United States Patent
Lavey et al.

(10) Patent No.: US 7,772,263 B2
(45) Date of Patent: Aug. 10, 2010

(54) COMPOUNDS FOR THE TREATMENT OF INFLAMMATORY DISORDERS

(75) Inventors: Brian J. Lavey, New Providence, NJ (US); Joseph A. Kozlowski, Princeton, NJ (US); Guowei Zhou, Somerset, NJ (US); Ling Tong, Warren, NJ (US); Wensheng Yu, Edison, NJ (US); Michael K. C. Wong, North Brunswick, NJ (US); Bandarpalle B. Shankar, Branchburg, NJ (US); Neng-Yang Shih, Lexington, MA (US); M. Arshad Siddiqui, Newton, MA (US); Kristin E. Rosner, Watertown, MA (US); Chaoyang Dai, Acton, MA (US); Janeta Popovici-Muller, Waltham, MA (US); Vinay M. Girijavallabhan, Denville, NJ (US); Dansu Li, Reading, MA (US); Razia Rizvi, Bloomfield, NJ (US); Lei Chen, Roselle Park, NJ (US); De-Yi Yang, Morris Plains, NJ (US); Robert Feltz, Jersey City, NJ (US); Seong Heon Kim, Livingston, NJ (US)

(73) Assignee: Schering Corporation, Kenilworth, NJ (US)

( * ) Notice: Subject to any disclaimer, the term of this patent is extended or adjusted under 35 U.S.C. 154(b) by 0 days.

(21) Appl. No.: 12/364,845

(22) Filed: Feb. 3, 2009

(65) Prior Publication Data

US 2009/0156586 A1    Jun. 18, 2009

Related U.S. Application Data

(63) Continuation of application No. 11/653,511, filed on Jan. 16, 2007, now Pat. No. 7,524,842.

(60) Provisional application No. 60/759,300, filed on Jan. 17, 2006.

(51) Int. Cl.
A61K 31/427   (2006.01)
A61K 31/4164  (2006.01)
A61K 31/4375  (2006.01)

(52) U.S. Cl. .................. 514/373; 514/405; 514/414
(58) Field of Classification Search .............. 514/227.8, 514/373, 405, 414; 544/60
See application file for complete search history.

(56) References Cited

U.S. PATENT DOCUMENTS

| | | | |
|---|---|---|---|
| 6,495,565 B2 | 12/2002 | Duan et al. |
| 6,534,491 B2 | 3/2003 | Levin et al. |
| 6,677,355 B1 | 1/2004 | Conrad et al. |
| 7,482,370 B2 | 1/2009 | Yu et al. |
| 7,488,745 B2 | 2/2009 | Yu et al. |
| 7,504,424 B2 | 3/2009 | Yu et al. |
| 7,524,842 B2 | 4/2009 | Lavey et al. |
| 2004/0067996 A1 | 4/2004 | Sheppeck |
| 2006/0276506 A1 | 12/2006 | Yu et al. |
| 2007/0265299 A1 | 11/2007 | Lavey et al. |
| 2008/0226618 A1 | 9/2008 | Mansoor et al. |
| 2009/0111803 A1 | 4/2009 | Yu et al. |
| 2009/0137586 A1 | 5/2009 | Yu et al. |
| 2009/0156586 A1 | 6/2009 | Lavey et al. |
| 2009/0170875 A1 | 7/2009 | Yu et al. |

FOREIGN PATENT DOCUMENTS

| | | |
|---|---|---|
| WO | WO02/074750 | 9/2002 |
| WO | WO 02/074751 | 9/2002 |
| WO | WO02/096426 | 12/2002 |
| WO | WO03/053940 | 7/2003 |
| WO | WO03/053941 | 7/2003 |
| WO | WO2004/012663 | 2/2004 |
| WO | WO2004/024698 | 3/2004 |
| WO | WO2004/024715 | 3/2004 |
| WO | WO2004/024721 | 3/2004 |
| WO | WO 2004/033632 | 4/2004 |
| WO | WO2004/056766 | 7/2004 |
| WO | WO2006/019768 | 2/2006 |
| WO | WO2007/084455 | 7/2007 |

OTHER PUBLICATIONS

Dinarello, C. A., et al., "Stopping the Cuts"; Current Biology; 5(6):587-590; 1995.

Doggrell, S., "TACE inhibition: a new approach to treating inflammation", Expert Opin. Invet. Drugs, 2002, vol. 11, No. 7, pp. 1003-1006, 2002.

Donnahoo, K., et al., "Review Article: The Role Of Tumor Necrosis Factor In Renal Ischemia-Reperfusion Injury", The Journal of Urology, vol. 62, pp. 196-203, 1999.

(Continued)

Primary Examiner—Taofiq A Solola
(74) Attorney, Agent, or Firm—Krishna G. Banerjee; Eric A. Meade

(57) ABSTRACT

This invention relates to compounds of the Formula (I):

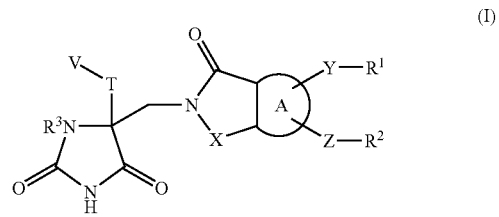

or a pharmaceutically acceptable salt, solvate or isomer thereof, which can be useful for the treatment of diseases or conditions mediated by MMPs, ADAMs, TACE, aggrecanase, TNF-α or combinations thereof.

31 Claims, No Drawings

OTHER PUBLICATIONS

Feldman, M. et al. "Discovery of TNF-α as a therapeutic target in rheumatoid arthritis: preclinical and clinical studies", Joint Bone Spine, vol. 69, pp. 12-18, 2002.

International Search Report for International Application No. PCT/US2005/024771 dated Nov. 9, 2005.

International Search Report for International Application No. PCT/US2007/000930 dated Aug. 22, 2007.

Knabe, J. et. al., Racemates and enantiomers of basic substituted 5-phenylhydantoins. Synthesis and antiarrhymic activity; Pharmazie, 1997, 52(12): 912-919—English abstract as it appears on p. 912.

Le, Giang T., et. al., "Inhibitors of TACE and Caspace-1 as Anti-Inflammatory Drugs"; Current Medicinal Chemistry; 12:2963-2977; 2005.

Leib, S., et al., "Inhibition of matrix metalloproteinases and tumour necrosis factor α converting enzyme as adjuvant therapy in pneumococcal meningitis" Brain, vol. 124, No. 9, pp. 1734-1742, 2001.

Morimoto, Y., et al., "KB-R7785, A Novel Matrix Metalloproteinase Inhibitor, Exerts Its Antidiabetic Effect By Inhibiting Tumor Necrosis Factor-α Production" Life Sciences, vol. 61, No. 8, pp. 795-803, 1997.

Moriyama, Hideki, et. al., "Azasugar-Based MMP/ADAM Inhibitors as Antipsoriatic Agents"; J. Med. Chem.; 47:1930-1938; 2004.

Moss, M. et al., "TACE and other ADAM Proteases as targets for drug discovery" Drug Discovery Today, vol. 6, No. 8, pp. 417-426, 2001.

Nelson, F. et al., "The therapeutic potential of small molecule TACE inhibitors" Exp. Opin. Invest. Drug, vol. 8, No. 4 pp. 383-392, 1999.

Newton, R. C. et al., "Biology of TACE Inhibition"; Ann. Rheum. Dis.; 60:iii25-iii32; 2001.

Olmarker, K., et al., "Selective Inhibition of Tumor Necrosis Factor-α Prevents Nucleus Pulposus-Induced Thrombus Formation, Intraneural Edema, and Reduction of Nerve Conduction Velocity" Spine, vol. 26, No. 8 pp. 863-869, 2001.

Reimold, A., et a., "New Indications for Treatment of Chronic Inflammation by TNF-[alpha] Blockade", American Journal of the Medical Sciences, vol. 325, No. 2, pp. 75-92, Abstract, 2003.

Satoh, M., et al., "Expression of Tumor Necrosis Factor-alpha-Converting Enzyme and Tumor Necrosis Factor-alpha in Human Myocarditis" Journal of American College of Cardiology, vol. 36, No. 4, pp. 1288-1294, 2000.

Seifert, T., et al., "TACE mRNA expression in peripheral mononuclear cells precedes new lesions on MRI in multiple sclerosis" Multiple Sclerosis, vol. 8, pp. 447-451, 2002.

Togashi, N., et al., "Effect of TNF-α Converting Enzyme Inhibitor on Insulin Resistance in Fructose-Fed Rats" Hypertension, vol. 39, Part 2, pp. 578-580, 2002.

Trifilieff, A., et al., "Pharmacological profile of PKF242-484 and PKF241-466, novel dual inhibitors of TNF-α converting enzyme and matrix metalloproteinases, in models of airway inflammation", British Journal of Pharmacology, vol. 135, No. 7, pp. 1655-1664, 2002.

Vandeventer, SJH, "A Place for TACE", GUT 2002 51: 5-6.

PCT International Search Report dated Jun. 1, 2007 for corresponding PCT Application No. PCT/US2007/001025.

COMPOUNDS FOR THE TREATMENT OF INFLAMMATORY DISORDERS

CROSS-REFERENCE TO RELATED APPLICATIONS

This Application, which is a continuation of U.S. application Ser. No. 11/653,511, filed Jan. 16, 2007, now U.S. Pat. No. 7,524,842, which claims the benefit of U.S. Provisional Application Ser. No. 60/759,300 filed Jan. 17, 2006, which is incorporated by reference in its entirety.

BACKGROUND OF THE INVENTION

1. Field of the Invention

This invention relates generally to novel hydantoin derivatives that can inhibit matrix metalloproteinases (MMPs), a disintegrin and metalloproteases (ADAMs) and/or tumor necrosis factor alpha-converting enzyme (TACE) and in so doing prevent the release of tumor necrosis factor alpha (TNF-α), pharmaceutical compositions comprising such compounds, and methods of treatment using such compounds.

2. Description

Osteo- and rheumatoid arthritis (OA and RA, respectively) are destructive diseases of articular cartilage characterized by localized erosion of the cartilage surface. Findings have shown that articular cartilage from the femoral heads of patients with OA, for example, had a reduced incorporation of radiolabeled sulfate over controls, suggesting that there must be an enhanced rate of cartilage degradation in OA (Mankin et al. J. Bone Joint Surg. 52A (1970) 424-434). There are four classes of protein degradative enzymes in mammalian cells: serine, cysteine, aspartic and metalloproteases. The available evidence supports the belief that it is the metalloproteases that are responsible for the degradation of the extracellular matrix of articullar cartilage in OA and RA. Increased activities of collagenases and stromelysin have been found in OA cartilage and the activity correlates with severity of the lesion (Mankin et al. Arthritis Rheum. 21, 1978, 761-766, Woessner et al. Arthritis Rheum. 26, 1983, 63-68 and Ibid. 27, 1984, 305-312). In addition, aggrecanase (a newly identified metalloprotease) has been identified that provides the specific cleavage product of proteoglycan, found in RA and OA patients (Lohmander L. S. et al. Arthritis Rheum. 36, 1993, 1214-22).

Metalloproteases (MPs) have been implicated as the key enzymes in the destruction of mammalian cartilage and bone. It can be expected that the pathogenesis of such diseases can be modified in a beneficial manner by the administration of MP inhibitors (see Wahl et al. Ann. Rep. Med. Chem. 25, 175-184, AP, San Diego, 1990).

MMPs are a family of over 20 different enzymes that are involved in a variety of biological processes important in the uncontrolled breakdown of connective tissue, including proteoglycan and collagen, leading to resorption of the extracellular matrix. This is a feature of many pathological conditions, such as RA and OA, corneal, epidermal or gastric ulceration; tumor metastasis or invasion; periodontal disease and bone disease. Normally these catabolic enzymes are tightly regulated at the level of their synthesis as well as at their level of extracellular activity through the action of specific inhibitors, such as alpha-2-macroglobulins and TIMPs (tissue inhibitor of MPs), which form inactive complexes with the MMP's.

Tumor necrosis factor alpha (TNF-α) is a cell-associated cytokine that is processed from a 26 kDa precursor form to a 17 kd active form. See Black R. A. "Tumor necrosis factor-alpha converting enzyme" Int J Biochem Cell Biol. 2002 January; 34(1):1-5 and Moss M L, White J M, Lambert M H, Andrews R C. "TACE and other ADAM proteases as targets for drug discovery" Drug Discov Today. 2001 Apr. 1; 6(8): 417-426, each of which is incorporated by reference herein.

TNF-α has been shown to play a pivotal role in immune and inflammatory responses. Inappropriate or over-expression of TNF-α is a hallmark of a number of diseases, including RA, Crohn's disease, multiple sclerosis, psoriasis and sepsis. Inhibition of TNF-α production has been shown to be beneficial in many preclinical models of inflammatory disease, making inhibition of TNF-α production or signaling an appealing target for the development of novel anti-inflammatory drugs.

TNF-α is a primary mediator in humans and animals of inflammation, fever and acute phase responses, similar to those observed during acute infection and shock. Excess TNF-α has been shown to be lethal. Blocking the effects of TNF-α with specific antibodies can be beneficial in a variety of conditions, including autoimmune diseases such as RA (Feldman et al, Lancet, (1994) 344, 1105), non-insulin dependent diabetes mellitus (Lohmander L. S. et al., Arthritis Rheum. 36 (1993) 1214-22) and Crohn's disease (Macdonald T. et al., Clin. Exp. Immunol. 81 (1990) 301).

Compounds that inhibit the production of TNF-α are therefore of therapeutic importance for the treatment of inflammatory disorders. Recently it has been shown that metalloproteases, such as TACE, are capable of converting TNF-α from its inactive to active form (Gearing et al Nature, 1994, 370, 555). Since excessive TNF-α production has been noted in several disease conditions also characterized by MMP-mediated tissue degradation, compounds which inhibit both MMPs and TNF-α production may also have a particular advantage in diseases where both mechanisms are involved.

One approach to inhibiting the harmful effects of TNF-α is to inhibit the enzyme, TACE before it can process TNF-α to its soluble form. TACE is a member of the ADAM family of type I membrane proteins and mediates the ectodomain shedding of various membrane-anchored signaling and adhesion proteins. TACE has become increasingly important in the study of several diseases, including inflammatory disease, because of its role in cleaving TNF-α from its "stalk" sequence and thus releasing the soluble form of the TNF-α protein (Black R. A. Int J Biochem Cell Biol. 2002 34, 1-5).

There are numerous patents and publications which disclose hydroxamate, sulphonamide, hydantoin, carboxylate and/or lactam based MMP inhibitors.

U.S. Pat. No. 6,677,355 and U.S. Pat. No. 6,534,491 (B2), describe compounds that are hydroxamic acid derivatives and MMP inhibitors.

U.S. Pat. No. 6,495,565 discloses lactam derivatives that are potential inhibitors of MMPs and/or TNF-α.

PCT Publications WO2002/074750, WO2002/096426, WO20040067996, WO2004012663, WO200274750 and WO2004024721 disclose hydantoin derivatives that are potential inhibitors of MMPs.

PCT Publications WO2004024698 and WO2004024715 disclose sulphonamide derivatives that are potential inhibitors of MMPs.

PCT Publications WO2004056766, WO2003053940 and WO2003053941 also describe potential inhibitors of TACE and MMPs.

PCT Publication WO2006/019768 refers to hydantoin derivatives that are TACE inhibitors.

There is a need in the art for inhibitors of MMPs, ADAMs, TACE, and TNF-α, which can be useful as anti-inflammatory compounds and cartilage protecting therapeutics. The inhibition of TNF-α, TACE and or other MMPs can prevent the degradation of cartilage by these enzymes, thereby alleviating the pathological conditions of OA and RA as well as many other auto-immune diseases.

SUMMARY OF THE INVENTION

In its many embodiments, the present invention provides a novel class of compounds as inhibitors of TACE, the production of TNF-α, MMPs, ADAMs, aggrecanase, or any combination thereof, methods of preparing such compounds, pharmaceutical compositions comprising one or more such compounds, methods of preparing pharmaceutical formulations comprising one or more such compounds, and methods of treatment, prevention, inhibition or amelioration of one or more diseases associated with TACE, aggrecanase TNF-α, MMPs, ADAMs or any combination thereof using such compounds or pharmaceutical compositions.

In one embodiment, the present application discloses a compound represented by Formula (I):

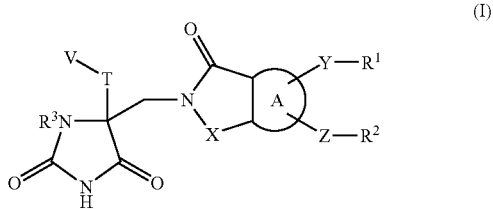

(I)

or a pharmaceutically acceptable salt, solvate, ester or isomer thereof, wherein:

ring A is selected from the group consisting of aryl and heteroaryl, each of which is substituted with —Y—$R^1$ and —Z—$R^2$ as shown;

X is selected from the group consisting of —S—, —O—, —S(O)$_2$—, S(O)—, —(C($R^3$)$_2$)$_m$—, and —N($R^3$)—;

T is alkynyl;

V is selected from the group consisting H, alkyl, cycloalkyl, cycloalkenyl, aryl, heteroaryl, heterocyclyl, and N-oxides of said heteroaryl and heterocyclyl, wherein when each of said cycloalkyl, cycloalkenyl, aryl, heteroaryl, heterocyclyl, and N oxides of said heteroaryl and heterocyclyl contains two radicals on same or adjacent carbon atoms, said radicals may optionally be taken together with the carbon atom(s) to which they are attached to form a five- to eight-membered cycloalkyl, cycloalkenyl, aryl, heterocyclyl or heteroaryl ring, wherein each of the aforementioned cycloalkyl, cycloalkenyl, aryl, heteroaryl, and heterocyclyl, optionally with said five- to eight-membered cycloalkyl, cycloalkenyl, aryl, heterocyclyl, or heteroaryl is independently unsubstituted or substituted with one to four $R^{10}$ moieties which can be the same or different;

Y is selected from the group consisting of a covalent bond, —(C($R^4$)$_2$)$_n$—, —N($R^4$)—, —C(O)N($R^4$)—, —N($R^4$)C(O)—, —N($R^4$)C(O)N($R^4$)—, —S(O)$_2$N($R^4$)—, —N($R^4$)—S(O)$_2$—, —O—, —S—, —C(O)—, —S(O)—, and —S(O)$_2$—;

Z is selected from the group consisting of a covalent bond, —(C($R^4$)$_2$)$_n$—, —N($R^4$)—, —C(O)N($R^4$)—, —N($R^4$)C(O)—, —N($R^4$)C(O)N($R^4$)—, —S(O)$_2$N($R^4$)—, —N($R^4$)—S(O)$_2$—, —O—, —S—, —C(O)—, —S(O)—, and —S(O)$_2$—;

m is 1 to 3:

n is 1 to 3;

$R^1$ is selected from the group consisting of H, cyano, alkynyl, halogen, alkyl, cycloalkyl, haloalkyl, aryl, heteroaryl, and heterocyclyl, wherein when each of said cycloalkyl, heterocyclyl, aryl and heteroaryl contains two radicals on adjacent carbon atoms, said radicals may optionally be taken together with the carbon atoms to which they are attached to form a five- to eight-membered cycloalkyl, aryl, heterocyclyl or heteroaryl ring; wherein each of the $R^1$ alkyl, alkynyl, aryl, heteroaryl, and heterocyclyl, optionally with the five or six-membered cycloalkyl, aryl, heterocyclyl or heteroaryl ring is unsubstituted or optionally independently substituted with one to four $R^{20}$ moieties which can be the same or different; with the proviso that when Y is —N($R^4$)—, —S— or —O—, then $R^1$ is not halogen or cyano;

$R^2$ is selected from the group consisting of H, cyano, alkynyl, halogen, alkyl, cycloalkyl, haloalkyl, aryl, heteroaryl, and heterocyclyl, wherein when each of said cycloalkyl, heterocyclyl, aryl and heteroaryl contains two radicals on adjacent carbon atoms, said radicals may optionally be taken together with the carbon atoms to which they are attached to form a five- to eight-membered cycloalkyl, aryl, heterocyclyl or heteroaryl ring; wherein each of the $R^2$ alkyl, cycloalkyl, aryl, heteroaryl, and heterocyclyl, optionally with the five or six-membered cycloalkyl, aryl, heterocyclyl or heteroaryl ring is unsubstituted or optionally independently substituted with one to four $R^{20}$ moieties which can be the same or different; with the proviso that when Y is —N($R^4$)—, —S— or —O—, then $R^2$ is not halogen or cyano;

each $R^3$ is the same of different and is independently selected from the group consisting of H, alkyl, and aryl;

each $R^4$ is the same or different and is independently selected from the group consisting of H, alkyl, cycloalkyl, haloalkyl, hydroxy, -alkylcycloalkyl, -alkyl-N(alkyl)$_2$, heterocyclyl, aryl, and heteroaryl;

$R^{10}$ is selected from the group consisting of hydrogen, cyano, nitro, —C($R^4$)=N—O$R^4$ —O$R^4$ —S$R^4$, —N($R^4$)$_2$, —S(O)$R^4$, —S(O)$_2R^4$, —N($R^4$)S(O)$_2R^4$, —N($R^4$)—C(O)—$R^4$, —C(O)N($R^4$)—S(O)$_2R^4$, —S(O)$_2$N($R_4$)—C(O)—$R^4$, —C(O)N($R^4$)C(O)$R^4$, —C(O)N($R^4$)C(O)N$R^4$—S(O)$_2$N($R^4$)$_2$, —N($R^4$)—C(O)O$R^4$, —OC(O)N($R^4$)$_2$, —N($R^4$)C(O)N($R^4$)$_2$, —S(O)$_2$N($R^4$)$_2$, —S(O)$_2$N($R_4$)—C(O)—$R^4$, —N($R^4$)—C(=N$R^4$)—N($R^4$)$_2$, —N($R^4$)—C(=N—CN)—N($R^4$)$_2$, -haloalkoxy, —C(O)O$R^4$, —C(O)$R^4$, —C(O)N($R^4$)$_2$, halogen, alkyl, haloalkyl, aryl, heteroaryl, heterocyclyl, and cycloalkyl, wherein each of the $R^{10}$ alkyl, aryl, heteroaryl, heterocyclyl, and cycloalkyl is unsubstituted or optionally independently substituted with one to four $R^{30}$ moieties which can be the same or different;

or wherein two $R^{10}$ moieties, when attached to the same or adjacent carbon atoms may optionally be taken together with the carbon atom(s) to which they are attached to form a cycloalkyl, cycloalkenyl, heterocyclyl, aryl, or heteroaryl ring;

$R^{20}$ is selected from the group consisting of cyano, nitro, —C($R^4$)=N—O$R^4$, —O$R^4$, —S$R^4$, —N($R^4$)$_2$, —S(O)$R^4$, —S(O)$_2R^4$, —N($R^4$)S(O)$_2R^4$, —N($R^4$)—C(O)—$R^4$, —C(O)N($R^4$)—S(O)$_2R^4$, —S(O)$_2$N($R_4$)—C(O)—$R^4$, —C(O)N($R^4$)C(O)$R^4$, —C(O)N($R^4$)C(O)N$R^4$—S(O)$_2$N($R^4$)$_2$, —N($R^4$)—C(O)O$R^4$, —OC(O)N($R^4$)$_2$, —N($R^4$)C(O)N($R^4$)$_2$, —S(O)$_2$N($R^4$)$_2$, —S(O)$_2$N($R^4$)—C(O)—$R^4$, —N($R^4$)—C(=N$R^4$)—N($R^4$)$_2$, —N($R^4$)—C(=N—CN)—N($R^4$)$_2$, -haloalkoxy, —C(O)O$R^4$, —C(O)$R^4$, —C(O)N($R^4$)$_2$, halogen, alkyl, haloalkyl, aryl, heteroaryl, heterocyclyl, and cycloalkyl; wherein when each of said $R^{20}$ aryl, heteroaryl, heterocyclyl and cycloalkyl contains two radicals on adjacent carbon atoms, said radicals may optionally be taken together with the carbon atoms to which they are attached to form a five- to eight-membered cycloalkyl, aryl, heterocyclyl or heteroaryl ring; wherein each of said $R^{20}$ alkyl, aryl, heteroaryl, heterocyclyl, and cycloalkyl, optionally with said five- to eight-membered cycloalkyl, aryl, heterocyclyl or heteroaryl ring is unsubstituted or substituted with one to four moieties selected independently from the group consisting of alkyl, halo, haloalkyl, hydroxy, alkoxy, haloalkoxy, hydroxyalkyl, cyano, nitro, —$NH_2$, —NH(alkyl), and —$N(alkyl)_2$;

or when two $R^{20}$ moieties when attached to the same or adjacent carbon atoms may optionally be taken together with the carbon atom(s) to which they are attached to form a cycloalkyl, cycloalkenyl, heterocyclyl, aryl, or heteroaryl ring;

$R^{30}$ is selected from the group consisting of cyano, nitro, —$C(R^4)$=N—$OR^4$, —$OR^4$, —$SR^4$, —$N(R^4)_2$, —$S(O)R^4$, —$S(O)_2R^4$, —$N(R^4)S(O)_2R^4$, —$N(R^4)$—$C(O)$—$R^4$, —$C(O)N(R^4)$—$S(O)_2R^4$, —$S(O)_2N(R_4)$—$C(O)$—$R^4$, —$C(O)N(R^4)C(O)R^4$, —$C(O)N(R^4)C(O)NR^4$—$S(O)_2N(R^4)_2$, —$N(R^4)$—$C(O)OR^4$, —$OC(O)N(R^4)_2$, —$N(R^4)C(O)N(R^4)_2$, —$S(O)_2N(R^4)_2$, —$S(O)_2N(R_4)$—$C(O)$—$R^4$, —$N(R^4)$—$C(=NR^4)$—$N(R^4)_2$, —$N(R^4)$—$C(=N$—$CN)$—$N(R^4)_2$, -haloalkoxy, —$C(O)OR^4$, —$C(O)R^4$, —$C(O)N(R^4)_2$, halogen, alkyl, haloalkyl, aryl, heteroaryl, heterocyclyl, and cycloalkyl; wherein when each of said $R^{30}$ aryl, heteroaryl, heterocyclyl and cycloalkyl contains two radicals on adjacent carbon atoms, said radicals may optionally be taken together with the carbon atoms to which they are attached to form a five- to eight-membered cycloalkyl, aryl, heterocyclyl or heteroaryl ring; wherein each of said $R^{30}$ alkyl, aryl, heteroaryl, heterocyclyl, and cycloalkyl, optionally with said five- to eight-membered cycloalkyl, aryl, heterocyclyl or heteroaryl ring is unsubstituted or substituted with one to four moieties selected independently from the group consisting of alkyl, halo, haloalkyl, hydroxy, alkoxy, haloalkoxy, cyano, nitro, —$NH_2$, —NH(alkyl), and —$N(alkyl)_2$;

or when two $R^{30}$ moieties when attached to the same or adjacent carbon atoms may optionally be taken together with the carbon atom(s) to which they are attached to form a cycloalkyl, cycloalkenyl, heterocyclyl, aryl, or heteroaryl ring.

In another embodiment, the present application discloses a compound having the general structure shown in Formula (II):

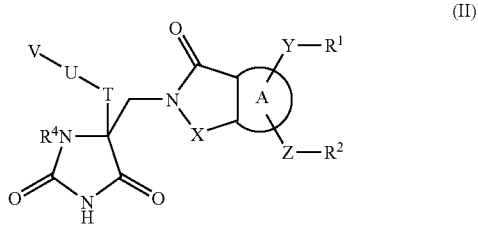

(II)

or a pharmaceutically acceptable salt, solvate, ester or isomer thereof, wherein:

the ring labeled A is selected from the group consisting of aryl and heteroaryl, each of which is substituted with —Y—$R^1$ and —Z—$R^2$ as shown;

X is selected from the group consisting of —S—, —O—, —$C(R^3)_2$— or —$N(R^3)$—;

T is absent or present, and if present, T is selected from the group consisting of H (with U and V being absent), alkyl, alkenyl, alkynyl, aryl, heteroaryl, heterocyclyl, cycloalkyl, alkylaryl-, and arylalkyl-, said aryl, heteroaryl, heterocyclyl, cycloalkyl, alkylaryl-, and arylalkyl- being optionally fused with one or more moieties selected from the group consisting of aryl, heteroaryl, heterocyclyl, cycloalkyl, alkylaryl and arylalkyl, wherein each of any of the aforementioned alkyl, alkenyl, aryl, heteroaryl, heterocyclyl, cycloalkyl, alkylaryl and arylalkyl groups of T is unsubstituted or optionally independently substituted with one to four $R^{10}$ moieties which can be the same or different, each $R^{10}$ moiety being independently selected from the group of $R^{10}$ moieties below;

U is absent or present, and if present U is selected from the group consisting of alkynyl, —C(O)—, —C(O)O—, and —$C(O)NR^4$—;

V is absent or present, and if present V is selected from the group consisting of hydrogen, alkyl, aryl, heteroaryl, heterocyclyl, heterocyclylalkyl-, cycloalkyl, alkylaryl-, and arylalkyl-, said aryl, heteroaryl, heterocyclyl, heterocyclylalkyl-, cycloalkyl, alkylaryl- and arylalkyl- being optionally fused with one or more moieties selected from the group consisting of aryl, heteroaryl, heterocyclyl, cycloalkyl, alkylaryl and arylalkyl, wherein each of any of the aforementioned alkyl, aryl, heteroaryl, heterocyclyl and cycloalkyl is unsubstituted or optionally independently substituted with one to four $R^{10}$ moieties which can be the same or different, each $R^{10}$ moiety being independently selected from the group of $R^{10}$ moieties below;

Y is selected from the group consisting of a covalent bond, —$(C(R^4)_2)_n$—, —$N(R^4)$—, —$C(O)N(R^4)$—, —$N(R^4)C(O)$—, —$N(R^4)C(O)N(R^4)$—, —$S(O)_2N(R^4)$—, —$N(R^4)$—$S(O)_2$, —O—, —S—, —C(O)—, —S(O)—, and —$S(O)_2$—;

Z is selected from the group consisting of a covalent bond, —$(C(R^4)_2)_n$—, —$N(R^4)$—, —$C(O)N(R^4)$—, —$N(R^4)C(O)$—, —$N(R^4)C(O)N(R^4)$—, —$S(O)_2N(R^4)$—, —$N(R^4)$—$S(O)_2$—, —O—, —S—, —C(O)—, —S(O)—, and —$S(O)_2$—;

n is 1 to 3;

$R^1$ is selected from the group consisting of H, —$OR^4$, cyano, —$C(O)OR^4$, —$C(O)N(R^4)_2$, halogen, alkyl, fluoroalkyl, aryl, heteroaryl, heterocyclyl, alkylaryl, alkylheteroaryl and arylalkyl, wherein each of the alkyl, fluoroalkyl, aryl, heteroaryl, heterocyclyl, alkylaryl, alkylheteroaryl and arylalkyl groups of $R^1$ is unsubstituted or optionally independently substituted with one to four $R^{20}$ moieties which can be the same or different, each $R^{20}$ moiety being independently selected from the group of $R^{20}$ moieties below, with the proviso that when Y is present and Y is N, S or O, then $R^1$ is not halogen or cyano;

$R^2$ is selected from the group consisting of H, —$OR^4$, cyano, —$C(O)OR^4$, —$C(O)N(R^4)_2$, halogen, alkyl, fluoroalkyl, aryl, heteroaryl, heterocyclyl, alkylaryl, alkylheteroaryl and arylalkyl, wherein each of the alkyl, fluoroalkyl, aryl, heteroaryl, heterocyclyl, alkylaryl, alkylheteroaryl and arylalkyl groups of $R^2$ is unsubstituted or optionally independently substituted with one to four $R^{20}$ moieties which can be the same or different, each $R^{20}$ moiety being independently selected from the group of $R^{20}$ moieties below, with the proviso that when Z is present and Z is N, S or O, then $R^2$ is not halogen;

each $R^3$ is the same of different and is independently selected from the group consisting of H, alkyl, and aryl;

each $R^4$ is the same or different and is independently selected from the group consisting of H, alkyl, heterocyclyl, aryl, and heteroaryl;

$R^{10}$ is selected from the group consisting of cyano, —$OR^4$, —$SR^4$, —$N(R^4)_2$, —$S(O)R^4$—, —$S(O)_2R^4$—, —$N(R^4)S(O)_2R^4$, —$S(O)_2N(R^4)_2$, —O(fluoroalkyl), —$C(O)OR^4$, —$C(O)N(R^4)_2$, halogen, alkyl, fluoroalkyl, aryl, heteroaryl, heterocyclyl, cycloalkyl, alkylaryl and arylalkyl, wherein each of the alkyl, fluoroalkyl, aryl, heteroaryl, heterocyclyl, cycloalkyl, alkylaryl and arylalkyl groups of $R^{10}$ is unsubstituted or optionally independently substituted with one to four $R^{30}$ moieties which can be the same or different, each $R^{30}$ moiety being independently selected from the group of $R^{30}$ moieties below;

$R^{20}$ is selected from the group consisting of halogen, alkyl, fluoroalkyl, —$N(R^4)_2$, and —$C(O)N(R^4)_2$; and $R^{30}$ is selected from the group consisting of halogen, alkyl, fluoroalkyl, —$N(R^4)_2$, and —$C(O)N(R^4)_2$.

The compounds of Formula I can be useful as inhibitors of TACE and may be useful in the treatment and prevention of diseases associated with TACE, TNF-α, MMPs, ADAMs or any combination thereof.

DETAILED DESCRIPTION OF THE INVENTION

In its several embodiments, the present invention provides a novel class of inhibitors of TACE, aggrecanase, the production of TNF-α, MMPs, ADAMs or any combination thereof, pharmaceutical compositions containing one or more of the compounds, methods of preparing pharmaceutical formulations comprising one or more such compounds, and methods of treatment, prevention or amelioration of one or more of the symptoms of inflammation.

In one embodiment, the present invention provides compounds which are represented by structural Formula (I)-(IV) above or a pharmaceutically acceptable salt, solvate, ester or isomer thereof, wherein the various moieties are as described above.

In another embodiment, the isomer referred to the in the preceding paragraph is a stereoisomer.

In one embodiment, the labeled ring A is selected from the group consisting of phenyl, thiophenyl, pyridyl, pyrimidyl, and

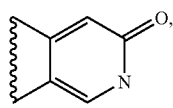

each of which is substituted with —Y—$R^1$ and —Z—$R^2$ as shown in Formula (I).

In another embodiment, in Formula (I), ring A is phenyl which is substituted with —Y—$R^1$ and —Z—$R^2$ as shown.

In another embodiment, in Formula (I), X is selected from the group consisting of —$(C(R^3)_2)_m$— and —$N(R^3)$—.

In another embodiment, in Formula (I), X is X is —$(C(R^3)_2)_m$, wherein m is 1 or 2.

In another embodiment, in Formula (I), X is —$(C(R^3)_2)_m$, wherein m is 1.

In another embodiment, in Formula (I), $R^3$ is H.

In another embodiment, in Formula (I), X is —$(C(R^3)_2)_m$, wherein m 1, and wherein $R^3$ is H.

In another embodiment, in Formula (I), T is —C≡C—.

In another embodiment, in Formula (I), wherein V is selected from the group consisting of H, aryl, heteroaryl, and N-oxide of said heteroaryl; wherein when each of the aforementioned aryl, and heteroaryl contains two radicals on same or adjacent carbon atoms, said radicals may optionally be taken together with the carbon atom(s) to which they are attached to form a five or six-membered cycloalkyl, aryl, heterocyclyl or heteroaryl ring; wherein said aryl and heteroaryl optionally with said five or six-membered cycloalkyl, aryl, heterocyclyl or heteroaryl ring is unsubstituted or optionally substituted with one to four $R^{10}$ moieties which can be the same or different.

In another embodiment, in Formula (I), V is selected from the group consisting of phenyl, naphthyl, pyrrolyl, furanyl, thiophenyl, pyrrazolyl, benzopyrazolyl, imidazoly, benzimidazolyl, furazanyl, pyridyl, pyridyl-N-oxide, pyridazinyl, pyrimidinyl, pyrazinyl, indolyl, isoindolyl, indazolyl, indolizinyl, quinolinyl, isopquinolinyl, quinazolinyl, pteridinyl, tetrazolyl, oxazolyl, isothiazolyl, thiazolyl,

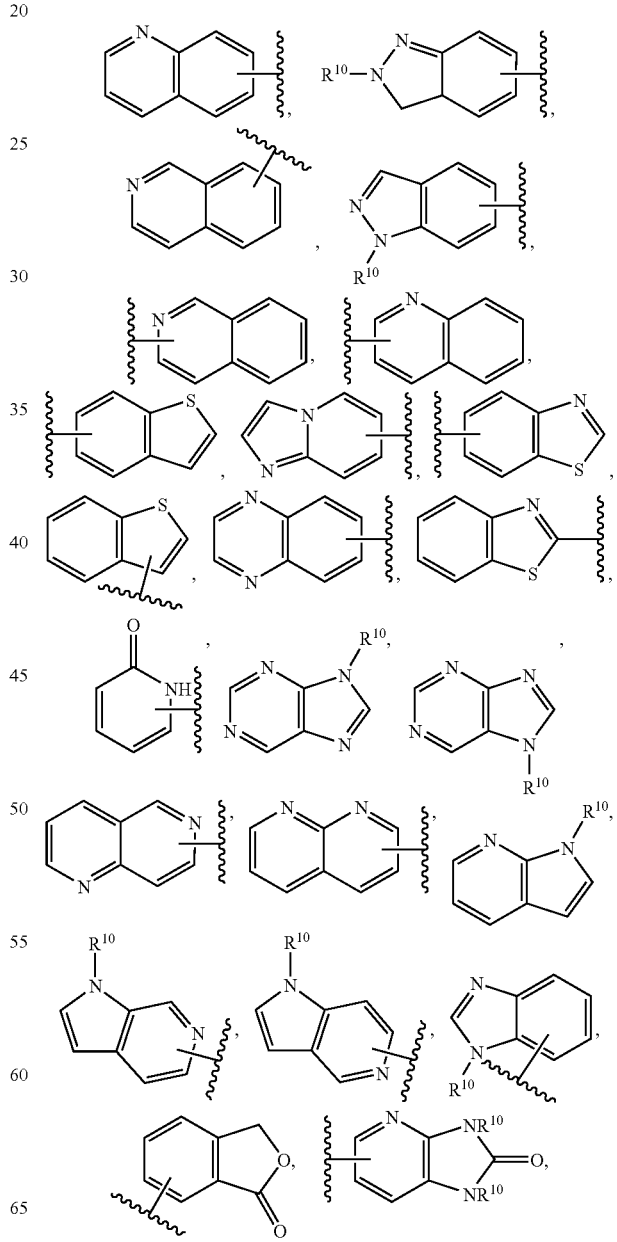

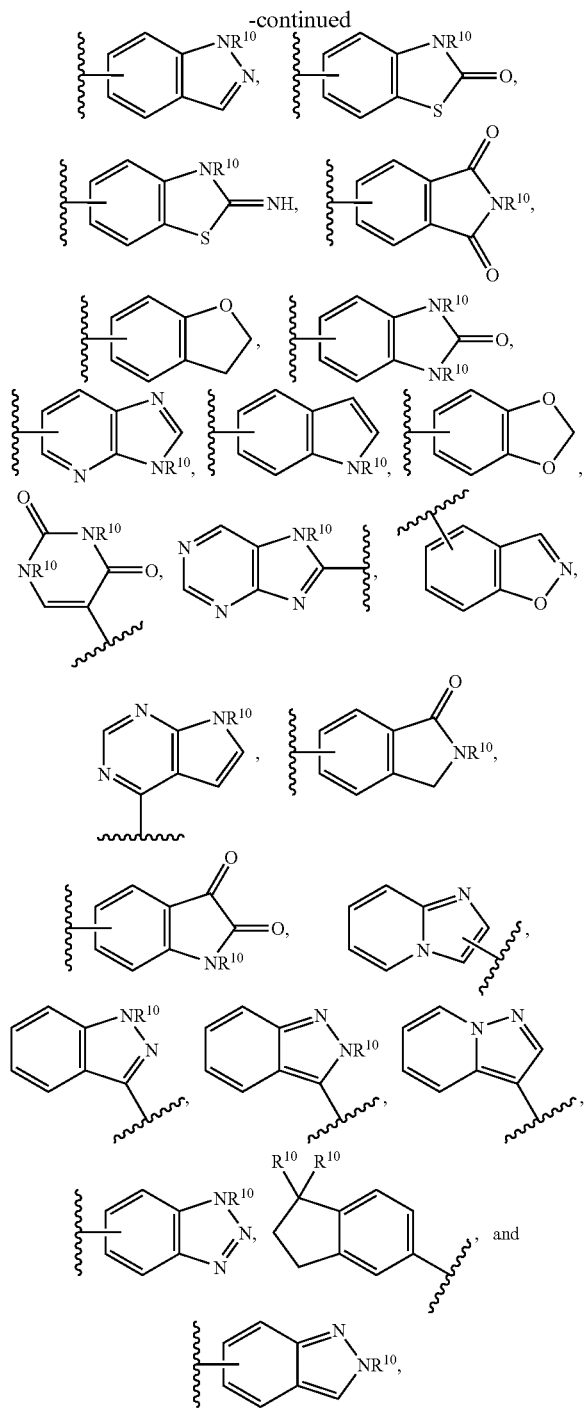

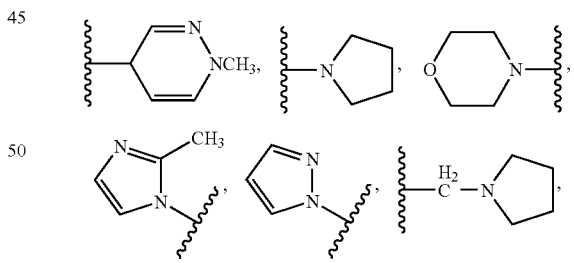

each of which is optionally substituted with one or more $R^{10}$ moieties such that the number of $R^{10}$ moieties per V group does not exceed four.

In another embodiment, in Formula (I), $R^{10}$ is selected from the group consisting of hydrogen, cyano, nitro, —$OR^4$, —$SR^4$, —$N(R^4)_2$, —$S(O)_2R^4$—, —$S(O)_2N(R^4)_2$, -haloalkoxy, —$C(O)OR^4$, —$C(O)R^4$, —$C(O)N(R^4)_2$, —$C(O)N(R^4)$—$S(O)_2R^4$, —$C(R^4)$=N—OR, halogen, alkyl, haloalkyl, aryl, heteroaryl, and heterocyclyl, wherein each of the alkyl, aryl, heteroaryl, and heterocyclyl is unsubstituted or optionally independently substituted with one to four $R^{30}$ moieties which can be the same or different;

or wherein two $R^{10}$ moieties, when attached to the same carbon atom are taken together with the carbon atom to which they are attached to form a heterocyclyl ring;

each $R^4$ is the same or different and is independently selected from the group consisting of H, alkyl, cycloalkyl, haloalkyl, hydroxy, -alkylcycloalkyl, -alkyl-N(alkyl)$_2$, heterocyclyl, aryl, and heteroaryl; and $R^{30}$ is selected from the group consisting of halogen, alkyl, haloalkyl, hydroxy, alkoxy, heterocyclyl, —$C(R^4)$=N—OR, —O-alkyl-cycloalkyl, —$N(R^4)_2$, and —$C(O)N(R^4)_2$, wherein said $R^{30}$ alkyl is substituted with a —$NH_2$. In another embodiment, in Formula (I), $R^{10}$ is selected from the group consisting of nitro, alkyl, halogen, haloalkyl, haloalkoxy, alkoxy, cyano, —$S(O)_2$-alkyl, —$NH_2$, —NH(alkyl), —N(alkyl)$_2$, cycloalkyl, aryl, heteroaryl, heterocyclyl, -alkyl-heterocyclyl, -cycloalkyl-$NH_2$, —$S(O)_2$—$NH_2$, —$S(O)_2$alkyl, —$C(O)NH_2$, hydroxy, —C(O)N(H)(cycloalkyl), —C(O)N(H)(alkyl), —N(H)(cycloalkyl), —C(O)O-alkyl, —C(O)OH, —$S(O)_2$N(H)(alkyl), —$S(O)_2$OH, —S-haloalkyl, —$S(O)_2$-haloalkyl, hydroxyalkyl, alkoxyalkyl, —O-alkyl-cycloalkyl, -alkyl-O-alkyl-cycloalkyl, —C(O)alkyl, aminoalkyl, -alkyl-NH(alkyl), -alkyl-N(alkyl)$_2$, —CH=N—O-alkyl, —C(O)NH-alkyl-N(alkyl)$_2$, —C(O)-heterocyclyl, and —NH—C(O)-alkyl, wherein each of said $R^{10}$ aryl and heteroaryl is optionally substituted with 1-2 moieties selected from the group consisting of alkyl, —$NH_2$, —NH(alkyl), and —N(alkyl)$_2$;

or wherein two $R^{10}$ moieties attached to the same carbon atom are taken together with the carbon atom to which they are attached to form a heterocyclyl ring.

In another embodiment, in Formula (I), $R^{10}$ is selected from the group consisting of hydrogen, nitro, methyl, fluoro, bromo, trifluoromethyl, chloro, difluoromethoxy, trifluoromethoxy, methoxy, hydroxyl, cyano, —$S(O)_2CH_3$, —$NH_2$, isopropyl, cyclopropyl, -cyclopropyl-$NH_2$, —NH(cyclopropyl), —NH(CH$_3$), —$S(O)_2$—$NH_2$, —C(O)NH$_2$, —C(O)OCH$_3$, —C(O)OH, —$S(O)_2$N(H)CH$_3$, —C(O)NH(CH$_3$), —C(O)NH(cyclopropyl), —$S(O)_2$OH, —S—CF$_3$, —$S(O)_2$—CF$_3$, ethoxy, hydroxymethyl, methoxymethyl, isopropoxy, —OCH$_2$-cyclopropyl, —CH$_2$O—CH$_2$-cyclopropyl, —C(O)CH$_3$, —C(O)CH$_3$, —CH(CH$_3$)OH, —CH$_2$NH$_2$, —CH(CH$_3$)NH$_2$, —CH$_2$NH—CH$_3$, —CH(CH$_3$)OH, —CH$_2$NHCH$_3$, —CH=N—OCH$_3$, —C(CH$_3$)=N—OCH$_3$, —C(O)OCH$_2$CH$_3$, —C(O)NHCH$_2$CH$_2$N(CH$_3$)$_2$, —NH—C(O)CH$_3$,

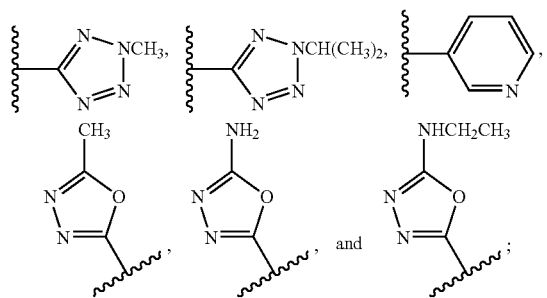

or wherein two R[10] moieties, when attached to the same carbon atom are taken together with the carbon atom to which they are attached to form

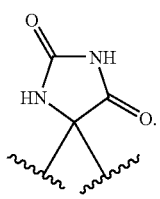

In another embodiment, in Formula (I), Y is selected from the group consisting of a covalent bond and —O—.

In another embodiment, in Formula (I), Y is a covalent bond.

In another embodiment, in Formula (I), Y is —O—.

In another embodiment, in Formula (I), Z is selected from the group consisting of a covalent bond and —O—.

In another embodiment, in Formula (I), Z is —O—.

In another embodiment, in Formula (I), R[1] is selected from the group consisting of hydrogen, cyano, halogen, alkyl, aryl, heteroaryl, haloalkyl, and alkynyl; wherein said R[1] alkyl is unsubstituted or substituted with an aryl, heteroaryl, or heterocyclyl, wherein when said aryl, heteroaryl, or heterocyclyl contains two radicals on adjacent carbon atoms, said radicals may optionally be taken together with the carbon atoms to which they are attached to form a five- to eight-membered cycloalkyl, aryl, heterocyclyl or heteroaryl ring; wherein said aryl, heteroaryl or heterocyclyl substitutent of said R[1] alkyl optionally with said five- to eight-membered cycloalkyl, aryl, heterocyclyl or heteroaryl ring is unsubstituted or optionally independently substituted with one to four R[20] moieties.

In another embodiment, in Formula (I), R[2] is selected from the group consisting of hydrogen, cyano, halogen, alkyl, aryl, heteroaryl, haloalkyl, and alkynyl; wherein said R[1] alkyl is unsubstituted or substituted with an aryl, heteroaryl, or heterocyclyl, wherein when said aryl, heteroaryl, or heterocyclyl contains two radicals on adjacent carbon atoms, said radicals may optionally be taken together with the carbon atoms to which they are attached to form a five- to eight-membered cycloalkyl, aryl, heterocyclyl or heteroaryl ring; wherein said aryl, heteroaryl or heterocyclyl substitutent of said R[1] alkyl optionally with said five- to eight-membered cycloalkyl, aryl, heterocyclyl or heteroaryl ring is unsubstituted or optionally independently substituted with one to four R[20] moieties.

In another embodiment, in Formula (I), R[1] is halogen or cyano.

In another embodiment, in Formula (I), R[1] is fluoro, chloro, or cyano.

In another embodiment, in Formula (I), Y is —O—, and R[1] is selected from the group consisting of alkyl, haloalkyl, and alkynyl; wherein said R[1] alkyl is unsubstituted or substituted with a heteroaryl, wherein when said heteroaryl contains two radicals on adjacent carbon atoms, said radicals may optionally be taken together with the carbon atoms to which they are attached to form a five- or six-membered aryl; wherein said heteroaryl substituent of said R[1] alkyl, optionally with said five- or six-membered aryl is substituted with alkyl. In another embodiment, in Formula (I), Y is —O—, and R[1] is selected from the group consisting of CH$_3$, —CH$_2$—C≡C—CH$_3$, difluoromethyl, and

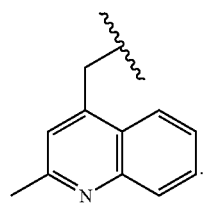

In another embodiment, the compound of Formula (I) is represented by the compound of formula (III):

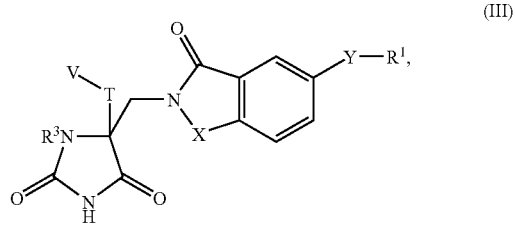

(III)

wherein in formula (III), X is —(CH$_2$)$_{1-2}$—, and T, V, Y, R[1], and R[3] are as set forth in Formula (I).

In another embodiment, in Formula (III), X is —CH$_2$—.

In another embodiment, the compound of Formula (I) is represented by the compound of formula (IV):

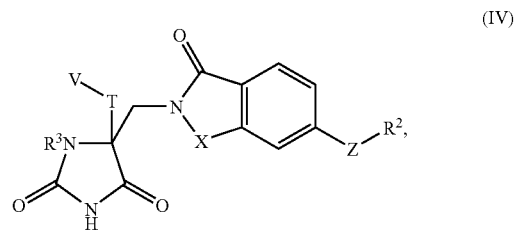

(IV)

wherein in formula (IV), X is —(CH$_2$)$_{1-2}$—, T, V, Y, R[1], and R[3] are as set forth in Formula (I).

In another embodiment, in Formula (IV), X is —CH$_2$—.

In another embodiment, the compound of Formula (I) is selected from the group consisting of compounds listed in the table below, or a pharmaceutically acceptable salt, solvate, ester or isomer thereof. This table also lists the mass spectroscopy data and the Ki rating for each compound. Those compounds having a Ki value of less than 5 nM (<5 nM) are designated with letter "A"; those with a Ki value of from 5 to less than 25 nM (5-<25 nM) are designated with letter "B"; those with a Ki value of from 25 to 100 nM are designated with letter "C"; and those with a Ki value of more than 100 nM (>100 nM) are designated with letter "D". The synthesis and characterization of these compounds is described hereinbelow in the "EXAMPLES" section of the present application.

TABLE 1001

| Compound ID | Structures | Exact Mass | Mass Obsvd | Ki Rating |
|---|---|---|---|---|
| 315A | 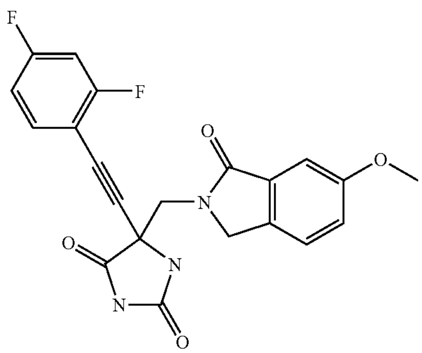 | 411.10 | 412.1 [M + H]+ | A |
| 315 | 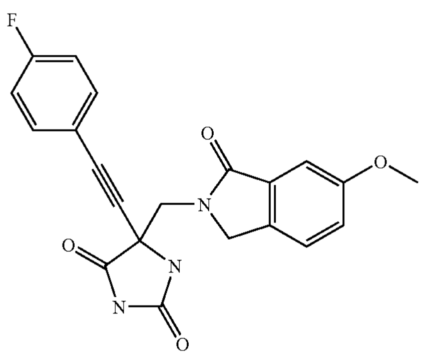 | 393.11 | 394.1 [M + H]+ | A |
| 312 | 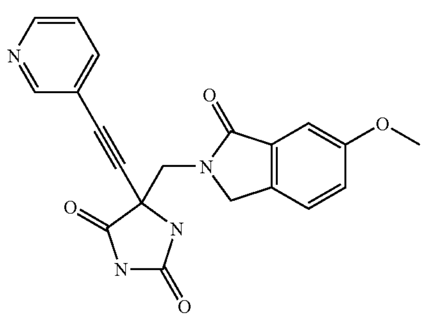 | 376.12 | 377 [M + H]+ | A |
| 312B | 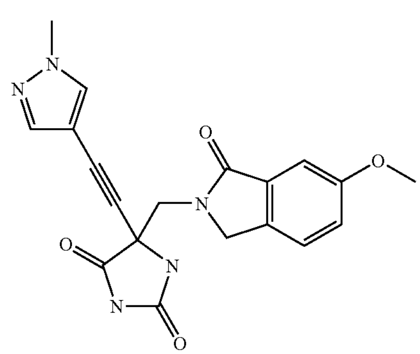 | 379.13 | 380 [M + H]+ | A |

TABLE 1001-continued
| Compound ID | Structures | Exact Mass | Mass Obsvd | Ki Rating |
|---|---|---|---|---|
| 421 | 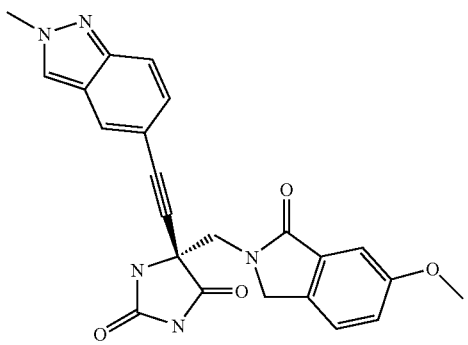 | 429.14 | 430.1 [M + H]+ | A |
| 422 | 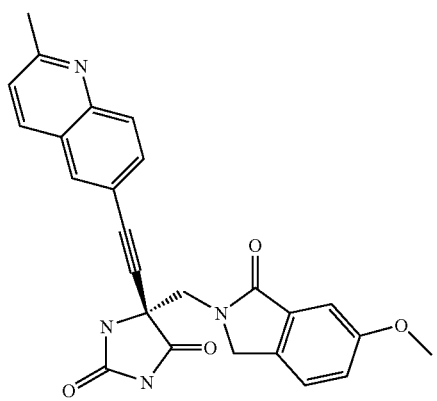 | 440.15 | 441.1 [M + H]+ | A |
| 423 | 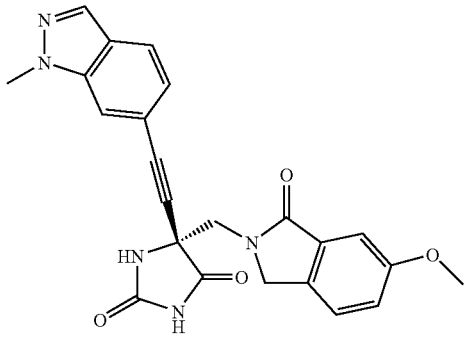 | 429.14 | 430.1 [M + H]+ | A |
| 424 | 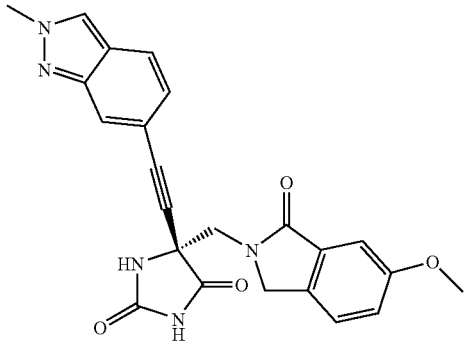 | 429.14 | 430.1 [M + H]+ | A |

TABLE 1001-continued

| Compound ID | Structures | Exact Mass | Mass Obsvd | Ki Rating |
|---|---|---|---|---|
| 425 | 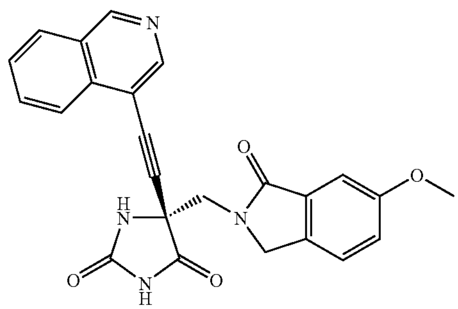 | 426.13 | 427.1 [M + H]+ | A |
| 426 | 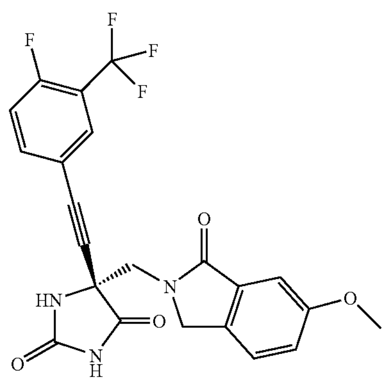 | 461.10 | 462.1 [M + H]+ | A |
| 427 | 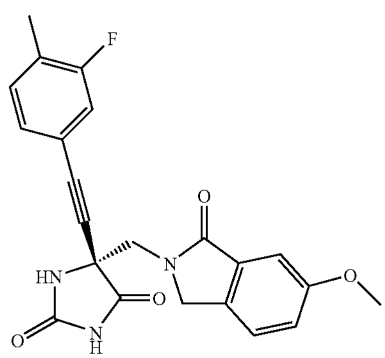 | 407.13 | 408.1 [M + H]+ | A |
| 428 | 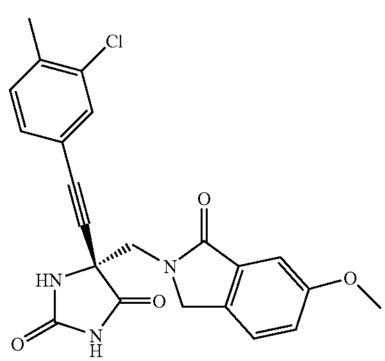 | 423.10 | 424.1 [M + H]+ | A |

TABLE 1001-continued

| Compound ID | Structures | Exact Mass | Mass Obsvd | Ki Rating |
|---|---|---|---|---|
| 429 | 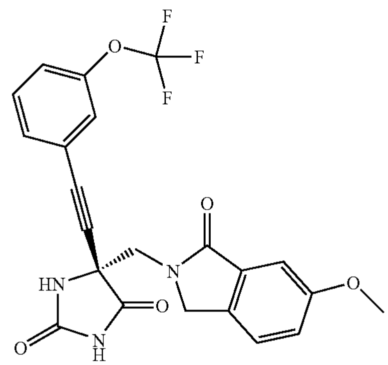 | 459.10 | 460.1 [M + H]+ | A |
| 430 | 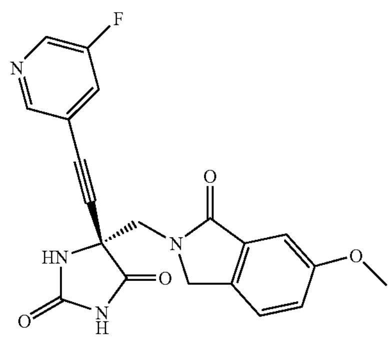 | 394.11 | 395.0 [M + H]+ | A |
| 432 | 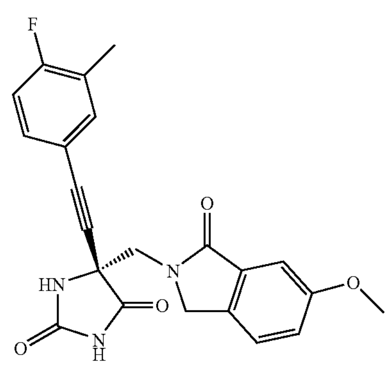 | 407.13 | 408.1 [M + H]+ | A |
| 433 | 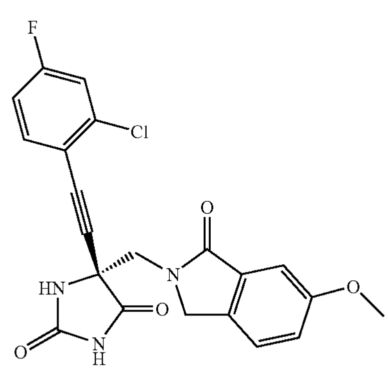 | 427.07 | 428.0 [M + H]+ | A |

TABLE 1001-continued

| Compound ID | Structures | Exact Mass | Mass Obsvd | Ki Rating |
|---|---|---|---|---|
| 434 | 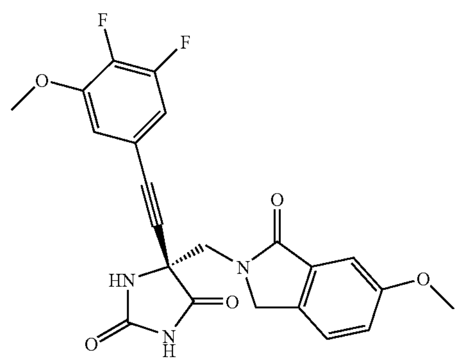 | 441.11 | 442.1 [M + H]⁺ | A |
| 435 | 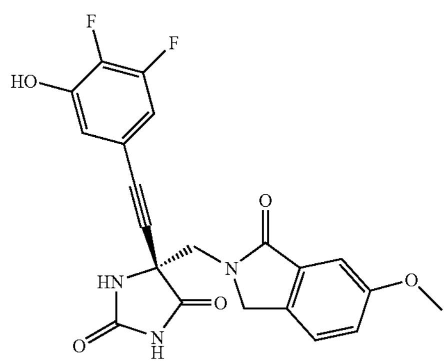 | 427.10 | 428.0 [M + H]⁺ | A |
| 436 | 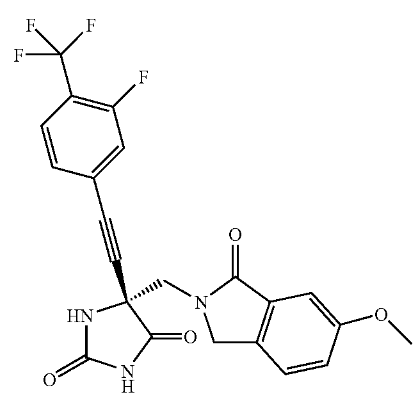 | 461.10 | 462.1 [M + H]⁺ | A |
| 437 | 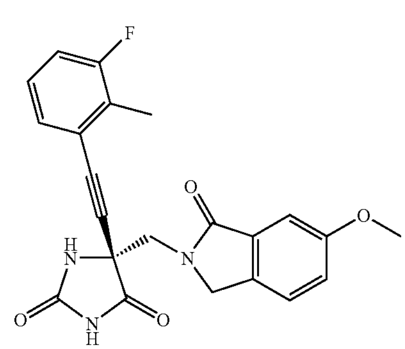 | 407.13 | 408.1 [M + H]⁺ | A |

TABLE 1001-continued

| Compound ID | Structures | Exact Mass | Mass Obsvd | Ki Rating |
|---|---|---|---|---|
| 438 | 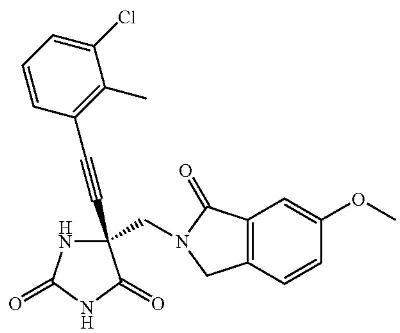 | 423.10 | 424.1 [M + H]+ | A |
| 439 | 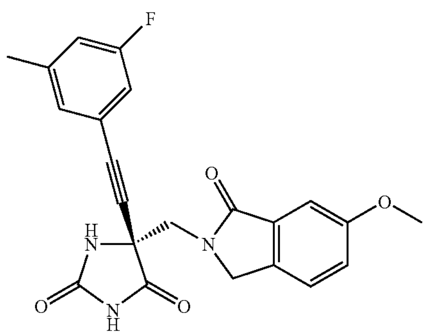 | 407.13 | 408.1 [M + H]+ | A |
| 440 | 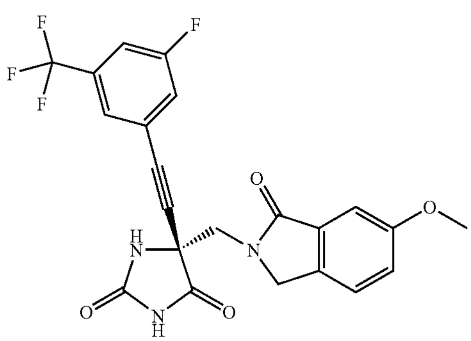 | 461.10 | 462.1 [M + H]+ | A |
| 441 | 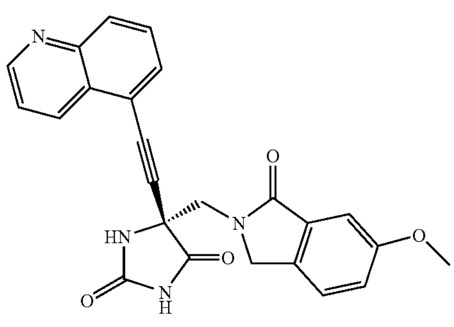 | 426.13 | 427.1 [M + H]+ | A |

TABLE 1001-continued

| Compound ID | Structures | Exact Mass | Mass Obsvd | Ki Rating |
|---|---|---|---|---|
| 442 | 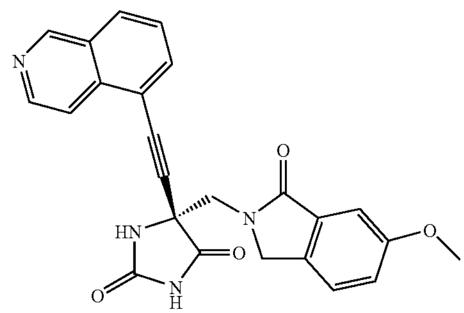 | 426.13 | 427.1 [M + H]+ | A |
| 443 | 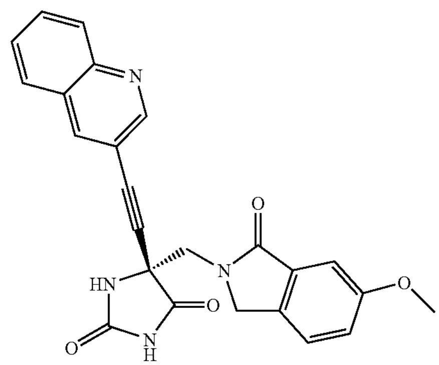 | 426.13 | 427.0 [M + H]+ | A |
| 444 | 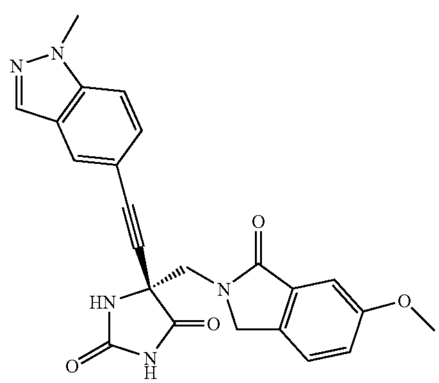 | 429.14 | 430.1 [M + H]+ | A |
| 401 | 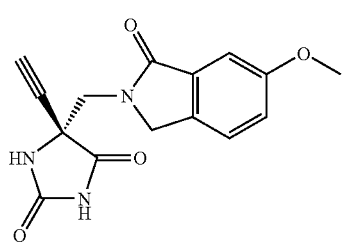 | 299.09 | 300.1 [M + H]+ | A |

TABLE 1001-continued

| Compound ID | Structures | Exact Mass | Mass Obsvd | Ki Rating |
|---|---|---|---|---|
| 445 | 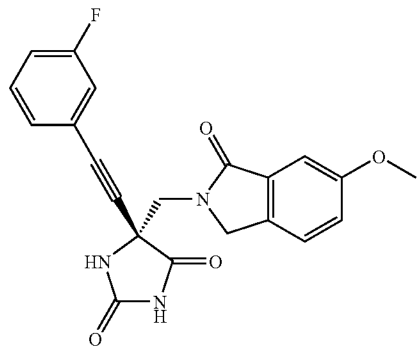 | 393.11 | 394.1 [M + H]+ | A |
| 446 | 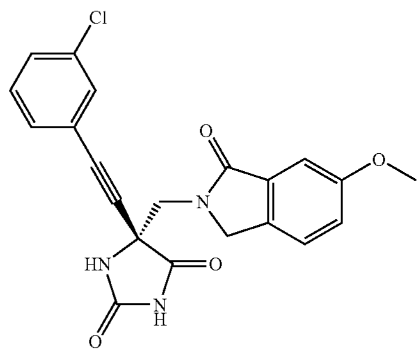 | 409.08 | 410.0 [M + H]+ | A |
| 447 | 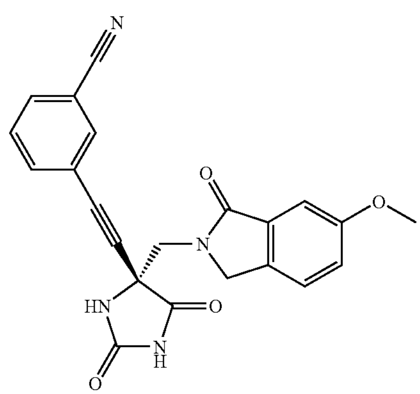 | 400.12 | 401.1 [M + H]+ | A |
| 448 | 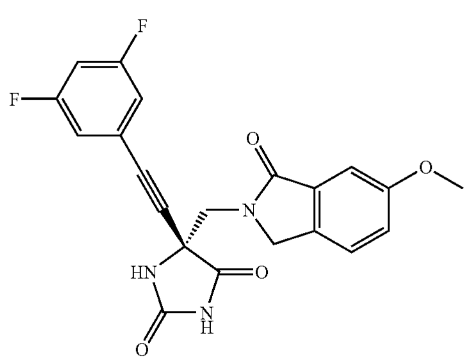 | 411.10 | 412.1 [M + H]+ | A |

TABLE 1001-continued

| Compound ID | Structures | Exact Mass | Mass Obsvd | Ki Rating |
|---|---|---|---|---|
| 449 | 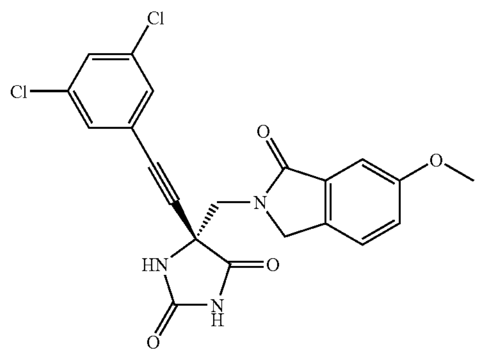 | 443.04 | 444.1 [M + H]+ | A |
| 450 | 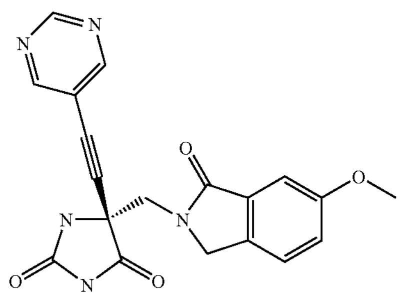 | 377.11 | 378.1 [M + H]+ | A |
| 451 | 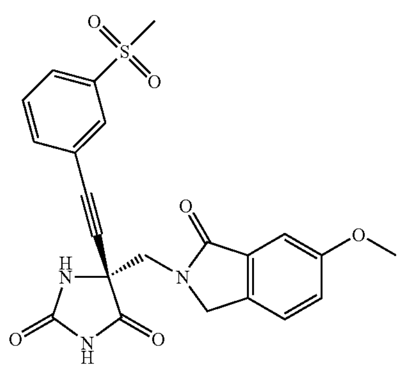 | 453.10 | 454.1 [M + H]+ | A |
| 452 | 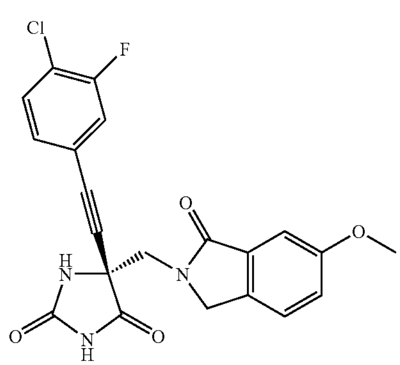 | 427.07 | 428.0 [M + H]+ | A |

TABLE 1001-continued

| Compound ID | Structures | Exact Mass | Mass Obsvd | Ki Rating |
|---|---|---|---|---|
| 453 | 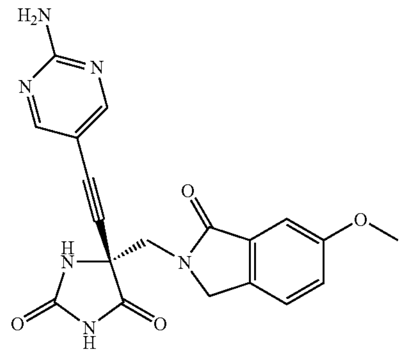 | 392.12 | 393.1 [M + H]+ | A |
| 454 | 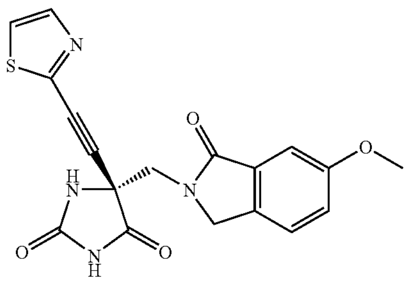 | 382.07 | 383.0 [M + H]+ | A |
| 455 | 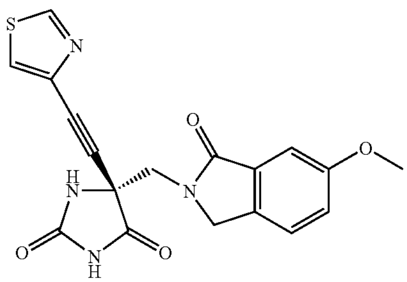 | 382.07 | 383.0 [M + H]+ | A |
| 456 | 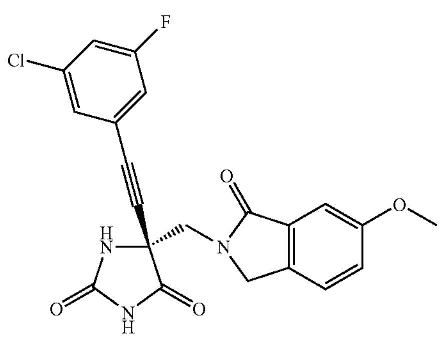 | 427.07 | 428.0 [M + H]+ | A |
| 457 | 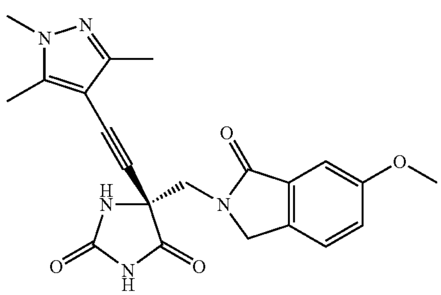 | 407.16 | 408.1 [M + H]+ | A |

TABLE 1001-continued

| Compound ID | Structures | Exact Mass | Mass Obsvd | Ki Rating |
|---|---|---|---|---|
| 458 | 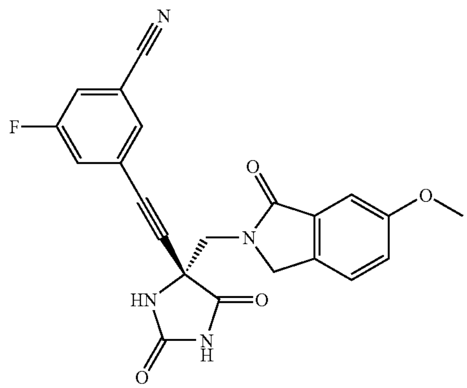 | 418.11 | 419.0 [M + H]+ | A |
| 459 | 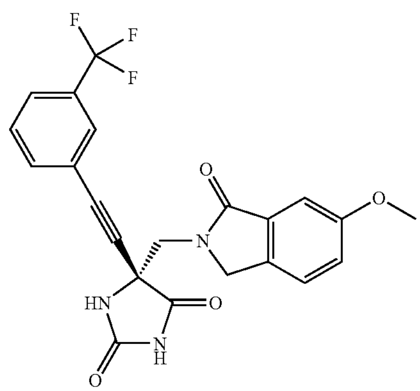 | 443.11 | 444.1 [M + H]+ | A |
| 460 | 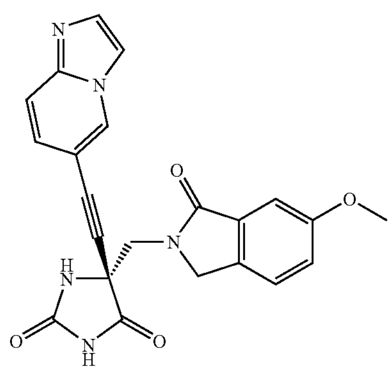 | 415.13 | 416.1 [M + H]+ | A |
| 461 | 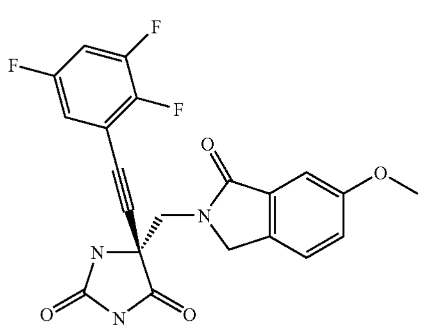 | 429.09 | 430.1 [M + H]+ | A |

TABLE 1001-continued

| Compound ID | Structures | Exact Mass | Mass Obsvd | Ki Rating |
|---|---|---|---|---|
| 462 | 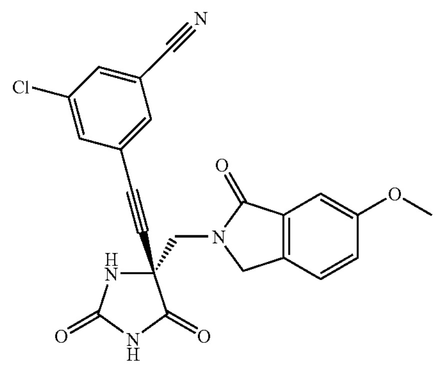 | 434.08 | 435.1 [M + H]+ | A |
| 463 | 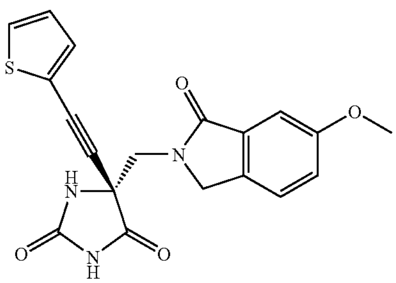 | 381.08 | 382.1 [M + H]+ | A |
| 464 | 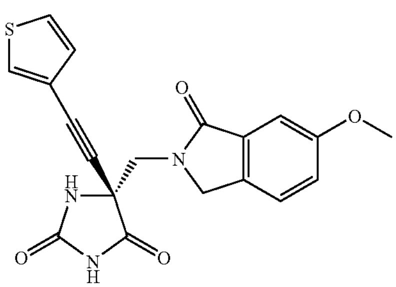 | 381.08 | 382.1 [M + H]+ | A |
| 465 | 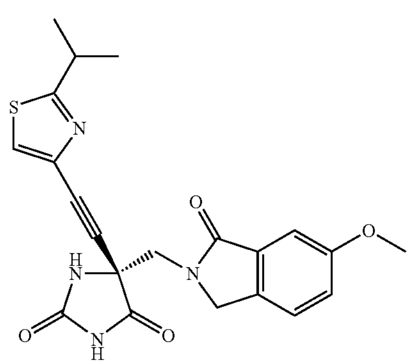 | 424.12 | 425.1 [M + H]+ | A |

TABLE 1001-continued

| Compound ID | Structures | Exact Mass | Mass Obsvd | Ki Rating |
|---|---|---|---|---|
| 466 | 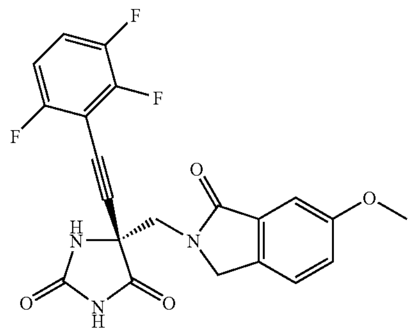 | 429.09 | 430.1 [M + H]+ | A |
| 467 | 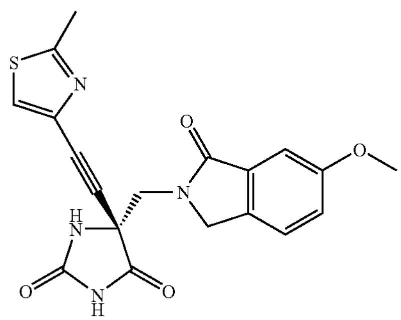 | 396.09 | 397.1 [M + H]+ | A |
| 468 | 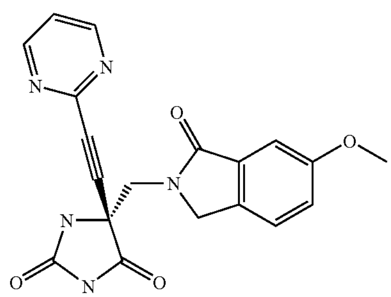 | 377.11 | 378.1 [M + H]+ | A |
| 469 | 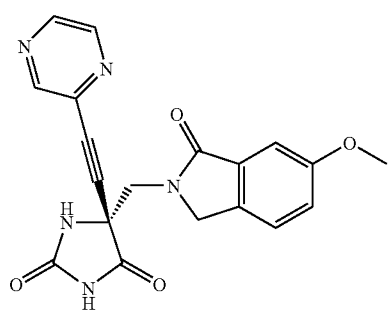 | 377.11 | 378.1 [M + H]+ | A |
| 470 | 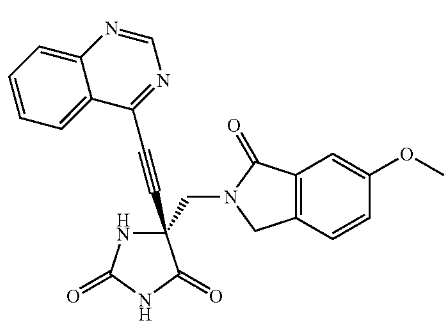 | 427.13 | 428.0 [M + H]+ | A |

TABLE 1001-continued

| Compound ID | Structures | Exact Mass | Mass Obsvd | Ki Rating |
|---|---|---|---|---|
| 471 | 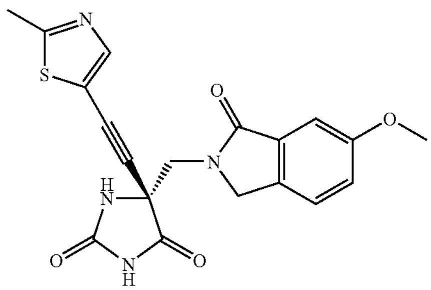 | 396.09 | 397.1 [M + H]⁺ | A |
| 472 | 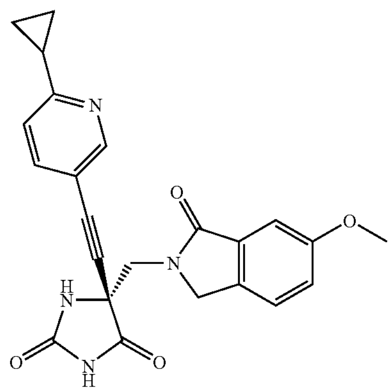 | 416.15 | 417.2 [M + H]⁺ | A |
| 409C | 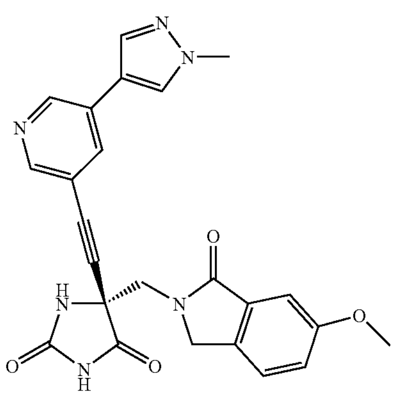 | 456.15 | 457.1 [M + H]⁺ | A |
| 480 | 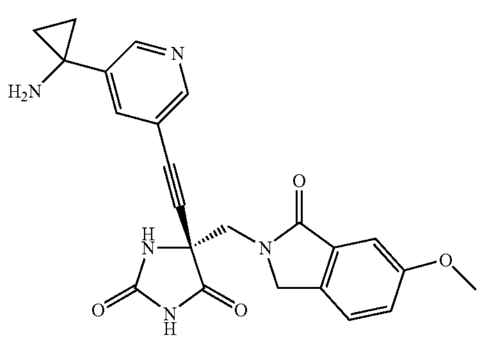 | 431.16 | 432.2 [M + H]⁺ | A |

TABLE 1001-continued

| Compound ID | Structures | Exact Mass | Mass Obsvd | Ki Rating |
|---|---|---|---|---|
| 481 | 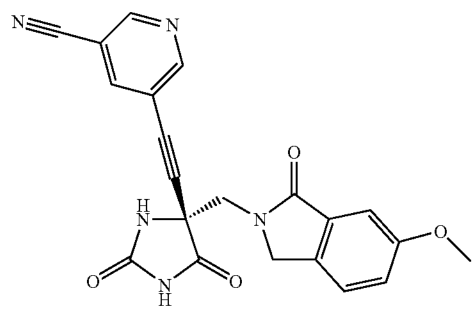 | 401.11 | 402.1 [M + H]+ | A |
| 410B | 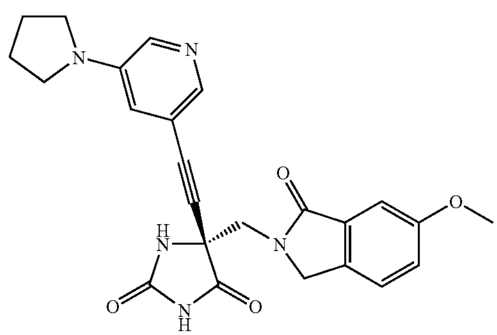 | 445.18 | 446.2 [M + H]+ | A |
| 482 | 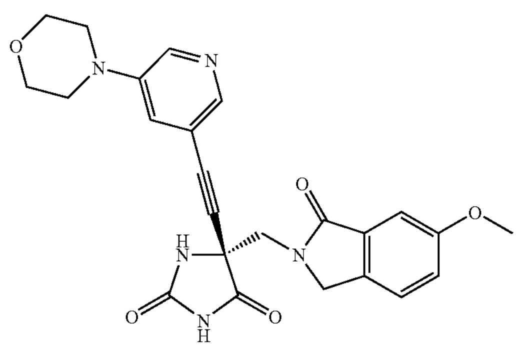 | 461.17 | 462.3 [M + H]+ | A |
| 482B | 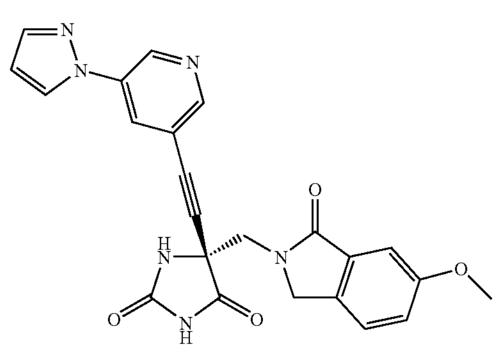 | 442.14 | 443.2 [M + H]+ | A |

TABLE 1001-continued
| Compound ID | Structures | Exact Mass | Mass Obsvd | Ki Rating |
|---|---|---|---|---|
| 482C | 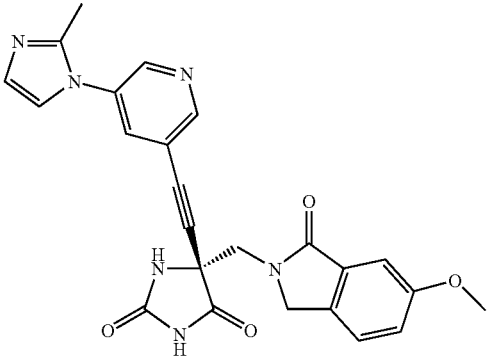 | 456.15 | 457.1 [M + H]+ | A |
| 411 | 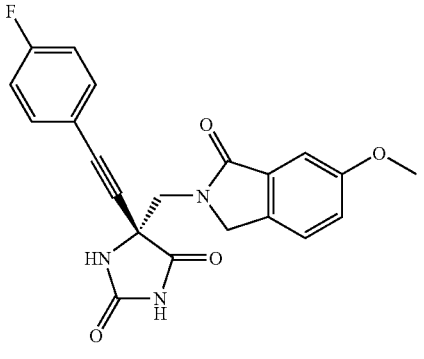 | 393.37 | 394.1 [M + H]+ | A |
| 400B | 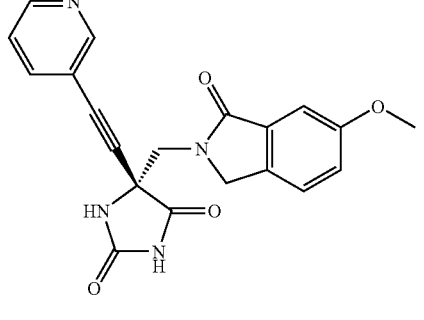 | 376.37 | 377.0 [M + H]+ | A |
| 483 | 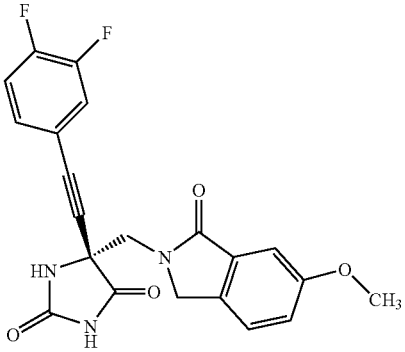 | 411.36 | 412.1 [M + H]+ | A |

TABLE 1001-continued

| Compound ID | Structures | Exact Mass | Mass Obsvd | Ki Rating |
|---|---|---|---|---|
| 484 | 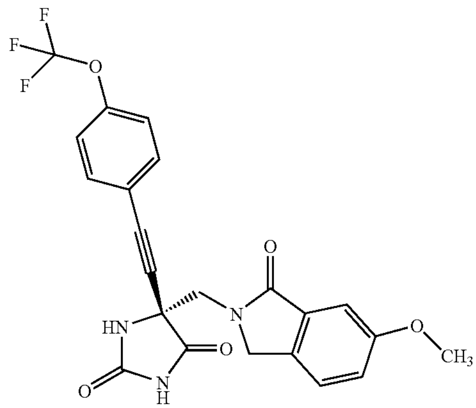 | 459.37 | 460.1 [M + H]+ | A |
| 485 | 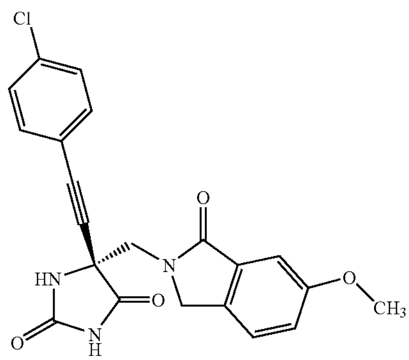 | 409.82 | 410.0 [M + H]+ | A |
| 486 | 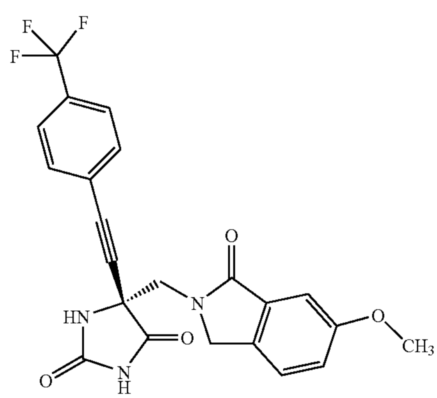 | 443.38 | 444.1 [M + H]+ | A |
| 487 | 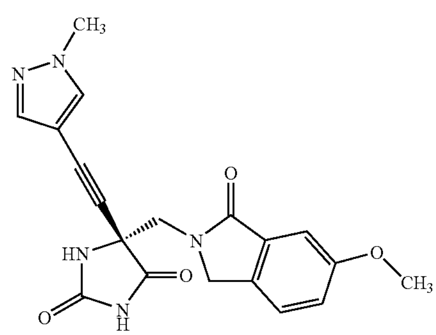 | 379.37 | 380.2 [M + H]+ | A |

TABLE 1001-continued

| Compound ID | Structures | Exact Mass | Mass Obsvd | Ki Rating |
|---|---|---|---|---|
| 488 | 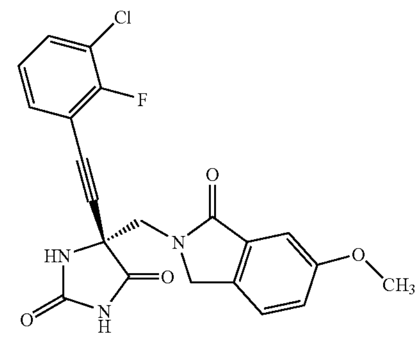 | 427.81 | 428.0 [M + H]+ | A |
| 489 | 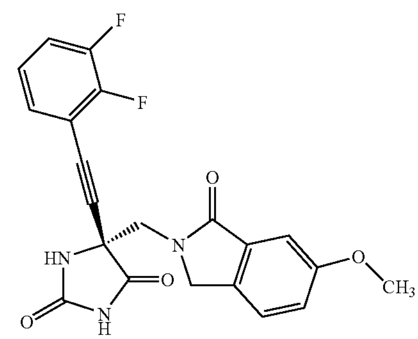 | 411.36 | 412.1 [M + H]+ | A |
| 490 | 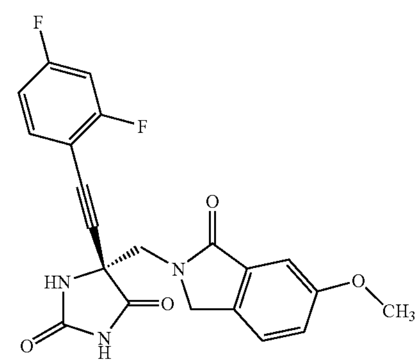 | 411.36 | 412.1 [M + H]+ | A |
| 491 | 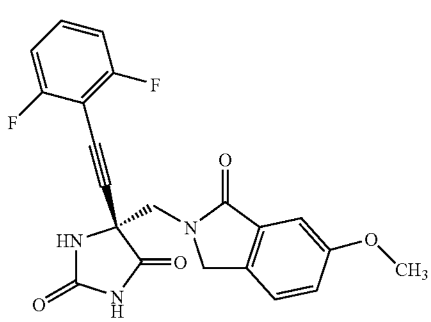 | 411.36 | 412.0 [M + H]+ | A |

TABLE 1001-continued

| Compound ID | Structures | Exact Mass | Mass Obsvd | Ki Rating |
|---|---|---|---|---|
| 492 | 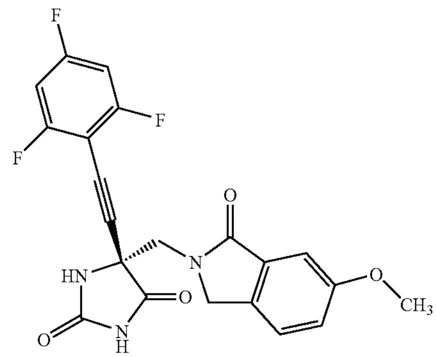 | 429.35 | 430.0 [M + H]+ | A |
| 493 | 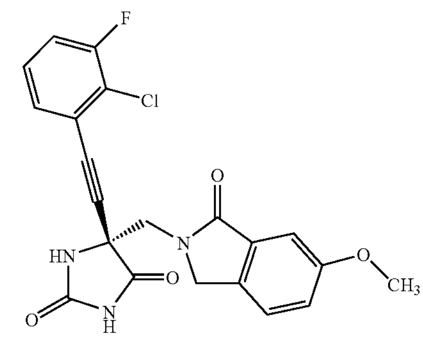 | 427.81 | 428.0 [M + H]+ | A |
| 494 | 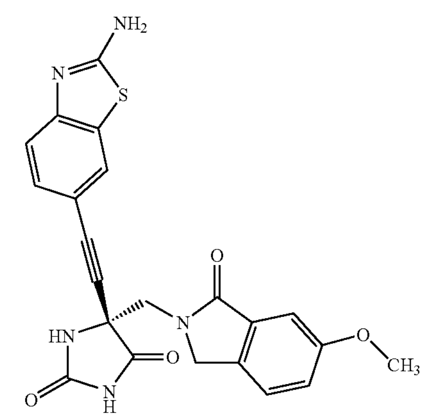 | 447.47 | 448.1 [M + H]+ | A |
| 495 | 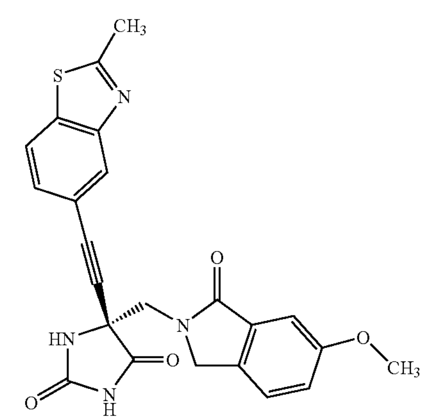 | 446.48 | 447.1 [M + H]+ | A |

TABLE 1001-continued

| Compound ID | Structures | Exact Mass | Mass Obsvd | Ki Rating |
|---|---|---|---|---|
| 496 | 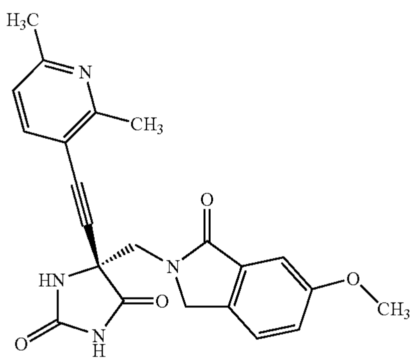 | 404.42 | 405.1 [M + H]+ | A |
| 497 | 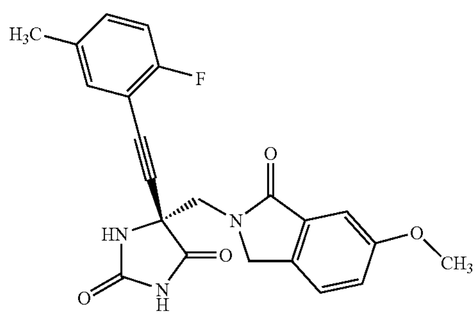 | 407.39 | 408.1 [M + H]+ | A |
| 498 | 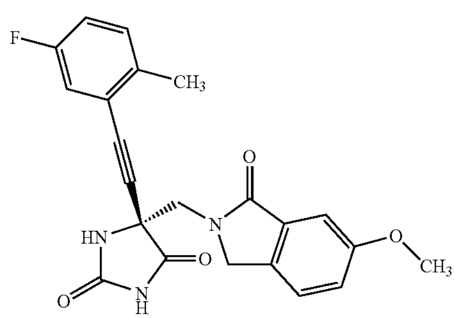 | 407.39 | 408.1 [M + H]+ | A |
| 499 | 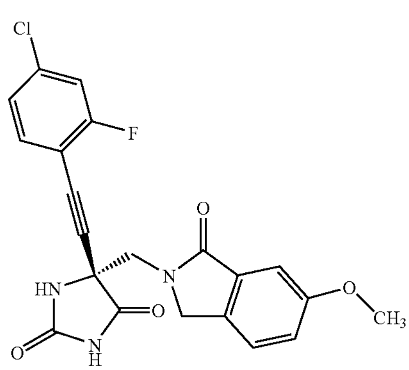 | 427.81 | 428.0 [M + H]+ | A |

TABLE 1001-continued
| Compound ID | Structures | Exact Mass | Mass Obsvd | Ki Rating |
|---|---|---|---|---|
| 500 | 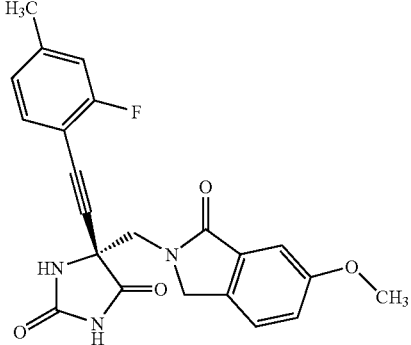 | 407.39 | 408.1 [M + H]+ | A |
| 503 | 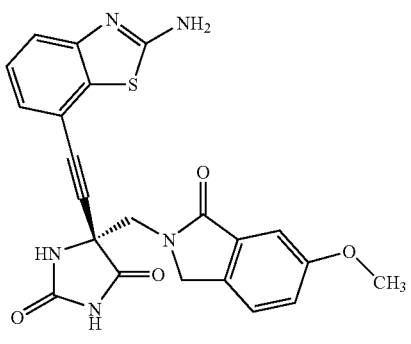 | 447.47 | 448.1 [M + H]+ | A |
| 504 | 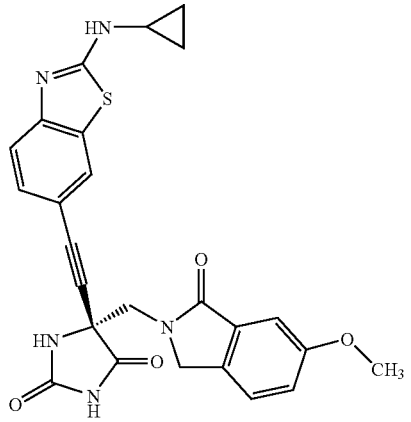 | 487.53 | 488.0 [M + H]+ | A |
| 505 | 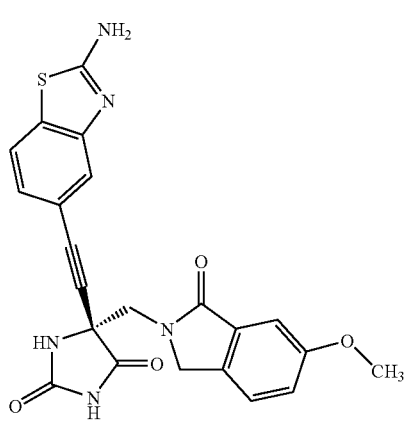 | 447.47 | 448.1 [M + H]+ | A |

TABLE 1001-continued

| Compound ID | Structures | Exact Mass | Mass Obsvd | Ki Rating |
|---|---|---|---|---|
| 412D | 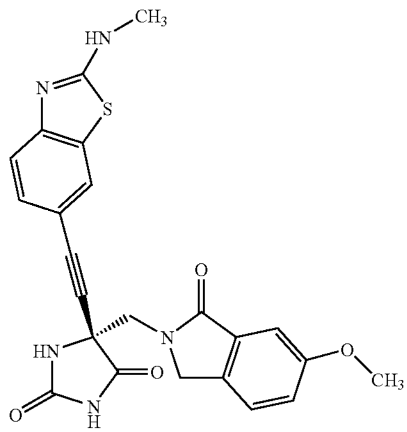 | 461.49 | 462.1 [M + H]+ | A |
| 506 | 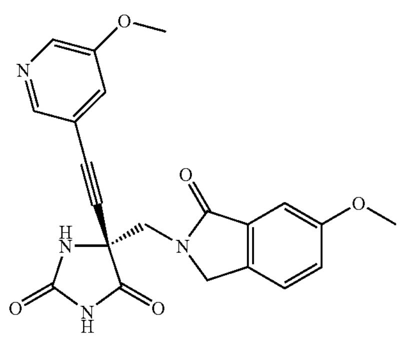 | 406.39 | 407.0 [M + H]+ | A |
| 507 | 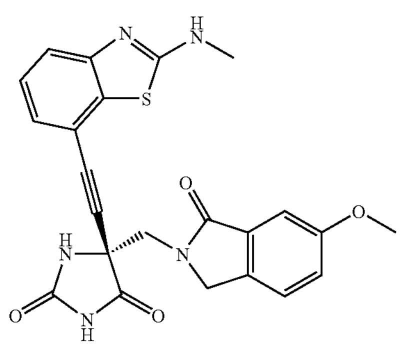 | 461.49 | 462.1 [M + H]+ | A |
| 508 | 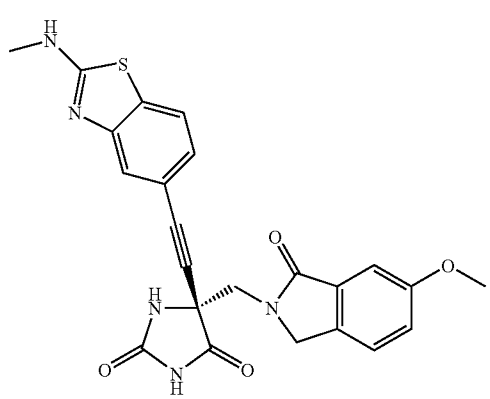 | 461.49 | 462.1 [M + H]+ | A |

TABLE 1001-continued

| Compound ID | Structures | Exact Mass | Mass Obsvd | Ki Rating |
|---|---|---|---|---|
| 509 | 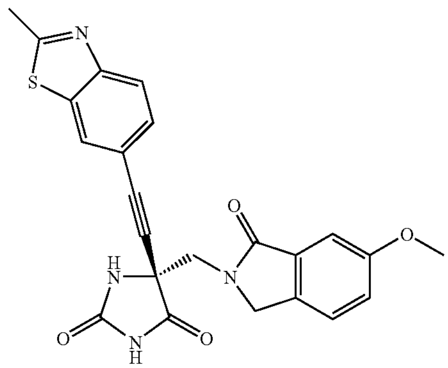 | 446.48 | 447.1 [M + H]+ | A |
| 413D | 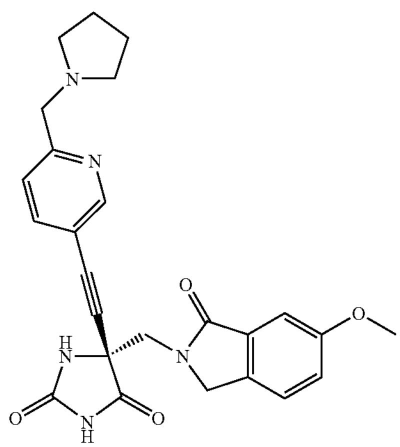 | 459.50 | 460.2 [M + H]+ | A |
| 510 | 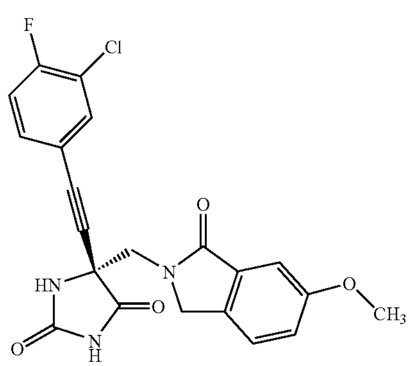 | 427.81 | 428.1 [M + H]+ | A |
| 414B | 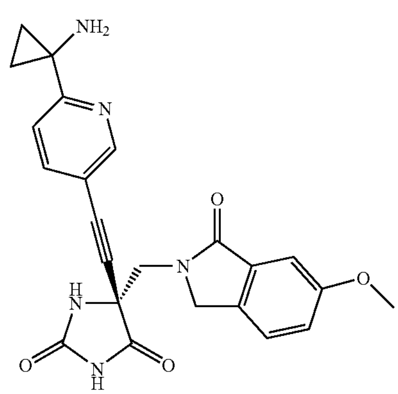 | 431.44 | 432.1 [M + H]+ | B |

TABLE 1001-continued

| Compound ID | Structures | Exact Mass | Mass Obsvd | Ki Rating |
|---|---|---|---|---|
| 513 | 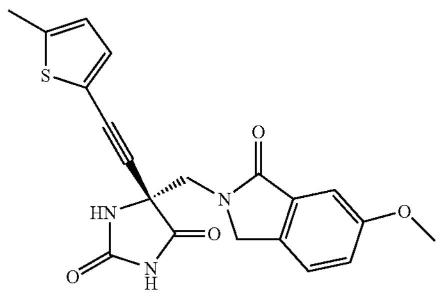 | 395.09 | 396.1 [M + H]+ | A |
| 514 | 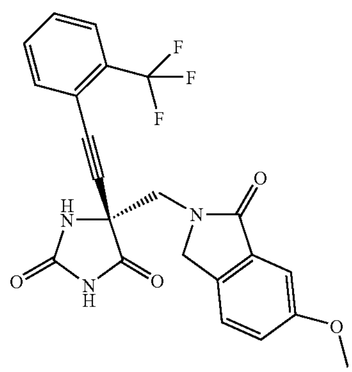 | 443.11 | 444.1 [M + H]+ | A |
| 515 | 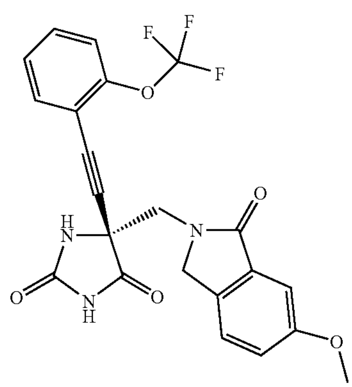 | 459.10 | 460.1 [M + H]+ | A |
| 516 | 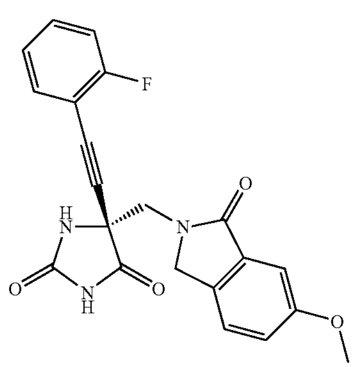 | 393.11 | 394.1 [M + H]+ | A |

TABLE 1001-continued

| Compound ID | Structures | Exact Mass | Mass Obsvd | Ki Rating |
|---|---|---|---|---|
| 517 | 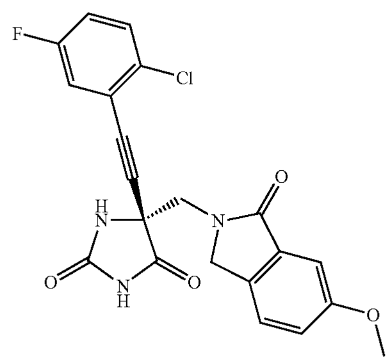 | 427.07 | 428.0 [M + H]+ | A |
| 518 | 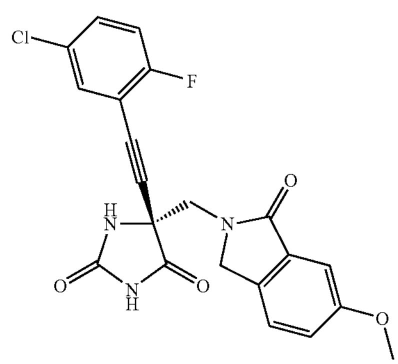 | 427.07 | 428.0 [M + H]+ | A |
| 519 | 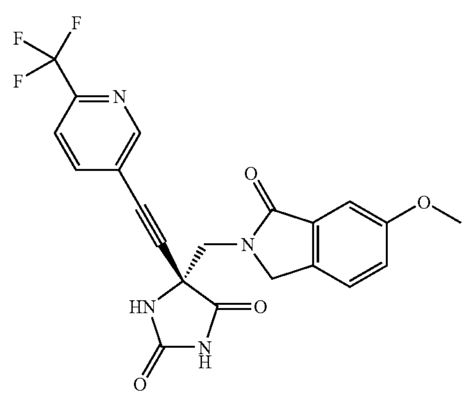 | 444.10 | 445.1 [M + H]+ | A |
| 520 | 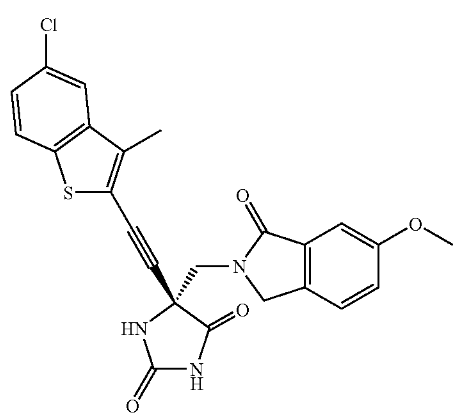 | 479.07 | 480.0 [M + H]+ | A |

TABLE 1001-continued

| Compound ID | Structures | Exact Mass | Mass Obsvd | Ki Rating |
|---|---|---|---|---|
| 521 | 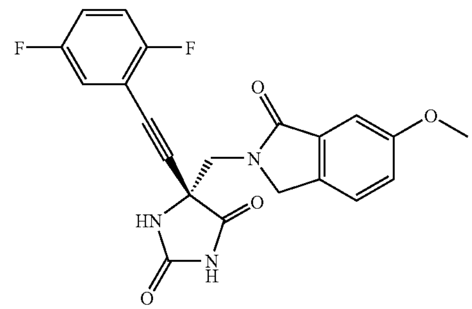 | 411.10 | 412.0 [M + H]+ | A |
| 522 | 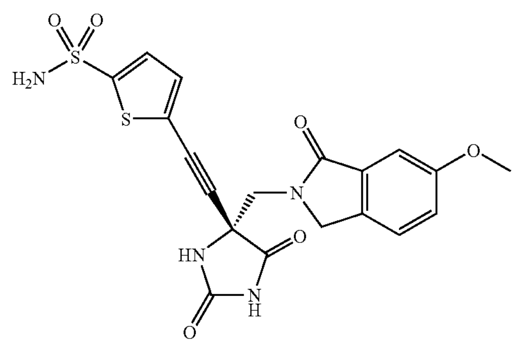 | 460.05 | 461.0 [M + H]+ | A |
| 523 | 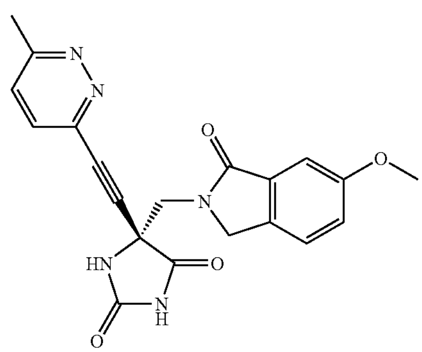 | 391.13 | 392.2 [M + H]+ | A |
| 524 | 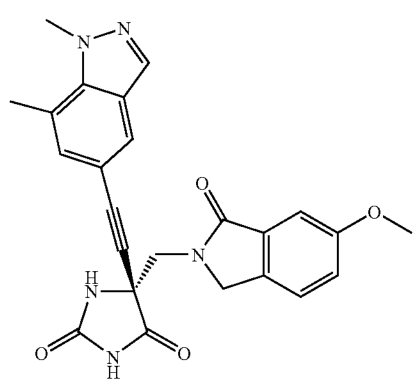 | 443.16 | 444.1 [M + H]+ | A |

TABLE 1001-continued

| Compound ID | Structures | Exact Mass | Mass Obsvd | Ki Rating |
|---|---|---|---|---|
| 525 | 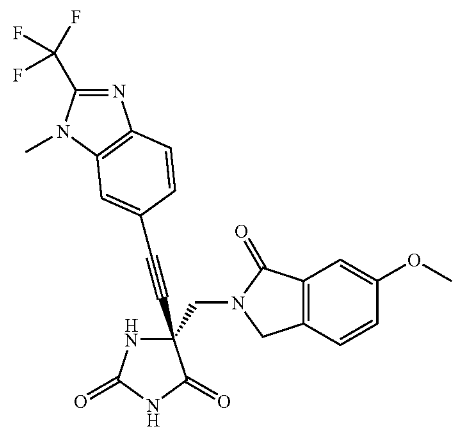 | 497.13 | 498.1 [M + H]+ | A |
| 526 | 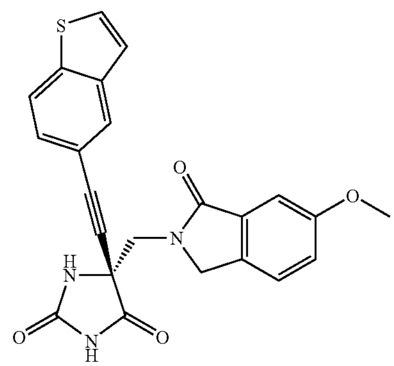 | 431.09 | 432.1 [M + H]+ | A |
| 527 | 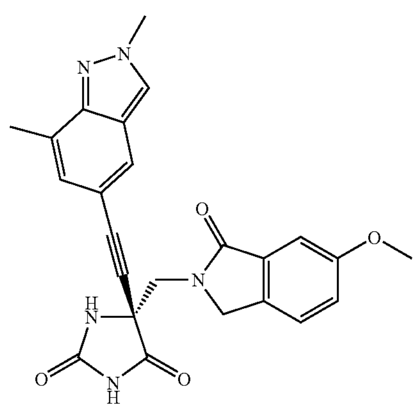 | 443.16 | 444.1 [M + H]+ | A |
| 528 | 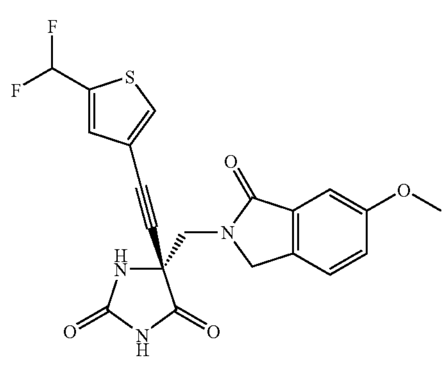 | 431.08 | 432.1 [M + H]+ | A |

TABLE 1001-continued

| Compound ID | Structures | Exact Mass | Mass Obsvd | Ki Rating |
|---|---|---|---|---|
| 529 | 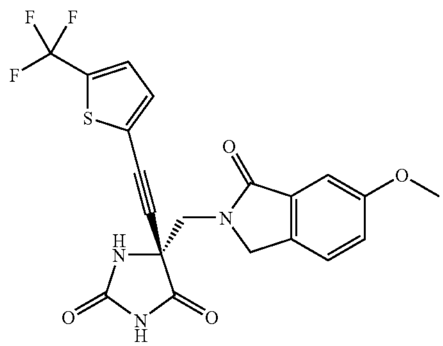 | 449.07 | 450.1 [M + H]+ | A |
| 530 | 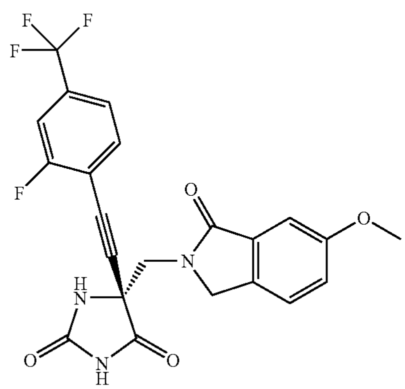 | 461.10 | 462.1 [M + H]+ | A |
| 531 | 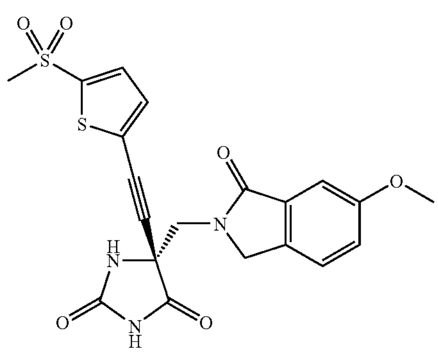 | 459.06 | 460.0 [M + H]+ | A |
| 532 | 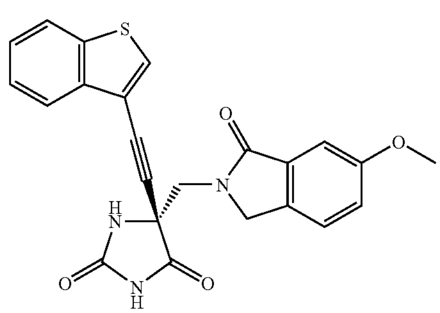 | 431.09 | 432.1 [M + H]+ | A |

TABLE 1001-continued

| Compound ID | Structures | Exact Mass | Mass Obsvd | Ki Rating |
|---|---|---|---|---|
| 533 | 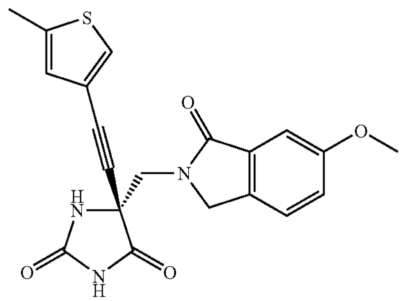 | 395.09 | 396.1 [M + H]+ | A |
| 417C | 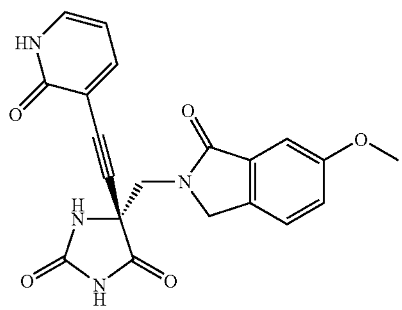 | 392.11 | 393.1 [M + H]+ | A |
| 535 | 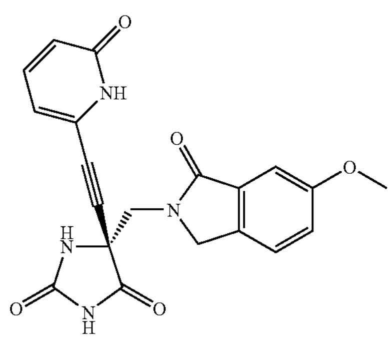 | 392.11 | 393.1 [M + H]+ | A |
| 536 | 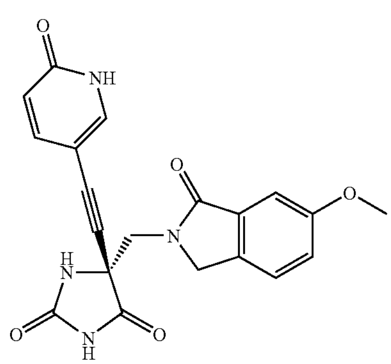 | 392.11 | 393.1 [M + H]+ | A |

TABLE 1001-continued
| Compound ID | Structures | Exact Mass | Mass Obsvd | Ki Rating |
|---|---|---|---|---|
| 537 | 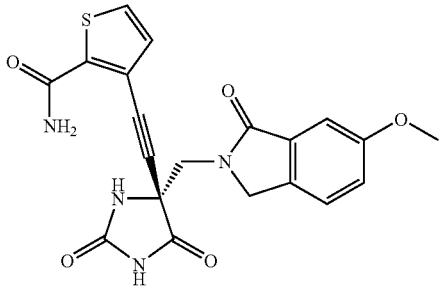 | 424.08 | 425.0 [M + H]+ | A |
| 538 | 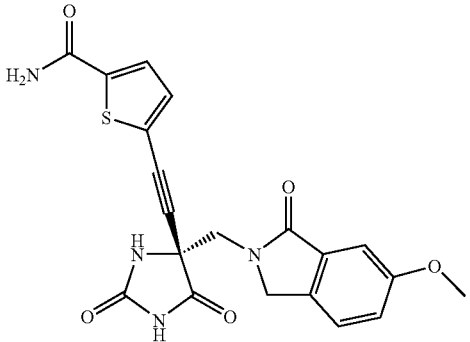 | 424.08 | 425.0 [M + H]+ | A |
| 539 | 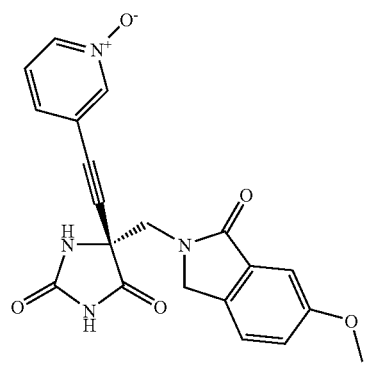 | 392.11 | 393.1 [M + H]+ | A |
| 540 | 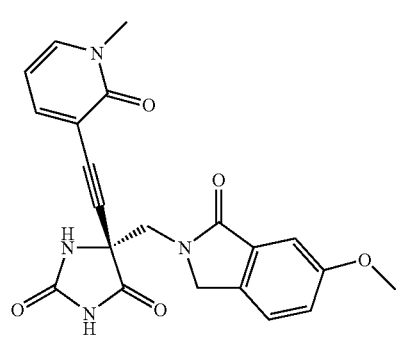 | 406.13 | 407.2 [M + H]+ | A |

TABLE 1001-continued

| Compound ID | Structures | Exact Mass | Mass Obsvd | Ki Rating |
|---|---|---|---|---|
| 554 | 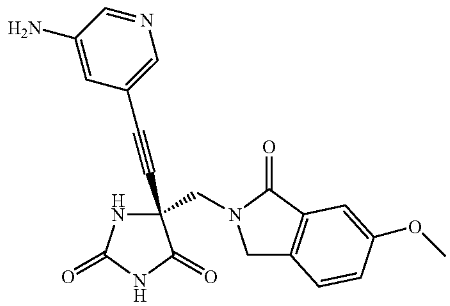 | 391.13 | 392.2 [M + H]⁺ | A |
| 555 | 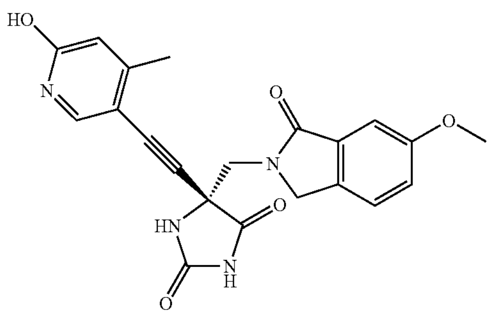 | 406.13 | 407.1 [M + H]⁺ | A |
| 900 | 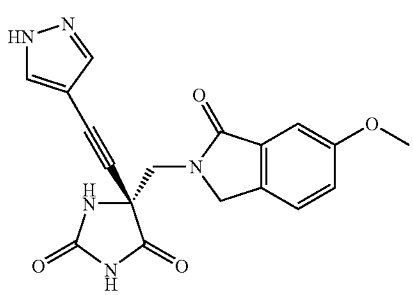 | 365.11 | 366.2 [M + H]⁺ | A |
| 901 | 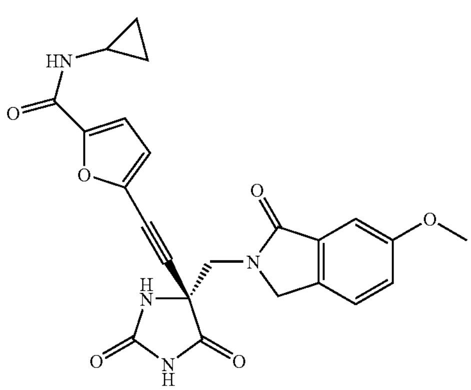 | 448.14 | 449.2 [M + H]⁺ | A |

TABLE 1001-continued
| Compound ID | Structures | Exact Mass | Mass Obsvd | Ki Rating |
|---|---|---|---|---|
| 902 | 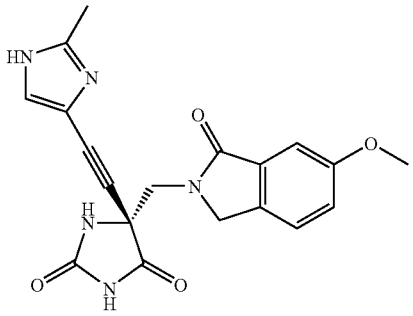 | 379.13 | 380.2 [M + H]+ | A |
| 903 | 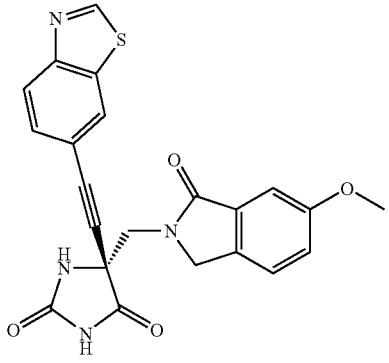 | 432.09 | 433.2 [M + H]+ | A |
| 904 | 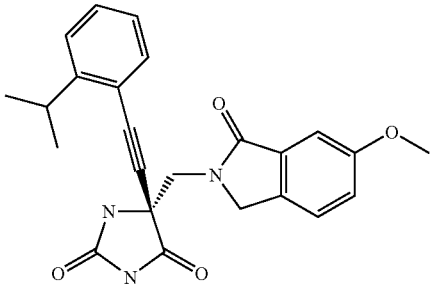 | 417.17 | 418.2 [M + H]+ | A |
| 905 | 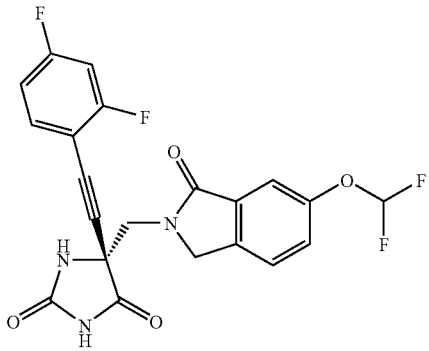 | 447.08 | 448.2 [M + H]+ | A |

TABLE 1001-continued

| Compound ID | Structures | Exact Mass | Mass Obsvd | Ki Rating |
|---|---|---|---|---|
| 906 | 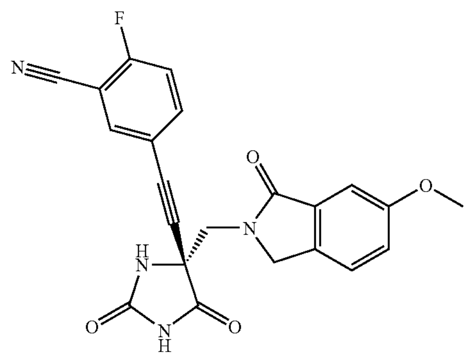 | 418.11 | 419.2 [M + H]+ | A |
| 907 | 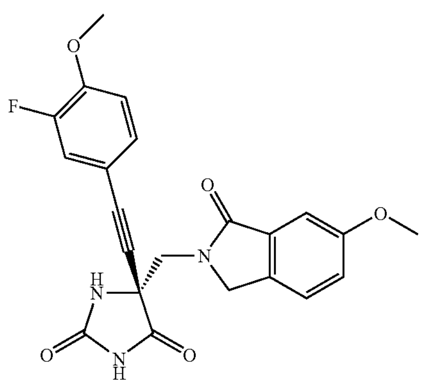 | 423.12 | 424.2 [M + H]+ | A |
| 908 | 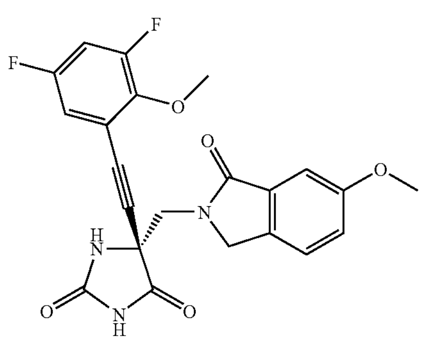 | 441.11 | 442.2 [M + H]+ | A |
| 909 | 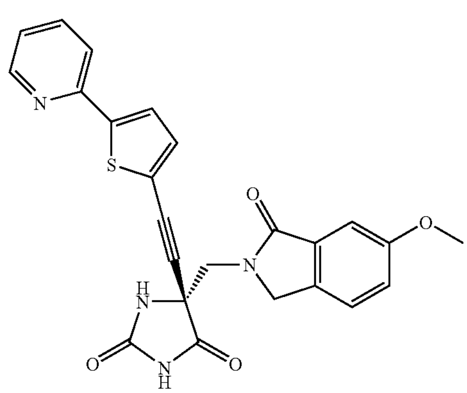 | 458.10 | 459.3 [M + H]+ | A |

TABLE 1001-continued
| Compound ID | Structures | Exact Mass | Mass Obsvd | Ki Rating |
|---|---|---|---|---|
| 910 | 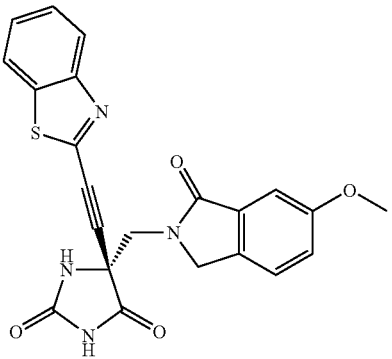 | 432.09 | 433.2 [M + H]+ | A |
| 911 | 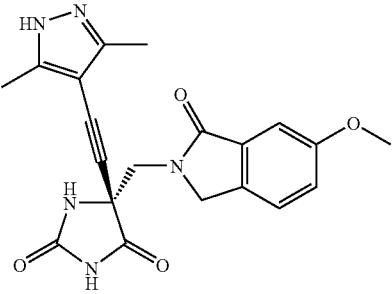 | 393.14 | 394.2 [M + H]+ | A |
| 912 | 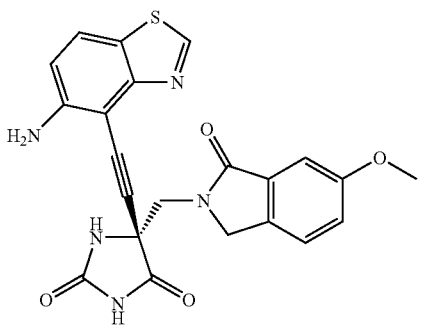 | 447.10 | 448.2 [M + H]+ | A |
| 913 | 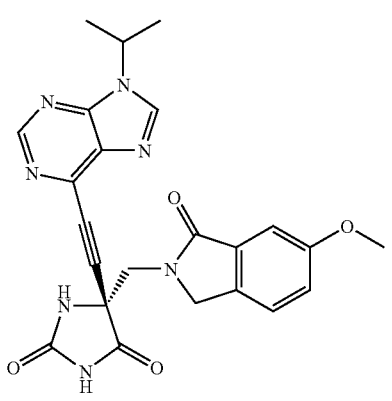 | 459.17 | 460.3 [M + H]+ | A |

TABLE 1001-continued

| Compound ID | Structures | Exact Mass | Mass Obsvd | Ki Rating |
|---|---|---|---|---|
| 914 | 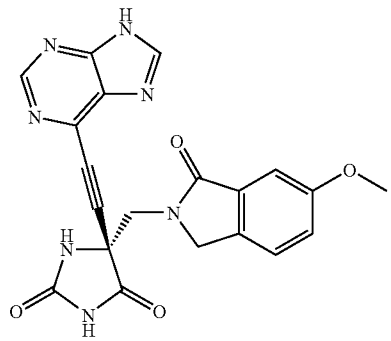 | 417.12 | 418.2 [M + H]⁺ | A |
| 915 | 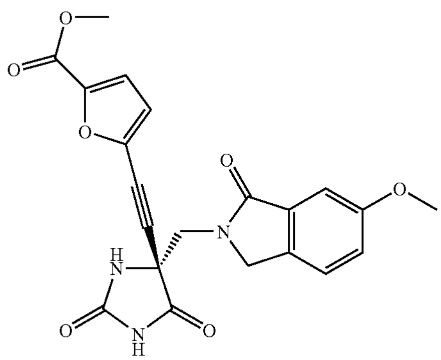 | 423.11 | 424.2 [M + H]⁺ | A |
| 916 | 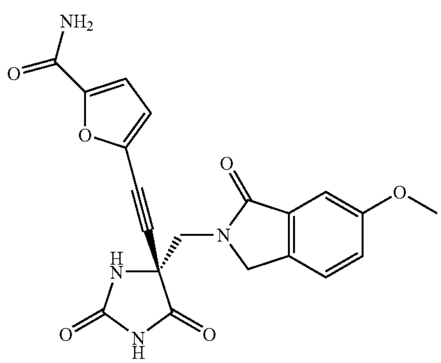 | 408.11 | 409.2 [M + H]⁺ | A |
| 917 | 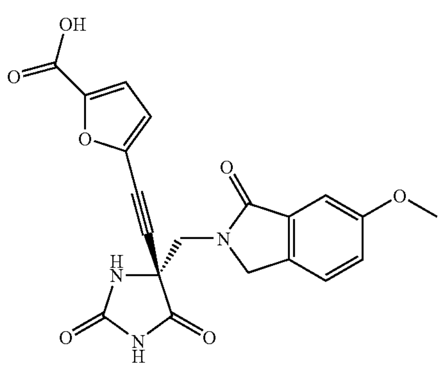 | 409.09 | 410.2 [M + H]⁺ | A |

TABLE 1001-continued

| Compound ID | Structures | Exact Mass | Mass Obsvd | Ki Rating |
|---|---|---|---|---|
| 918 | 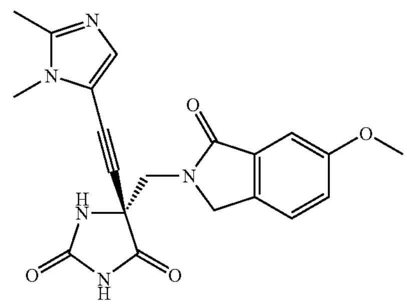 | 393.14 | 394.2 [M + H]+ | A |
| 919 | 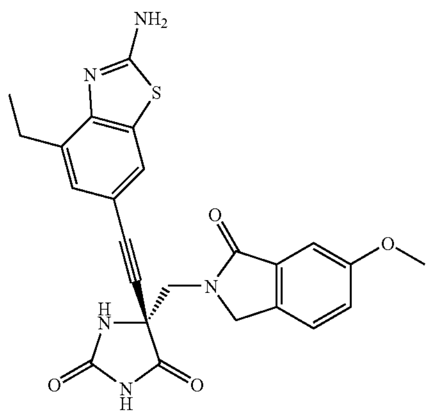 | 475.13 | 476.3 [M + H]+ | A |
| 920 | 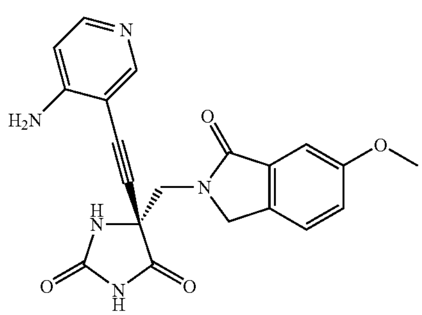 | 391.13 | 392.2 [M + H]+ | A |
| 922 | 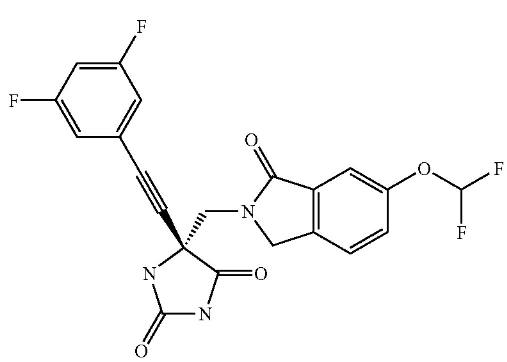 | 447.08 | 448.2 [M + H]+ | A |

TABLE 1001-continued

| Compound ID | Structures | Exact Mass | Mass Obsvd | Ki Rating |
|---|---|---|---|---|
| 924 | 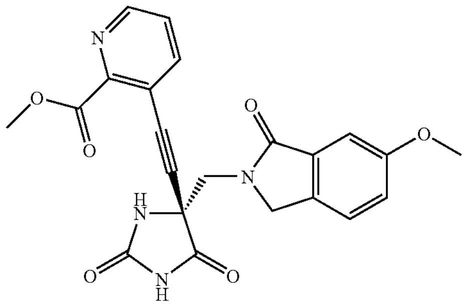 | 434.12 | 435.2 [M + H]+ | A |
| 925 | 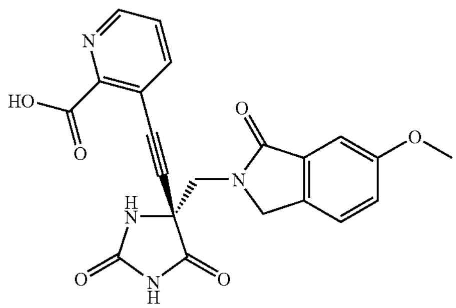 | 421.11 | 421.2 M+ | A |
| 926 | 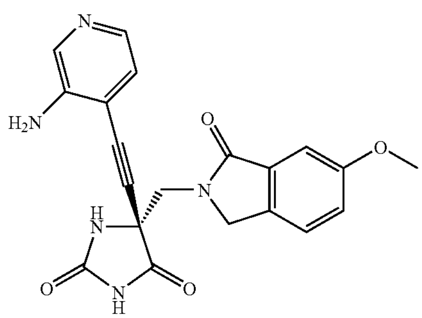 | 391.13 | 392.2 [M + H]+ | B |
| 928 | 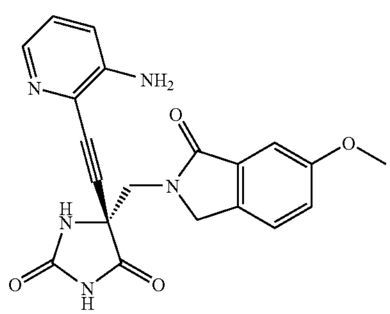 | 391.13 | 392.2 [M + H]+ | A |
| 930 | 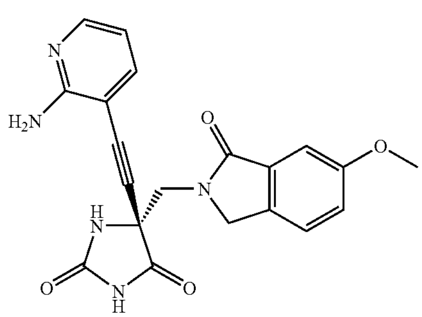 | 392.14 | 392.2 [M + H]+ | A |

TABLE 1001-continued

| Compound ID | Structures | Exact Mass | Mass Obsvd | Ki Rating |
|---|---|---|---|---|
| 931 | 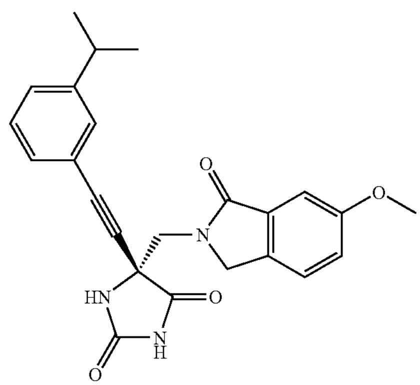 | 417.17 | 418.2 [M + H]+ | A |
| 932 | 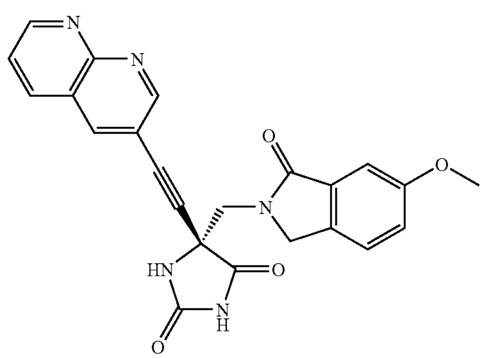 | 427.13 | 428.2 [M + H]+ | A |
| 933 | 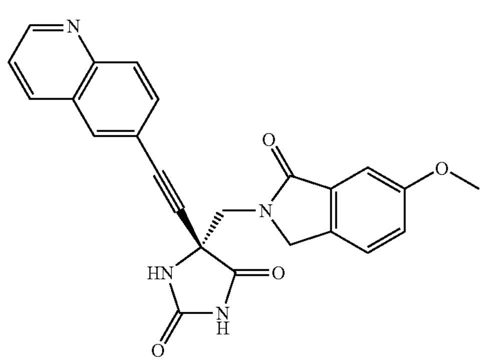 | 426.13 | 427.2 [M + H]+ | A |
| 934 | 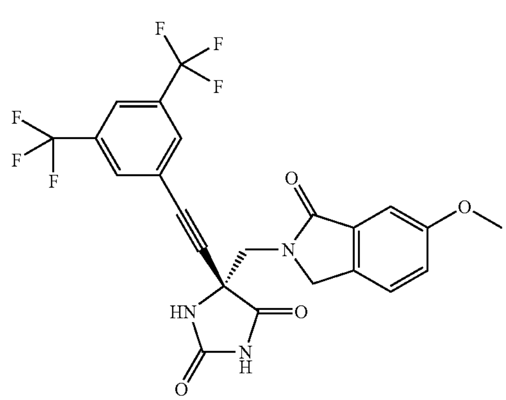 | 511.10 | 512.3 [M + H]+ | A |

TABLE 1001-continued

| Compound ID | Structures | Exact Mass | Mass Obsvd | Ki Rating |
|---|---|---|---|---|
| 935 | 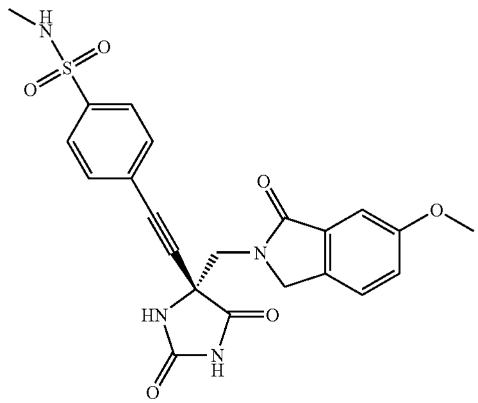 | 482.13 | 483.3 [M + H]+ | A |
| 937 | 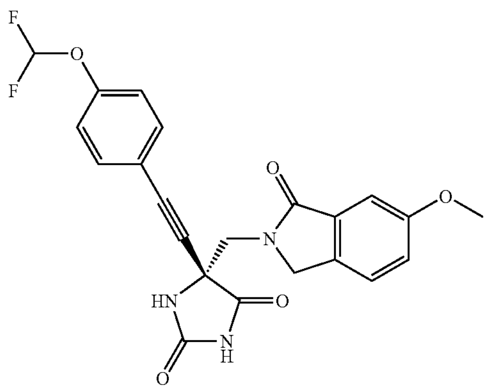 | 441.11 | 442.2 [M + H]+ | A |
| 938 | 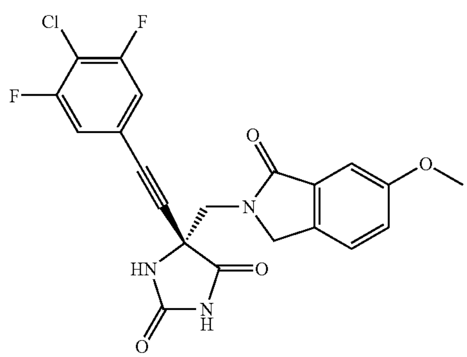 | 445.06 | 446.2 [M + H]+ | A |
| 939 | 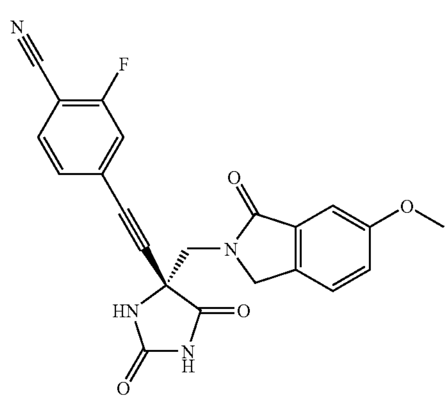 | 418.11 | 419.2 [M + H]+ | A |

//

TABLE 1001-continued

| Compound ID | Structures | Exact Mass | Mass Obsvd | Ki Rating |
|---|---|---|---|---|
| 940 | 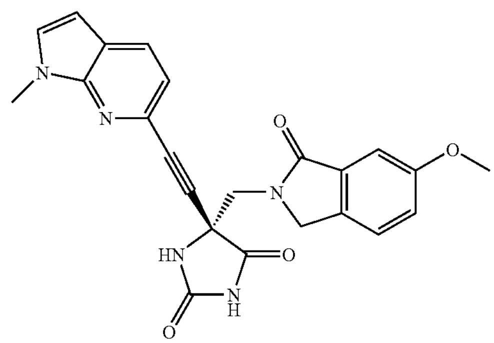 | 429.14 | 430.2 [M + H]+ | A |
| 941 | 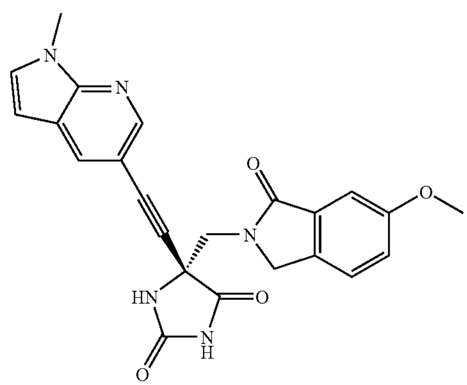 | 429.14 | 430.2 [M + H]+ | A |
| 942 | 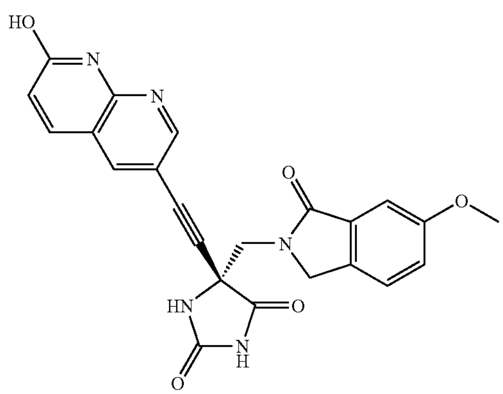 | 443.12 | 444.2 [M + H]+ | A |
| 943 | 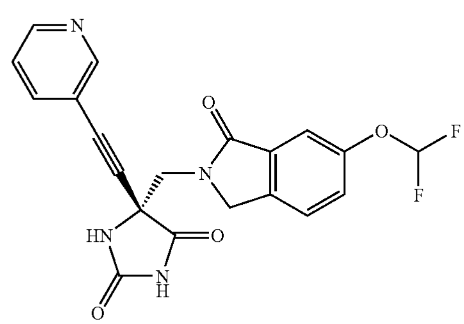 | 412.10 | 413.2 [M + H]+ | A |

TABLE 1001-continued

| Compound ID | Structures | Exact Mass | Mass Obsvd | Ki Rating |
|---|---|---|---|---|
| 944 | 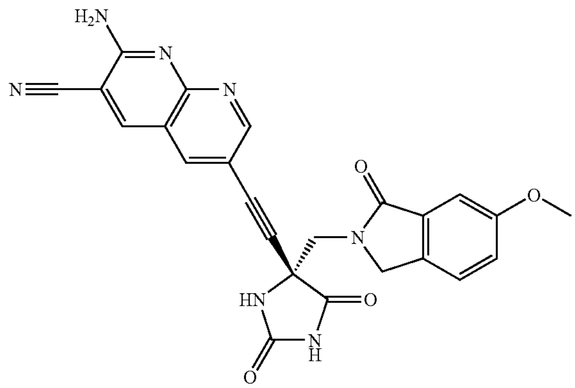 | 467.13 | 468.3 [M + H]⁺ | A |
| 945 | 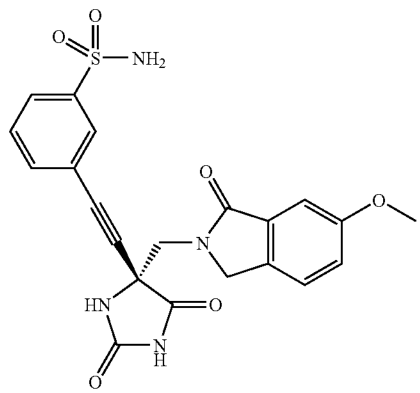 | 454.09 | 455.3 [M + H]⁺ | A |
| 946 | 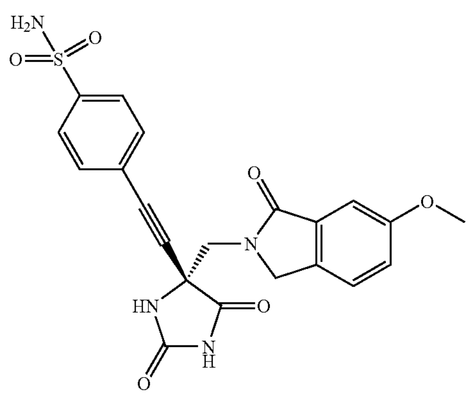 | 454.09 | 455.3 [M + H]⁺ | A |
| 947 | 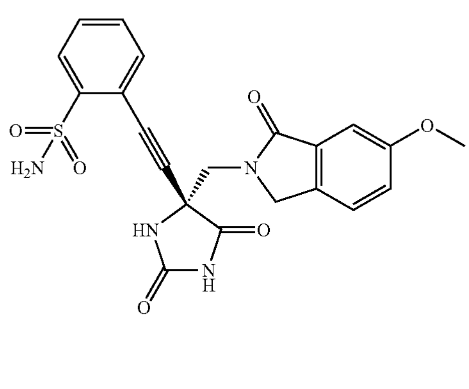 | 454.09 | 455.3 [M + H]⁺ | A |

TABLE 1001-continued
| Compound ID | Structures | Exact Mass | Mass Obsvd | Ki Rating |
|---|---|---|---|---|
| 948 | 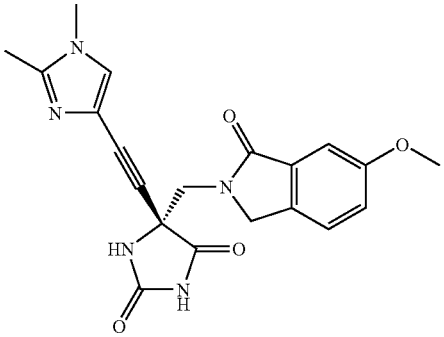 | 393.14 | 394.2 [M + H]+ | A |
| 949 | 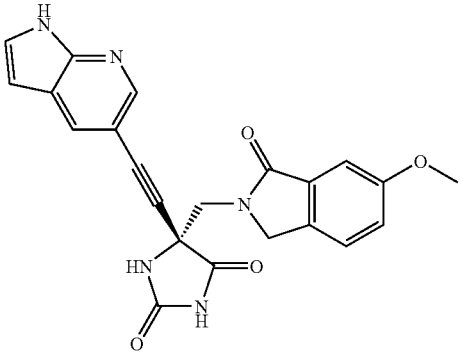 | 415.13 | 416.2 [M + H]+ | A |
| 950 | 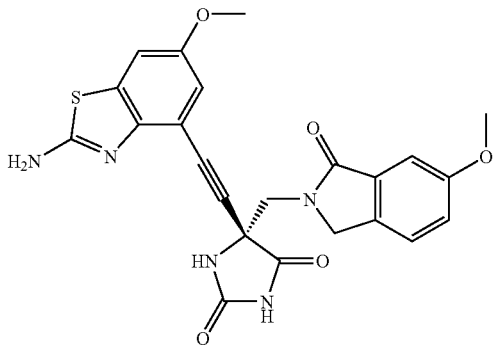 | 477.11 | 478.3 [M + H]+ | A |
| 951 | 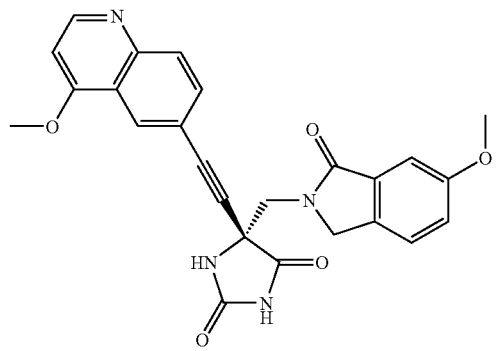 | 456.14 | 457.3 [M + H]+ | A |

TABLE 1001-continued

| Compound ID | Structures | Exact Mass | Mass Obsvd | Ki Rating |
| --- | --- | --- | --- | --- |
| 952 | 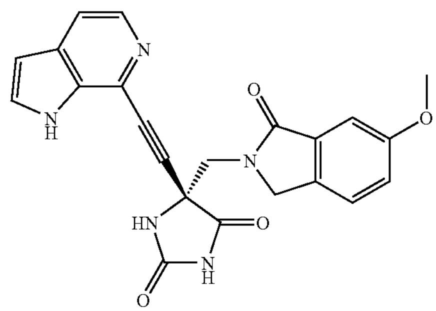 | 415.13 | 416.2 [M + H]⁺ | A |
| 953 | 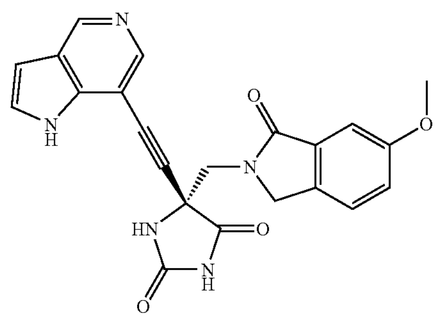 | 415.13 | 416.2 [M + H]⁺ | A |
| 954 | 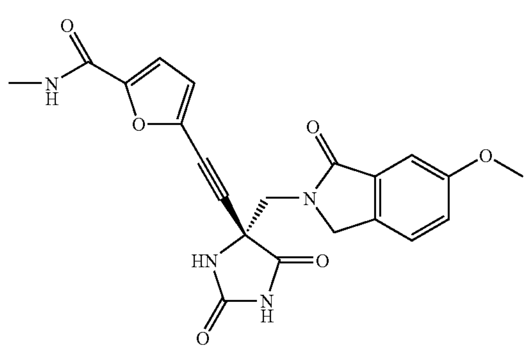 | 422.12 | 423.2 [M + H]⁺ | A |
| 955 | 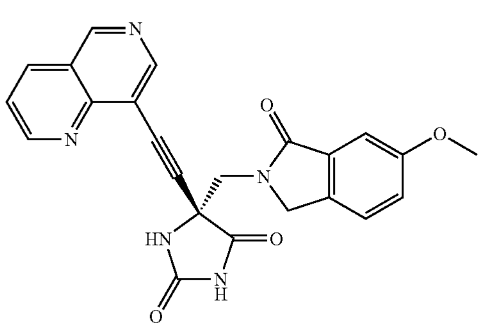 | 427.13 | 428.2 [M + H]⁺ | A |

TABLE 1001-continued

| Compound ID | Structures | Exact Mass | Mass Obsvd | Ki Rating |
|---|---|---|---|---|
| 956 | 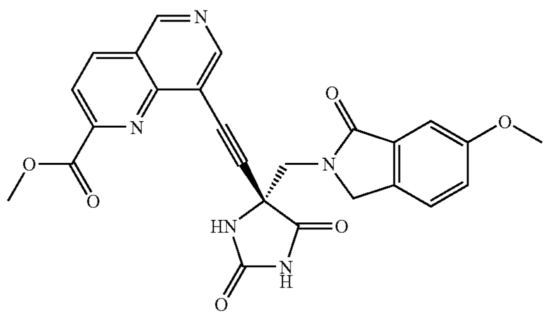 | 485.13 | 485.3 [M + H]+ | A |
| 957 | 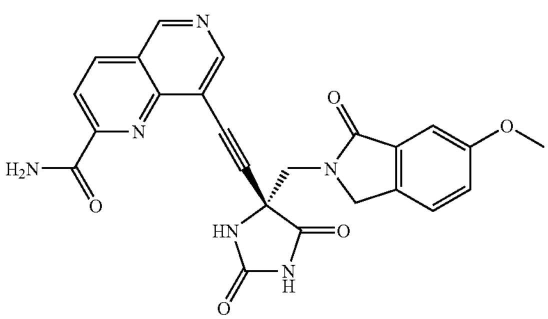 | 470.13 | 471.3 [M + H]+ | A |
| 958 | 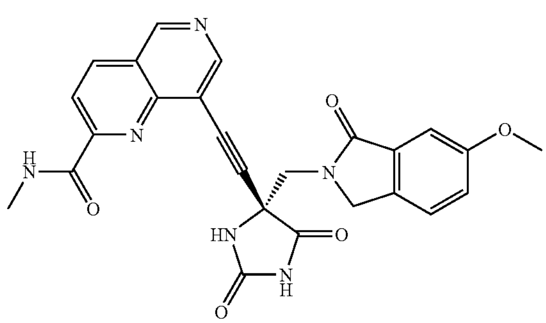 | 484.15 | 485.3 [M + H]+ | A |
| 959 | 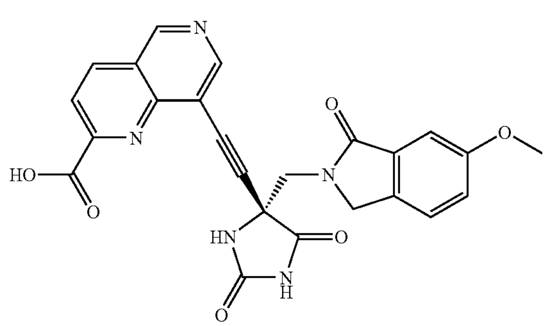 | 471.12 | 472.3 [M + H]+ | A |

TABLE 1001-continued

| Compound ID | Structures | Exact Mass | Mass Obsvd | Ki Rating |
|---|---|---|---|---|
| 960 | 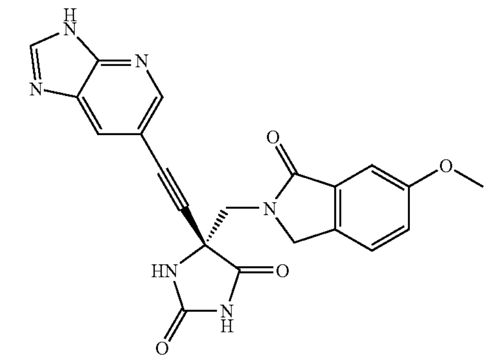 | 416.39 | 417.2 [M + H]+ | A |
| 961 | 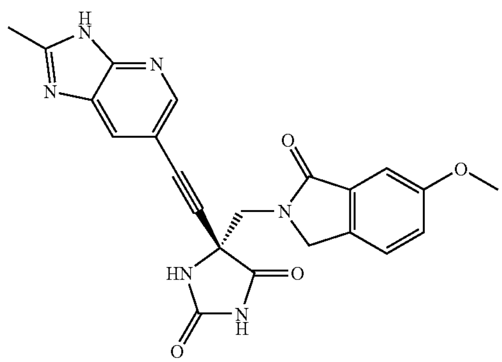 | 430.14 | 431.2 [M + H]+ | A |
| 962 | 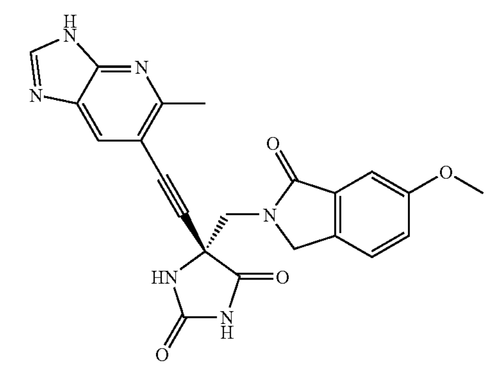 | 430.14 | 431.2 [M + H]+ | A |
| 963 | 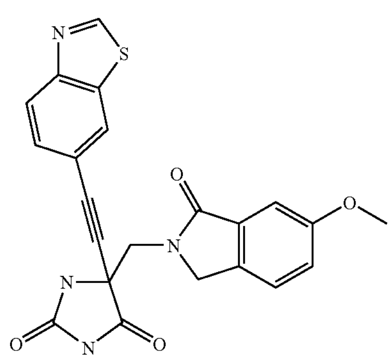 | 432.09 | 433.2 [M + H]+ | A |

TABLE 1001-continued

| Compound ID | Structures | Exact Mass | Mass Obsvd | Ki Rating |
|---|---|---|---|---|
| 964 | 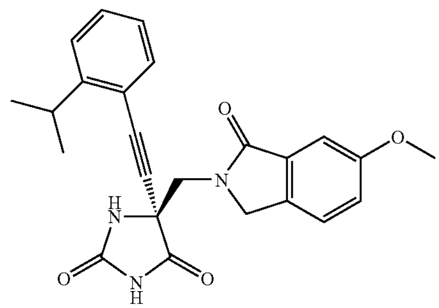 | 417.17 | 418.2 [M + H]+ | B |
| 965 | 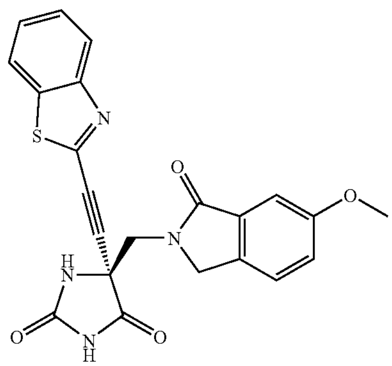 | 432.09 | 433.2 [M + H]+ | C |
| 966 | 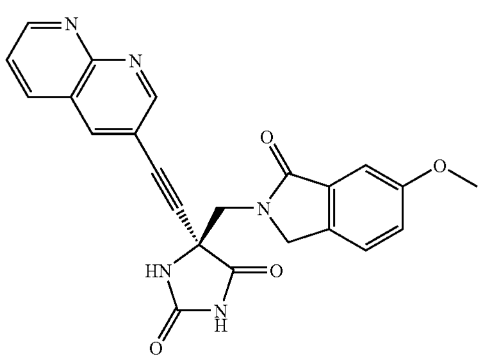 | 427.13 | 428.2 [M + H]+ | C |
| 967 | 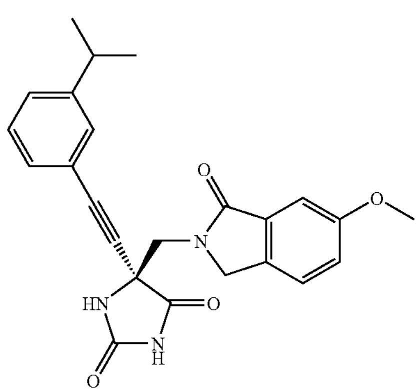 | 417.17 | 418.2 [M + H]+ | C |

| Compound ID | Structures | Exact Mass | Mass Obsvd | Ki Rating |
|---|---|---|---|---|
| 968 | 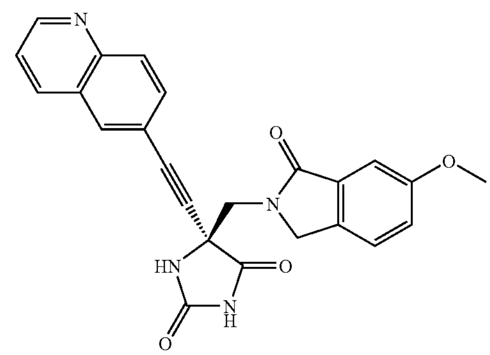 | 426.13 | 427.2 [M + H]+ | C |
| 969 | 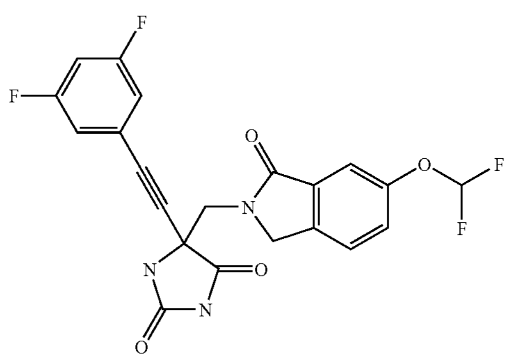 | 447.08 | 448.2 [M + H]+ | A |
| 970 | 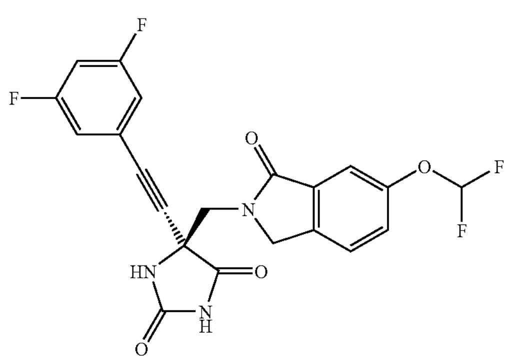 | 447.08 | 448.2 [M + H]+ | D |
| 971 | 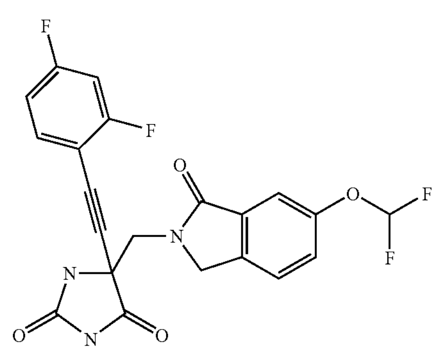 | 447.08 | 448.2 [M + H]+ | A |

TABLE 1001-continued

| Compound ID | Structures | Exact Mass | Mass Obsvd | Ki Rating |
|---|---|---|---|---|
| 973 | 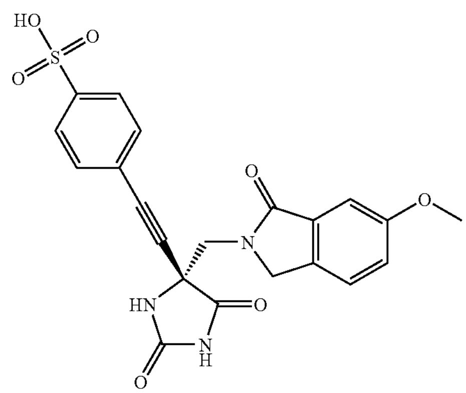 | 455.08 | 456.3 [M + H]+ | A |
| 1002 | 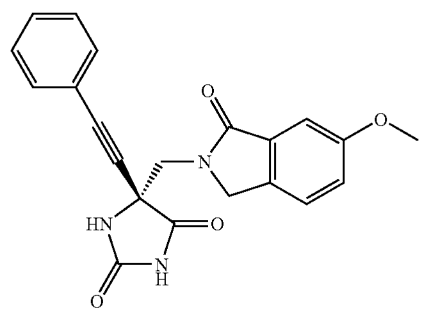 | 375.12 | 376.2 [M + H]+ | A |
| 1003 | 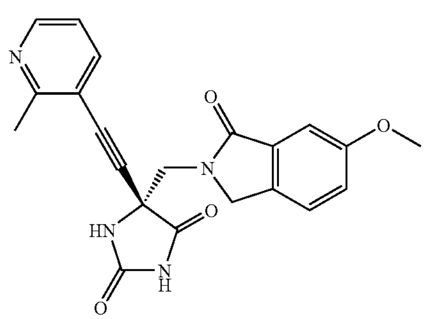 | 390.13 | 391.2 [M + H]+ | A |
| 1003B | 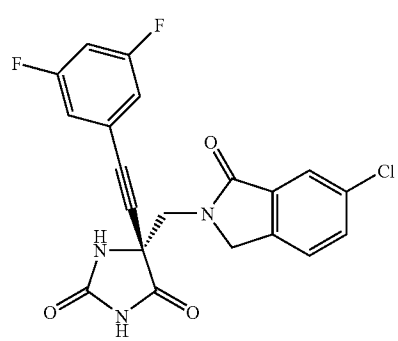 | 415.05 | 416.2 [M + H]+ | A |

TABLE 1001-continued

| Compound ID | Structures | Exact Mass | Mass Obsvd | Ki Rating |
|---|---|---|---|---|
| 1003C | 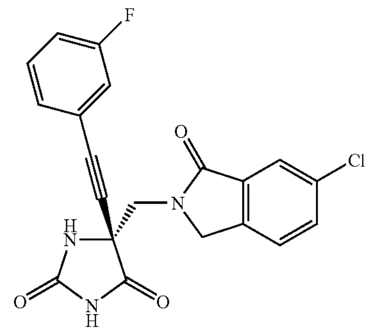 | 397.06 | 398.2 [M + H]+ | A |
| 1004 | 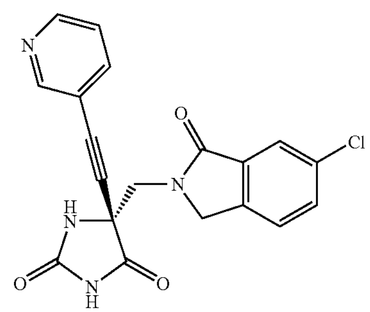 | 380.07 | 381.2 [M + H]+ | A |
| 1005 | 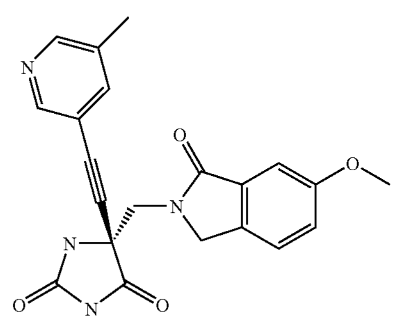 | 390.13 | 391.2 [M + H]+ | A |
| 1006 | 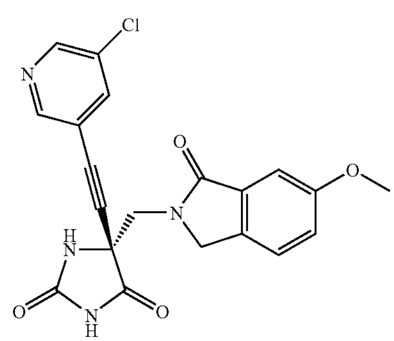 | 410.08 | 411.2 [M + H]+ | A |

TABLE 1001-continued

| Compound ID | Structures | Exact Mass | Mass Obsvd | Ki Rating |
|---|---|---|---|---|
| 1007 | 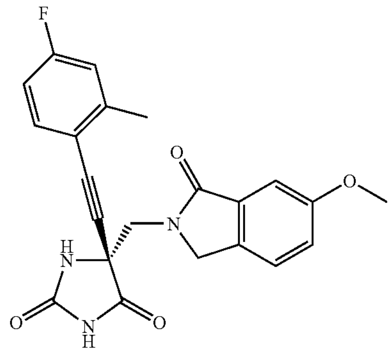 | 407.13 | 408.2 [M + H]+ | A |
| 1008 | 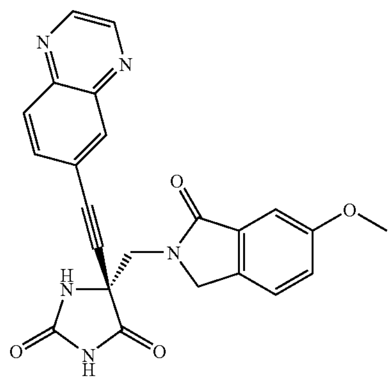 | 427.13 | 428.2 [M + H]+ | A |
| 1009 | 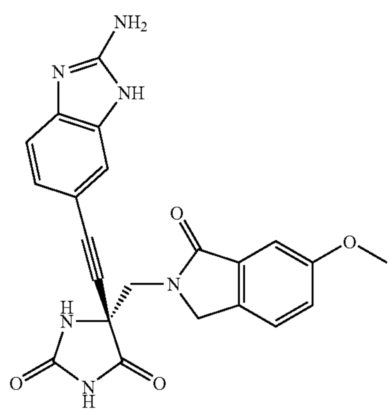 | 430.14 | 431.2 [M + H]+ | A |
| 1010 | 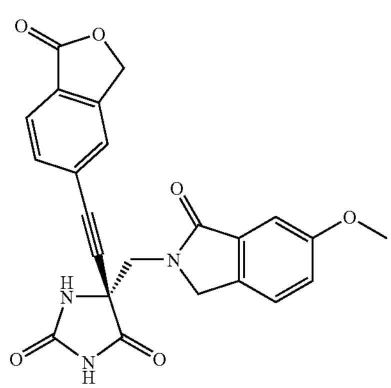 | 431.11 | 432.2 [M + H]+ | A |

TABLE 1001-continued

| Compound ID | Structures | Exact Mass | Mass Obsvd | Ki Rating |
|---|---|---|---|---|
| 1011 | 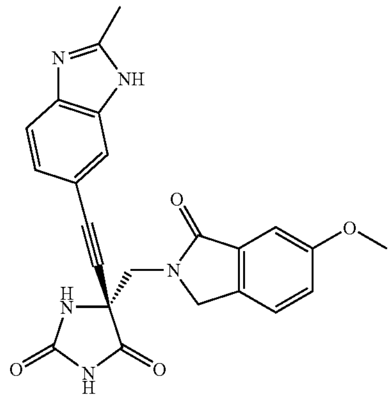 | 429.14 | 430.2 [M + H]+ | A |
| 1012 | 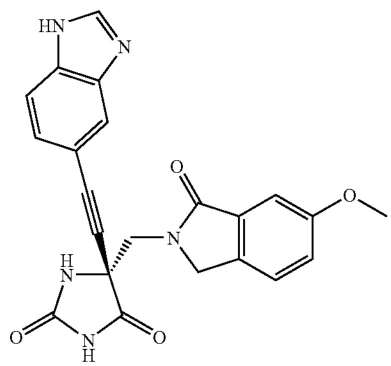 | 415.13 | 416.2 [M + H]+ | A |
| 1013 | 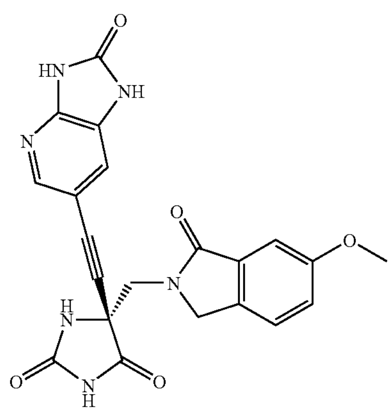 | 432.12 | 433.2 [M + H]+ | A |
| 1014 | 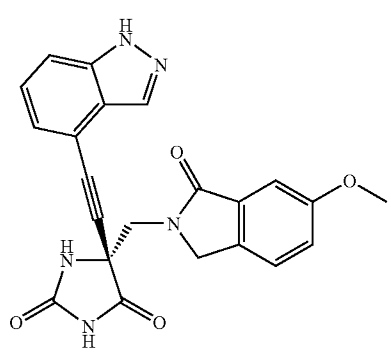 | 415.13 | 416.2 [M + H]+ | A |

TABLE 1001-continued

| Compound ID | Structures | Exact Mass | Mass Obsvd | Ki Rating |
|---|---|---|---|---|
| 1015 | 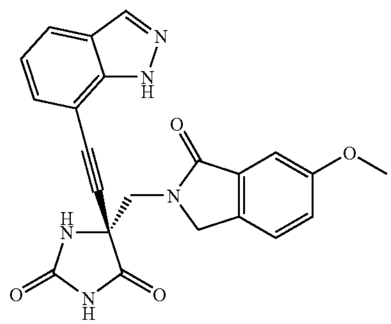 | 415.13 | 416.2 [M + H]+ | A |
| 1016 | 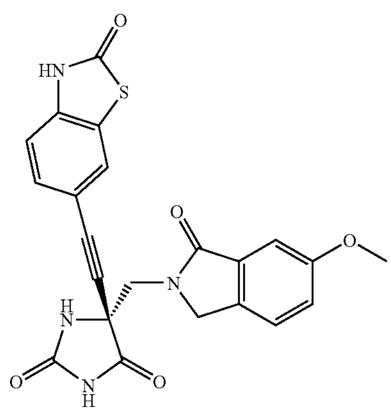 | 448.08 | 449.2 [M + H]+ | A |
| 1017 | 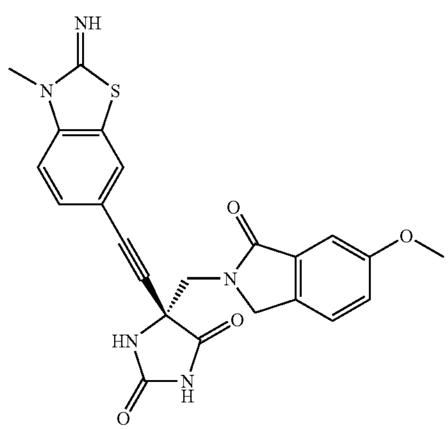 | 461.12 | 462.3 [M + H]+ | A |
| 1018 | 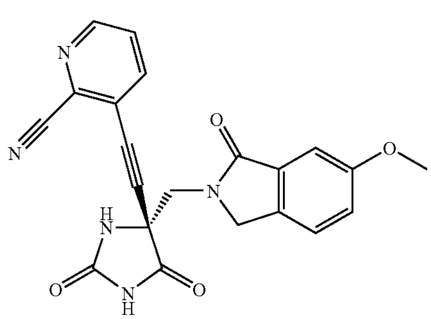 | 401.11 | 402.2 [M + H]+ | A |

TABLE 1001-continued

| Compound ID | Structures | Exact Mass | Mass Obsvd | Ki Rating |
|---|---|---|---|---|
| 1019 | 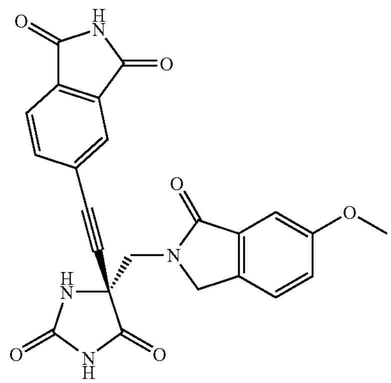 | 444.11 | 445.2 [M + H]+ | A |
| 1036 | 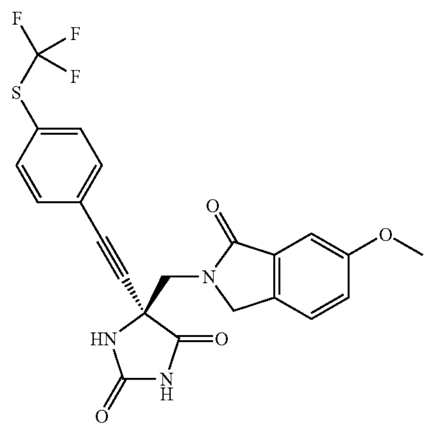 | 475.44 | 476.3 [M + H]+ | D |
| 1037 | 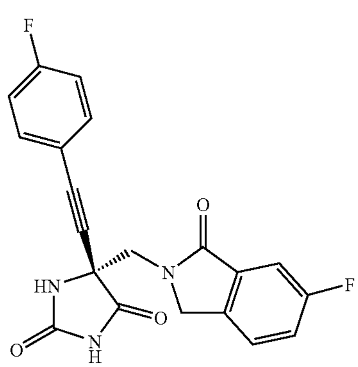 | 381.33 | 382.3 [M + H]+ | A |

TABLE 1001-continued
| Compound ID | Structures | Exact Mass | Mass Obsvd | Ki Rating |
|---|---|---|---|---|
| 1038 | 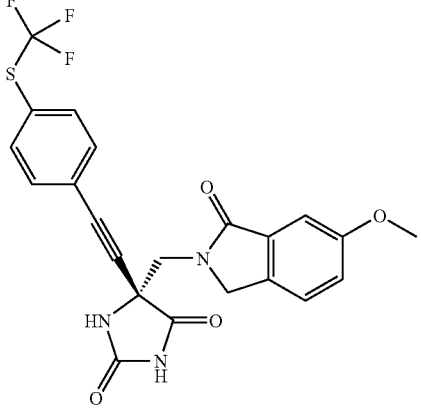 | 475.44 | 476.3 [M + H]+ | A |
| 1039 | 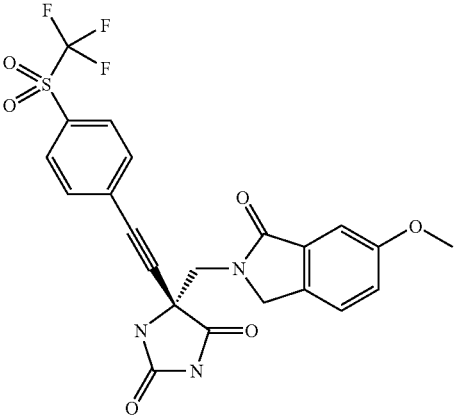 | 507.44 | 508.3 [M + H]+ | B |
| 1040 | 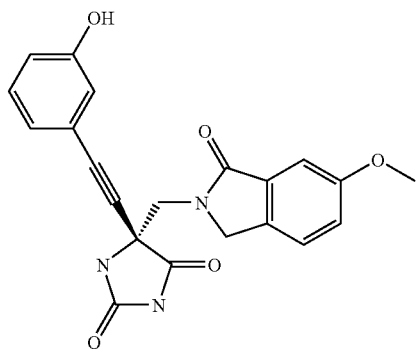 | 391.38 | 392.2 [M + H]+ | A |
| 1041 | 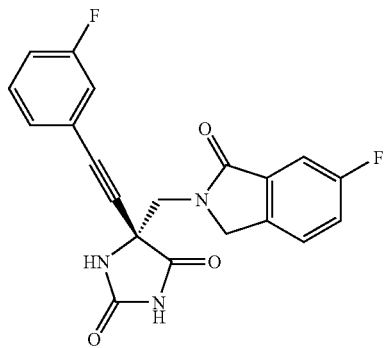 | 381.33 | 382.2 [M + H]+ | A |

TABLE 1001-continued

| Compound ID | Structures | Exact Mass | Mass Obsvd | Ki Rating |
|---|---|---|---|---|
| 1042 | 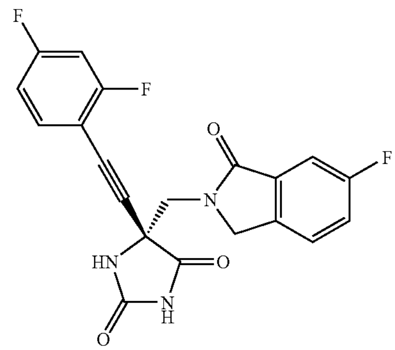 | 399.32 | 400.2 [M + H]+ | A |
| 1043 | 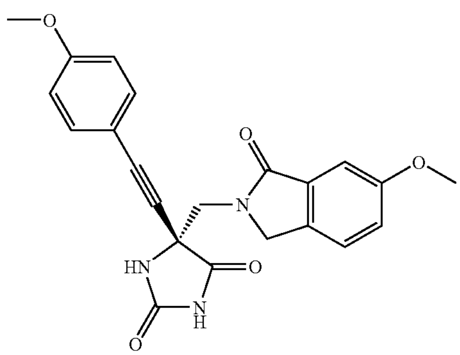 | 405.40 | 406.2 [M + H]+ | A |
| 1044 | 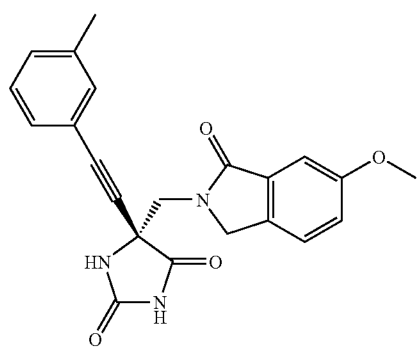 | 389.40 | 390.2 [M + H]+ | A |
| 1045 | 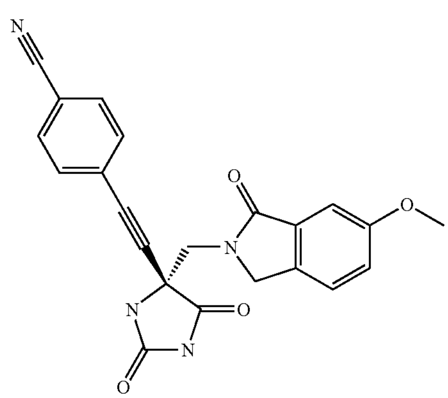 | 400.39 | 401.2 [M + H]+ | A |

TABLE 1001-continued
| Compound ID | Structures | Exact Mass | Mass Obsvd | Ki Rating |
|---|---|---|---|---|
| 1046 | 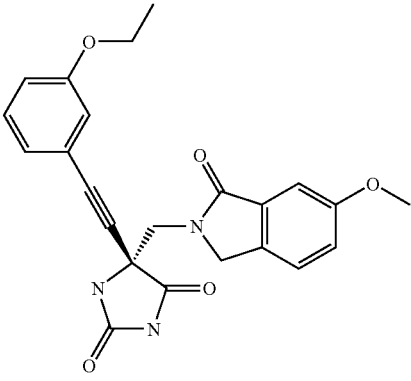 | 419.43 | 420.2 [M + H]+ | A |
| 1047 | 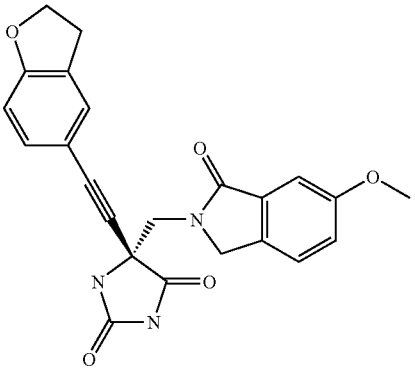 | 417.41 | 418.2 [M + H]+ | A |
| 1048 | 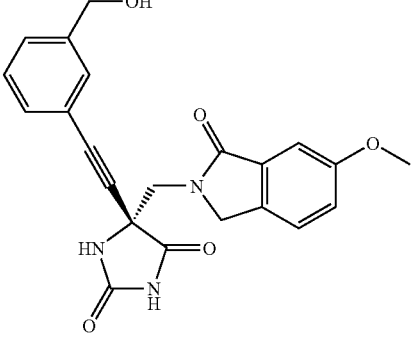 | 405.40 | 406.2 [M + H]+ | A |
| 1049 | 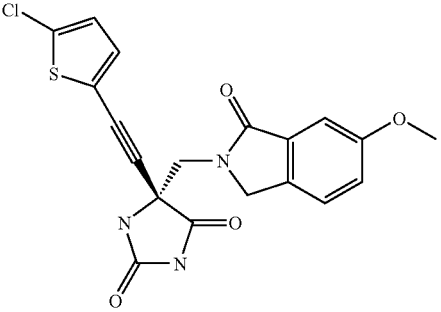 | 415.85 | 416.2 [M + H]+ | A |

TABLE 1001-continued

| Compound ID | Structures | Exact Mass | Mass Obsvd | Ki Rating |
|---|---|---|---|---|
| 1050 | 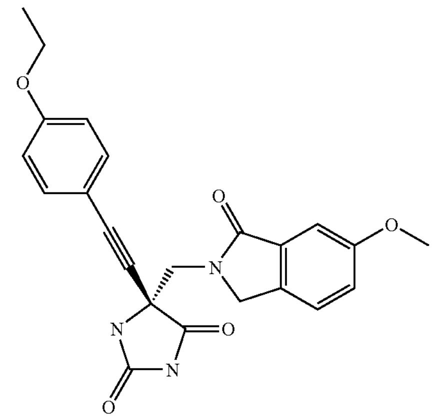 | 419.43 | 420.2 [M + H]⁺ | A |
| 1051 | 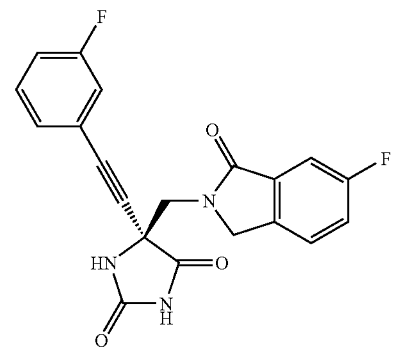 | 381.33 | 382.2 [M + H]⁺ | C |
| 1052 | 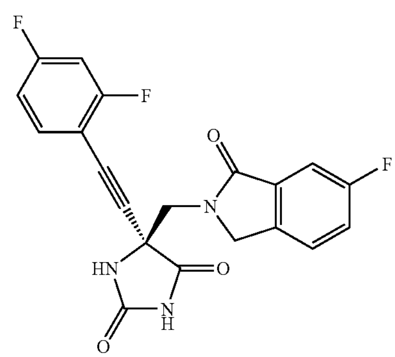 | 399.32 | 400.2 [M + H]⁺ | C |
| 1053 | 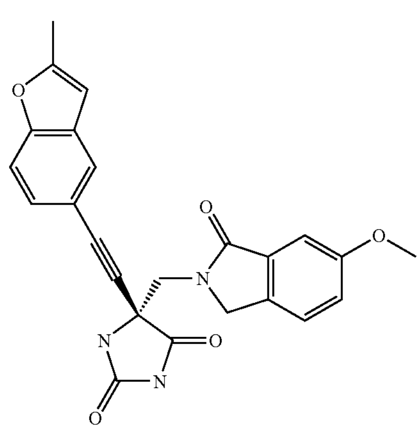 | 429.42 | 430.2 [M + H]⁺ | A |

TABLE 1001-continued

| Compound ID | Structures | Exact Mass | Mass Obsvd | Ki Rating |
|---|---|---|---|---|
| 1054 | 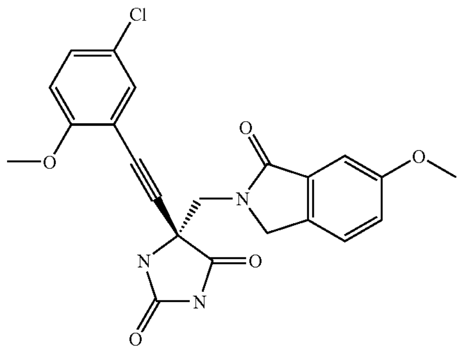 | 439.85 | 440.2 [M + H]+ | A |
| 1055 | 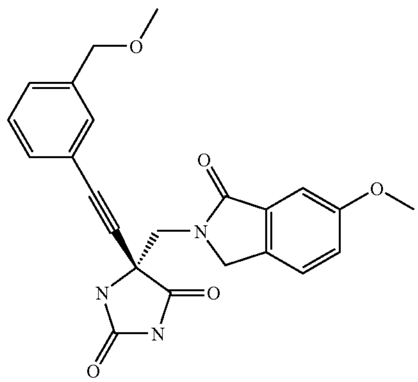 | 419.43 | 420.2 [M + H]+ | A |
| 1056 | 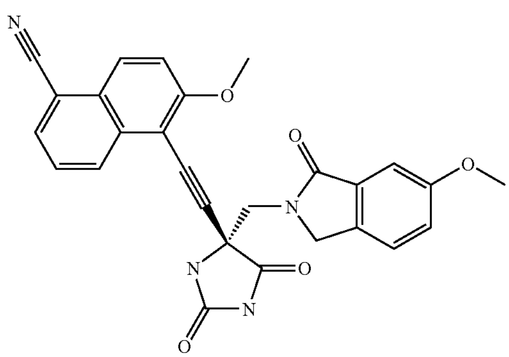 | 480.47 | 481.3 [M + H]+ | A |
| 1057 | 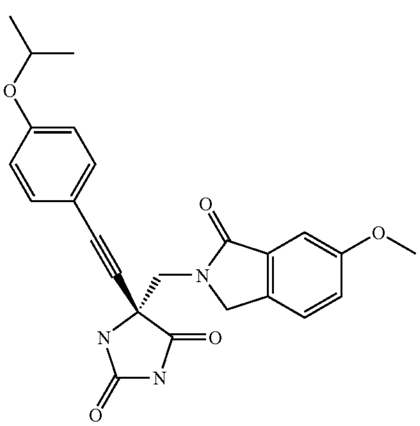 | 433.46 | 434.2 [M + H]+ | A |

TABLE 1001-continued

| Compound ID | Structures | Exact Mass | Mass Obsvd | Ki Rating |
|---|---|---|---|---|
| 1058 | 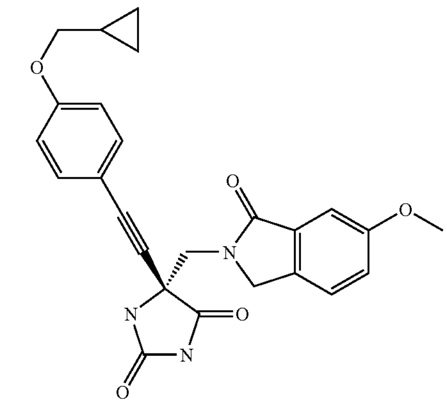 | 445.47 | 446.2 [M + H]⁺ | A |
| 1059 | 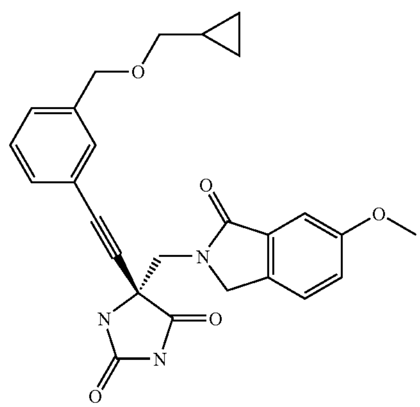 | 459.49 | 460.3 [M + H]⁺ | A |
| 1060 | 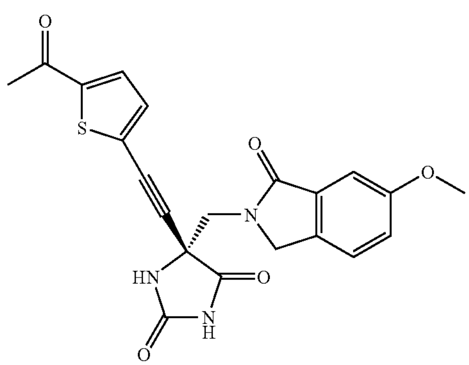 | 423.44 | 424.2 [M + H]⁺ | A |
| 1061 | 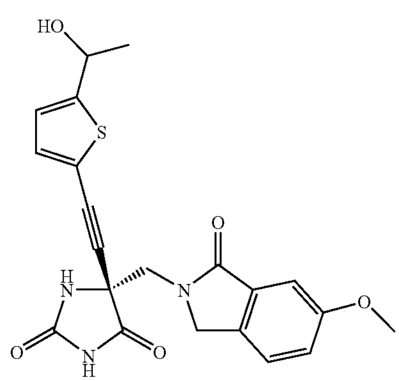 | 425.46 | 426.2 [M + H]⁺ | A |

TABLE 1001-continued

| Compound ID | Structures | Exact Mass | Mass Obsvd | Ki Rating |
|---|---|---|---|---|
| 1062 | 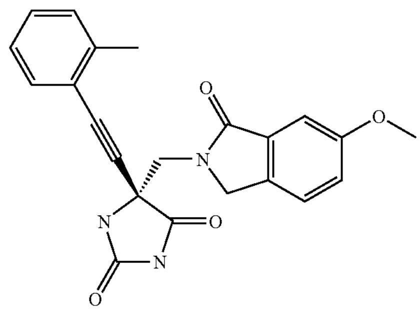 | 389.40 | 390.2 [M + H]⁺ | A |
| 1063 | 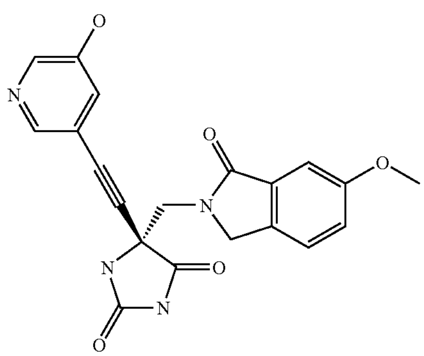 | 392.36 | 393.2 [M + H]⁺ | A |
| 1064 | 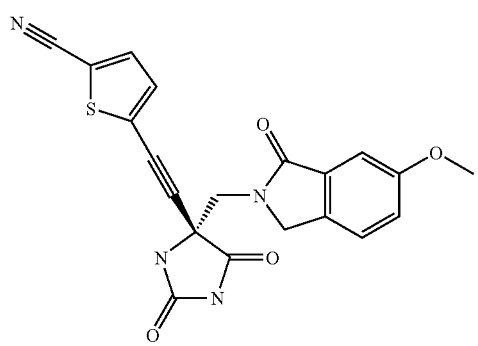 | 406.41 | 407.2 [M + H]⁺ | A |
| 1065 | 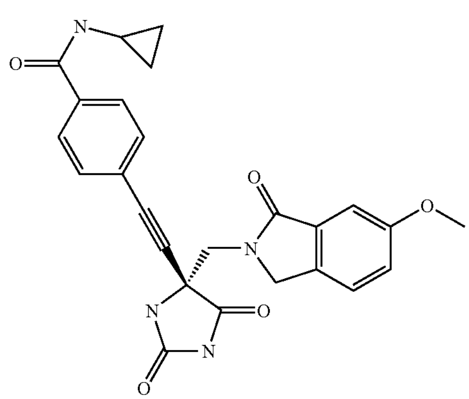 | 458.47 | 459.3 [M + H]⁺ | A |

TABLE 1001-continued

| Compound ID | Structures | Exact Mass | Mass Obsvd | Ki Rating |
|---|---|---|---|---|
| 1066 | 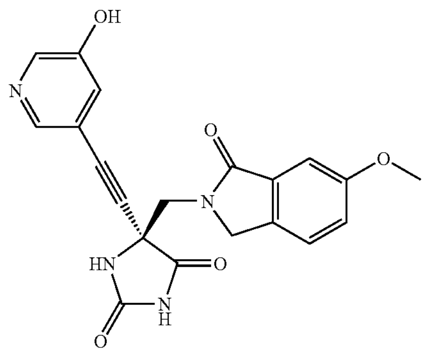 | 392.36 | 393.2 [M + H]+ | D |
| 1067 | 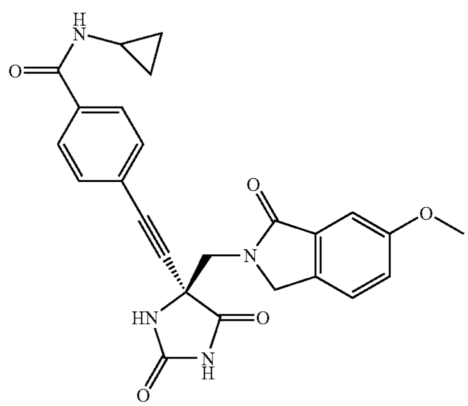 | 458.47 | 459.3 [M + H]+ | D |
| 1068 | 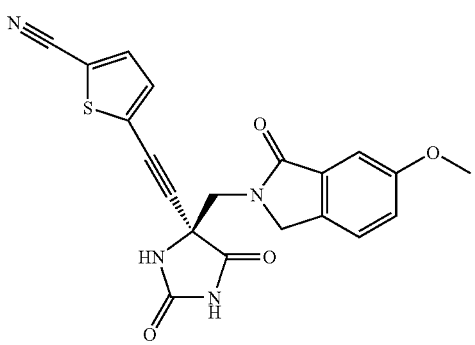 | 406.41 | 407.2 [M + H]+ | D |
| 1069 | 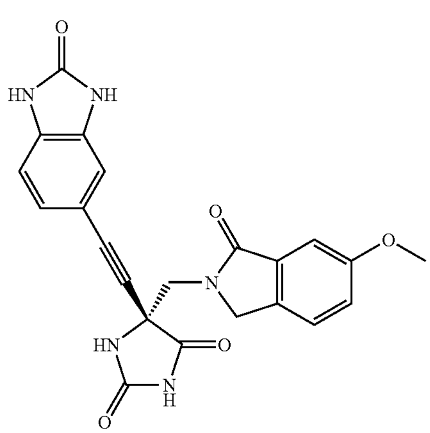 | 431.40 | 432.2 [M + H]+ | A |

TABLE 1001-continued

| Compound ID | Structures | Exact Mass | Mass Obsvd | Ki Rating |
|---|---|---|---|---|
| 1070 | 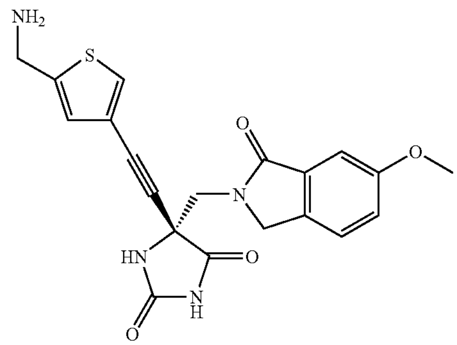 | 410.45 | 411.2 [M + H]+ | A |
| 1071 | 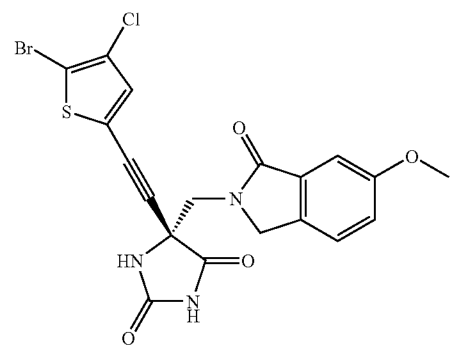 | 494.95 | 496.3 [M + H]+ | A |
| 1072 | 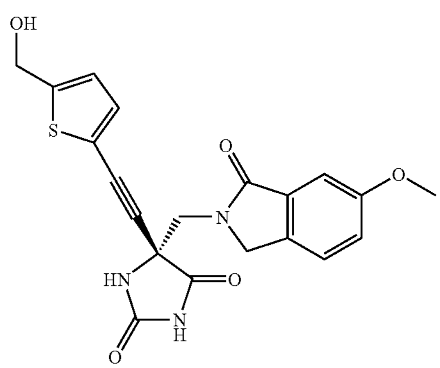 | 411.43 | 412.2 [M + H]+ | A |
| 1073 | 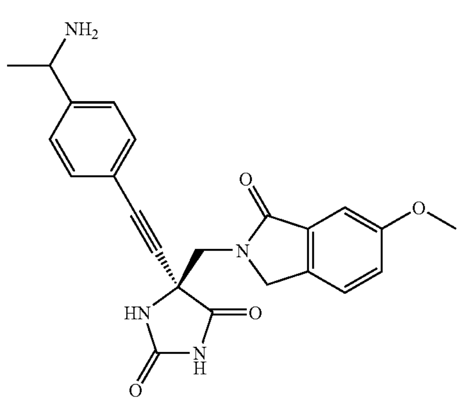 | 418.45 | 419.2 [M + H]+ | D |

TABLE 1001-continued

| Compound ID | Structures | Exact Mass | Mass Obsvd | Ki Rating |
|---|---|---|---|---|
| 1074 | 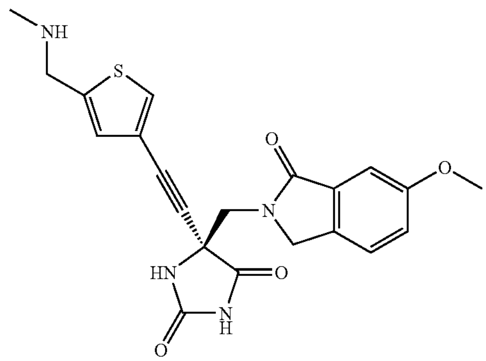 | 424.47 | 425.2 [M + H]+ | D |
| 1075 | 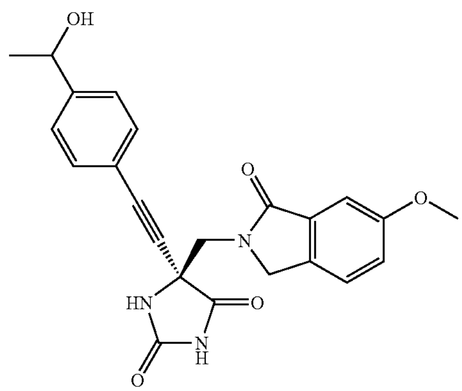 | 419.43 | 420.2 [M + H]+ | D |
| 1076 | 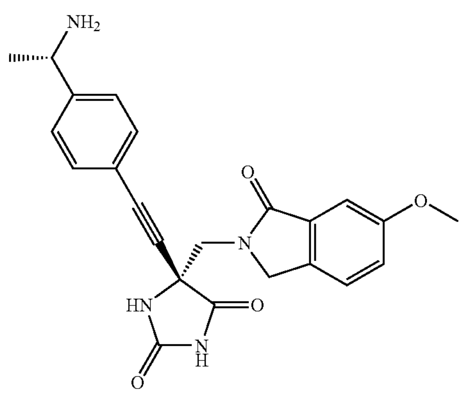 | 418.45 | 419.2 [M + H]+ | A |
| 1077 | 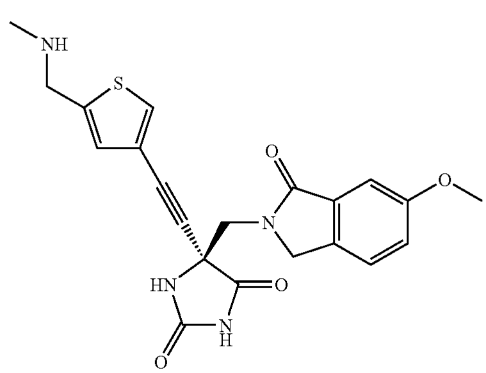 | 424.47 | 425.2 [M + H]+ | A |

TABLE 1001-continued
| Compound ID | Structures | Exact Mass | Mass Obsvd | Ki Rating |
|---|---|---|---|---|
| 1078 | 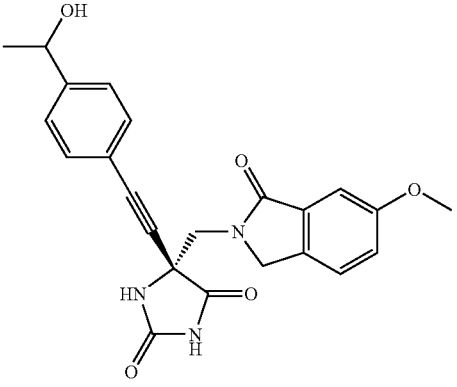 | 419.43 | 420.2 [M + H]+ | A |
| 1079 | 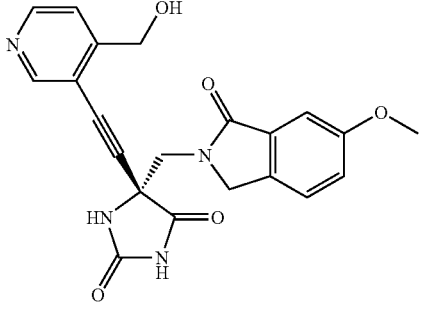 | 406.39 | 407.2 [M + H]+ | A |
| 1080 | 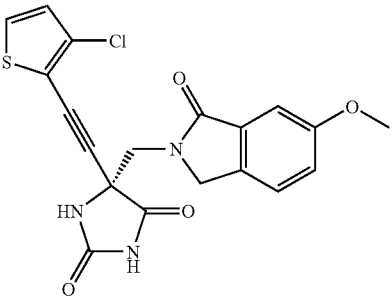 | 415.85 | 416.2 [M + H]+ | A |
| 1081 | 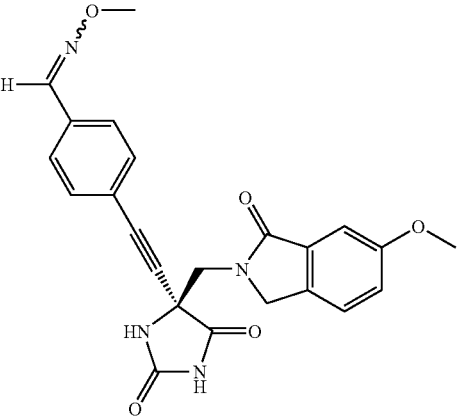 | 432.43 | 433.2 [M + H]+ | D |

TABLE 1001-continued

| Compound ID | Structures | Exact Mass | Mass Obsvd | Ki Rating |
|---|---|---|---|---|
| 1082 | 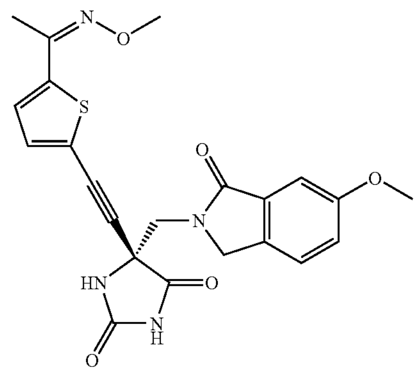 | 452.48 | 453.2 [M + H]⁺ | A |
| 1083 | 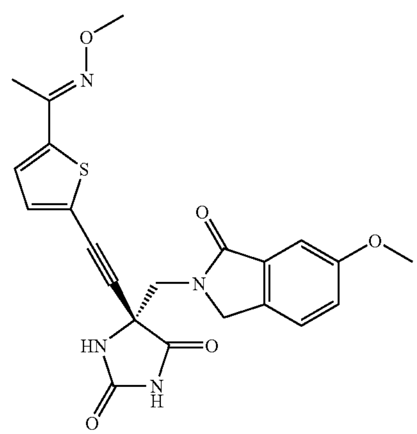 | 452.48 | 453.2 [M + H]⁺ | A |
| 1084 | 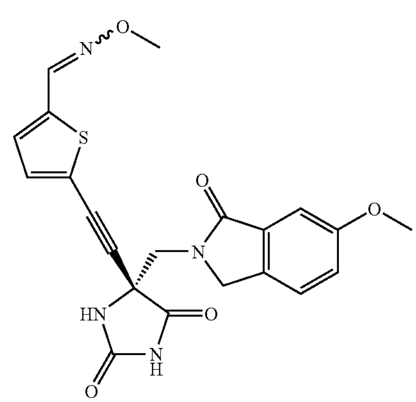 | 438.46 | 439.2 [M + H]⁺ | A |

TABLE 1001-continued

| Compound ID | Structures | Exact Mass | Mass Obsvd | Ki Rating |
|---|---|---|---|---|
| 1085 | 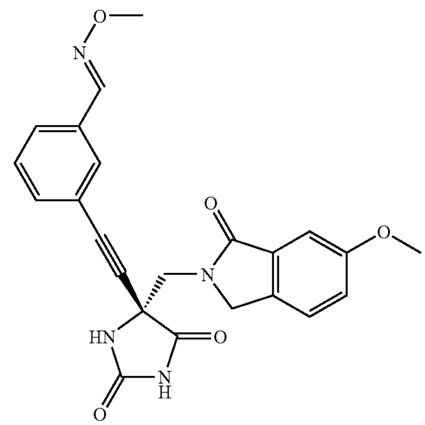 | 432.43 | 433.2 [M + H]+ | A |
| 1086 | 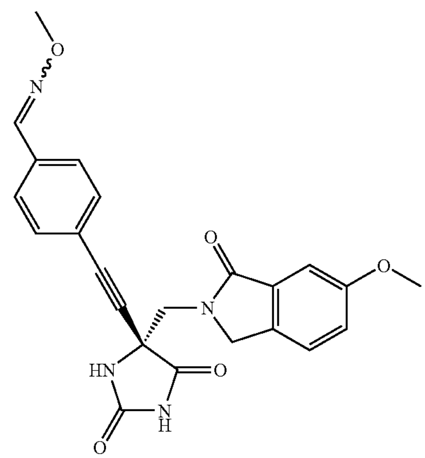 | 432.43 | 433.2 [M + H]+ | A |
| 1087 | 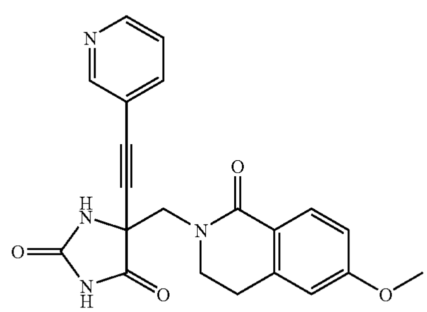 | 390.39 | 391.2 [M + H]+ | A |
| 1088 | 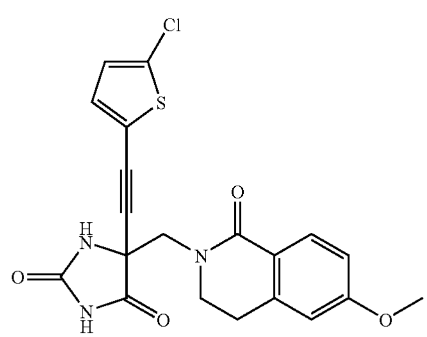 | 429.88 | 430.2 [M + H]+ | B |

TABLE 1001-continued

| Compound ID | Structures | Exact Mass | Mass Obsvd | Ki Rating |
|---|---|---|---|---|
| 1089 | 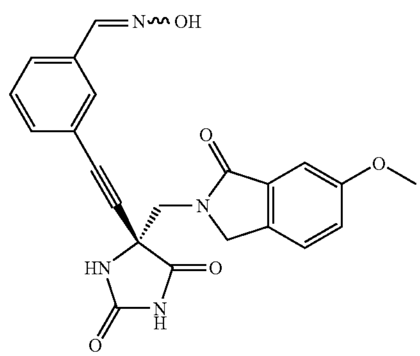 | 418.40 | 419.2 [M + H]+ | A |
| 1090 | 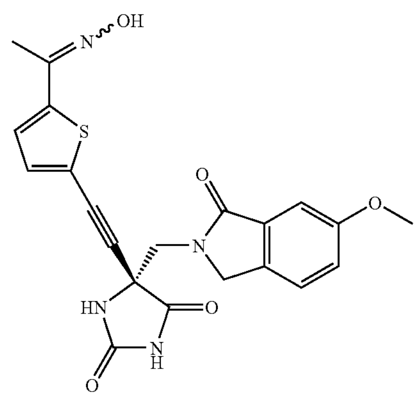 | 438.46 | 439.2 [M + H]+ | A |
| 1091 | 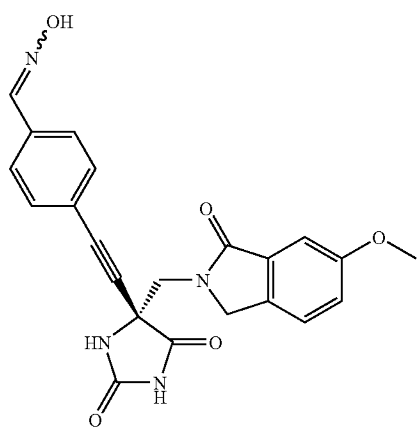 | 418.40 | 419.2 [M + H]+ | A |
| 1092 | 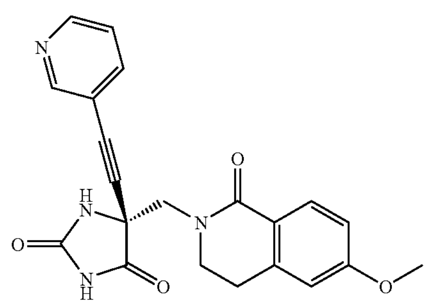 | 390.39 | 391.2 [M + H]+ | A |

TABLE 1001-continued

| Compound ID | Structures | Exact Mass | Mass Obsvd | Ki Rating |
|---|---|---|---|---|
| 1093 | 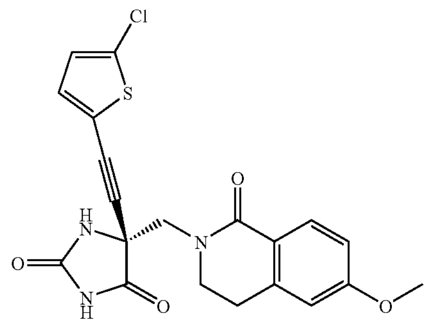 | 429.88 | 430.2 [M + H]+ | A |
| 1094 | 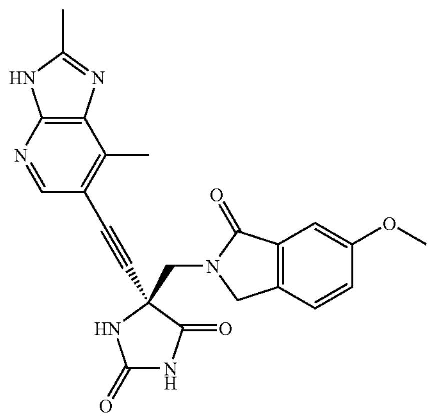 | 444.44 | 445.2 [M + H]+ | D |
| 1095 | 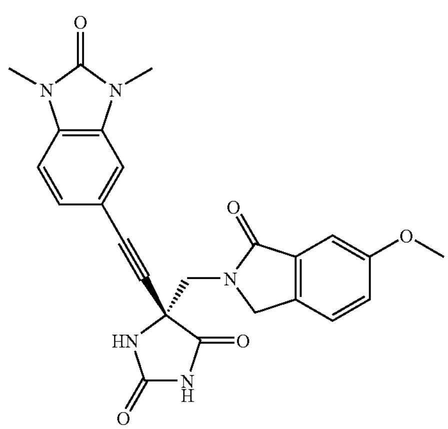 | 459.45 | 460.3 [M + H]+ | A |
| 1096 | 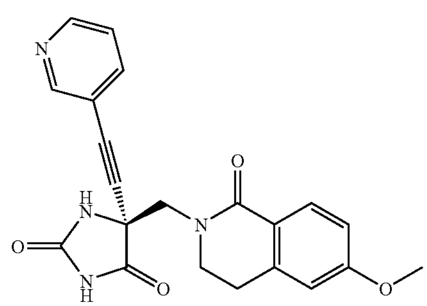 | 390.39 | 391.2 [M + H]+ | D |

TABLE 1001-continued

| Compound ID | Structures | Exact Mass | Mass Obsvd | Ki Rating |
|---|---|---|---|---|
| 1097 | 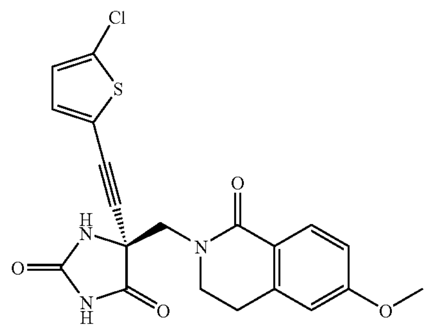 | 429.88 | 430.2 [M + H]⁺ | D |
| 1098 | 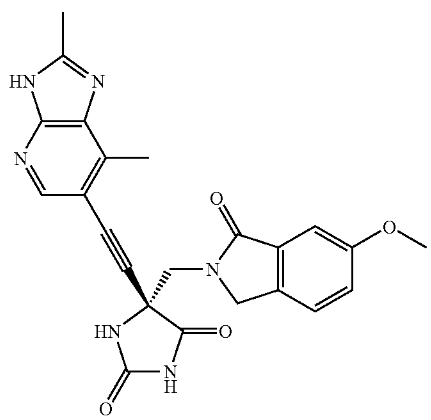 | 444.44 | 445.2 [M + H]⁺ | A |
| 1099 | 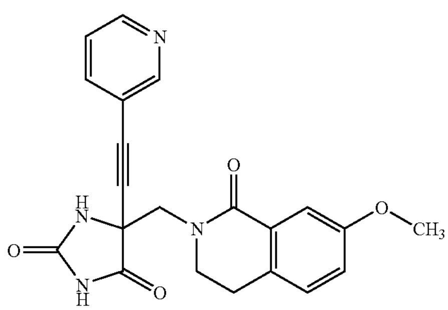 | 390.39 | 391.2 [M + H]⁺ | n/a |
| 1129 | 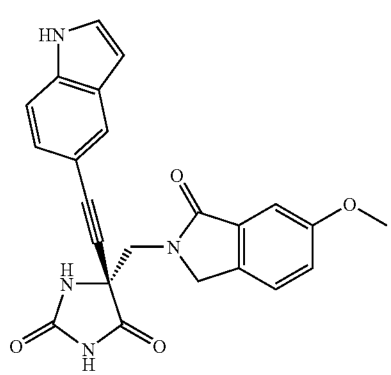 | 414.1 | 415.2 [M + H]⁺ | A |

TABLE 1001-continued

| Compound ID | Structures | Exact Mass | Mass Obsvd | Ki Rating |
|---|---|---|---|---|
| 1130 | 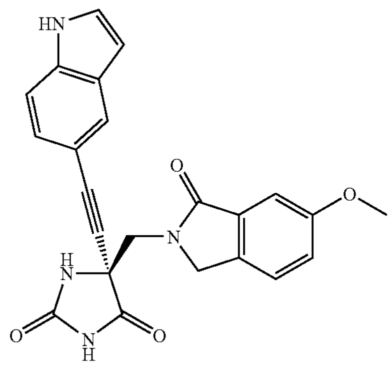 | 414.1 | 415.2 [M + H]+ | B |
| 1131 | 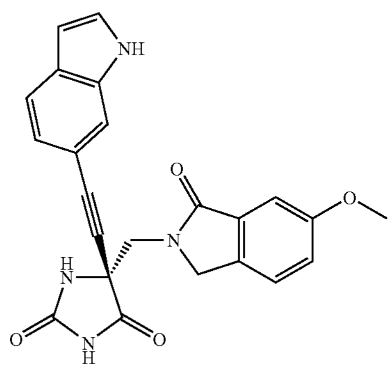 | 414.1 | 415.2 [M + H]+ | A |
| 1132 | 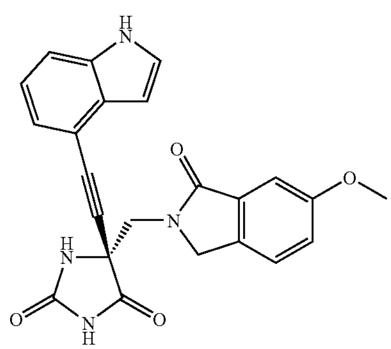 | 414.1 | 415.2 [M + H]+ | A |
| 1133 | 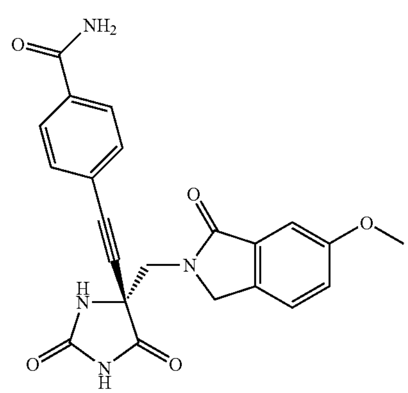 | 418.13 | 419.2 [M + H]+ | A |

TABLE 1001-continued

| Compound ID | Structures | Exact Mass | Mass Obsvd | Ki Rating |
|---|---|---|---|---|
| 1134 | 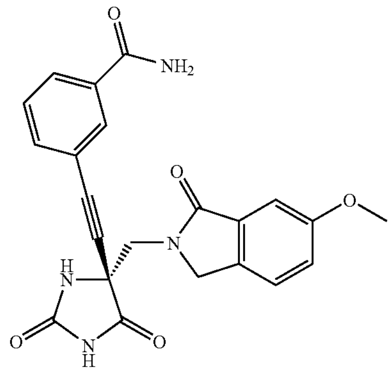 | 418.13 | 419.2 [M + H]⁺ | A |
| 1135 | 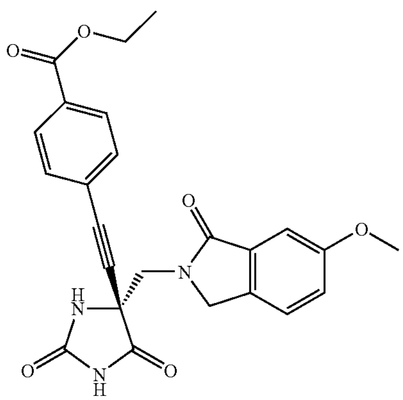 | 447.14 | 448.2 [M + H]⁺ | A |
| 1136 | 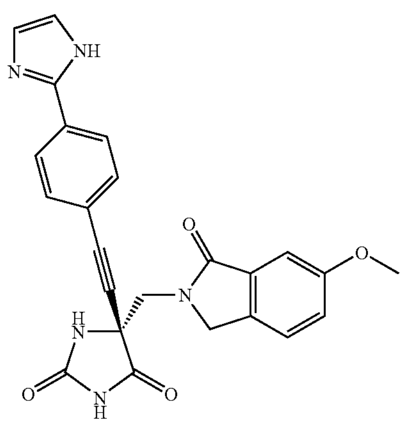 | 441.1 | 442.2 [M + H]⁺ | A |
| 1137 | 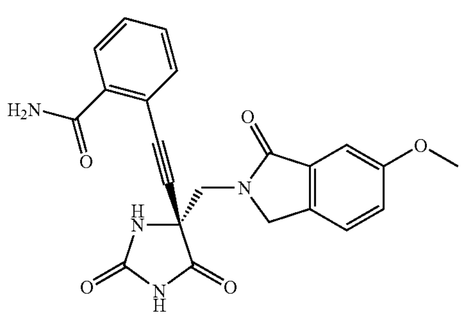 | 418.1 | 419.2 [M + H]⁺ | A |

TABLE 1001-continued

| Compound ID | Structures | Exact Mass | Mass Obsvd | Ki Rating |
|---|---|---|---|---|
| 1138 1380269 | | 419.1 | 420.2 [M + H]+ | A |
| 1139 | 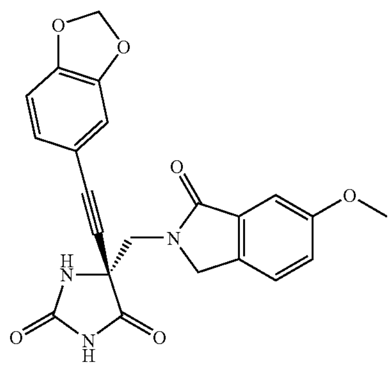 | 419.1 | 420.2 [M + H]+ | A |
| 1140 | 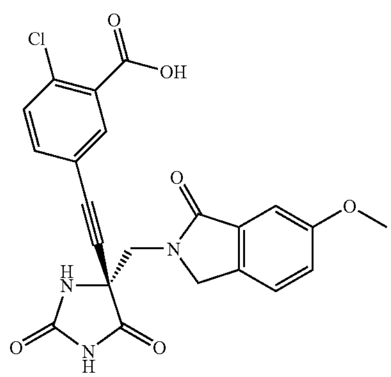 | 453.1 | 454.2 [M + H]+ | A |
| 1141 | 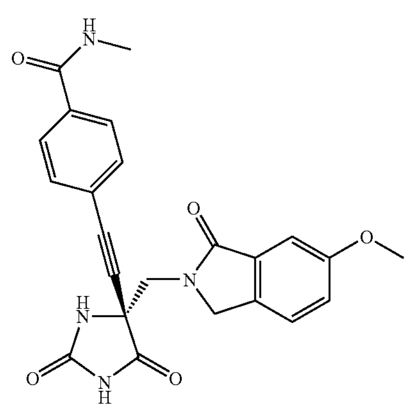 | 432.1 | 433.2 [M + H]+ | A |

TABLE 1001-continued

| Compound ID | Structures | Exact Mass | Mass Obsvd | Ki Rating |
|---|---|---|---|---|
| 1142 | 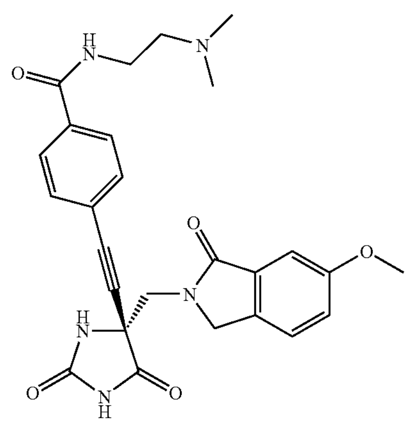 | 489.2 | 490.3 [M + H]⁺ | A |
| 1143 | 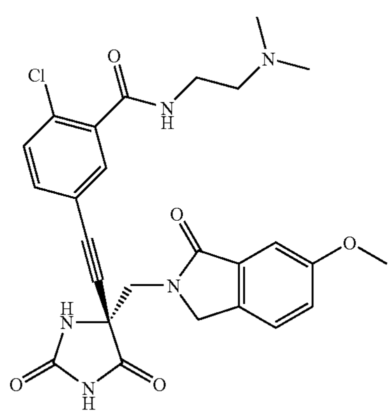 | 523.2 | 524.3 [M + H]⁺ | A |
| 1144 | 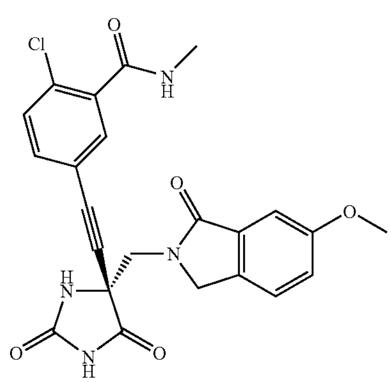 | 466.1 | 467.3 [M + H]⁺ | A |

TABLE 1001-continued

| Compound ID | Structures | Exact Mass | Mass Obsvd | Ki Rating |
|---|---|---|---|---|
| 1145 | 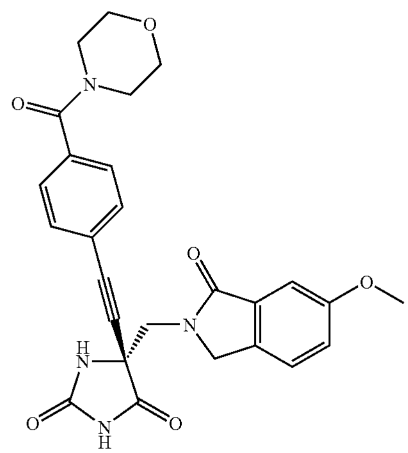 | 488.2 | 489.3 [M + H]+ | A |
| 1146 | 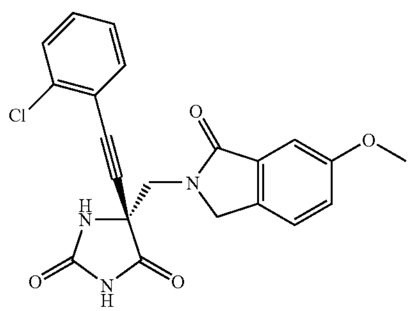 | 409.1 | 410.2 [M + H]+ | A |
| 1147 | 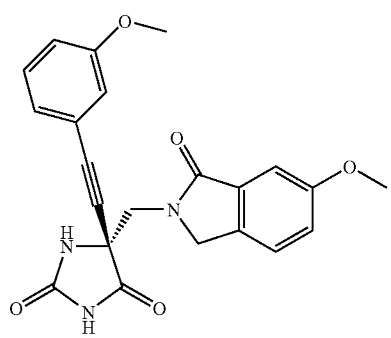 | 405.1 | 406.2 [M + H]+ | A |
| 1148 | 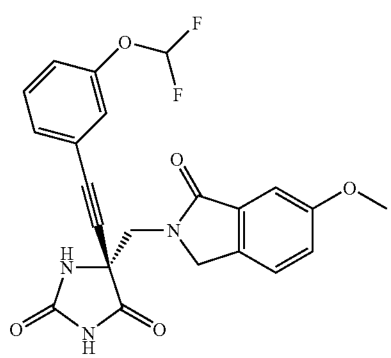 | 441.1 | 442.2 [M + H]+ | A |

TABLE 1001-continued

| Compound ID | Structures | Exact Mass | Mass Obsvd | Ki Rating |
|---|---|---|---|---|
| 1149 | 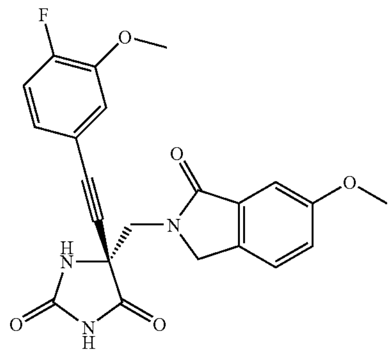 | 423.1 | 424.2 [M + H]+ | A |
| 1150 | 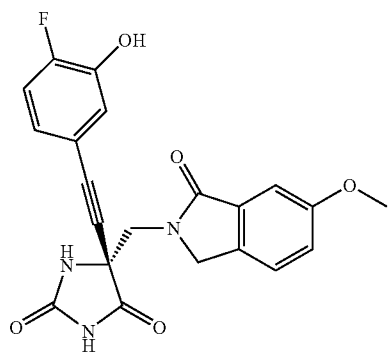 | 409.1 | 410.2 [M + H]+ | A |
| 1151 | 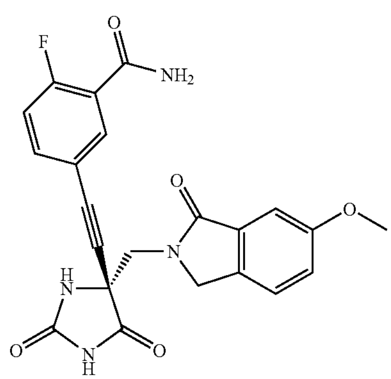 | 436.1 | 437.2 [M + H]+ | A |
| 1152 | 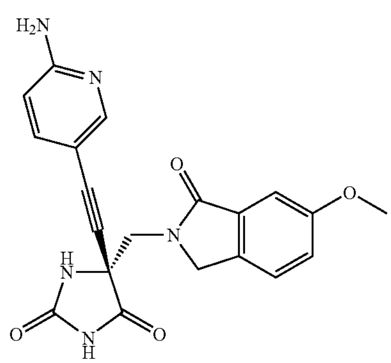 | 391.1 | 392.2 [M + H]+ | A |

TABLE 1001-continued

| Compound ID | Structures | Exact Mass | Mass Obsvd | Ki Rating |
|---|---|---|---|---|
| 1153 | 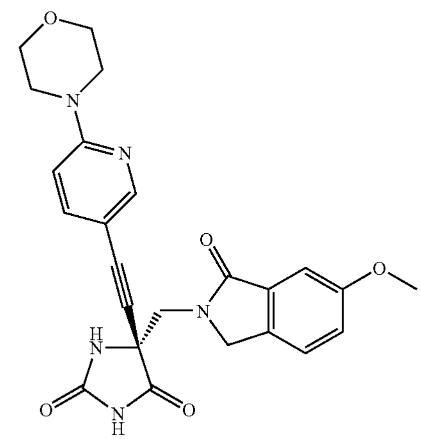 | 461.2 | 462.3 [M + H]+ | A |
| 1154 | 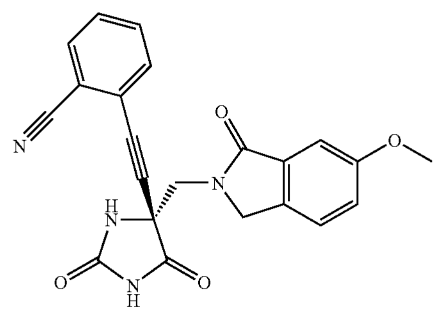 | 400.1 | 401.2 [M + H]+ | A |
| 1155 | 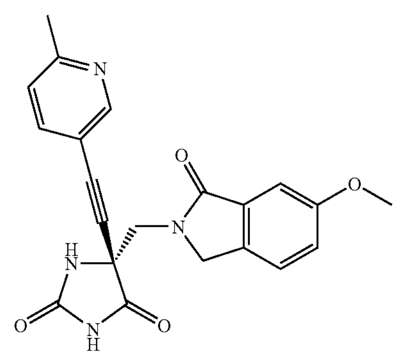 | 390.1 | 391.2 [M + H]+ | A |
| 1156 | 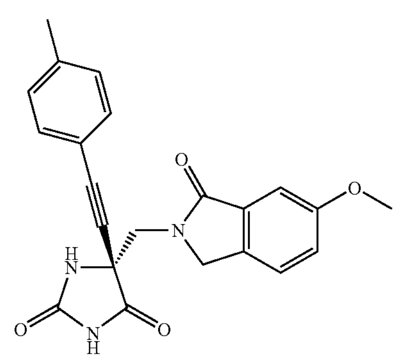 | 389.1 | 390.2 [M + H]+ | A |

TABLE 1001-continued

| Compound ID | Structures | Exact Mass | Mass Obsvd | Ki Rating |
|---|---|---|---|---|
| 1157 | 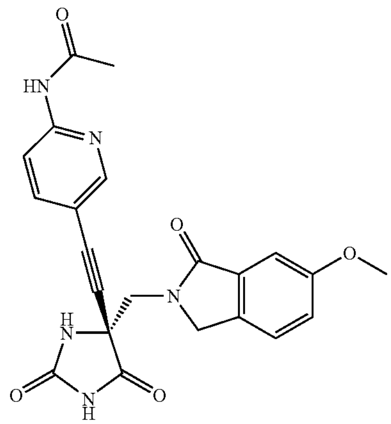 | 433.1 | 434.2 [M + H]+ | A |
| 1200 | 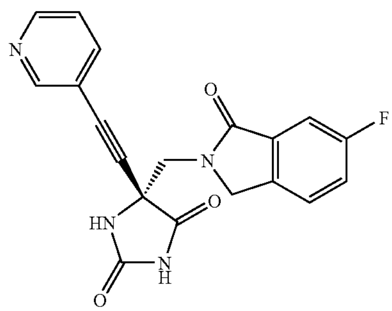 | 364.3 | 365.2 [M + H]+ | A |
| 1201 | 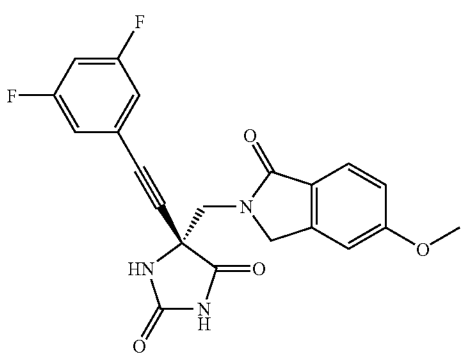 | 411.4 | 412.2 [M + H]+ | A |
| 1202 | 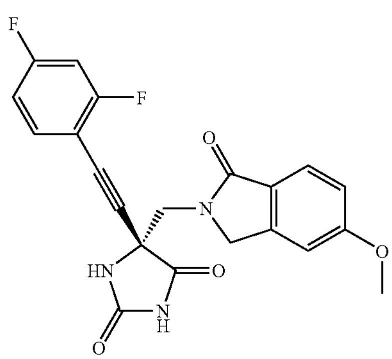 | 411.4 | 412.2 [M + H]+ | A |

TABLE 1001-continued

| Compound ID | Structures | Exact Mass | Mass Obsvd | Ki Rating |
|---|---|---|---|---|
| 1203 | 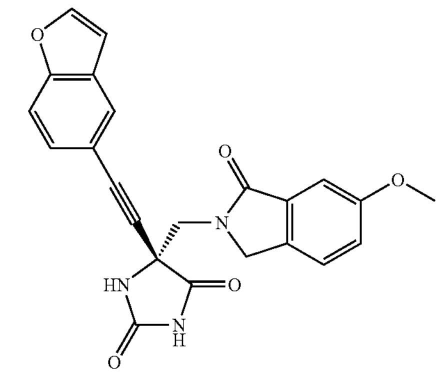 | 415.4 | 416.2 [M + H]⁺ | A |
| 1204 | 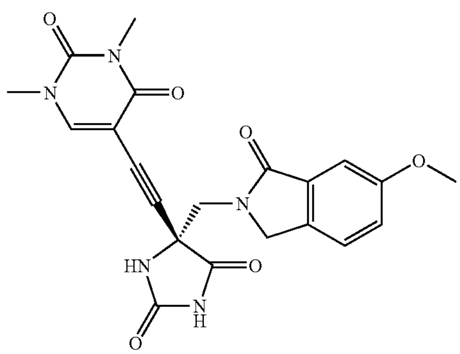 | 437.4 | 438.2 [M + H]⁺ | A |
| 1205 | 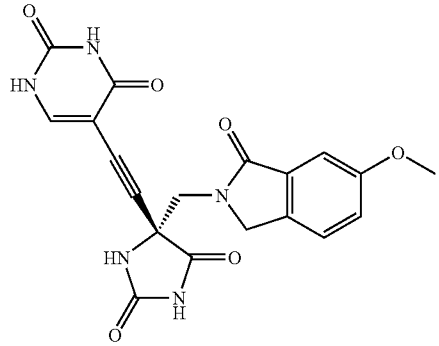 | 409.4 | 410.2 [M + H]⁺ | A |
| 1206 | 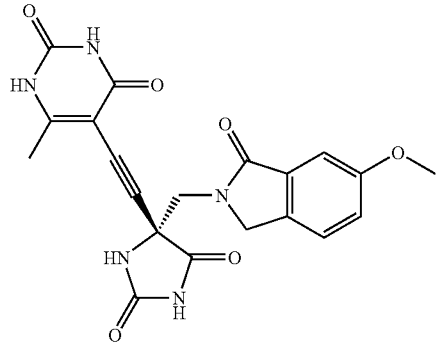 | 495.5 | 496.2 [M + H]⁺ | A |

TABLE 1001-continued
| Compound ID | Structures | Exact Mass | Mass Obsvd | Ki Rating |
|---|---|---|---|---|
| 1208 | 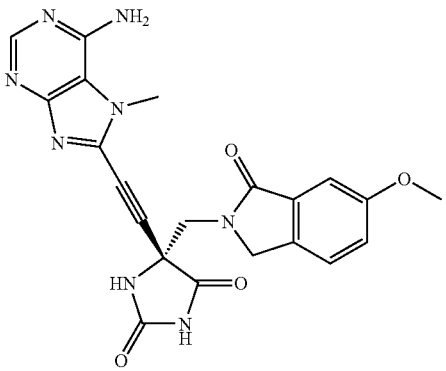 | 446.4 | 447.3 [M + H]+ | A |
| 1211 | 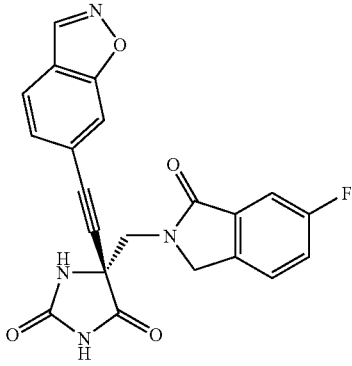 | 404.4 | 405.2 [M + H]+ | A |
| 1212 | 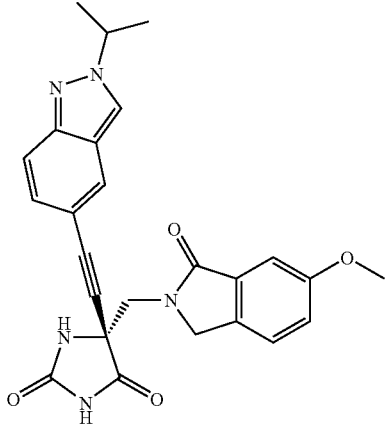 | 457.5 | 458.3 [M + H]+ | A |

TABLE 1001-continued

| Compound ID | Structures | Exact Mass | Mass Obsvd | Ki Rating |
|---|---|---|---|---|
| 1213 | 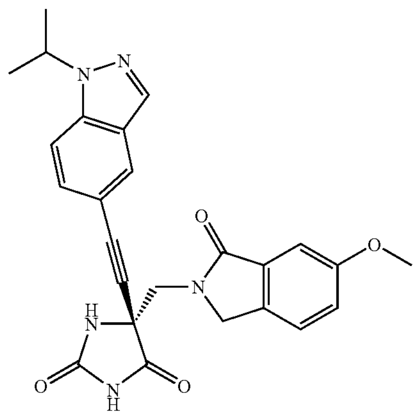 | 457.5 | 458.3 [M + H]⁺ | A |
| 1214 | 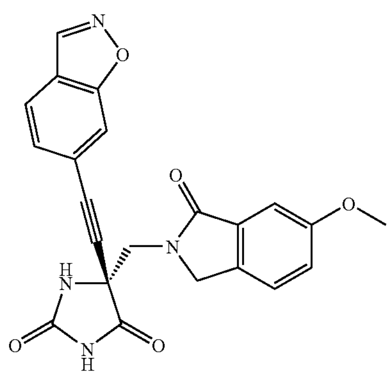 | 416.4 | 417.3 [M + H]⁺ | A |
| 1215 | 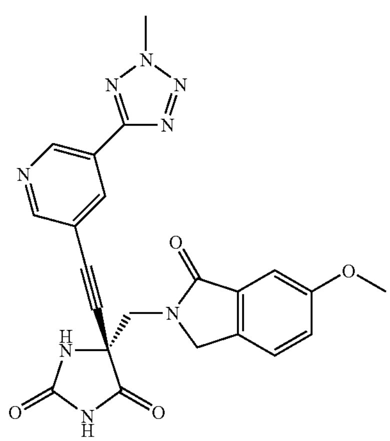 | 458.4 | 459.3 [M + H]⁺ | A |

TABLE 1001-continued

| Compound ID | Structures | Exact Mass | Mass Obsvd | Ki Rating |
|---|---|---|---|---|
| 1216 | 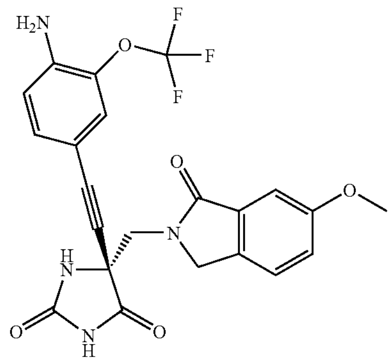 | 474.4 | 475.3 [M + H]+ | A |
| 1217 | 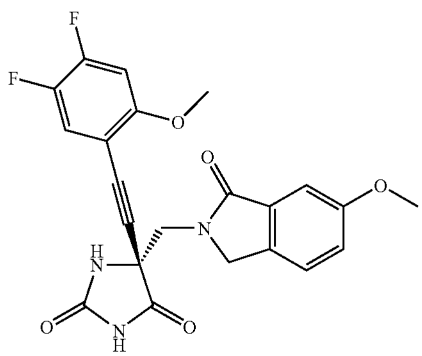 | 441.4 | 422.2 [M + H]+ | A |
| 1218 | 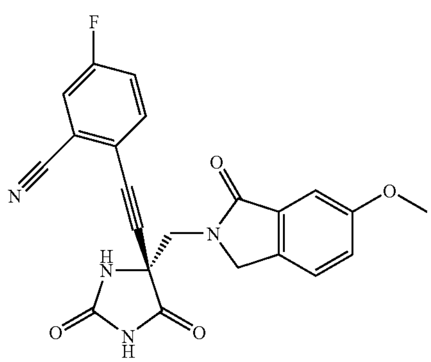 | 418.4 | 419.2 [M + H]+ | A |
| 1219 | 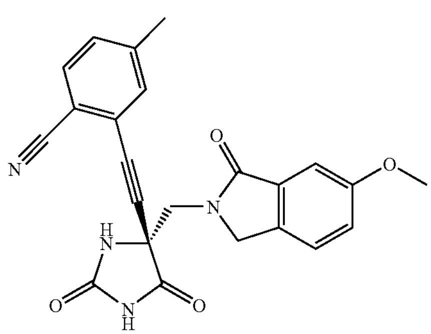 | 414.4 | 415 [M + H]+ | A |

TABLE 1001-continued
| Compound ID | Structures | Exact Mass | Mass Obsvd | Ki Rating |
|---|---|---|---|---|
| 1220 | 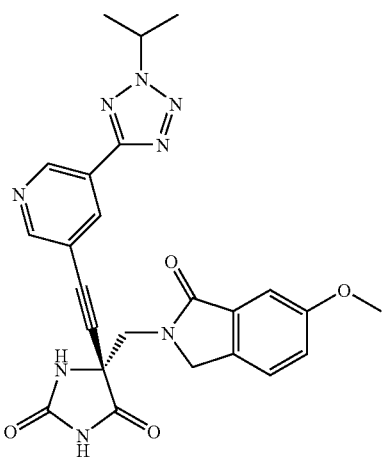 | 486.5 | 487.5 [M + H]+ | A |
| 1220A | 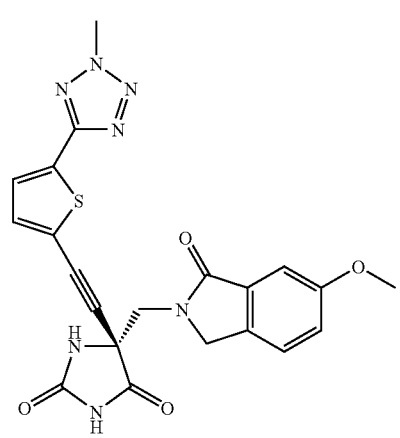 | 463.5 | 464.5 [M + H]+ | A |
| 1220B | 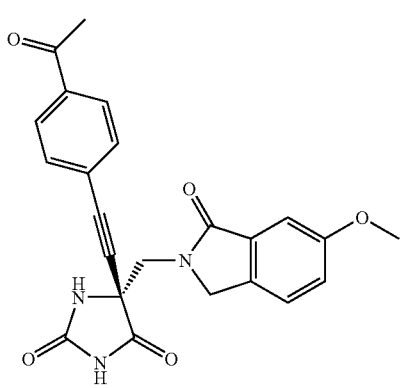 | 417.4 | 418.4 [M + H]+ | A |

TABLE 1001-continued

| Compound ID | Structures | Exact Mass | Mass Obsvd | Ki Rating |
|---|---|---|---|---|
| 1220C | 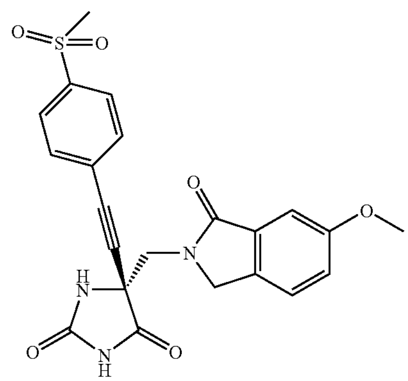 | 453.5 | 454.5 [M + H]+ | D |
| 1220D | 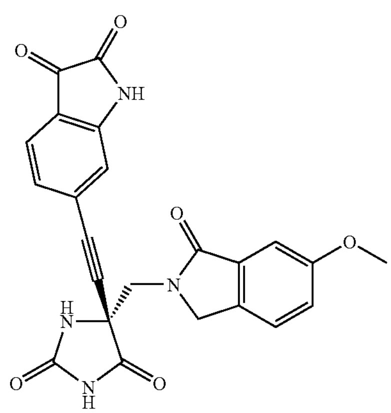 | 444.11 | 445.2 [M + H]+ | A |
| 1220E | 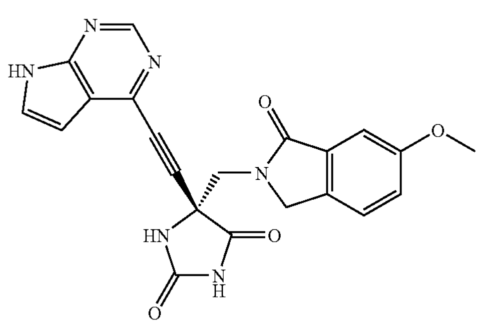 | 416.12 | 417.2 [M + H]+ | A |
| 1221 | 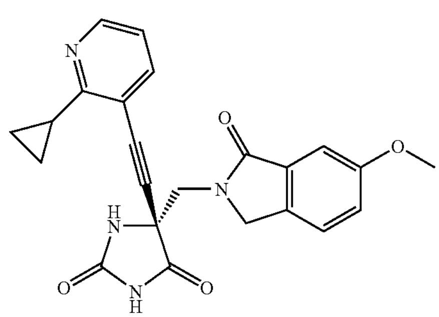 | 416.15 | 417.2 [M + H]+ | A |

TABLE 1001-continued
| Compound ID | Structures | Exact Mass | Mass Obsvd | Ki Rating |
|---|---|---|---|---|
| 1222 | 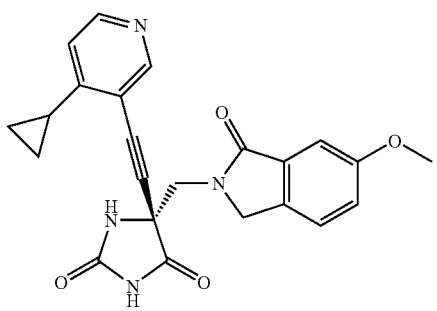 | 416.15 | 417.2 [M + H]+ | A |
| 1250 | 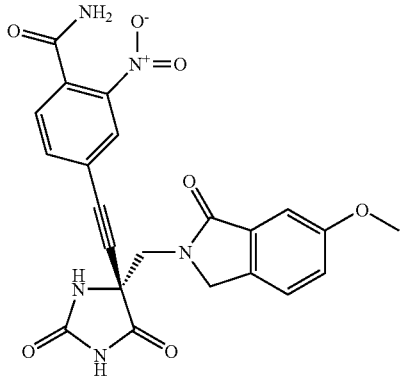 | 463.11 | 464.3 [M + H]+ | A |
| 1251 | 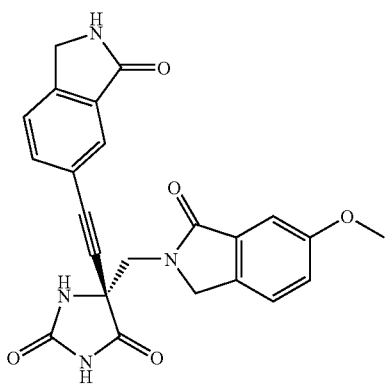 | 430.13 | 431.2 [M + H]+ | A |
| 1252 | 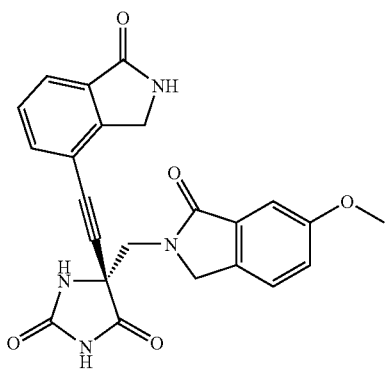 | 430.13 | 431.2 [M + H]+ | A |

TABLE 1001-continued

| Compound ID | Structures | Exact Mass | Mass Obsvd | Ki Rating |
|---|---|---|---|---|
| 1253 | 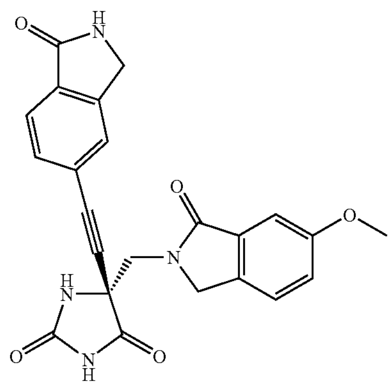 | 430.13 | 431.2 [M + H]+ | A |
| 1254 | 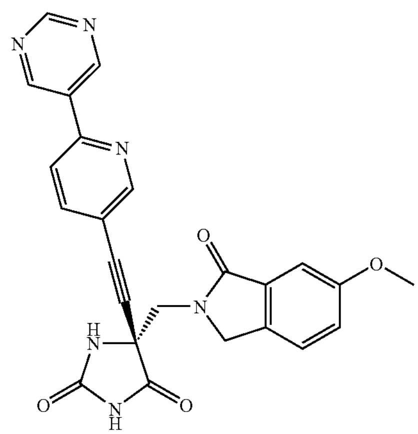 | 454.14 | 455.3 [M + H]+ | A |
| 1255 | 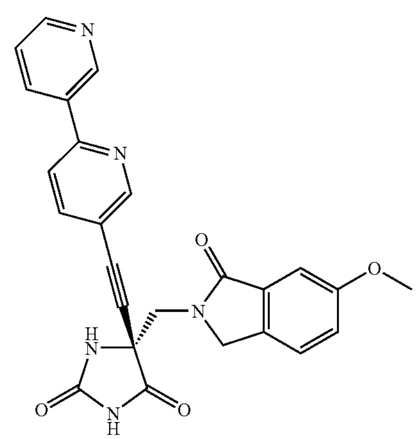 | 453.14 | 454.2 [M + H]+ | 0.75 |

TABLE 1001-continued

| Compound ID | Structures | Exact Mass | Mass Obsvd | Ki Rating |
|---|---|---|---|---|
| 1256 | 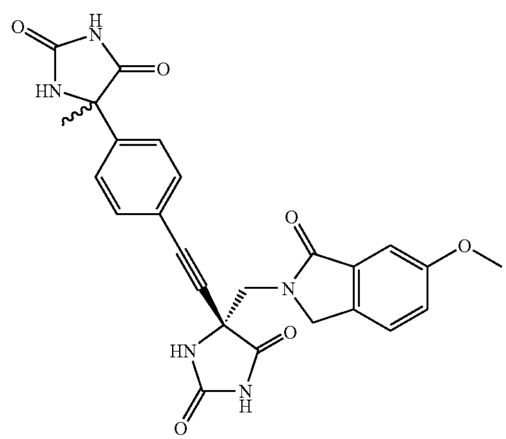 | 487.15 | 488.3 [M + H]⁺ | 0.03 |
| 1256C | 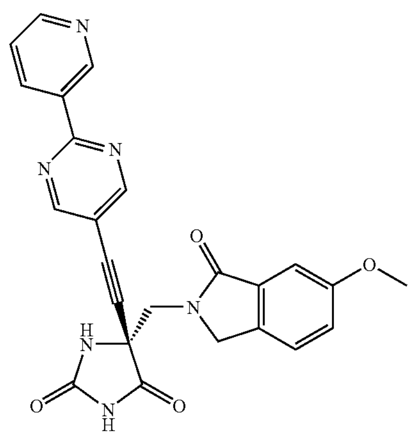 | 454.14 | 455.2 [M + H]⁺ | A |
| 1500 | 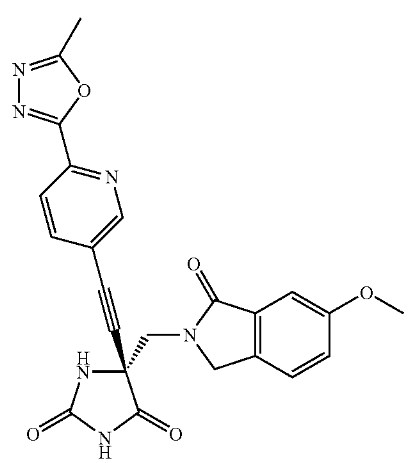 | 458.42 | 459.4 [M + H]⁺ | A |

TABLE 1001-continued

| Compound ID | Structures | Exact Mass | Mass Obsvd | Ki Rating |
|---|---|---|---|---|
| 1501 | 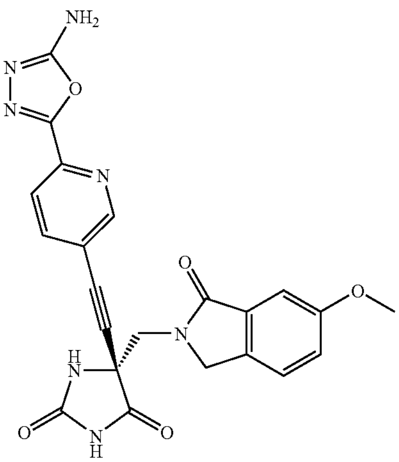 | 459.41 | 460.5 [M + H]+ | A |
| 1502 | 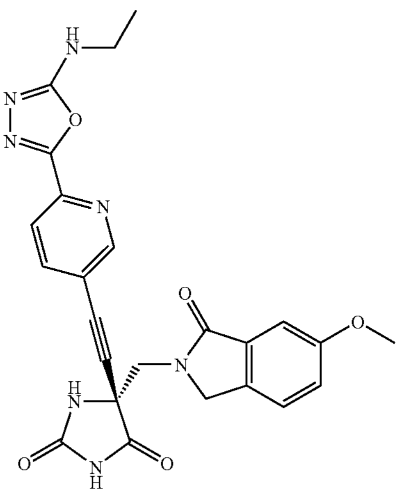 | 487.46 | 488.5 [M + H]+ | A |
| 1503 | 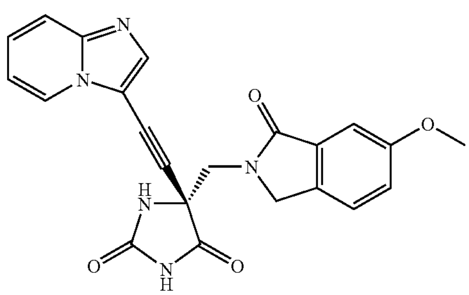 | 415.40 | 416.5 [M + H]+ | A |
| 1504 | 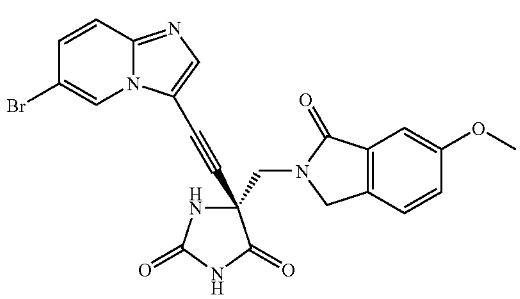 | 494.29 | 495.4 [M + H]+ | A |

TABLE 1001-continued

| Compound ID | Structures | Exact Mass | Mass Obsvd | Ki Rating |
|---|---|---|---|---|
| 1505 | 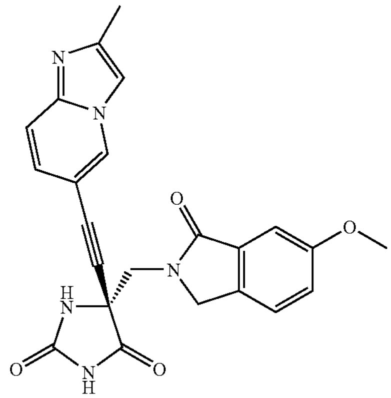 | 429.42 | 430.5 [M + H]+ | A |
| 1506 | 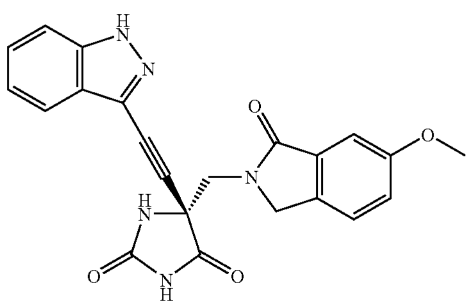 | 415.40 | 416.4 [M + H]+ | A |
| 1507 | 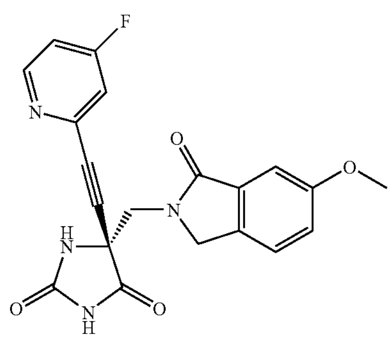 | 394.35 | 395.4 [M + H]+ | A |
| 1508 | 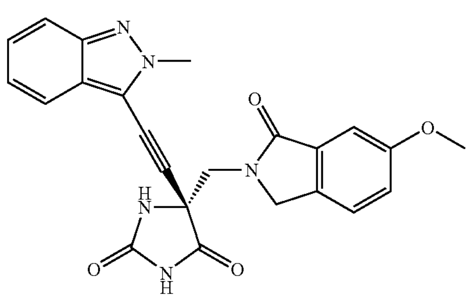 | 429.42 | 430.4 [M + H]+ | A |

TABLE 1001-continued

| Compound ID | Structures | Exact Mass | Mass Obsvd | Ki Rating |
|---|---|---|---|---|
| 1509 | 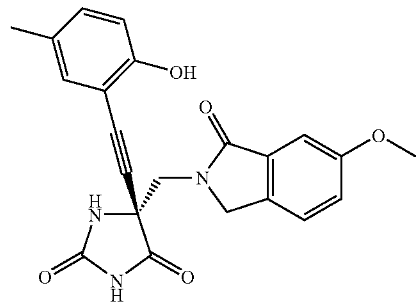 | 405.40 | 406.4 [M + H]+ | A |
| 1510 | 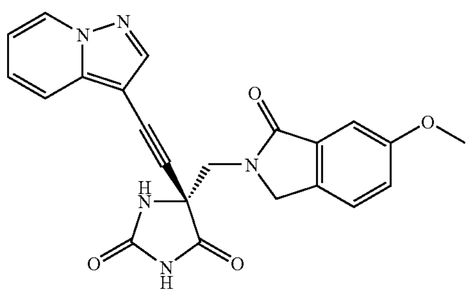 | 415.40 | 416.5 [M + H]+ | A |
| 1511 | 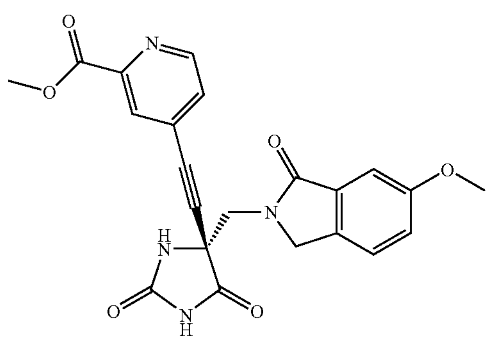 | 434.40 | 435.5 [M + H]+ | A |
| 1512 | 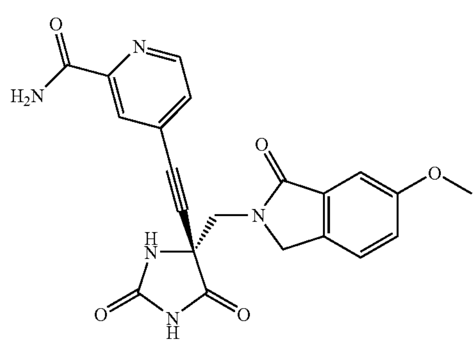 | 419.39 | 420.4 [M + H]+ | A |

TABLE 1001-continued

| Compound ID | Structures | Exact Mass | Mass Obsvd | Ki Rating |
|---|---|---|---|---|
| 1513 | 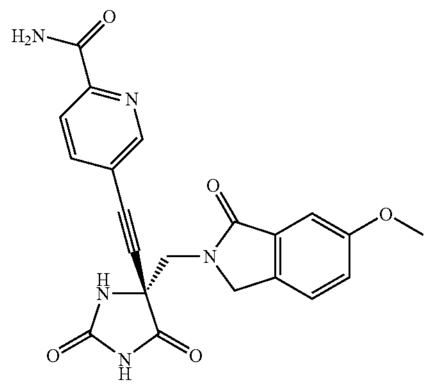 | 419.39 | 420.4 [M + H]+ | A |
| 1514 | 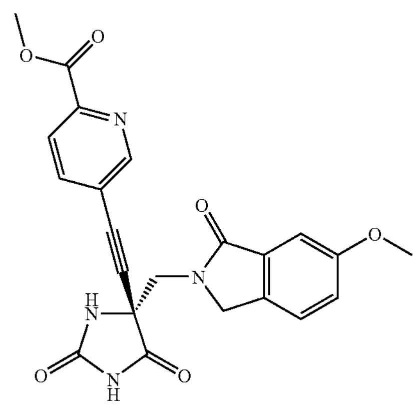 | 434.40 | 435.5 [M + H]+ | A |
| 1515 | 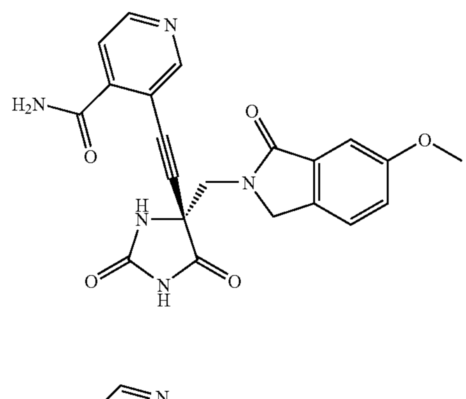 | 419.39 | 420.4 [M + H]+ | A |
| 1516 | 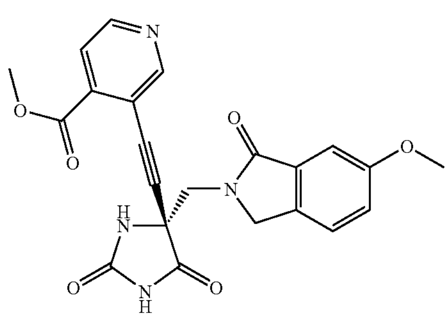 | 434.40 | 435.5 [M + H]+ | A |

TABLE 1001-continued

| Compound ID | Structures | Exact Mass | Mass Obsvd | Ki Rating |
|---|---|---|---|---|
| 1517 | 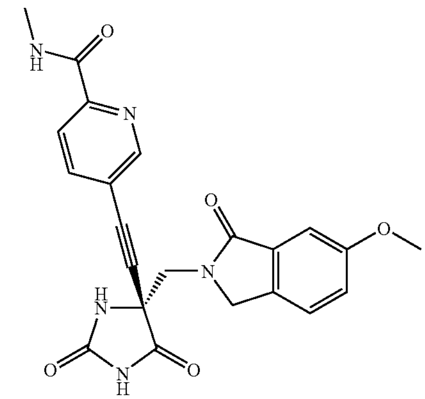 | 433.41 | 434.4 [M + H]+ | A |
| 1518 | 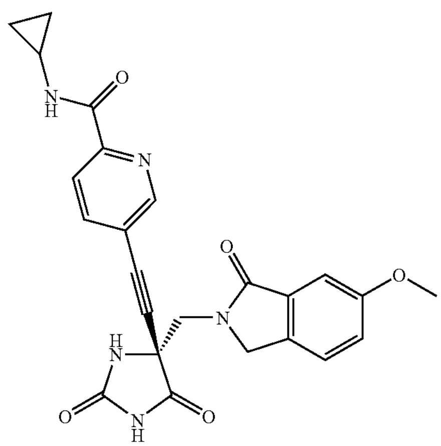 | 459.45 | 460.5 [M + H]+ | A |
| 1519 | 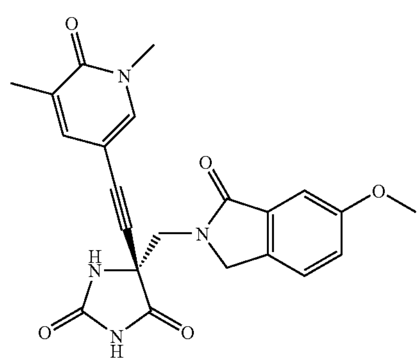 | 420.41 | 421.4 [M + H]+ | A |
| 1520 | 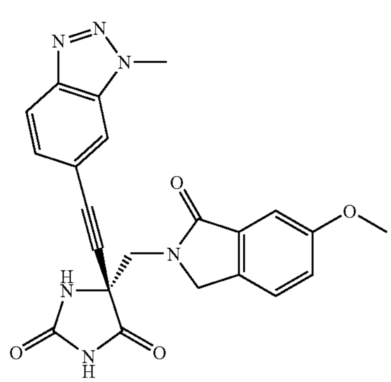 | 430.41 | 431.4 [M + H]+ | A |

TABLE 1001-continued

| Compound ID | Structures | Exact Mass | Mass Obsvd | Ki Rating |
|---|---|---|---|---|
| 1521 | 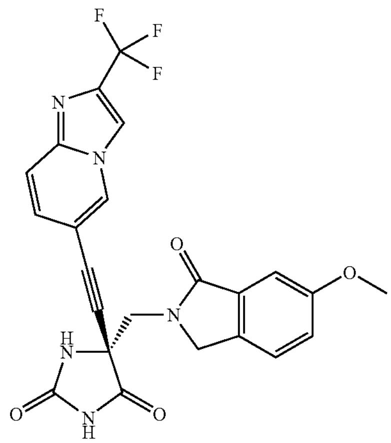 | 483.4 | 484.4 [M + H]+ | A |
| 1522 | 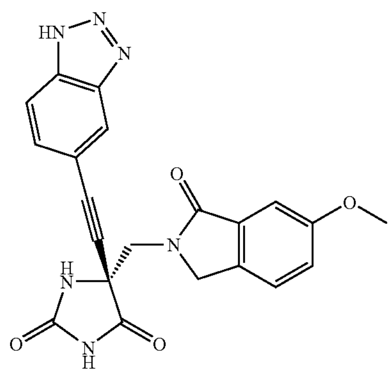 | 416.38 | 417.5 [M + H]+ | A |
| 1523 | 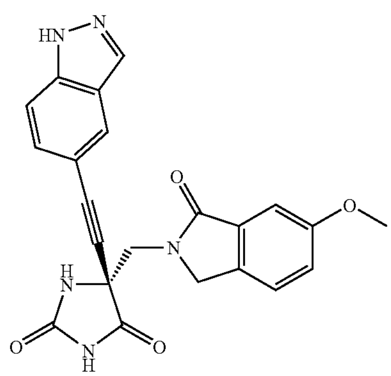 | 415.40 | 416.4 [M + H]+ | A |
| 1524 | 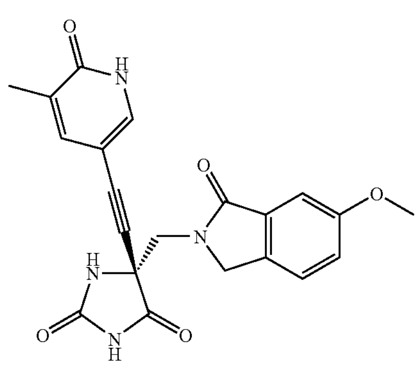 | 406.39 | 407.4 [M + H]+ | A |

TABLE 1001-continued

| Compound ID | Structures | Exact Mass | Mass Obsvd | Ki Rating |
|---|---|---|---|---|
| 1533 | 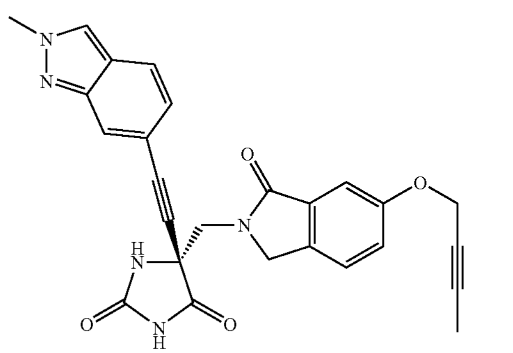 | 467.47 | 468.5 [M + H]+ | A |
| 1534 | 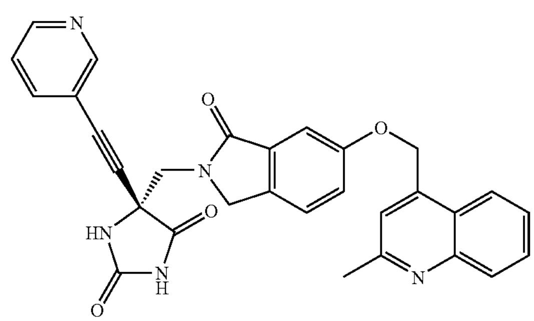 | 517.53 | 518.5 [M + H]+ | A |
| 1535 | 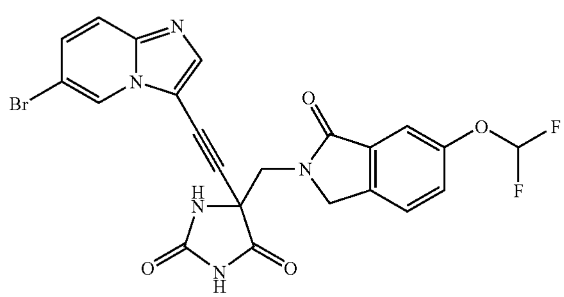 | 530.28 | 531.4 [M + H]+ | B |
| 1550 | 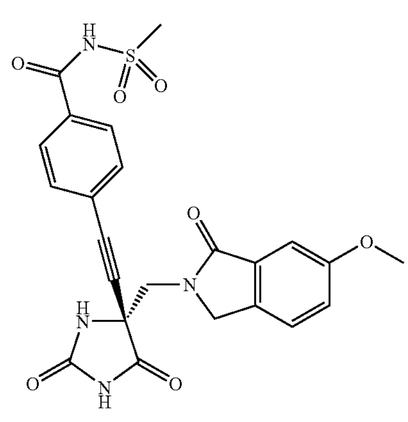 | 496.11 | 497.3 [M + H]+ | B |

TABLE 1001-continued

| Compound ID | Structures | Exact Mass | Mass Obsvd | Ki Rating |
|---|---|---|---|---|
| 1551 | 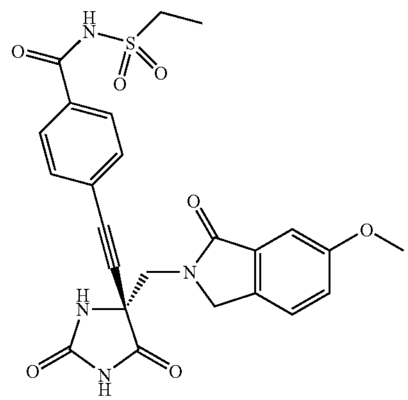 | 510.12 | 511.3 [M + H]⁺ | A |
| 1552 | 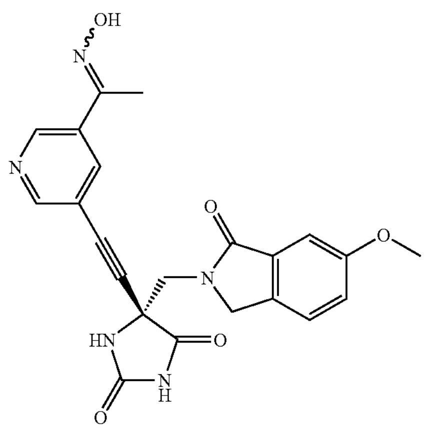 | 433.14 | 434.2 [M + H]⁺ | A |
| 1553 | 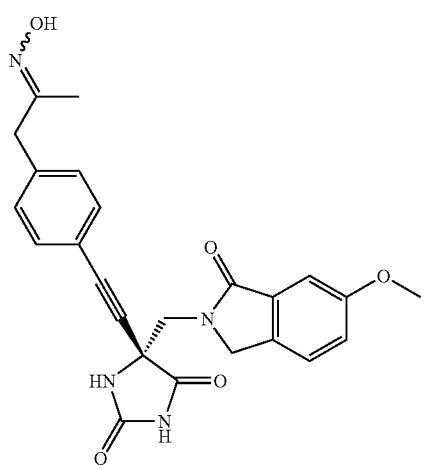 | 446.16 | 447.2 [M + H]⁺ | A |

TABLE 1001-continued

| Compound ID | Structures | Exact Mass | Mass Obsvd | Ki Rating |
|---|---|---|---|---|
| 1554 | 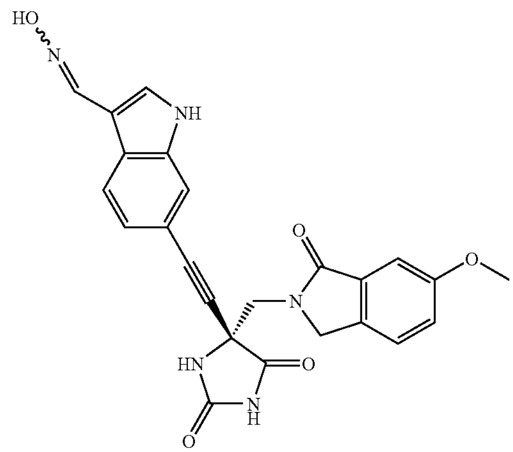 | 457.14 | 458.3 [M + H]⁺ | A |
| 1555 | 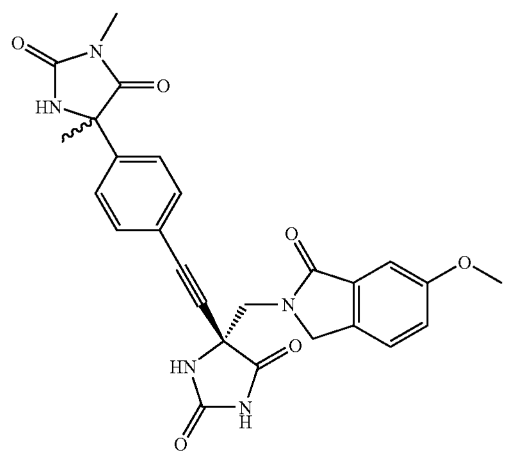 | 501.16 | 502.3 [M + H]⁺ | A |
| 1556 | 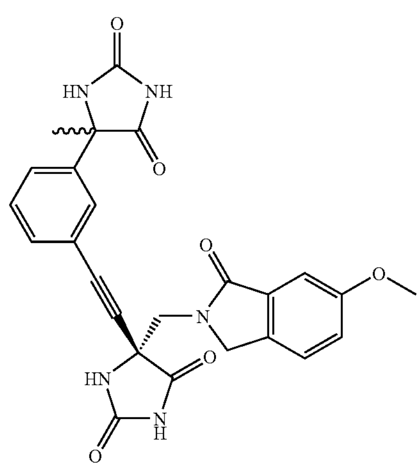 | 487.15 | 488.3 [M + H]⁺ | A |

TABLE 1001-continued

| Compound ID | Structures | Exact Mass | Mass Obsvd | Ki Rating |
|---|---|---|---|---|
| 1557 | 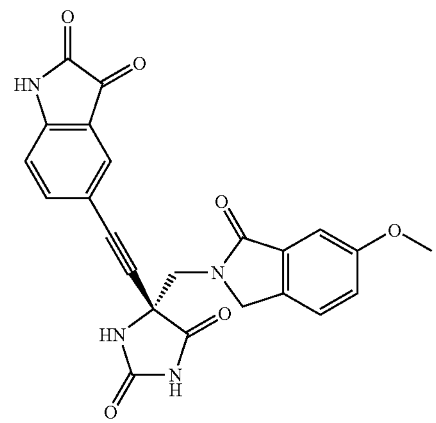 | 444.11 | 445.2 [M + H]⁺ | A |
| 1558 | 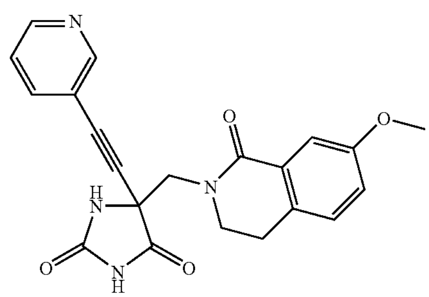 | 390.13 | 391.2 [M + H]⁺ | B |
| 1559 | 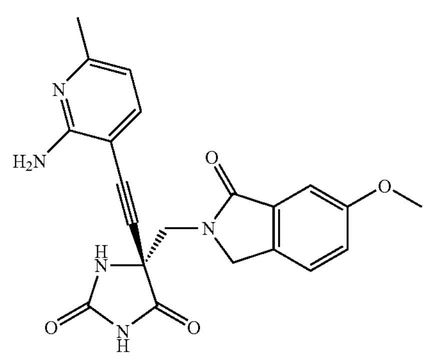 | 405.14 | 406.2 [M + H]⁺ | A |
| 1560 | 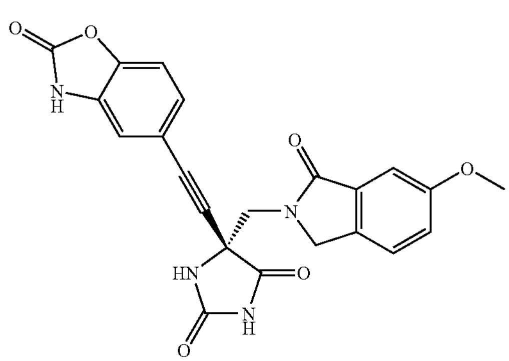 | 432.11 | 433.2 [M + H]⁺ | A |

TABLE 1001-continued

| Compound ID | Structures | Exact Mass | Mass Obsvd | Ki Rating |
|---|---|---|---|---|
| 1561 | 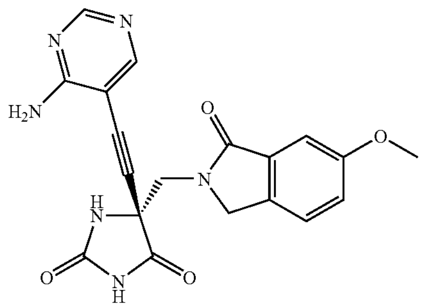 | 392.12 | 393.2 [M + H]+ | A |
| 1562 | 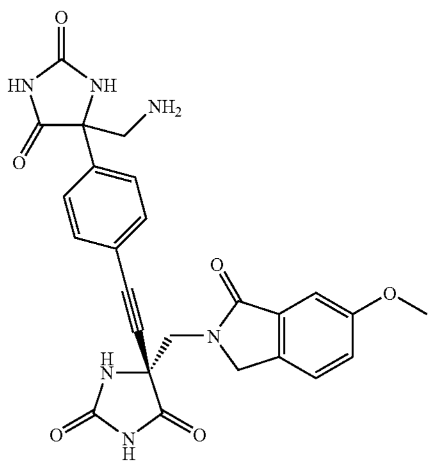 | 502.16 | 503.3 [M + H]+ | A |
| 1563 | 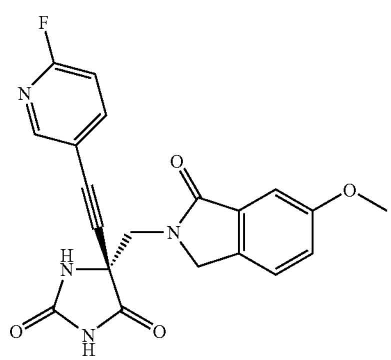 | 394.35 | 395.2 [M + H]+ | A |
| 1564 | 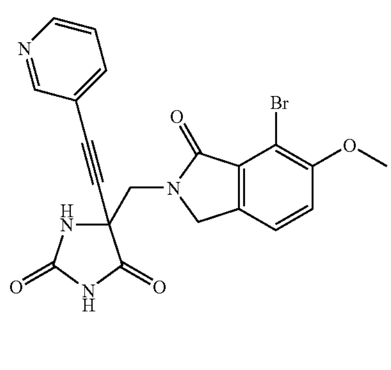 | 455.26 | 455.3 [M + H]+ | B |

TABLE 1001-continued

| Compound ID | Structures | Exact Mass | Mass Obsvd | Ki Rating |
|---|---|---|---|---|
| 1565 | 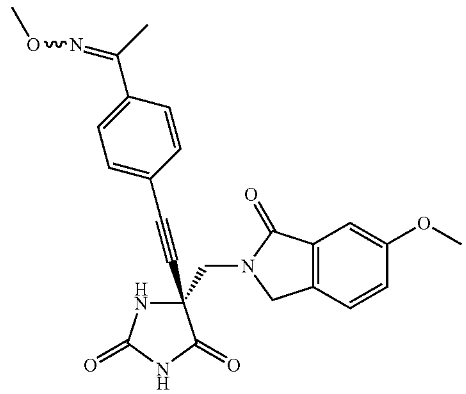 | 446.45 | 447.2 [M + H]+ | A |
| 1566 | 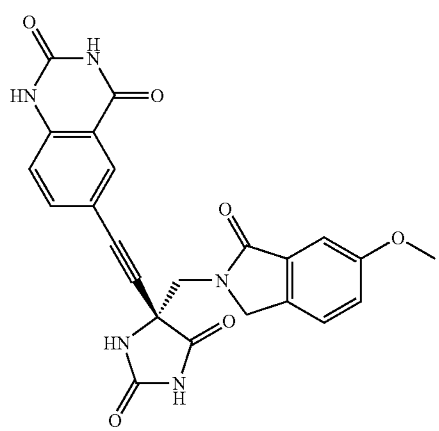 | 459.12 | 460.3 [M + H]+ | A |
| 1567 | 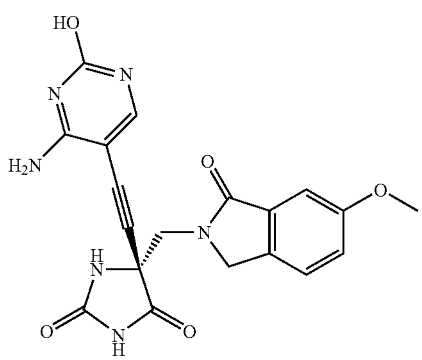 | 408.12 | 409.2 [M + H]+ | A |
| 1568 | 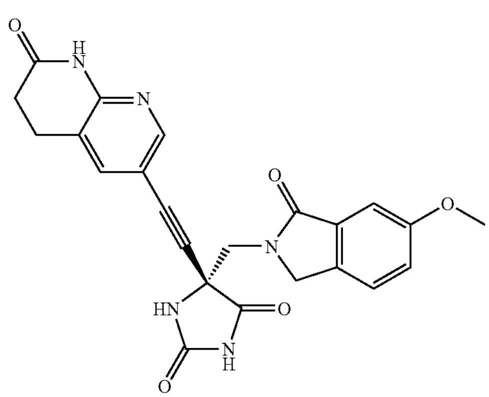 | 445.14 | 446.2 [M + H]+ | A |

TABLE 1001-continued

| Compound ID | Structures | Exact Mass | Mass Obsvd | Ki Rating |
|---|---|---|---|---|
| 1569 | 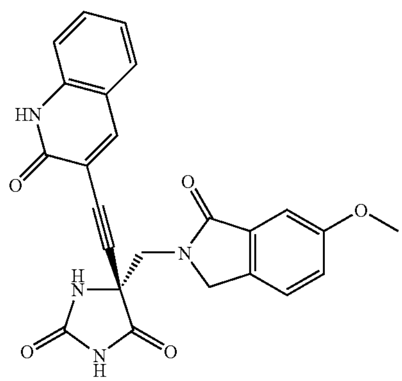 | 442.13 | 443.2 [M + H]⁺ | A |
| 1570 | 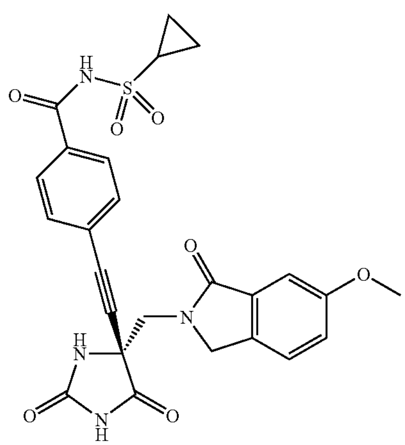 | 522.12 | 523.3 [M + H]⁺ | A |
| 1571 | 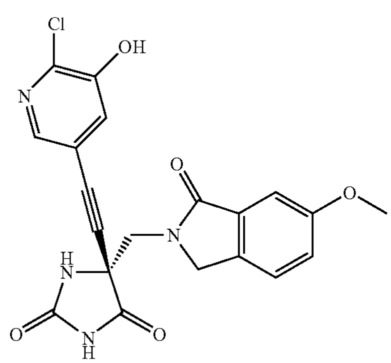 | 426.80 | 427.2 [M + H]⁺ | A |

TABLE 1001-continued

| Compound ID | Structures | Exact Mass | Mass Obsvd | Ki Rating |
|---|---|---|---|---|
| 1572 | 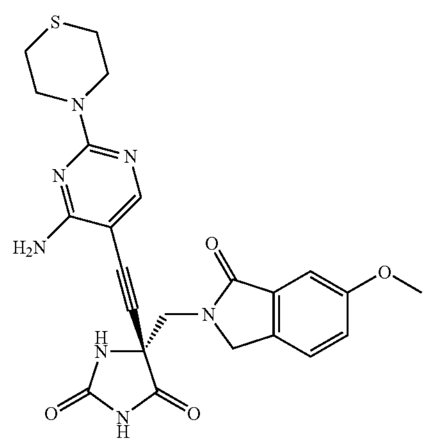 | 493.15 | 494.3 [M + H]+ | A |
| 1573 | 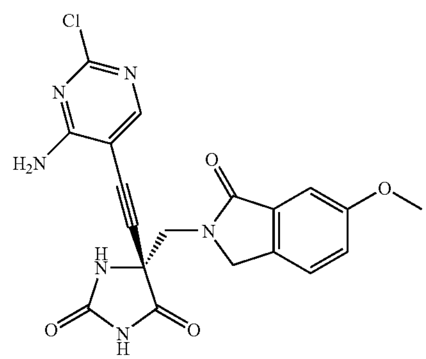 | 426.08 | 427.2 [M + H]+ | A |
| 1574 | 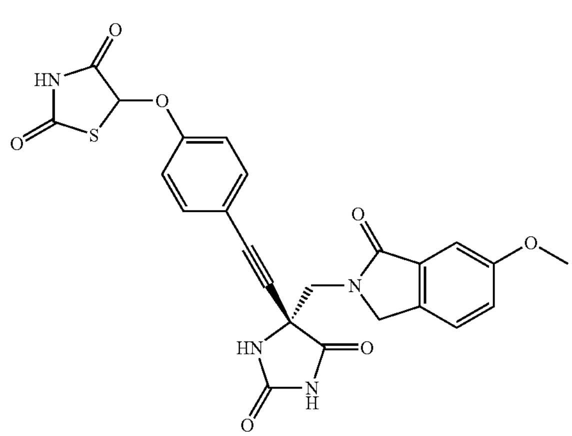 | 506.09 | 507.3 [M + H]+ | A |

TABLE 1001-continued

| Compound ID | Structures | Exact Mass | Mass Obsvd | Ki Rating |
|---|---|---|---|---|
| 1575 | 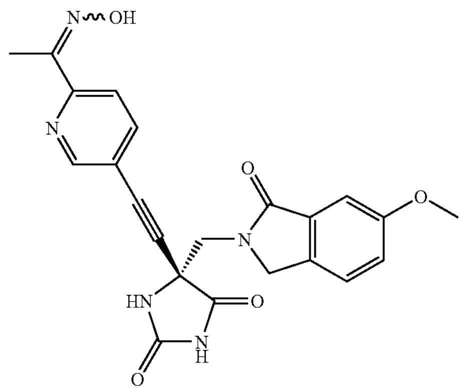 | 433.14 | 434.2 [M + H]⁺ | A |
| 1576 | 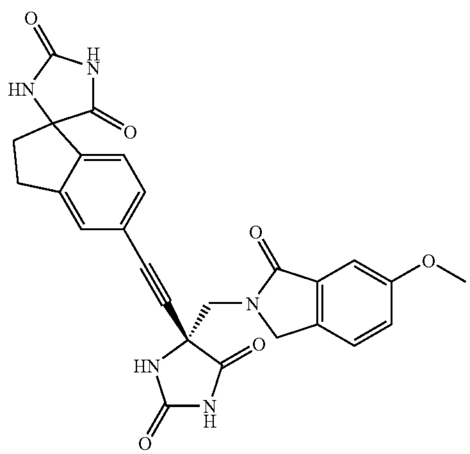 | 499.15 | 500.3 [M + H]⁺ | A |
| 1577 | 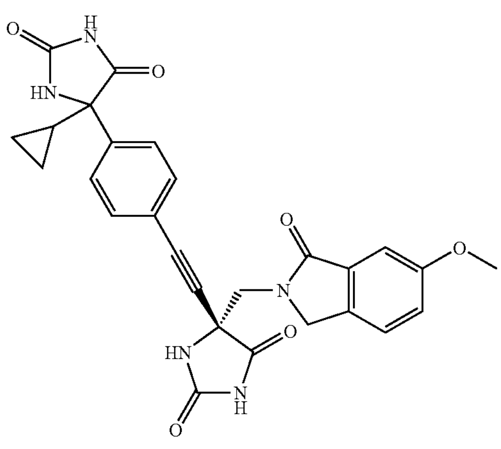 | 513.16 | 514.3 [M + H]⁺ | A |

TABLE 1001-continued

| Compound ID | Structures | Exact Mass | Mass Obsvd | Ki Rating |
|---|---|---|---|---|
| 1578 | 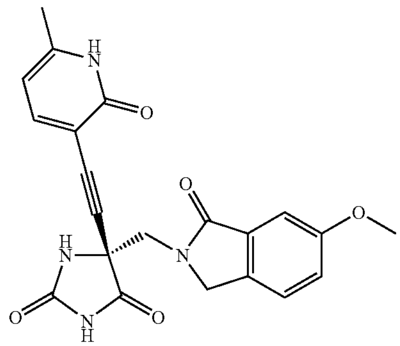 | 406.13 | 407.1 [M + H]$^+$ | A |
| 1579 | 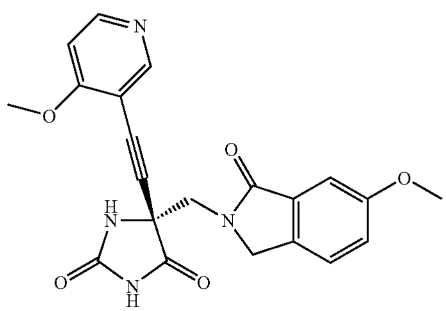 | 406.13 | 407.0 [M + H]$^+$ | A |
| 1580 | 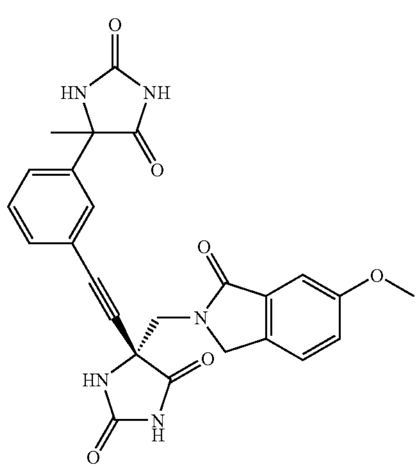 | 487.15 | 488.3 [M + H]$^+$ | A |

In another embodiment, the compounds of Formula (I) are selected from the group consisting of;

| Compound ID | Structures |
|---|---|
| 400B | 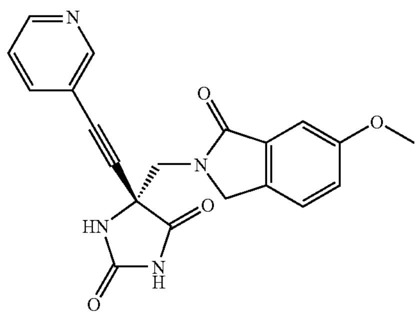 |
| 417C | 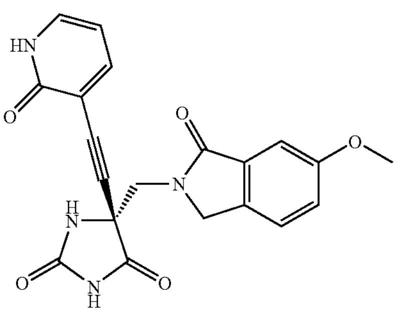 |
| 424 | 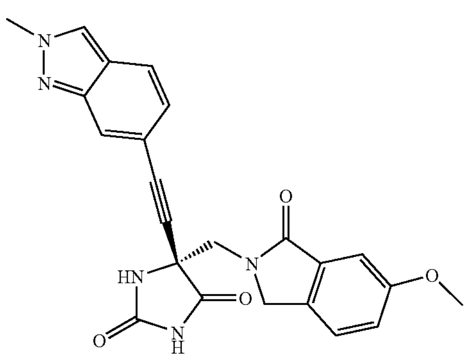 |
| 447 | 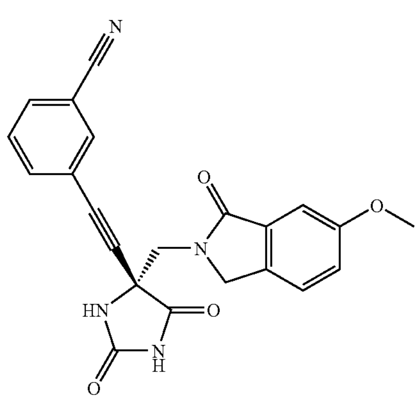 |
| 494 | |
| 507 | |
| 555 | |
| 554 | |

-continued
| Compound ID | Structures |
|---|---|
| 1003 | 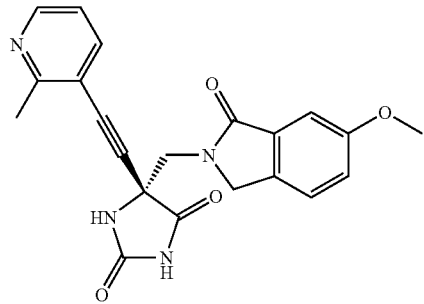 |
| 1256 | 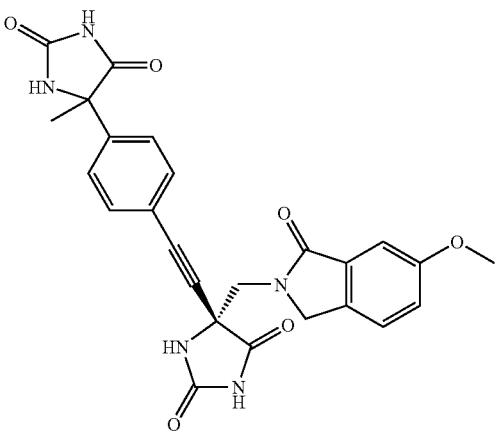 |
| 1009 | 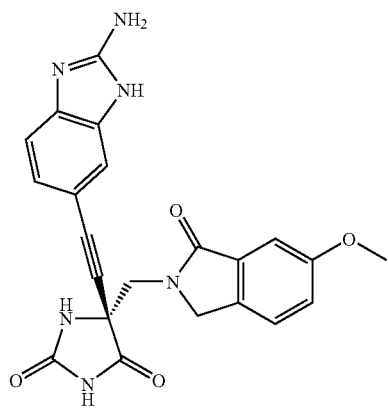 |
| 1012 | 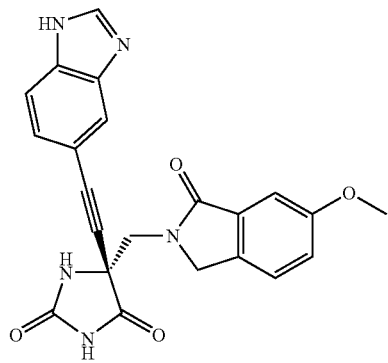 |
-continued
| Compound ID | Structures |
|---|---|
| 1253 | 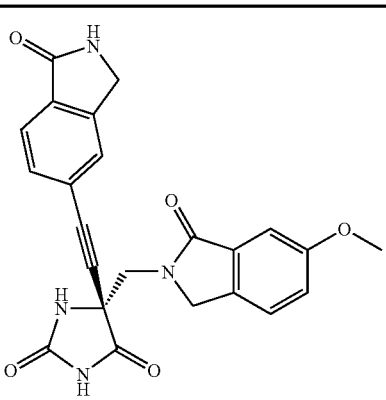 |
| 1015 | 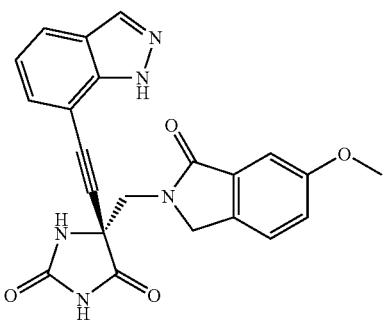 |
| 1091 | 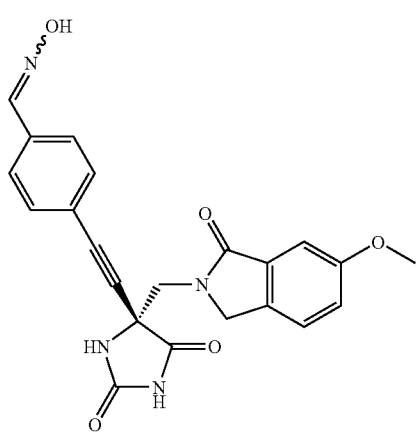 |
| 1063 | 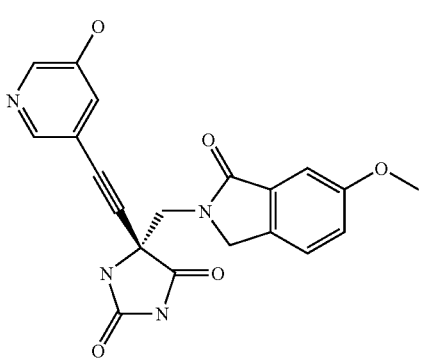 |

-continued
| Compound ID | Structures |
|---|---|
| 1070 | 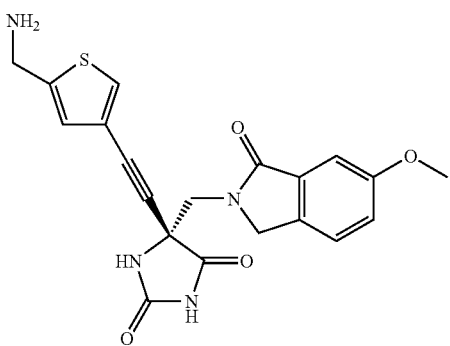 |
| 1090 | 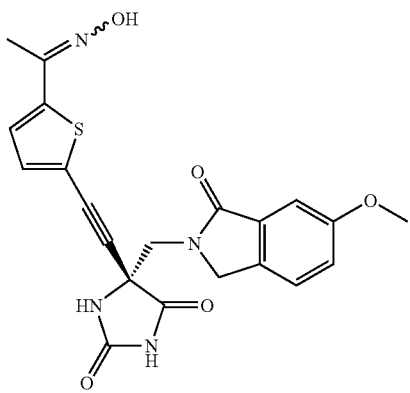 |
| 1092 | 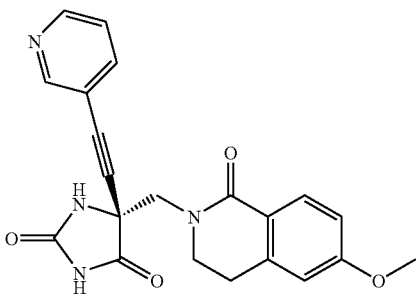 |
| 1098 | 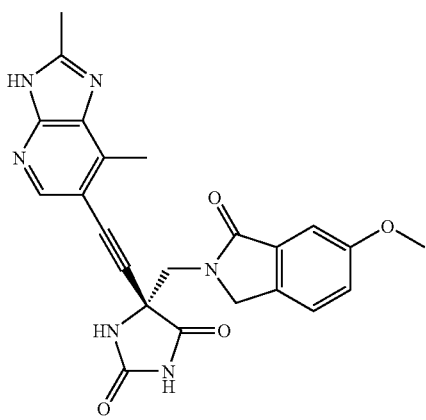 |
-continued
| Compound ID | Structures |
|---|---|
| 1069 | 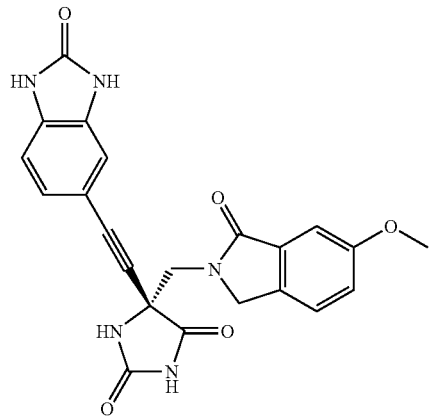 |
| 1099 | 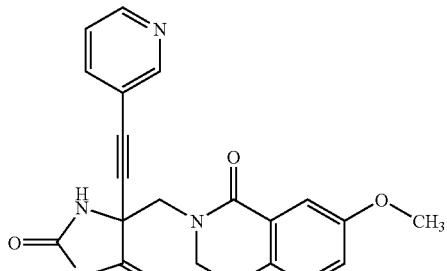 |
| 1505 | 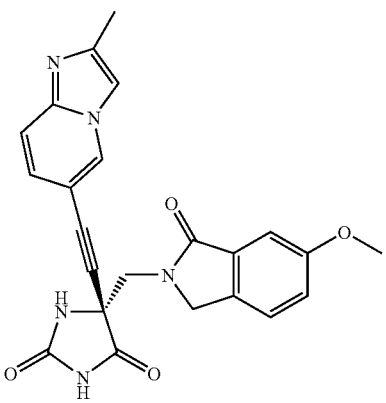 |
| 1513 | 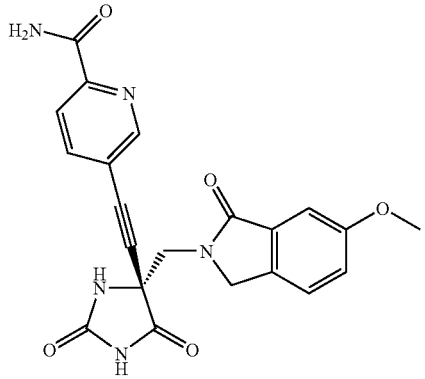 |

-continued
| Compound ID | Structures |
|---|---|
| 1520 | 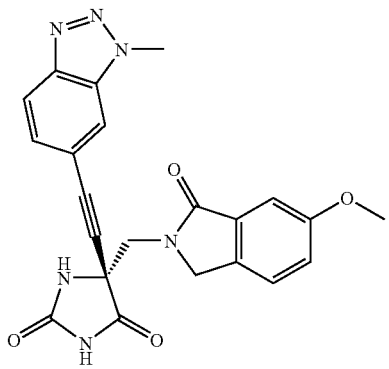 |
| 1519 | 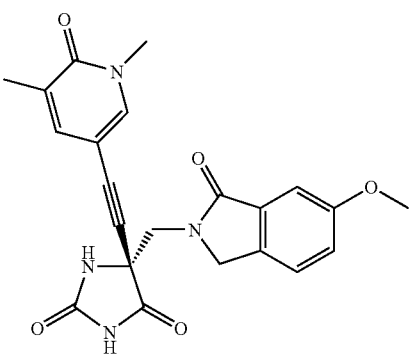 |
| 1523 | 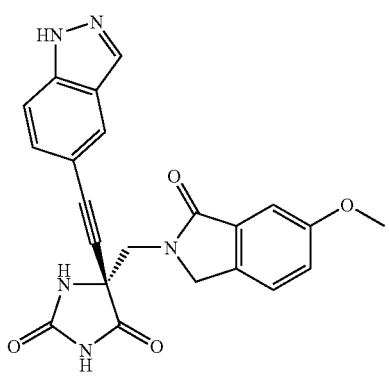 |
-continued
| Compound ID | Structures |
|---|---|
| 1502 | 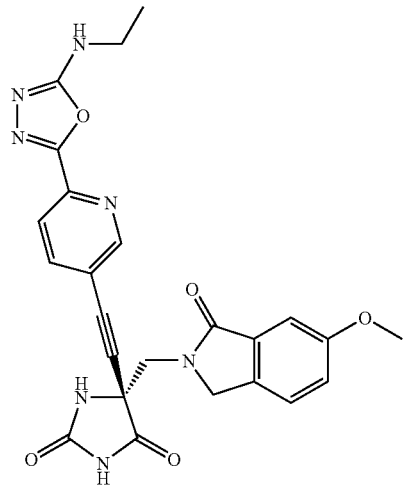 |
| 972 | 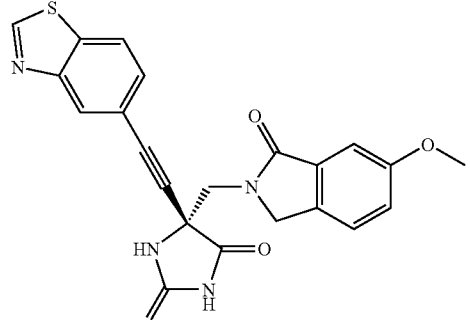 |
| 930 | 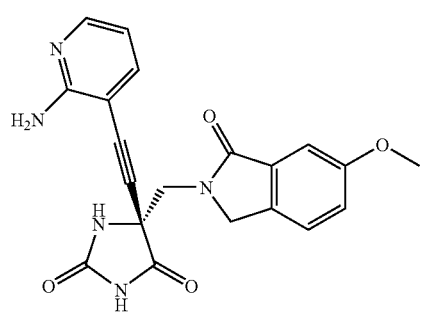 |
| 943 | 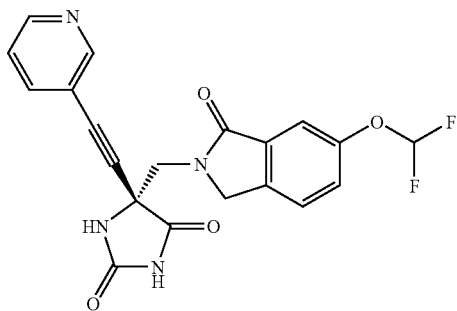 |

-continued
| Compound ID | Structures |
|---|---|
| 960 | 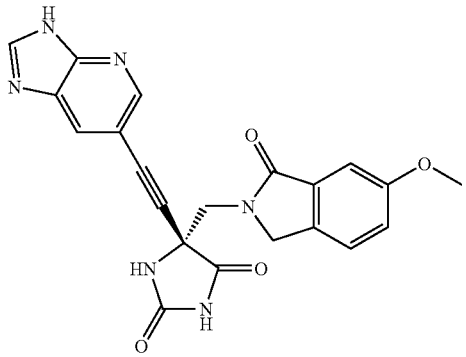 |
| 1220B | 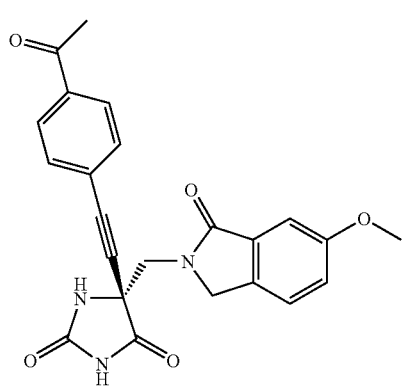 |
| 1206 | 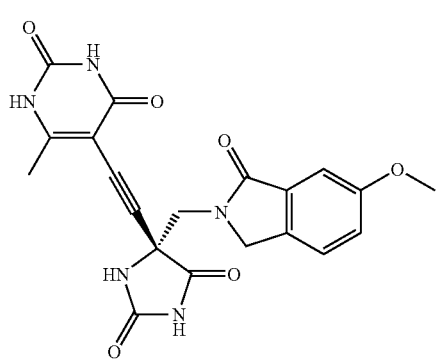 |
| 1220 | 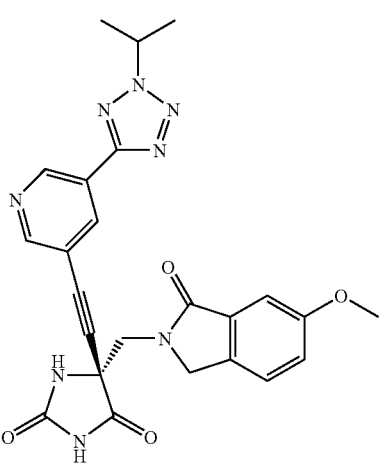 |
-continued
| Compound ID | Structures |
|---|---|
| 1201 | 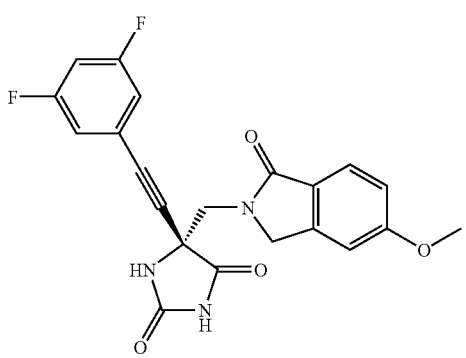 |
| 1200 | 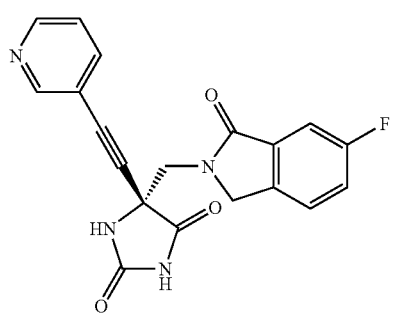 |
| 1155 | 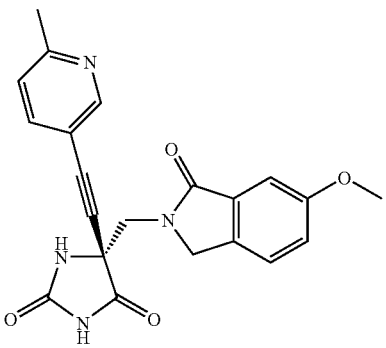 |
| 1152 | 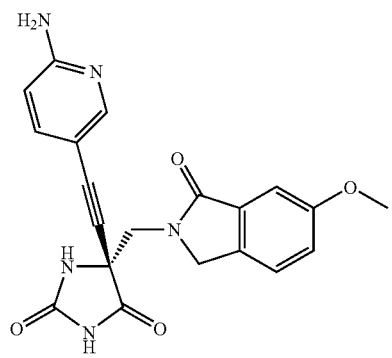 |

-continued
| Compound ID | Structures |
|---|---|
| 1129 | 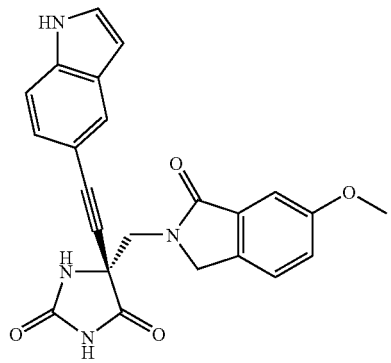 |
| 1133 | 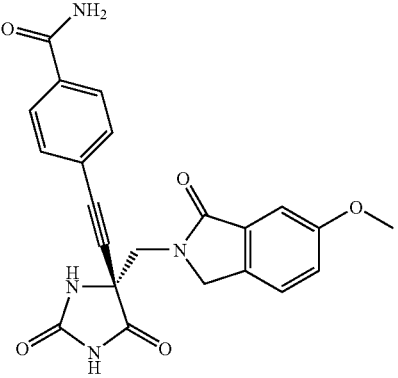 |
| 1134 | 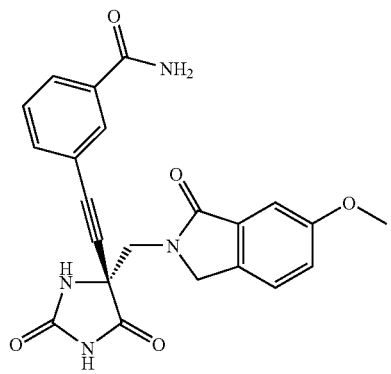 |
| 1146 | 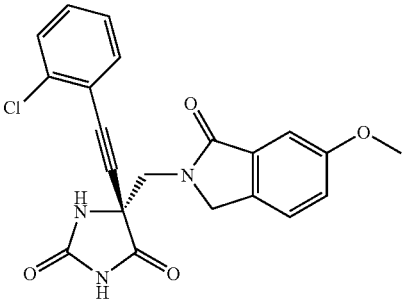 |
-continued
| Compound ID | Structures |
|---|---|
| 1136 | 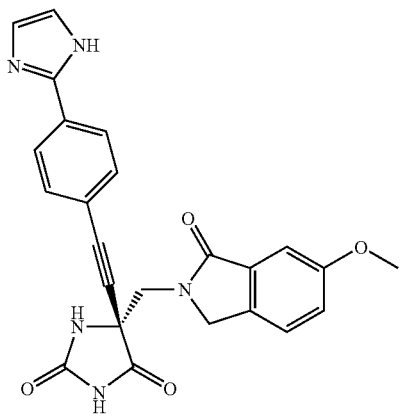 |
| 1132 | 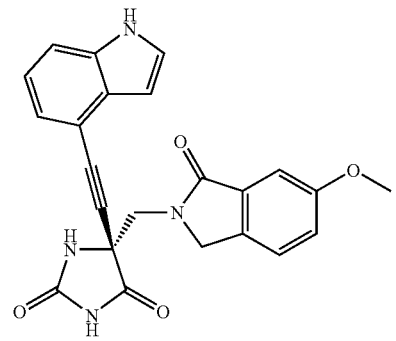 |
| 490 | 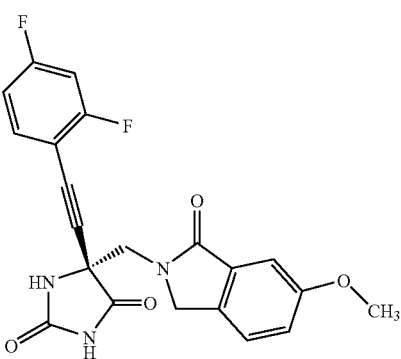 |
| 442 | 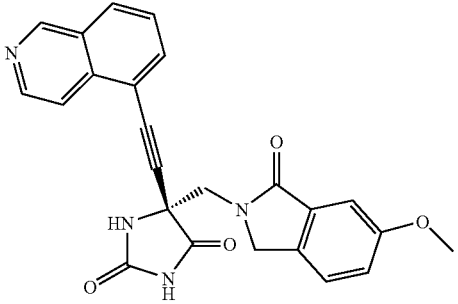 |

-continued
| Compound ID | Structures |
|---|---|
| 1562 | 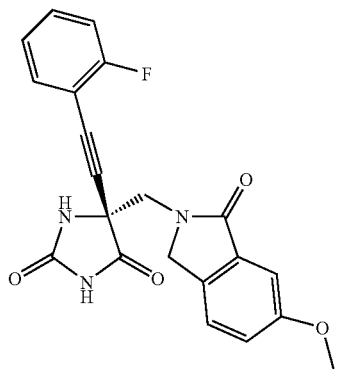 |
| 1552 | 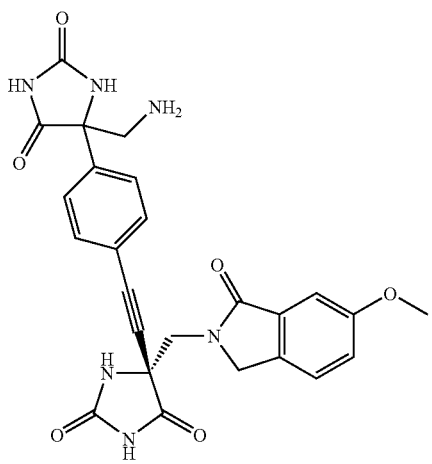 |
| | 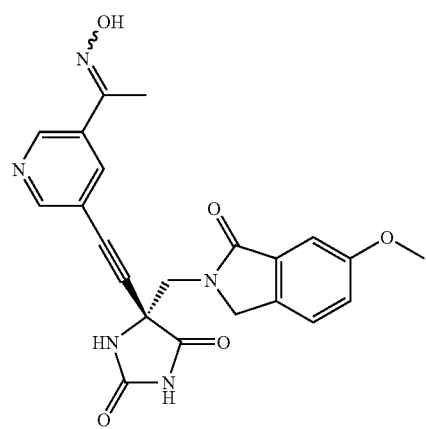 |
-continued
| Compound ID | Structures |
|---|---|
| 1576 | 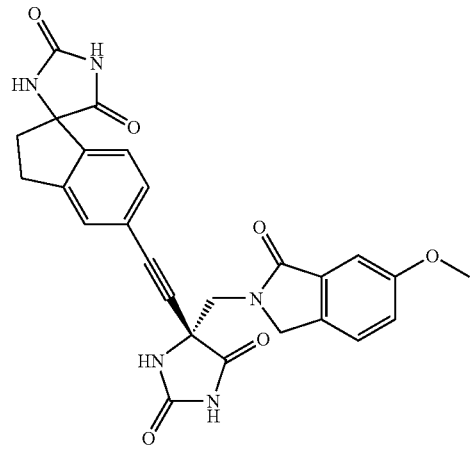 |
or a pharmaceutically acceptable salt, solvate, or ester thereof.
In another embodiment, the compounds of Formula (I) are selected from the group consisting of:
| Compound ID | Structures |
|---|---|
| 400B | 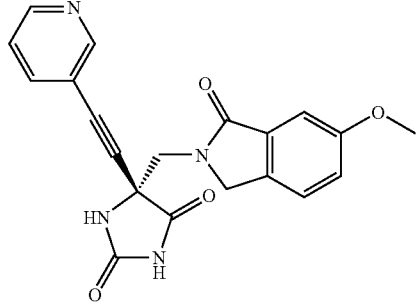 |
| 516 | 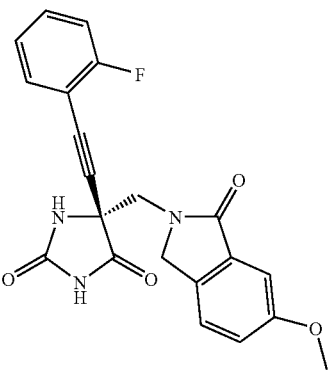 |

-continued
| Compound ID | Structures |
|---|---|
| 490 | 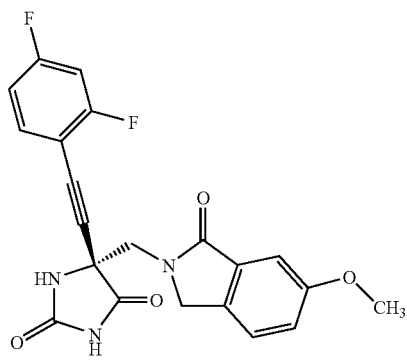 |
| 1003 | 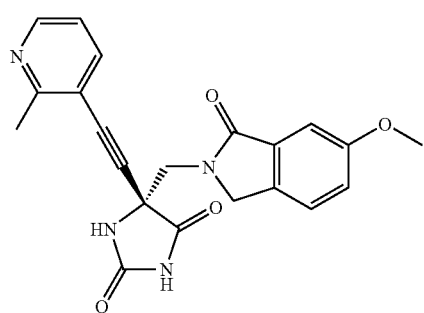 |
| 1132 | 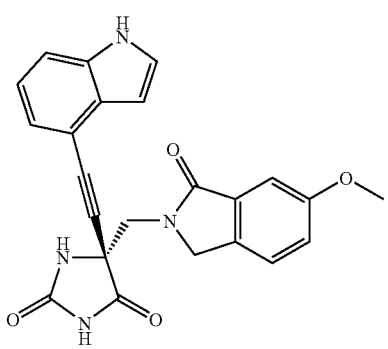 |
| 442 | 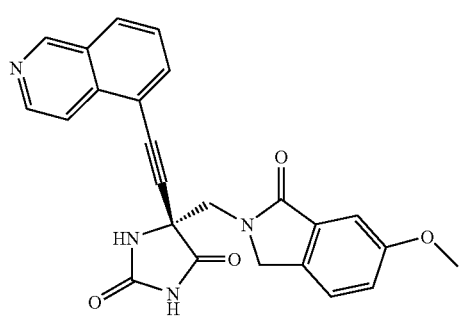 |
-continued
| Compound ID | Structures |
|---|---|
| 1155 | 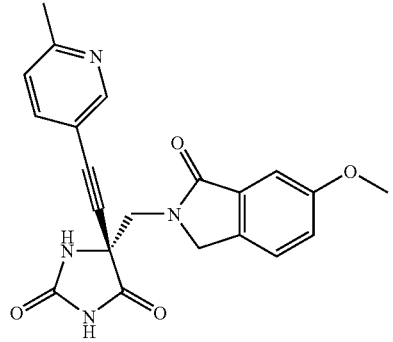 |
| 930 | 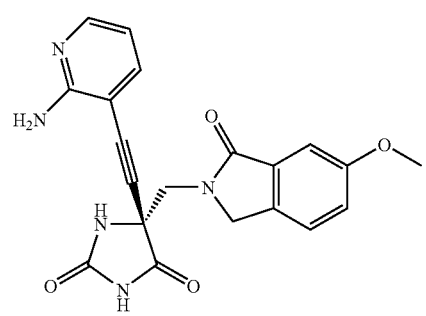 |
| 1256 | 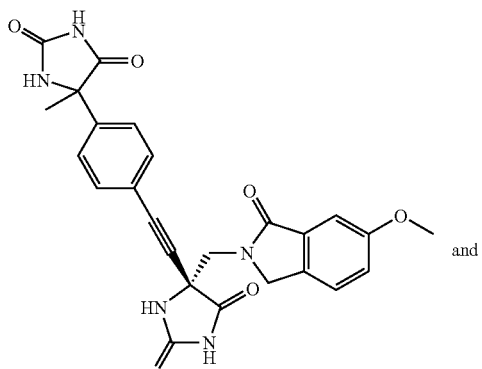 |
| 1576 | 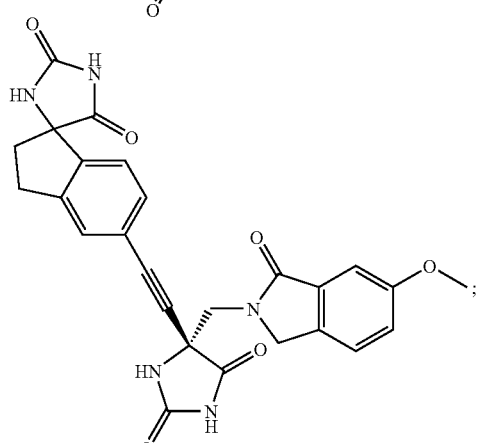 and |
or a pharmaceutically acceptable salt, solvate, or ester thereof.

Specific TACE inhibitory activity (Ki values) of some representative compounds of the present invention are set forth below.

TABLE 1002

| Compound ID | Structures | Exact Mass | Mass Obsvd | Ki (nM) |
|---|---|---|---|---|
| 400B | 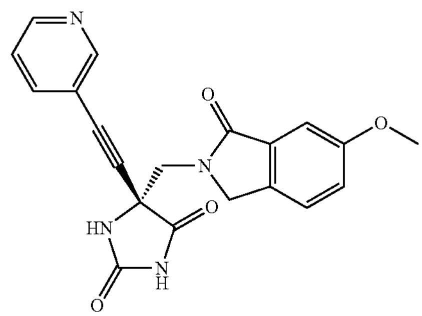 | 376.37 | 377.0 [M + H]+ | 0.44 |
| 516 | 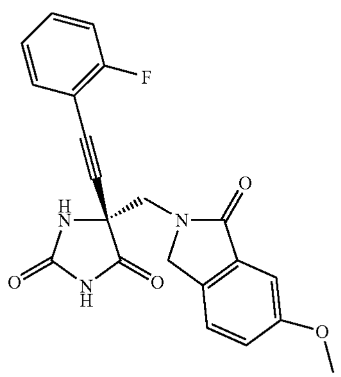 | 393.11 | 394.1 [M + H]+ | 0.13 |
| 490 | 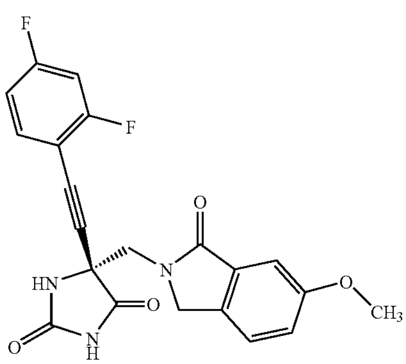 | 411.36 | 412.1 [M + H]+ | 0.23 |
| 1003 | 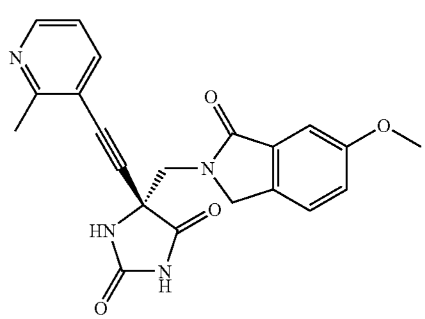 | 390.13 | 391.2 [M + H]+ | 0.11 |

TABLE 1002-continued

| Compound ID | Structures | Exact Mass | Mass Obsvd | Ki (nM) |
|---|---|---|---|---|
| 1132 | 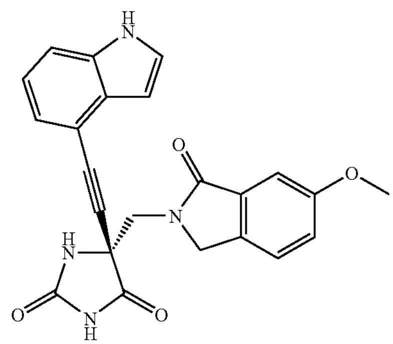 | 414.1 | 415.2 [M + H]+ | 1.8 |
| 442 | 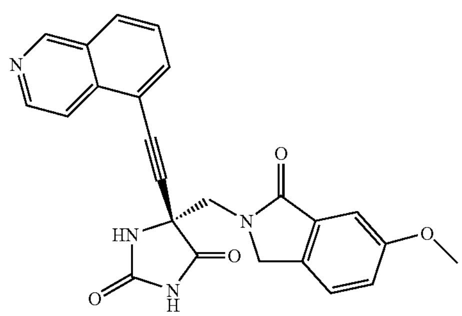 | 426.13 | 427.1 [M + H]+ | 0.11 |
| 1155 | 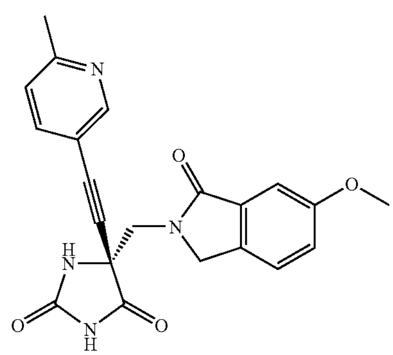 | 390.1 | 391.2 [M + H]+ | 0.41 |
| 930 | 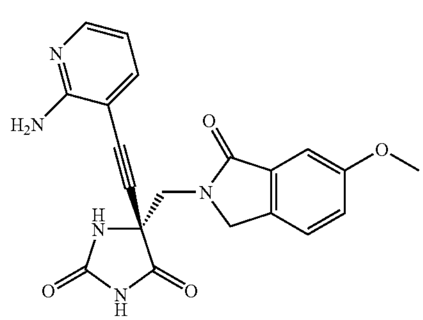 | 392.14 | 392.2 [M + H]+ | 0.56 |

TABLE 1002-continued

| Compound ID | Structures | Exact Mass | Mass Obsvd | Ki (nM) |
| --- | --- | --- | --- | --- |
| 1256 | 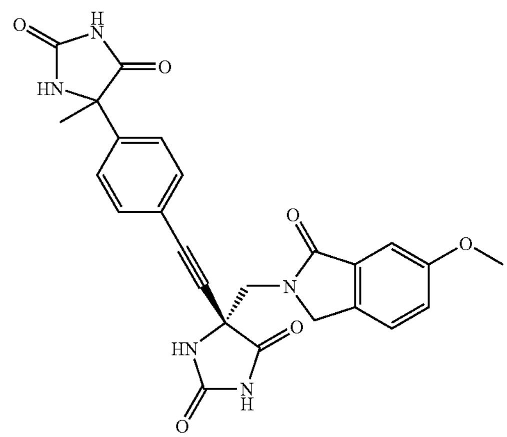 | 487.15 | 488.3 [M + H]+ | 0.03 |
| 1576 | 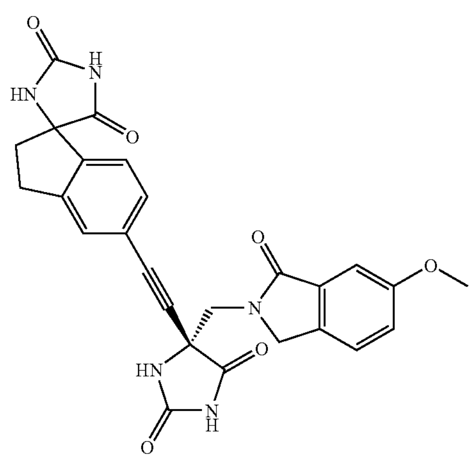 | 499.15 | 500.3 [M + H]+ | 0.27 |
| 1152 | 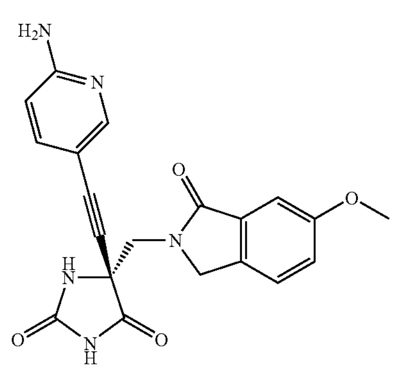 | 391.1 | 392.2 [M + H]+ | 0.03 |

… TABLE 1002-continued
| Compound ID | Structures | Exact Mass | Mass Obsvd | Ki (nM) |
|---|---|---|---|---|
| 1129 | 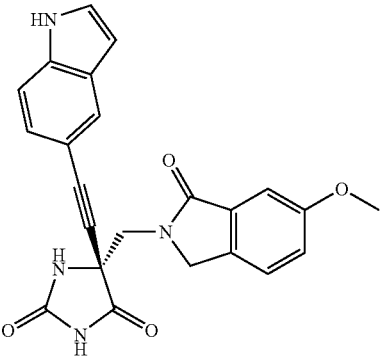 | 414.1 | 415.2 [M + H]+ | 0.17 |
| 1502 | 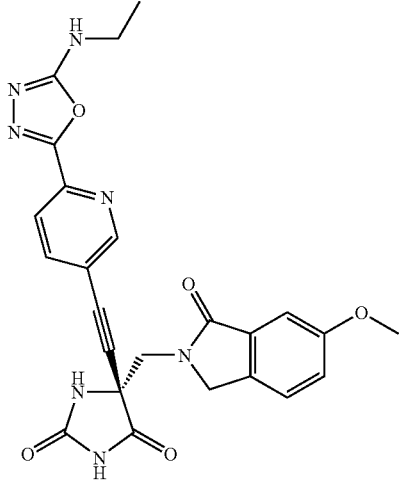 | 487.46 | 488.5 [M + H]+ | 0.094 |
| 972 | 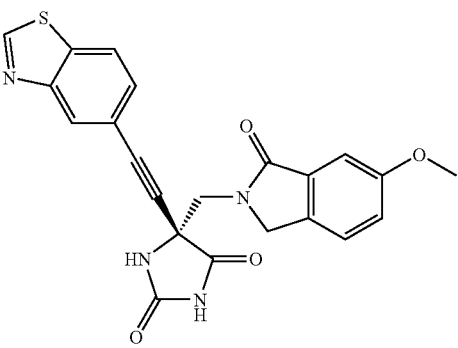 | 432.09 | 433.2 [M + H]+ | 0.12 |

TABLE 1002-continued

| Compound ID | Structures | Exact Mass | Mass Obsvd | Ki (nM) |
|---|---|---|---|---|
| 1090 | 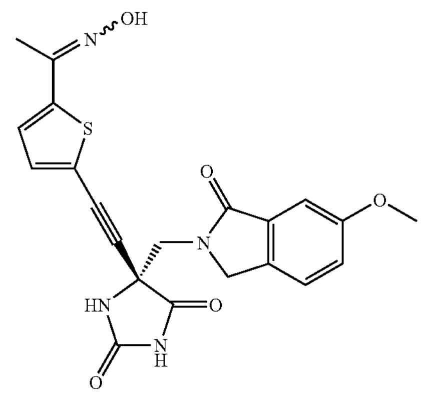 | 438.46 | 439.2 [M + H]+ | 0.3 |
| 1092 | 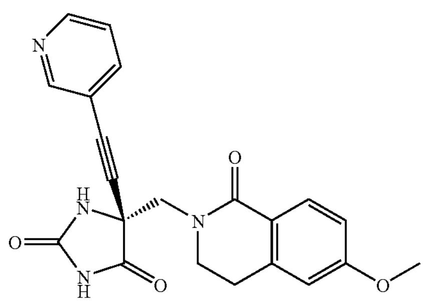 | 390.39 | 391.2 [M + H]+ | 0.37 |
| 554 | 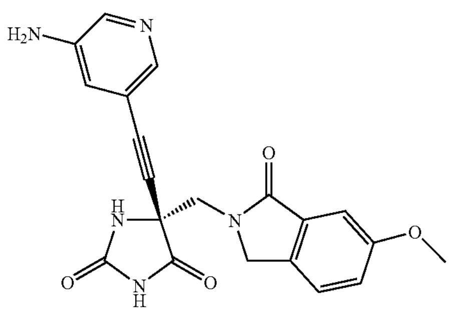 | 391.13 | 392.2 [M + H]+ | 0.31 |
| 1003 | 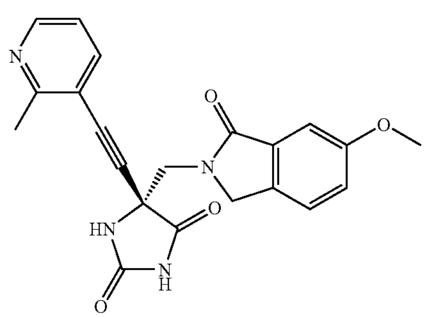 | 390.13 | 391.2 [M + H]+ | 0.11 |

TABLE 1002-continued

| Compound ID | Structures | Exact Mass | Mass Obsvd | Ki (nM) |
|---|---|---|---|---|
| 1256 | 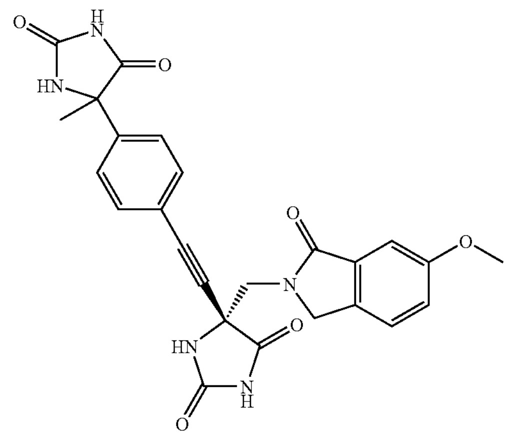 | 487.15 | 488.3 [M + H]⁺ | 0.03 |
| 1009 | 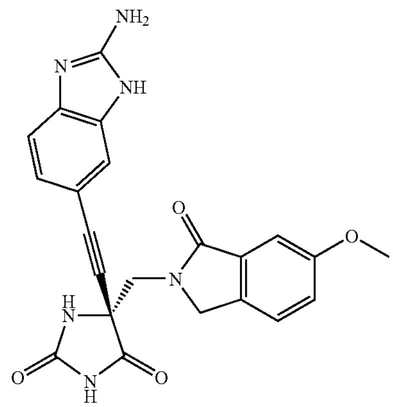 | 430.14 | 431.2 [M + H]⁺ | 1.33 |

As used above, and throughout this disclosure, the following terms, unless otherwise indicated, shall be understood to have the following meanings:

"Patient" includes both human and animals.

"Mammal" means humans and other mammalian animals.

"Alkyl" means an aliphatic hydrocarbon group which may be straight or branched and comprising about 1 to about 20 carbon atoms in the chain. Preferred alkyl groups contain about 1 to about 12 carbon atoms in the chain. More preferred alkyl groups contain about 1 to about 6 carbon atoms in the chain. Branched means that one or more lower alkyl groups such as methyl, ethyl or propyl, are attached to a linear alkyl chain. "Lower alkyl" means a group having about 1 to about 6 carbon atoms in the chain which may be straight or branched. The alkyl group may be substituted by one or more substituents which may be the same or different, each substituent being independently selected from the group consisting of halo, alkyl, aryl, cycloalkyl, cyano, hydroxy, alkoxy, alkylthio, amino, —NH(alkyl), —NH(cycloalkyl), —N(alkyl)$_2$, carboxy and —C(O)O-alkyl. Non-limiting examples of suitable alkyl groups include methyl, ethyl, n-propyl, isopropyl and t-butyl.

"Alkenyl" means an aliphatic hydrocarbon group containing at least one carbon-carbon double bond and which may be straight or branched and comprising about 2 to about 15 carbon atoms in the chain. Preferred alkenyl groups have about 2 to about 12 carbon atoms in the chain; and more preferably about 2 to about 6 carbon atoms in the chain. Branched means that one or more lower alkyl groups such as methyl, ethyl or propyl, are attached to a linear alkenyl chain. "Lower alkenyl" means about 2 to about 6 carbon atoms in the chain which may be straight or branched. Non-limiting examples of suitable alkenyl groups include ethenyl, propenyl, n-butenyl, 3-methylbut-2-enyl, n-pentenyl, octenyl and decenyl.

"Alkynyl" means an aliphatic hydrocarbon group containing at least one carbon-carbon triple bond and which may be straight or branched and comprising about 2 to about 15 carbon atoms in the chain. Preferred alkynyl groups have about 2 to about 12 carbon atoms in the chain; and more preferably about 2 to about 4 carbon atoms in the chain. Branched means that one or more lower alkyl groups such as methyl, ethyl or propyl, are attached to a linear alkynyl chain. "Lower alkynyl" means about 2 to about 6 carbon atoms in the chain which may be straight or branched. Non-limiting examples of suitable alkynyl groups include ethynyl, propynyl, 2-butynyl and 3-methylbutynyl. The term "substituted alkynyl" means that the alkynyl group may be substituted by one or more substituents which may be the same or different, each substituent being independently selected from the group consisting of alkyl, aryl and cycloalkyl.

"Aryl" means an aromatic monocyclic or multicyclic ring system comprising about 6 to about 14 carbon atoms, preferably about 6 to about 10 carbon atoms. The aryl group can be optionally substituted with one or more "ring system substituents" which may be the same or different, and are as defined herein. Non-limiting examples of suitable aryl groups include phenyl and naphthyl.

"Heteroaryl" means an aromatic monocyclic or multicyclic ring system comprising about 5 to about 14 ring atoms, preferably about 5 to about 10 ring atoms, in which one or more of the ring atoms is an element other than carbon, for example nitrogen, oxygen or sulfur, alone or in combination. Preferred heteroaryls contain about 5 to about 6 ring atoms. The "heteroaryl" can be optionally substituted by one or more "ring system substituents" which may be the same or different, and are as defined herein. The prefix aza, oxa or thia before the heteroaryl root name means that at least a nitrogen, oxygen or sulfur atom respectively, is present as a ring atom. A nitrogen atom of a heteroaryl can be optionally oxidized to the corresponding N-oxide. "Heteroaryl" may also include a heteroaryl as defined above fused to an aryl as defined above. Non-limiting examples of suitable heteroaryls include pyridyl, pyrazinyl, furanyl, thienyl, pyrimidinyl, pyridone (including N-substituted pyridones), isoxazolyl, isothiazolyl, oxazolyl, thiazolyl, pyrazolyl, furazanyl, pyrrolyl, pyrazolyl, triazolyl, 1,2,4-thiadiazolyl, pyrazinyl, pyridazinyl, quinoxalinyl, phthalazinyl, oxindolyl, imidazo[1,2-a]pyridinyl, imidazo[2,1-b]thiazolyl, benzofurazanyl, indolyl, azaindolyl, benzimidazolyl, benzothienyl, quinolinyl, imidazolyl, thienopyridyl, quinazolinyl, thienopyrimidyl, pyrrolopyridyl, imidazopyridyl, isoquinolinyl, benzoazaindolyl, 1,2,4-triazinyl, benzothiazolyl and the like. The term "heteroaryl" also refers to partially saturated heteroaryl moieties such as, for example, tetrahydroisoquinolyl, tetrahydroquinolyl and the like.

"Aralkyl" or "arylalkyl" means an aryl-alkyl- group in which the aryl and alkyl are as previously described. Preferred aralkyls comprise a lower alkyl group. Non-limiting examples of suitable aralkyl groups include benzyl, 2-phenethyl and naphthalenylmethyl. The bond to the parent moiety is through the alkyl.

"Alkylaryl" means an alkyl-aryl- group in which the alkyl and aryl are as previously described. Preferred alkylaryls comprise a lower alkyl group. Non-limiting example of a suitable alkylaryl group is tolyl. The bond to the parent moiety is through the aryl.

"Cycloalkyl" means a non-aromatic mono- or multicyclic ring system comprising about 3 to about 10 carbon atoms, preferably about 5 to about 10 carbon atoms. Preferred cycloalkyl rings contain about 5 to about 7 ring atoms. The cycloalkyl can be optionally substituted with one or more "ring system substituents" which may be the same or different, and are as defined above. Non-limiting examples of suitable monocyclic cycloalkyls include cyclopropyl, cyclopentyl, cyclohexyl, cycloheptyl and the like. Non-limiting examples of suitable multicyclic cycloalkyls include 1-decalinyl, norbornyl, adamantyl and the like.

"Cycloalkenyl" means a non-aromatic mono or multicyclic ring system comprising about 3 to about 10 carbon atoms, preferably about 5 to about 10 carbon atoms which contains at least one carbon-carbon double bond. Preferred cycloalkenyl rings contain about 5 to about 7 ring atoms. The cycloalkenyl can be optionally substituted with one or more "ring system substituents" which may be the same or different, and are as defined above. Non-limiting examples of suitable monocyclic cycloalkenyls include cyclopentenyl, cyclohexenyl, cyclohepta-1,3-dienyl, and the like. Non-limiting example of a suitable multicyclic cycloalkenyl is norbornylenyl.

"Halogen" (or "halo") means fluorine, chlorine, bromine, or iodine. Preferred are fluorine, chlorine and bromine.

"Ring system substituent" means a substituent attached to an aromatic or non-aromatic ring system which, for example, replaces an available hydrogen on the ring system. Ring system substituents may be the same or different, each being independently selected from the group consisting of alkyl, alkenyl, alkynyl, aryl, heteroaryl, aralkyl, alkylaryl, heteroaralkyl, heteroarylalkenyl, heteroarylalkynyl, alkylheteroaryl, hydroxy, hydroxyalkyl, alkoxy, aryloxy, aralkoxy, acyl, aroyl, halo, nitro, cyano, carboxy, alkoxycarbonyl, aryloxycarbonyl, aralkoxycarbonyl, alkylsulfonyl, arylsulfonyl, heteroarylsulfonyl, alkylthio, arylthio, heteroarylthio, aralkylthio, heteroaralkylthio, cycloalkyl, heterocyclyl, —C(=N—CN)—NH$_2$, —C(=NH)—NH$_2$, —C(=NH)—NH(alkyl), $G_1G_2N$—, $G_1G_2N$-alkyl-, $G_1G_2NC(O)$—, $G_1G_2NSO_2$— and —SO$_2$NG$_1$G$_2$, wherein $G_1$ and $G_2$ can be the same or different and are independently selected from the group consisting of hydrogen, alkyl, aryl, cycloalkyl, and aralkyl. "Ring system substituent" may also mean a single moiety which simultaneously replaces two available hydrogens on two adjacent carbon atoms (one H on each carbon) on a ring system. Examples of such moiety are methylene dioxy, ethylenedioxy, —C(CH$_3$)$_2$— and the like which form moieties such as, for example:

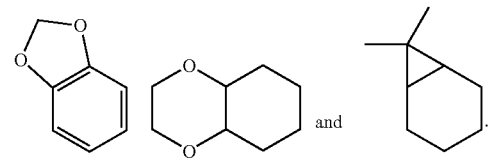

"Heterocyclyl" means a non-aromatic saturated monocyclic or multicyclic ring system comprising about 3 to about 10 ring atoms, preferably about 5 to about 10 ring atoms, in which one or more of the atoms in the ring system is an element other than carbon, for example nitrogen, oxygen or sulfur, alone or in combination. There are no adjacent oxygen and/or sulfur atoms present in the ring system. Preferred heterocyclyls contain about 5 to about 6 ring atoms. The prefix aza, oxa or thia before the heterocyclyl root name means that at least a nitrogen, oxygen or sulfur atom respectively is present as a ring atom. Any —NH in a heterocyclyl ring may exist protected such as, for example, as an —N(Boc), —N(CBz), —N(Tos) group and the like; such protections are also considered part of this invention. The heterocyclyl can be optionally substituted by one or more "ring system substituents" which may be the same or different, and are as defined herein. The nitrogen or sulfur atom of the heterocyclyl can be optionally oxidized to the corresponding N-oxide, S-oxide or S,S-dioxide. Non-limiting examples of suitable monocyclic heterocyclyl rings include piperidyl, pyrrolidinyl, piperazinyl, morpholinyl, thiomorpholinyl, thiazolidinyl, 1,4-dioxanyl, tetrahydrofuranyl, tetrahydrothiophenyl, lactam, lactone, and the like. "Heterocyclyl" may also mean a single moiety (e.g., carbonyl) which simultaneously replaces two available hydrogens on the same carbon atom on a ring system. Example of such moiety is pyrrolidone:

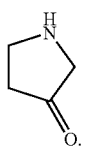

It should be noted that tautomeric forms such as, for example, the moieties:

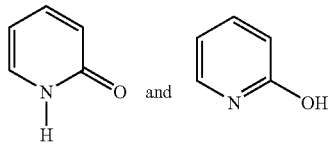

are considered equivalent in certain embodiments of this invention.

"Alkynylalkyl" means an alkynyl-alkyl- group in which the alkynyl and alkyl are as previously described. Preferred alkynylalkyls contain a lower alkynyl and a lower alkyl group. The bond to the parent moiety is through the alkyl. Non-limiting examples of suitable alkynylalkyl groups include propargylmethyl.

"Heteroaralkyl" means a heteroaryl-alkyl- group in which the heteroaryl and alkyl are as previously described. Preferred heteroaralkyls contain a lower alkyl group. Non-limiting examples of suitable aralkyl groups include pyridylmethyl, and quinolin-3-ylmethyl. The bond to the parent moiety is through the alkyl.

"Hydroxyalkyl" means a HO-alkyl- group in which alkyl is as previously defined. Preferred hydroxyalkyls contain lower alkyl. Non-limiting examples of suitable hydroxyalkyl groups include hydroxymethyl and 2-hydroxyethyl.

"Acyl" means an H—C(O)—, alkyl-C(O)— or cycloalkyl-C(O)—, group in which the various groups are as previously described. The bond to the parent moiety is through the carbonyl. Preferred acyls contain a lower alkyl. Non-limiting examples of suitable acyl groups include formyl, acetyl and propanoyl.

"Aroyl" means an aryl-C(O)— group in which the aryl group is as previously described. The bond to the parent moiety is through the carbonyl. Non-limiting examples of suitable groups include benzoyl and 1-naphthoyl.

"Alkoxy" means an alkyl-O— group in which the alkyl group is as previously described. Non-limiting examples of suitable alkoxy groups include methoxy, ethoxy, n-propoxy, isopropoxy and n-butoxy. The bond to the parent moiety is through the ether oxygen.

"Aryloxy" means an aryl-O— group in which the aryl group is as previously described. Non-limiting examples of suitable aryloxy groups include phenoxy and naphthoxy. The bond to the parent moiety is through the ether oxygen.

"Aralkyloxy" means an aralkyl-O— group in which the aralkyl group is as previously described. Non-limiting examples of suitable aralkyloxy groups include benzyloxy and 1- or 2-naphthalenemethoxy. The bond to the parent moiety is through the ether oxygen.

"Alkylthio" means an alkyl-S— group in which the alkyl group is as previously described. Non-limiting examples of suitable alkylthio groups include methylthio and ethylthio. The bond to the parent moiety is through the sulfur.

"Arylthio" means an aryl-S— group in which the aryl group is as previously described. Non-limiting examples of suitable arylthio groups include phenylthio and naphthylthio. The bond to the parent moiety is through the sulfur.

"Aralkylthio" means an aralkyl-S— group in which the aralkyl group is as previously described. Non-limiting example of a suitable aralkylthio group is benzylthio. The bond to the parent moiety is through the sulfur.

"Alkoxycarbonyl" means an alkyl-O—CO— group. Non-limiting examples of suitable alkoxycarbonyl groups include methoxycarbonyl and ethoxycarbonyl. The bond to the parent moiety is through the carbonyl.

"Aryloxycarbonyl" means an aryl-O—C(O)— group. Non-limiting examples of suitable aryloxycarbonyl groups include phenoxycarbonyl and naphthoxycarbonyl. The bond to the parent moiety is through the carbonyl.

"Aralkoxycarbonyl" means an aralkyl-O—C(O)— group. Non-limiting example of a suitable aralkoxycarbonyl group is benzyloxycarbonyl. The bond to the parent moiety is through the carbonyl.

"Alkylsulfonyl" means an alkyl-S($O_2$)— group. Preferred groups are those in which the alkyl group is lower alkyl. The bond to the parent moiety is through the sulfonyl.

"Arylsulfonyl" means an aryl-S($O_2$)— group. The bond to the parent moiety is through the sulfonyl.

The term "substituted" means that one or more hydrogens on the designated atom is replaced with a selection from the indicated group, provided that the designated atom's normal valency under the existing circumstances is not exceeded, and that the substitution results in a stable compound. Combinations of substituents and/or variables are permissible only if such combinations result in stable compounds. By "stable compound" or "stable structure" is meant a compound that is sufficiently robust to survive isolation to a useful degree of purity from a reaction mixture, and formulation into an efficacious therapeutic agent.

The term "optionally substituted" means optional substitution with the specified groups, radicals or moieties.

The term "isolated" or "in isolated form" for a compound refers to the physical state of said compound after being isolated from a synthetic process or natural source or combination thereof. The term "purified" or "in purified form" for a compound refers to the physical state of said compound after being obtained from a purification process or processes described herein or well known to the skilled artisan, in sufficient purity to be characterizable by standard analytical techniques described herein or well known to the skilled artisan.

It should also be noted that any carbon as well as heteroatom with unsatisfied valences in the text, schemes, examples and Tables herein is assumed to have the sufficient number of hydrogen atom(s) to satisfy the valences.

When a functional group in a compound is termed "protected", this means that the group is in modified form to preclude undesired side reactions at the protected site when the compound is subjected to a reaction. Suitable protecting groups will be recognized by those with ordinary skill in the art as well as by reference to standard textbooks such as, for example, T. W. Greene et al, *Protective Groups in organic Synthesis* (1991), Wiley, New York.

When any variable (e.g., aryl, heterocycle, $R^2$, etc.) occurs more than one time in any constituent or in Formula I, its definition on each occurrence is independent of its definition at every other occurrence.

As used herein, the term "composition" is intended to encompass a product comprising the specified ingredients in the specified amounts, as well as any product which results, directly or indirectly, from combination of the specified ingredients in the specified amounts.

Prodrugs and solvates of the compounds of the invention are also contemplated herein. The term "prodrug", as employed herein, denotes a compound that is a drug precursor which, upon administration to a subject, undergoes chemical conversion by metabolic or chemical processes to yield a compound of Formula I or a salt and/or solvate thereof. A discussion of prodrugs is provided in T. Higuchi and V. Stella, *Pro-drugs as Novel Delivery Systems* (1987) 14 of the A.C.S. Symposium Series, and in *Bioreversible Carriers in Drug Design*, (1987) Edward B. Roche, ed., American Pharmaceutical Association and Pergamon Press, both of which are incorporated herein by reference thereto. The term "prodrug" means a compound (e.g., a drug precursor) that is transformed in vivo to yield a compound of Formula (I) or a pharmaceutically acceptable salt, hydrate or solvate of the compound. The transformation may occur by various mechanisms (e.g., by metabolic or chemical processes), such as, for example, through hydrolysis in blood. A discussion of the use of pro-drugs is provided by T. Higuchi and W. Stella, "Pro-drugs as Novel Delivery Systems," Vol. 14 of the A.C.S. Symposium Series, and in Bioreversible Carriers in Drug Design, ed. Edward B. Roche, American Pharmaceutical Association and Pergamon Press, 1987.

For example, if a compound of Formula (I) or a pharmaceutically acceptable salt, hydrate or solvate of the compound contains a carboxylic acid functional group, a prodrug can comprise an ester formed by the replacement of the hydrogen atom of the acid group with a group such as, for example, $(C_1-C_8)$alkyl, $(C_2-C_{12})$alkanoyloxymethyl, 1-(alkanoyloxy) ethyl having from 4 to 9 carbon atoms, 1-methyl-1-(alkanoyloxy)-ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-(alkoxycarbonyl)amino)ethyl having from 4 to 10 carbon atoms, 3-phthalidyl, 4-crotonolactonyl, gamma-butyrolacton-4-yl, di-N,N—$(C_1-C_2)$alkylamino$(C_2-C_3)$alkyl (such as β-dimethylaminoethyl), carbamoyl-$(C_1-C_2)$alkyl, N,N-di$(C_1-C_2)$alkylcarbamoyl-(C1-C2)alkyl and piperidino-, pyrrolidino- or morpholino$(C_2-C_3)$ alkyl, and the like.

Similarly, if a compound of Formula (I) contains an alcohol functional group, a prodrug can be formed by the replacement of the hydrogen atom of the alcohol group with a group such as, for example, $(C_1-C_6)$alkanoyloxymethyl, 1-(($C_1-C_6$)alkanoyloxy)ethyl, 1-methyl-1-(($C_1-C_6$)alkanoyloxy)ethyl, $(C_1-C_6)$alkoxycarbonyloxymethyl, N—$(C_1-C_6)$alkoxycarbonylaminomethyl, succinoyl, $(C_1-C_6)$alkanoyl, α-amino $(C_1-C_4)$alkanyl, arylacyl and α-aminoacyl, or α-aminoacyl-α-aminoacyl, where each α-aminoacyl group is independently selected from the naturally occurring L-amino acids, P(O)(OH)$_2$, —P(O)(O$(C_1-C_6)$alkyl)$_2$ or glycosyl (the radical resulting from the removal of a hydroxyl group of the hemiacetal form of a carbohydrate), and the like.

If a compound of Formula (I) incorporates an amine functional group, a prodrug can be formed by the replacement of a hydrogen atom in the amine group with a group such as, for example, R-carbonyl, RO-carbonyl, NRR'-carbonyl where R and R' are each independently $(C_1-C_{10})$alkyl, $(C_3-C_7)$ cycloalkyl, benzyl, or R-carbonyl is a natural α-aminoacyl or natural α-aminoacyl, —C(OH)C(O)OY$^1$ wherein Y$^1$ is H, $(C_1-C_6)$alkyl or benzyl, —C(OY$^2$)Y$^3$ wherein Y$^2$ is $(C_1-C_4)$ alkyl and Y$^3$ is $(C_1-C_6)$alkyl, carboxy$(C_1-C_6)$alkyl, amino $(C_1-C_4)$alkyl or mono-N— or di-N,N—$(C_1-C_6)$alkylaminoalkyl, —C(Y$^4$)Y$^5$ wherein Y$^4$ is H or methyl and Y$^5$ is mono-N— or di-N,N—$(C_1-C_6)$alkylamino morpholino, piperidin-1-yl or pyrrolidin-1-yl, and the like.

"Solvate" means a physical association of a compound of this invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolatable solvates. Non-limiting examples of suitable solvates include ethanolates, methanolates, and the like. "Hydrate" is a solvate wherein the solvent molecule is H$_2$O.

"Effective amount" or "therapeutically effective amount" is meant to describe an amount of compound or a composition of the present invention effective in inhibiting TACE, the production of TNF-α, MMPs, ADAMS or any combination thereof and thus producing the desired therapeutic, ameliorative, inhibitory or preventative effect.

The compounds of Formula I can form salts which are also within the scope of this invention. Reference to a compound of Formula I herein is understood to include reference to salts thereof, unless otherwise indicated. The term "salt(s)", as employed herein, denotes acidic salts formed with inorganic and/or organic acids, as well as basic salts formed with inorganic and/or organic bases. In addition, when a compound of Formula I contains both a basic moiety, such as, but not limited to a pyridine or imidazole, and an acidic moiety, such as, but not limited to a carboxylic acid, zwitterions ("inner salts") may be formed and are included within the term "salt(s)" as used herein. Pharmaceutically acceptable (i.e., non-toxic, physiologically acceptable) salts are preferred, although other salts are also useful. Salts of the compounds of the Formula I may be formed, for example, by reacting a compound of Formula I with an amount of acid or base, such as an equivalent amount, in a medium such as one in which the salt precipitates or in an aqueous medium followed by lyophilization.

Exemplary acid addition salts include acetates, ascorbates, benzoates, benzenesulfonates, bisulfates, borates, butyrates, citrates, camphorates, camphorsulfonates, fumarates, hydrochlorides, hydrobromides, hydroiodides, lactates, maleates, methanesulfonates, naphthalenesulfonates, nitrates, oxalates, phosphates, propionates, salicylates, succinates, sulfates, tartarates, thiocyanates, toluenesulfonates (also known as tosylates,) and the like. Additionally, acids which are generally considered suitable for the formation of pharmaceutically useful salts from basic pharmaceutical compounds are discussed, for example, by P. Stahl et al, Camille G. (eds.) *Handbook of Pharmaceutical Salts. Properties, Selection and Use*. (2002) Zurich: Wiley-VCH; S. Berge et al, *Journal of Pharmaceutical Sciences* (1977) 66(1) 1-19; P. Gould, *International J. of Pharmaceutics* (1986) 33 201-217; Anderson et al, *The Practice of Medicinal Chemistry* (1996), Academic Press, New York; and in *The Orange Book* (Food & Drug Administration, Washington, D.C. on their website). These disclosures are incorporated herein by reference thereto.

Exemplary basic salts include ammonium salts, alkali metal salts such as sodium, lithium, and potassium salts, alkaline earth metal salts such as calcium and magnesium salts, salts with organic bases (for example, organic amines) such as dicyclohexylamines, t-butyl amines, and salts with amino acids such as arginine, lysine and the like. Basic nitrogen-containing groups may be quarternized with agents such as lower alkyl halides (e.g. methyl, ethyl, and butyl chlorides, bromides and iodides), dialkyl sulfates (e.g. dimethyl, diethyl, and dibutyl sulfates), long chain halides (e.g. decyl, lauryl, and stearyl chlorides, bromides and iodides), aralkyl halides (e.g. benzyl and phenethyl bromides), and others.

All such acid salts and base salts are intended to be pharmaceutically acceptable salts within the scope of the invention and all acid and base salts are considered equivalent to the free forms of the corresponding compounds for purposes of the invention.

Compounds of Formula I, and salts, solvates and prodrugs thereof, may exist in their tautomeric form (for example, as an amide or imino ether). All such tautomeric forms are contemplated herein as part of the present invention.

All stereoisomers (for example, geometric isomers, optical isomers and the like) of the present compounds (including those of the salts, solvates and prodrugs of the compounds as well as the salts and solvates of the prodrugs), such as those which may exist due to asymmetric carbons on various substituents, including enantiomeric forms (which may exist even in the absence of asymmetric carbons), rotameric forms, atropisomers, and diastereomeric forms, are contemplated within the scope of this invention, as are positional isomers (such as, for example, 4-pyridyl and 3-pyridyl). Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the *IUPAC* 1974 Recommendations. The use of the terms "salt", "solvate" "prodrug" and the like, is intended to equally apply to the salt, solvate and prodrug of enantiomers, stereoisomers, rotamers, tautomers, positional isomers, racemates or prodrugs of the inventive compounds.

Polymorphic forms of the compounds of Formula I, and of the salts, solvates and prodrugs of the compounds of Formula I, are intended to be included in the present invention.

The compounds according to the invention have pharmacological properties; in particular, the compounds of Formula I can be inhibitors of TACE, aggrecanase, TNF-α and/or MMP activity.

In one aspect, the invention provides a pharmaceutical composition comprising as an active ingredient at least one compound of formula (I).

In another aspect, the invention provides a pharmaceutical composition of formula (I) additionally comprising at least one pharmaceutically acceptable carrier.

In another aspect, the invention provides a method of treating disorders associated with TACE, aggrecanase, TNF-α, MMPs, ADAMs or any combination thereof, said method comprising administering to a patient in need of such treatment an effective amount of at least one compound of formula (I).

In another aspect, the invention provides a use of a compound of formula (I) for the manufacture of a medicament to treat disorders associated with TACE, aggrecanase, TNF-α, MMPs, ADAMs or any combination thereof.

The compounds of Formula (I) can have anti-inflammatory activity and/or immunomodulatory activity and can be useful in the treatment of diseases including but not limited to septic shock, haemodynamic shock, sepsis syndrome, post ischaemic reperfusion injury, malaria, mycobacterial infection, meningitis, psoriasis, congestive heart failure, fibrotic diseases, cachexia, graft rejection, cancers such as cutaneous T-cell lymphoma, diseases involving angiogenesis, autoimmune diseases, skin inflammatory diseases, inflammatory bowel diseases such as Crohn's disease and colitis, OA and RA, ankylosing spondylitis, psoriatic arthritis, adult Still's disease, ureitis, Wegener's granulomatosis, Behcehe disease, Sjogren's syndrome, sarcoidosis, polymyositis, dermatomyositis, multiple sclerosis, sciatica, complex regional pain syndrome, radiation damage, hyperoxic alveolar injury, periodontal disease, HIV, non-insulin dependent diabetes mellitus, systemic lupus erythematosus, glaucoma, sarcoidosis, idiopathic pulmonary fibrosis, bronchopulmonary dysplasia, retinal disease, scleroderma, osteoporosis, renal ischemia, myocardial infarction, cerebral stroke, cerebral ischemia, nephritis, hepatitis, glomerulonephritis, cryptogenic fibrosing aveolitis, psoriasis, transplant rejection, atopic dermatitis, vasculitis, allergy, seasonal allergic rhinitis, reversible airway obstruction, adult respiratory distress syndrome, asthma, chronic obstructive pulmonary disease (COPD) and/or bronchitis. It is contemplated that a compound of this invention may be useful in treating one or more of the diseases listed.

In another aspect, the invention provides a method of preparing a pharmaceutical composition for treating the disorders associated with TACE, aggrecanase, TNF-α, MMPs, ADAMs or any combination thereof, said method comprising bringing into intimate contact at least one compound of formula (I) and at least one pharmaceutically acceptable carrier.

In another aspect, the invention provides a compound of formula (I) exhibiting TACE, TNF-α, MMPs, ADAMs or any combination thereof inhibitory activity, including enantiomers, stereoisomers and tautomers of said compound, and pharmaceutically acceptable salts, solvates, or esters of said compound, said compound being selected from the compounds of structures listed in Table 1001 set forth above.

In another aspect, the invention provides a pharmaceutical composition for treating disorders associated with TACE, aggrecanase, TNF-α, MMP, ADAM or any combination thereof in a subject comprising, administering to the subject in need of such treatment a therapeutically effective amount of at least one compound of formula (I) or a pharmaceutically acceptable salt, solvate, ester, or isomer thereof.

In another aspect, the invention provides a compound of formula (I) in purified form.

In another aspect, the invention provides a method of treating a condition or disease mediated by TACE, MMPs, TNF-α, aggrecanase, or any combination thereof in a subject comprising: administering to the subject in need of such treatment a therapeutically effective amount of at least one compound of formula (I) or a pharmaceutically acceptable salt, solvate, ester or isomer thereof.

In another aspect, the invention provides a method of treating a condition or disease selected from the group consisting of rheumatoid arthritis, osteoarthritis, periodontitis, gingivitis, corneal ulceration, solid tumor growth and tumor invasion by secondary metastases, neovascular glaucoma, inflammatory bowel disease, multiple sclerosis and psoriasis in a subject, comprising: administering to the subject in need of such treatment a therapeutically effective amount of at least one compound of formula (I) or a pharmaceutically acceptable salt, solvate, ester or isomer thereof.

In another aspect, the invention provides a method of treating a condition or disease selected from the group consisting of fever, cardiovascular conditions, hemorrhage, coagulation, cachexia, anorexia, alcoholism, acute phase response, acute infection, shock, graft versus host reaction, autoimmune disease and HIV infection in a subject comprising administering to the subject in need of such treatment a therapeutically effective amount of at least one compound of formula (I) or a pharmaceutically acceptable salt, solvate, ester, or isomer thereof.

In another aspect, the invention provides a method of treating a condition or disease selected from the group consisting of septic shock, haemodynamic shock, sepsis syndrome, post ischaemic reperfusion injury, malaria, mycobacterial infection, meningitis, psoriasis, congestive heart failure, fibrotic diseases, cachexia, graft rejection, cancers such as cutaneous T-cell lymphoma, diseases involving angiogenesis, autoimmune diseases, skin inflammatory diseases, inflammatory bowel diseases such as Crohn's disease and colitis, osteo and rheumatoid arthritis, ankylosing spondylitis, psoriatic arthritis, adult Still's disease, ureitis, Wegener's granulomatosis, Behcehe disease, Sjogren's syndrome, sarcoidosis, polymyositis, dermatomyositis, multiple sclerosis, sciatica, complex regional pain syndrome, radiation damage, hyperoxic alveolar injury, periodontal disease, HIV, non-insulin dependent diabetes mellitus, systemic lupus erythematosus, glaucoma, sarcoidosis, idiopathic pulmonary fibrosis, bronchopulmonary dysplasia, retinal disease, scleroderma, osteoporosis, renal ischemia, myocardial infarction, cerebral stroke, cerebral ischemia, nephritis, hepatitis, glomerulonephritis, cryptogenic fibrosing aveolitis, psoriasis, transplant rejection, atopic dermatitis, vasculitis, allergy, seasonal allergic rhinitis, reversible airway obstruction, adult respiratory distress syndrome, asthma, chronic obstructive pulmonary disease (COPD) and bronchitis in a subject comprising administering to the subject in need of such treatment a therapeutically effective amount of at least one compound of formula (I) or a pharmaceutically acceptable salt, solvate, ester or isomer thereof.

In another aspect, the invention provides a method of treating a condition or disease associated with COPD, comprising: administering to the subject in need of such treatment a therapeutically effective amount of at least one compound of Formula (I) or a pharmaceutically acceptable salt, solvate, ester or isomer thereof.

In another aspect, the invention provides a method of treating a condition or disease associated with rheumatoid arthritis, comprising: administering to the subject in need of such treatment a therapeutically effective amount of at least one compound of formula (I) or a pharmaceutically acceptable salt, solvate, ester, or isomer thereof.

In another aspect, the invention provides a method of treating a condition or disease associated with Crohn's disease, comprising: administering to the subject in need of such treatment a therapeutically effective amount of at least one compound of formula (I) or a pharmaceutically acceptable salt, solvate, ester or isomer thereof.

In another aspect, the invention provides a method of treating a condition or disease associated with psoriasis, comprising: administering to the subject in need of such treatment a therapeutically effective amount of at least one compound of formula (I) or a pharmaceutically acceptable salt, solvate, ester, or isomer thereof.

In another aspect, the invention provides a method of treating a condition or disease associated with ankylosing spondylitis, comprising: administering to the subject in need of such treatment a therapeutically effective amount of at least one compound of formula (I) or a pharmaceutically acceptable salt, solvate, ester or isomer thereof.

In another aspect, the invention provides a method of treating a condition or disease associated with sciatica, comprising: administering to the subject in need of such treatment a therapeutically effective amount of at least one compound of formula (I) or a pharmaceutically acceptable salt, solvate, ester or isomer thereof.

In another aspect, the invention provides a method of treating a condition or disease associated with complex regional pain syndrome, comprising: administering to the subject in need of such treatment a therapeutically effective amount of at least one compound of formula (I) or a pharmaceutically acceptable salt, solvate, ester, or isomer thereof.

In another aspect, the invention provides a method of treating a condition or disease associated with psoriatic arthritis, comprising: administering to the subject in need of such treatment a therapeutically effective amount of at least one compound of formula (I), or a pharmaceutically acceptable salt, solvate, ester, or isomer thereof.

In another aspect, the invention provides a method of treating a condition or disease associated with multiple sclerosis, comprising: administering to the subject in need of such treatment a therapeutically effective amount of at least one compound of formula (I) or a pharmaceutically acceptable salt, solvate, ester or isomer thereof, in combination with a compound selected from the group consisting of Avonex®, Betaseron, Copaxone or other compounds indicated for the treatment of multiple sclerosis.

Additionally, a compound of the present invention may be co-administered or used in combination with disease-modifying antirheumatic drugs (DMARDS) such as methotrexate, azathioprine, leflunomide, pencillinamine, gold salts, mycophenolate mofetil, cyclophosphamide and other similar drugs. They may also be co-administered with or used in combination with non-steroidal anti-inflammatory drugs (NSAIDs) such as piroxicam, naproxen, indomethacin, ibuprofen and the like; cycloxygenase-2 selective (COX-2) inhibitors such as Vioxx® and Celebrex®; immunosuppressives such as steroids, cyclosporin, Tacrolimus, rapamycin and the like; biological response modifiers (BRMS) such as Enbrel®, Remicade®, IL-1 antagonists, anti-CD40, anti-CD28, IL-10, anti-adhesion molecules and the like; and other anti-inflammatory agents such as p38 kinase inhibitors, PDE4 inhibitors, other chemically different TACE inhibitors, chemokine receptor antagonists, Thalidomide and other small molecule inhibitors of pro-inflammatory cytokine production.

Also, a compound of the present invention may be co-administered or used in combination with an H1 antagonist for the treatment of seasonal allergic rhinitis and/or asthma. Suitable H1 antagonists may be, for example, Claritin®, Clarinex®, Allegra®, or Zyrtec®.

In another aspect, the invention provides a method of treating a condition or disease mediated by TACE, MMPs, TNF-α, aggrecanase, or any combination thereof in a subject comprising: administering to the subject in need of such treatment a therapeutically effective amount of at least one compound of formula (I) or a pharmaceutically acceptable salt, solvate or isomer thereof in combination with a therapeutically effective amount of at least one medicament selected from the group consisting of disease modifying anti-rheumatic drugs (DMARDS), NSAIDs, COX-2 inhibitors, COX-1 inhibitors, immunosuppressives, biological response modifiers (BRMs), anti-inflammatory agents and H1 antagonists.

In another aspect, the invention provides a method of treating a condition or disease selected from the group consisting of rheumatoid arthritis, osteoarthritis, periodontitis, gingivitis, corneal ulceration, solid tumor growth and tumor invasion by secondary metastases, neovascular glaucoma, inflammatory bowel disease, multiple sclerosis and psoriasis in a subject, comprising: administering to the subject in need of such treatment a therapeutically effective amount of at least one compound of Formula (I) or a pharmaceutically acceptable salt, solvate, ester, or isomer thereof in combination with a therapeutically effective amount of at least one medicament selected from the group consisting of DMARDS, NSAIDs, COX-2 inhibitors, COX-1 inhibitors, immunosuppressives, BRMs, anti-inflammatory agents and H1 antagonists.

In another aspect, the invention provides a method of treating a condition or disease selected from the group consisting of septic shock, haemodynamic shock, sepsis syndrome, post ischaemic reperfusion injury, malaria, mycobacterial infection, meningitis, psoriasis, congestive heart failure, fibrotic diseases, cachexia, graft rejection, cancers such as cutaneous T-cell lymphoma, diseases involving angiogenesis, autoimmune diseases, skin inflammatory diseases, inflammatory bowel diseases such as Crohn's disease and colitis, osteo and rheumatoid arthritis, ankylosing spondylitis, psoriatic arthritis, adult Still's disease, ureitis, Wegener's granulomatosis, Behcehe disease, Sjogren's syndrome, sarcoidosis, polymyositis, dermatomyositis, multiple sclerosis, sciatica, complex regional pain syndrome, radiation damage, hyperoxic alveolar injury, periodontal disease, HIV, non-insulin dependent diabetes mellitus, systemic lupus erythematosus, glaucoma, sarcoidosis, idiopathic pulmonary fibrosis, bronchopulmonary dysplasia, retinal disease, scleroderma, osteoporosis, renal ischemia, myocardial infarction, cerebral stroke, cerebral ischemia, nephritis, hepatitis, glomerulonephritis, cryptogenic fibrosing aveolitis, psoriasis, transplant rejection, atopic dermatitis, vasculitis, allergy, seasonal allergic rhinitis, reversible airway obstruction, adult respiratory distress syndrome, asthma, chronic obstructive pulmonary disease (COPD) and bronchitis in a subject comprising administering to the subject in need of such treatment a therapeutically effective amount of at least one compound of Formula (I), or a pharmaceutically acceptable salt, solvate, ester or isomer thereof in combination with a therapeutically effective amount of at least one medicament selected from the group consisting of DMARDS, NSAIDs, COX-2 inhibitors, COX-1 inhibitors, immunosuppressives, BRMs, anti-inflammatory agents and H1 antagonists.

In another aspect, the invention provides a method for treating RA comprising administering a compound of the formula I in combination with compound selected from the class consisting of a COX-2 inhibitor e.g. Celebrex® or Vioxx®; a COX-1 inhibitor e.g. Feldene®; an immunosuppressive e.g. methotrexate or cyclosporin; a steroid e.g. β-methasone; and anti-TNF-α compound, e.g. Enbrel® or Remicade®; a PDE IV inhibitor, or other classes of compounds indicated for the treatment of RA.

In another aspect, the invention provides a method for treating multiple sclerosis comprising administering a compound of the formula (I) in combination with a compound selected from the group consisting of Avonex®, Betaseron, Copaxone or other compounds indicated for the treatment of multiple sclerosis.

TACE activity is determined by a kinetic assay measuring the rate of increase in fluorescent intensity generated by TACE catalyzed cleavage of an internally quenched peptide substrate (SPDL-3). The purified catalytic domain of recombinant human TACE (rhTACEc, Residue 215 to 477 with two mutation (S266A and N4520) and a 6×His tail) is used in the assay. It is purified from the baculovirus/Hi5 cells expression system using affinity chromatography. The substrate SPDL-3 is an internally quenched peptide (MCA-Pro-Leu-Ala-Gln-Ala-Val-Arg-Ser-Ser-Ser-Dpa-Arg-NH2), with its sequence derived from the pro-TNFα cleavage site. MCA is (7-Methoxycoumarin-4-yl)acetyl. Dpa is N-3-(2,4-Dinitrophenyl)-L-2,3-diaminopropionyl.

A 50 µl assay mixture contains 20 mM HEPES, pH 7.3, 5 mM $CaCl_2$, 100 µM $ZnCl_2$, 2% DMSO, 0.04% Methylcellulose, 30 µM SPDL-3, 70 pM rhTACEc and a test compound. RhTACEc is pre-incubated with the testing compound for 90 min. at 25° C. Reaction is started by addition of the substrate. The fluorescent intensity (excitation at 320 nm, emission at 405 nm) was measured every 45 seconds for 30 min. using a fluorospectrometer (GEMINI XS, Molecular Devices). Rate of enzymatic reaction is shown as Units per second. Effect of a test compound is shown as % of TACE activity in the absence of the compound.

The pharmaceutical compositions containing the active ingredient may be in a form suitable for oral use, for example, as tablets, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients that are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the technique described in the U.S. Pat. Nos. 4,256,108; 4,166,452; and 4,265,874 to form osmotic therapeutic tablets for controlled release.

The term pharmaceutical composition is also intended to encompass both the bulk composition and individual dosage units comprised of more than one (e.g., two) pharmaceutically active agents such as, for example, a compound of the present invention and an additional agent selected from the lists of the additional agents described herein, along with any pharmaceutically inactive excipients. The bulk composition and each individual dosage unit can contain fixed amounts of the afore-said "more than one pharmaceutically active agents". The bulk composition is material that has not yet been formed into individual dosage units. An illustrative dosage unit is an oral dosage unit such as tablets, pills and the like. Similarly, the herein-described method of treating a patient by administering a pharmaceutical composition of the present invention is also intended to encompass the administration of the afore-said bulk composition and individual dosage units.

Formulations for oral use may also be presented as hard gelatin capsules wherein the active ingredients is mixed with an inert solid diluent, for example, calcium carbonate, calcium phosphate or kaolin, or a soft gelatin capsules where in the active ingredient is mixed with water or an oil medium, for example peanut oil, liquid paraffin or olive oil.

Aqueous suspensions contain the active material in admixture with excipients suitable for the manufacture of aqueous suspensions. Such excipients are suspending agents, for example, sodium carboxymethylcellulose, methylcellulose, hydroxypropylmethyl-cellulose, sodium alginate, polyvinyl-pyrrolidone, gum tragacanth and gum acacia; dispersing or wetting agents may be a naturally-occurring phosphatide, for example, lecithin, or condensation products of an alkylene oxide with fatty acids, for example polyoxyethylene stearate, or condensation products of ethylene oxide with long chain aliphatic alcohols, for example, heptadecaethylene-oxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example, polyethylene sorbitan monooleate. The aqueous suspensions may also contain one or more preservatives, for example, ethyl or n-propyl, p-hydroxybenzoate, one or more coloring agents, one or more flavoring agents, and one or more sweetening agents, such as sucrose, saccharin or aspartame.

Oily suspensions may be formulated by suspending the active ingredient in a vegetable oil, for example, arachis oil, olive oil, sesame oil or coconut oil, or in mineral oil such as liquid paraffin. The oily suspensions may contain a thickening agent, for example, beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, e.g., sweetening, flavoring and coloring agents, may also be present.

The pharmaceutical compositions of the invention may also be in the form of an oil-in-water emulsion. The oily phase may be a vegetable oil, e.g., olive oil or arachis oil, or a mineral oil, e.g., liquid paraffin or mixtures of these. Suitable emulsifying agents may be naturally-occurring phosphatides, e.g., soy beans, lecithin, and esters or partial esters derived from fatty acids and hexitol anhydrides, for example, sorbitan monooleate, and condensation products of the said partial esters with ethylene oxide, e.g., polyoxyethylene sorbitan monooleate. The emulsions may also contain sweetening and flavoring agents.

Syrups and elixirs may be formulated with sweetening agents, for example, glycerol, propylene glycol, sorbitol or sucrose. Such formulations may also contain a demulcent, a preservative and flavoring and coloring agents.

The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, e.g., as a solution in 1,3-butane diol. Among the acceptable vehicles and solvents that may be employed are water, Ringer's solution and isotonic sodium chloride solution. In addition, sterile fixed oils are conventionally employed as a solvent or suspending medium. For this purpose any bland fixed oil may be employed including synthetic mono- or diglycerides. In addition, fatty acids such as oleic acid find use in the preparation of injectables.

Compounds of the invention may also be administered in the form of suppositories for rectal administration of the drug. The compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

For topical use, creams, ointments, jellies, solutions or suspensions, etc., containing the compounds of the invention are employed. (For purposes of this application, topical application shall include mouthwashes and gargles.)

The compounds for the present invention can be administered in the intranasal form via topical use of suitable intranasal vehicles, or via transdermal routes, using those forms of transdermal skin patches well known to those of ordinary skill in the art. To be administered in the form of a transdermal delivery system, the dosage administration will, of course, be continuous rather than intermittent throughout the dosage regimen. Compounds of the present invention may also be delivered as a suppository employing bases such as cocoa butter, glycerinated gelatin, hydrogenated vegetable oils, mixtures of polyethylene glycols of various molecular weights and fatty acid esters of polyethylene glycol.

The dosage regimen utilizing the compounds of the present invention is selected in accordance with a variety of factors including type, species, weight, sex and medical condition of the patient; the severity of the condition to be treated; the route of administration; the renal and hepatic function of the patient; and the particular compound thereof employed. A physician or veterinarian of ordinary skill can readily determine and prescribe the effective amount of the drug required to prevent, counter, arrest or reverse the progress of the condition. Optimal precision in achieving concentration of drug within the range that yields efficacy without toxicity requires a regimen based on the kinetics of the drug's availability to target sites. This involves a consideration of the distribution, equilibrium, and elimination of a drug. Preferably, doses of the compound of Formula I useful in the method of the present invention range from 0.01 to 1000 mg per day. More preferably, dosages range from 0.1 to 1000 mg/day. Most preferably, dosages range from 0.1 to 500 mg/day. For oral administration, the compositions are preferably provided in the form of tablets containing 0.01 to 1000 milligrams of the active ingredient, particularly 0.01, 0.05, 0.1, 0.5, 1.0, 2.5, 5.0, 10.0, 15.0, 25.0, 50.0, 100 and 500 milligrams of the active ingredient for the symptomatic adjustment of the dosage to the patient to be treated. An effective amount of the drug is ordinarily supplied at a dosage level of from about 0.0002 mg/kg to about 50 mg/kg of body weight per day. The range is more particularly from about 0.001 mg/kg to 1 mg/kg of body weight per day.

Advantageously, the active agent of the present invention may be administered in a single daily dose, or the total daily dosage may be administered in dividend doses of two, three or four time daily.

The amount of active ingredient that may be combined with the carrier materials to produce single dosage form will vary depending upon the host treated and the particular mode of administration.

It will be understood, however, that the specific dose level for any particular patient will depend upon a variety of factors including the age, body weight, general health, sex, diet, time of administration, route or administration, rate of excretion, drug combination and the severity of the particular disease undergoing therapy.

The compounds of the invention may be produced by processes known to those skilled in the art and as shown in the following reaction schemes and in the preparations and examples described below.

EXAMPLES

The following abbreviations may be used in the procedures and schemes:
ACN Acetonitrile
AcOH Acetic acid
Aq Aqueous
BOC tert-Butoxycarbonyl
$BOC_2O$ BOC Anhydride
C degrees Celsius CBZCl Benzyl chloroformate
DBU 1,8-Diazabicyclo[5.4.0]undec-7-ene
DCM Dichloromethane
DEAD Diethyl azodicarboxylate
(DHQ)2PHAL Hydroquinine 1,4-phthalazinediyl diether
DIAD Diisopropylazodicarboxylate
DIPEA Diisopropylethylamine
DMA N,N-Dimethylacetamide
DMAP 4-Dimethylaminopyridine
DME Dimethoxyethane
DMF Dimethylformamide
DMPU 1,3-Dimethyl-3,4,5,6-tetrahydro-2(1 h)-pyrimidinone
DMSO Dimethyl sulfoxide
EDCl 1-(3-Dimethylaminopropyl)-3-ethylcarbodiimide hydrochloride
EI Electron ionization
Eq Equivalents
EtOAc Ethyl acetate
EtOH Ethanol
g grams
h hours
hr hours
$^1$H proton
HATU N,N,N',N'-Tetramethyl-O-(7-Azabenzotriazol-1-yl) Uronium hexafluorophosphate
Hex hexanes
HOBT 1-Hydroxybenzotriazole
HPLC High pressure liquid chromatography
LAH Lithium aluminum hydride
LDA Lithium diisopropylamide
M Molar
mmol milimolar
mCPBA meta-Chloroperoxybenzoic acid
Me Methyl
MeCN Acetonitrile
MeOH Methanol
min Minutes
mg Milligrams
MHZ Megahertz
mL Milliliter
MPLC Medium Pressure Liquid Chromatography
NMR Nuclear Magnetic Resonance
MS Mass Spectroscopy
NBS N-Bromosuccinimide
NMM N-Methylmorpholine
NMP 1-methyl-2-pyrrolidone
ON Overnight
PCC Pyridinium Chlorochromate
PTLC Preparative thin layer chromatography
PyBrOP Bromo-tris-pyrrolidino-phosphonium hexafluorophosphate
Pyr Pyridine
RT Room temperature
sgc Silica gel 60 chromatography
tBOC tert-Butoxycarbonyl
TACE TNF-alpha converting enzyme
TEA Triethylamine
TFA Trifluoroacetic acid
THF Tetrahydrofuran
TLC Thin layer chromatography Example 300A

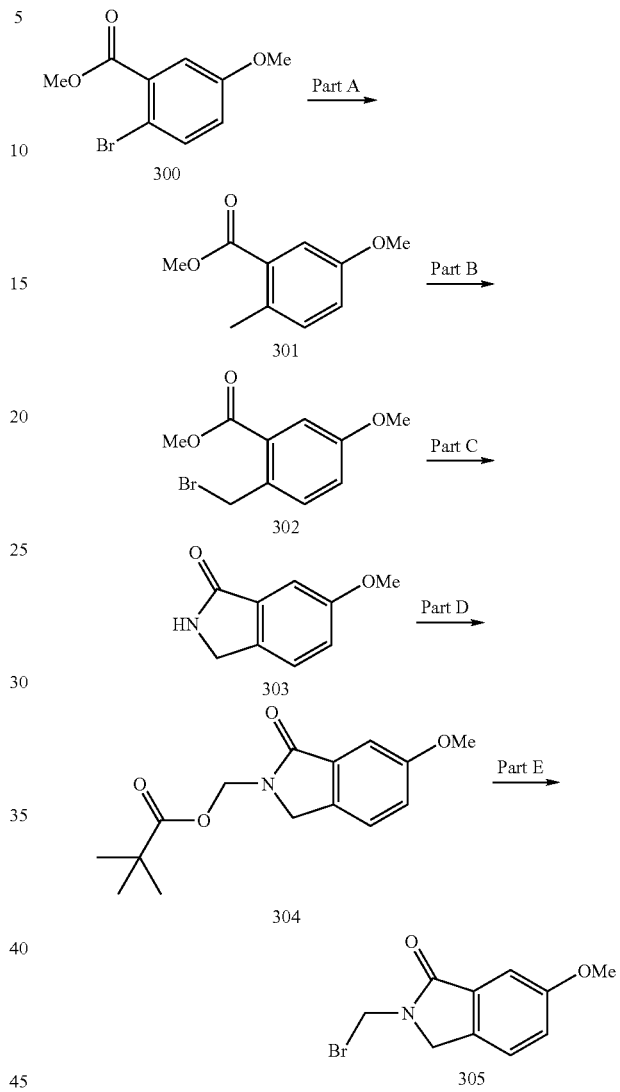

Part A:

Compound 300 (20.0 g, 81.61 mmol), trimethylboroxine (13.36 mL, 97.93 mmol), Pd(dppf)Cl$_2$ (1.0 g, 1.36 mmol), dioxane (350 mL), water (50 mL), and cesium carbonate (22.5 g, 163 mmol) were stirred at 110° C. (oil bath) under nitrogen for 16 hours. After cooling, the solid was removed by filtration. The solution was concentrated and purified by sgc (10:1 EtOAc/hexanes) to give 301 (12.1 g, 80%).

Part B:

Compound 301 (4.4 g, 24.2 mmol) was dissolved in carbon tetrachloride (80 mL) and N-bromosuccinimide (4.48 g, 24.2 mmol) and benzoyl peroxide (276 mg, 1.13 mmol) were added. The reaction mixture was stirred at reflux for 3 hours and then solids were filtered and washed with ether. The combined organic layers were washed with water, dried over sodium sulfate, and concentrated to provide the desired product 302 (6.1 g, 98%).

Part C:

Compound 302 (32.0 g, 124.0 mmol) was dissolved in 7 M ammonia in MeOH (150 mL) and stirred in a sealed pressure flask at 60° C. overnight. The reaction mixture was cooled and the solvent was removed under reduced pressure. The residue was suspended in ethyl acetate and stirred for 30 minutes. The solids were filtered and dissolved in methylene chloride. The methylene chloride was washed with water, dried over sodium sulfate, and concentrated to provide the desired product 303 (13.5 g, 67%).

Part D:

Compound 303 (2.2 g, 13.4 mmol) was dissolved in THF (250 mL) and DMPU (40 mL). Sodium t-butoxide (1.55 g, 16.13 mmol) was added and stirred for 5 hours. Chloromethylpivalate (3.0 mL, 20.1 mmol) was added dropwise and stirred overnight. The reaction was quenched with saturated ammonium chloride and extracted with ethyl acetate. The combined ethyl acetate layers were washed with water, brine, dried over sodium sulfate and concentrated. Purification by column chromatography ($SiO_2$, 25% ethyl acetate/hexanes) afforded the desired product 304 (2.5 g, 67%).

Part E:

Compound 304 (288 mg, 1.04 mmol) was dissolved in methylene chloride (5 mL) and cooled in an ice bath. Bromotrimethylsilane (0.3 mL, 2.08 mmol) was added dropwise and stirred in the ice bath for 30 minutes followed by 2 hours at room temperature. The reaction mixture was concentrated and re-dissolved in methylene chloride (2 mL). Hexanes (8 mL) was added and the solids were filtered to provide the desired product 305 (218 mg, 83%).

Example 300B

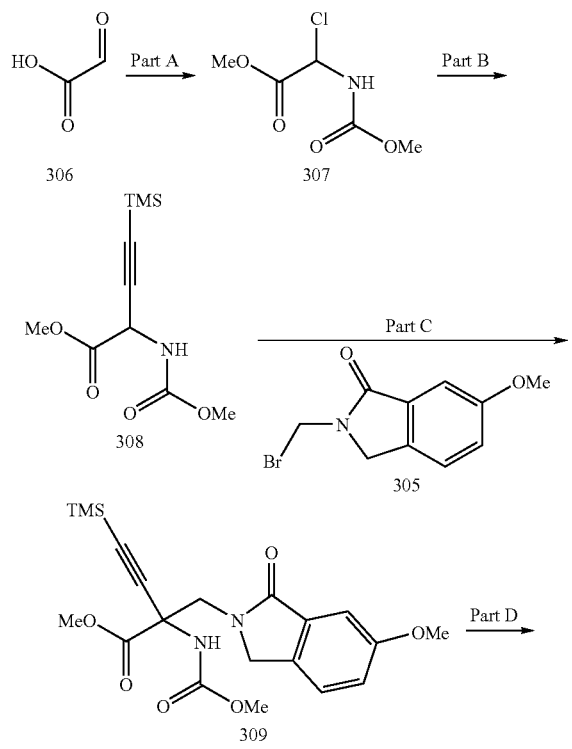

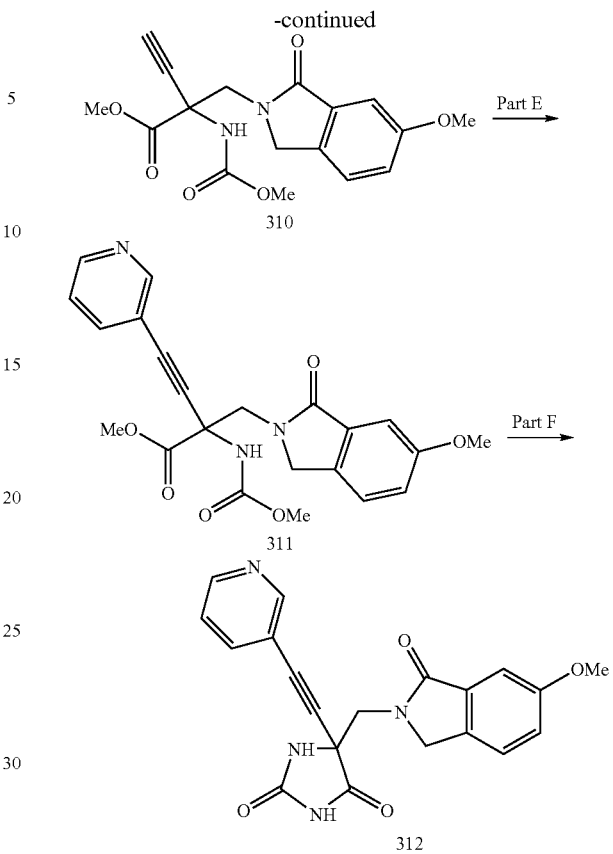

Part A:

Compound 307 was prepared from compound 306 using the procedure found in *Tetrahedron* 1975, 31, 863-866.

Part B:

Compound 308 was prepared from compound 307 using the procedure found in *J. Med. Chem.* 1981, 24, 16-20. HPLC-MS $t_R$=1.839 min (ELSD); mass calculated for formula $C_{10}H_{17}NO_4Si$ 243.09, observed LCMS m/z 244.1 (M+H).

Part C:

Diisopropylamine (0.80 mL, 5.8 mmol) and HMPA (2.3 mL) were dissolved in THF (10 mL) and cooled to −78° C. A solution of n-BuLi (2.5 M, 2.0 mL, 5 mmol) was added to the reaction dropwise and stirred for 20 minutes. Compound 308 (425 mg, 1.66 mmol) was dissolved in THF (5 mL) and added dropwise. After 20 minutes, compound 305 (470 mg, 1.83 mmol) in THF (10 mL) was added dropwise and the reaction was stirred for 2 hours at the same temperature. Saturated ammonium chloride solution was added slowly and the reaction was allowed to warm to room temperature. The aqueous layer was extracted with ethyl acetate. The combined organic layers were washed with water, brine, dried over sodium sulfate, and concentrated. Purification by column chromatography ($SiO_2$, 33% ethyl acetate/hexanes to 50% ethyl acetate/hexanes) afforded the desired product 309 (0.360 g, 52%). HPLC-MS $t_R$=1.904 min ($UV_{254\ nm}$); mass calculated for formula $C_{20}H_{26}N_2O_6Si$ 418.15, observed LCMS m/z 419.2 (M+H).

Part D:

Compound 309 (100 mg, 0.23 mmol) was dissolved in THF (5 mL) and cooled to 0° C. Tetrabutylammonium fluoride (1 M in THF, 0.3 mL, 0.3 mmol) was added dropwise and the reaction was stirred for 1 hour at room temperature. The reaction mixture was diluted with ethyl acetate and water. The organic layer was washed with water, saturated sodium bicarbonate, brine, dried over sodium sulfate and concentrated to provide compound 310 (70 mg, 88%). The product was used without purification.

Part E:

Compound 310 (627 mg, 1.87 mmol) was combined with 3-iodopyridine (561 mg, 2.8 mmol), Pd(dppf)Cl$_2$ (76 mg, 0.093 mmol), X-PHOS (88 mg, 0.186 mmol), piperidine (321 mg, 3.74 mmol) in acetonitrile (20 mL) and stirred overnight at 80° C. The reaction mixture was cooled to room temperature and concentrated. Purification by column chromatography (SiO$_2$, ethyl acetate to 2% methanol/ethyl acetate) afforded the desired product 311 (0.630 g, 80%). HPLC-MS $t_R$=1.389 min (UV$_{254\ nm}$); mass calculated for formula $C_{22}H_{21}N_3O_6$ 423.14, observed LCMS m/z 424.1 (M+H).

Part F:

Compound 311 (60 mg, 0.14 mmol) was dissolved in 7 M ammonia in methanol solution (5 mL) and stirred in a sealed pressure tube at 90° C. overnight. The reaction mixture was cooled to room temperature and concentrated. Trituration with ethyl acetate provided the desired product 312 (49.5 mg, 93%). HPLC-MS $t_R$=1.086 min (UV$_{254\ nm}$); mass calculated for formula $C_{20}H_{16}N_4O_4$ 376.11, observed LCMS m/z 377.0 (M+H).

Example 300C

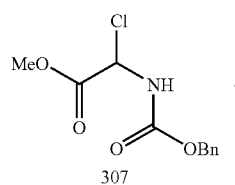

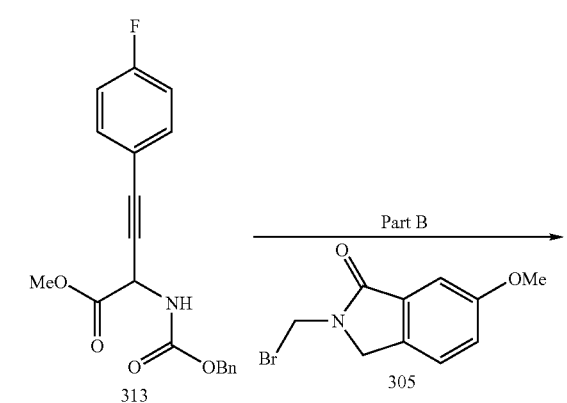

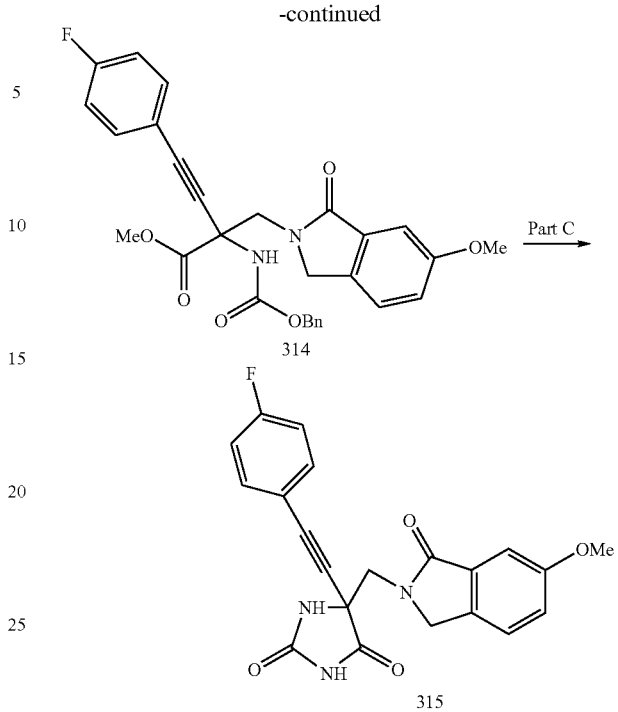

Part A:

Compound 313 was prepared using the procedure found in *J. Org. Chem.* 1990, 55, 4657-4663.

Part B:

Compound 314 was prepared using a procedure found in Part C of Example 300B.

Part C:

Compound 314 (100 mg, 0.23 mmol) was dissolved in 7 M ammonia in methanol solution (5 mL) and stirred in a sealed pressure tube at 90° C. overnight. The reaction mixture was cooled to room temperature and concentrated. Trituration with ethyl acetate provided the desired product (57 mg, 63%). HPLC-MS $t_R$=1.533 min (UV$_{254\ nm}$); mass calculated for formula $C_{21}H_{16}N_3O_4F$ 393.1, observed LCMS m/z 394.1 (M+H).

Example 400

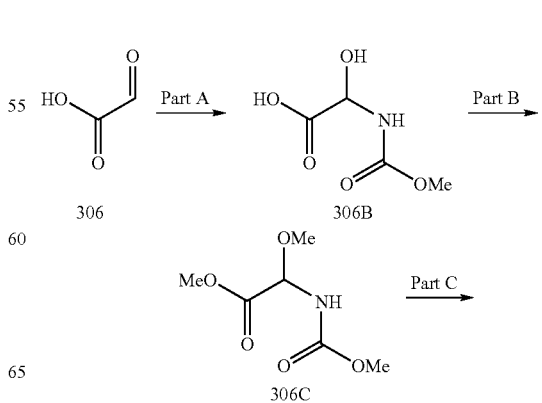

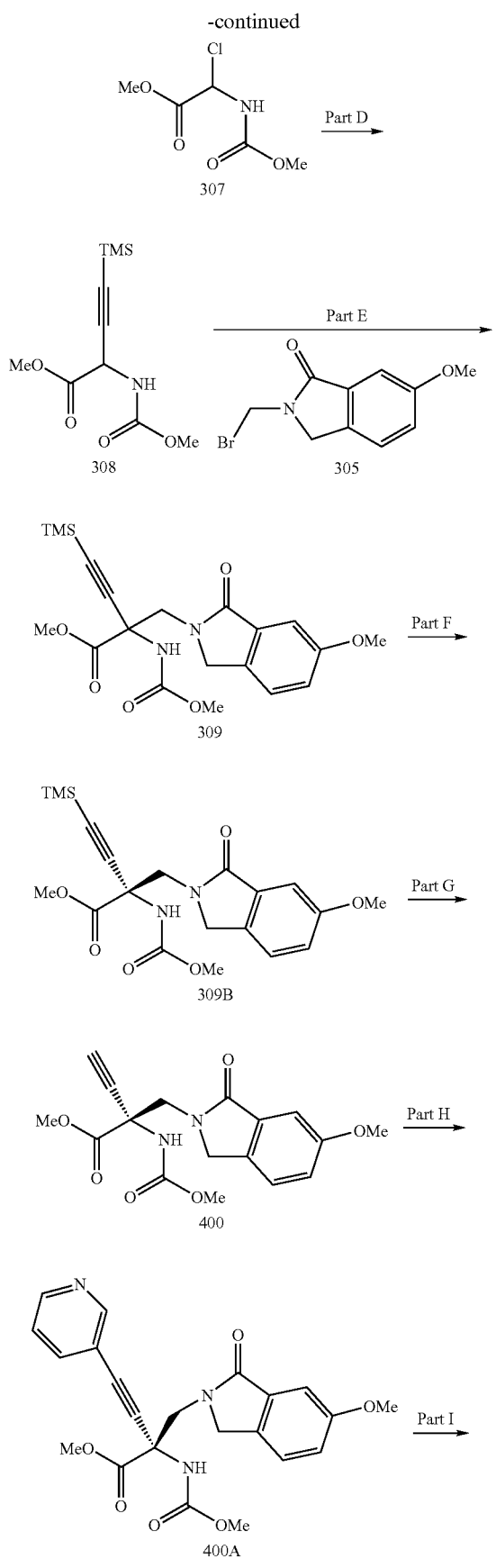

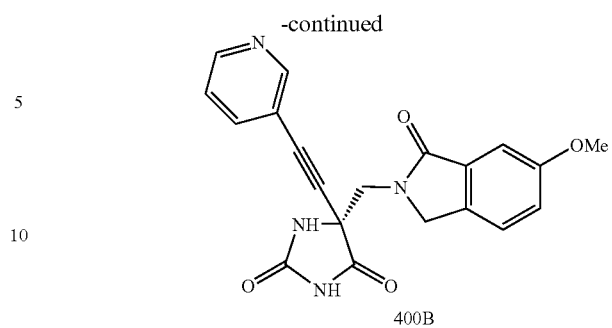

400B

Part A:

Glyoxylic acid monohydrate (20.0 g, 218 mmol) and methyl carbamate (16.3 g, 218 mmol) were dissolved in diethyl ether (200 mL) and stirred overnight. The solids were filtered to provide the desired product 306B (32.0 g, 98%).

Part B:

Compound 306B (32.0 g, 214 mmol) was dissolved in MeOH (200 mL) and cooled in an ice bath. Concentrated sulfuric acid (8 mL) was added dropwise and the reaction was stirred overnight. The reaction mixture was diluted with ethyl acetate and water. The organic layer was washed with brine, dried over sodium sulfate, and concentrated to provide compound 306C that was used without purification (27.0 g, 71%).

Part C:

Compound 306C (27.0 g, 152 mmol) was dissolved in carbon tetrachloride (700 mL). Phosphorus pentachloride (50 g, 240 mmol) was added and the suspension was stirred for 18 hours (solution became clear over time). The solvent was removed under reduced pressure and the residue was stirred in petroleum ether (500 mL) overnight. The solids were filtered to provide compound 307 with no need for purification (26.5 g, 96%). Trituration step was repeated if mass yield was too high.

Part D:

Compound 307 (15.0 g, 82.7 mmol) was dissolved in methylene chloride (140 mL) and cooled in an ice bath. Bis(trimethylsilyl)acetylene (15.0 g, 88.2 mmol) was added in methylene chloride (20 mL). Freshly crushed aluminum chloride (11.0 g, 82.7 mmol) was added in portions over 20 minutes. The reaction mixture was allowed to slowly warm to room temperature and stirred overnight. The reaction was cooled in an ice bath and slowly quenched with water. The organic layer was washed several times with water, dried over sodium sulfate, and concentrated. The residue was triturated/recrystallized from hexanes to provide the desired product 308 (14.8 g, 69%). HPLC-MS $t_R$=1.84 min (ELSD); mass calculated for formula $C_{10}H_{17}NO_4Si$ 243.09, observed LCMS m/z 244.1 (M+H).

Part E:

Compound 308 (24.0 g, 98.7 mmol) and compound 305 (25.1 g, 99.0 mmol) were dissolved in THF (300 mL) and cooled to −78° C. A 1M solution of LiHMDS (198 mL, 198 mmol) was added dropwise over 30 minutes and the reaction mixture was stirred for 2 hours. Saturated ammonium chloride solution was added slowly and the reaction was allowed to warm to room temperature. The aqueous layer was extracted with ethyl acetate. The combined organic layers were washed with water, brine, dried over sodium sulfate, and concentrated. Purification by column chromatography (SiO₂, 33% ethyl acetate/hexanes to 50% ethyl acetate/hexanes) afforded the desired product 309 (26.0 g, 63%). HPLC-MS $t_R$=1.90 min (UV$_{254\ nm}$); mass calculated for formula $C_{20}H_{26}N_2O_6Si$ 418.15, observed LCMS m/z 419.2 (M+H).

The synthesis for compound 305 was described in Example 300A.

Part F:

The two isomers were separated using a chiral OD column. One gram of material was injected into the column and the two peaks were separated by using a solvent mixture of 85% hexanes/ethanol. The second isomer was the desired compound 309B (400 mg, 80%).

Part G:

Compound 309B (8.0 g, 19.1 mmol) was dissolved in THF (250 mL) and cooled to 0° C. Tetrabutylammonium fluoride (1 M in THF, 22.9 mL, 22.9 mmol) was added dropwise and the reaction was stirred for 1 hour at room temperature. The reaction mixture was diluted with ethyl acetate and water. The organic layer was washed with water, saturated sodium bicarbonate, brine, dried over sodium sulfate and concentrated to provide compound 400 (5.8 g, 88%). The product was used without purification.

Part H:

Compound 400 (500 mg, 1.45 mmol) was combined with 3-iodopyridine (434 mg, 2.16 mmol), Pd(PPh$_3$)$_2$Cl$_2$ (50 mg, 0.072 mmol), CuI (14 mg, 0.072 mmol), diisopropylamine (0.4 mL, 2.9 mmol) in DMF (5 mL) and stirred overnight at room temperature. The reaction mixture was diluted with ethyl acetate and water. The organic layer was washed with water, brine, dried over sodium sulfate and concentrated. Purification by column chromatography (SiO$_2$, ethyl acetate to 2% methanol/ethyl acetate) afforded the desired product 400A (0.520 g, 84%). HPLC-MS $t_R$=1.39 min (UV$_{254\ nm}$); mass calculated for formula $C_{22}H_{21}N_3O_6$ 423.14, observed LCMS m/z 424.1 (M+H).

Part I:

Compound 400A (480 mg, 1.13 mmol) was dissolved in 7 M ammonia solution (5 mL) and stirred in a sealed pressure tube at 90° C. overnight. The reaction mixture was cooled to room temperature and concentrated. The residue was treated with 1M HCl (2 mL) and then diluted with acetonitrile (10 mL) and water (3 mL). The solvent was removed by lyophilization to provide compound 400B as the HCl salt (437.4 mg, 93%). HPLC-MS $t_R$=1.09 min (UV$_{254\ nm}$); mass calculated for formula $C_{20}H_{16}N_4O_4$ 376.11, observed LCMS m/z 377.0 (M+H).

Example 401

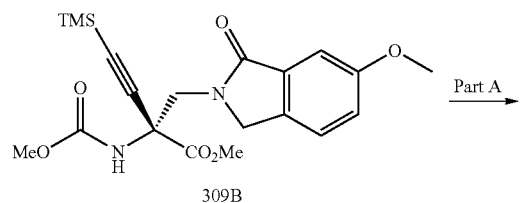

309B

-continued

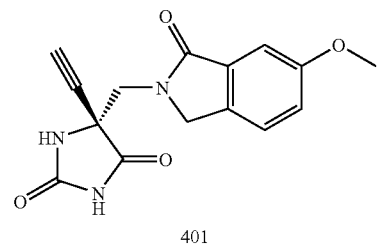

401

Part A:

Compound 309B (1.26 g, 3.0 mmol) in 7 M ammonia in methanol (20 mL) was heated to 85° C. in a pressure bottle overnight. The reaction mixture was concentrated to afford 401 (900 mg, 100%) which was used without further purification. HPLC-MS $t_R$=1.00 min (UV$_{254\ nm}$); mass calculated for formula $C_{15}H_{13}N_3O_4$ 299.09, observed LCMS m/z 300.1 (M+H).

Example 402

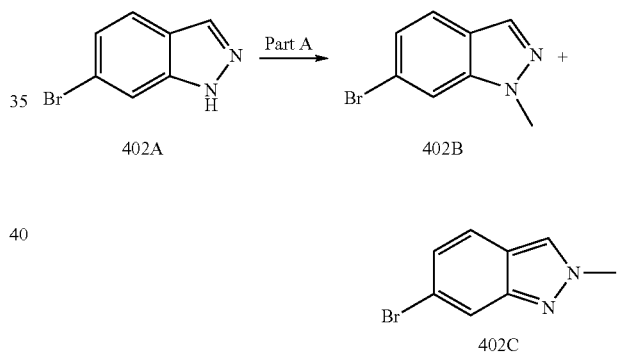

Part A:

To 6-bromoindazole (402A) (5.0 g, 25.4 mmol) in THF (50 mL) was added sodium hydride (95%, 672 mg, 26.6 mmol) with ice bath cooling. The mixture was stirred for 30 minutes. Methyl iodide (6.36 mL, 102 mmol) was added at room temperature. The reaction mixture was quenched with ammonium chloride solution and the layers were separated. The aqueous layer was extracted with ethyl acetate. The combined organic layer was washed with brine, dried over sodium sulfate and concentrated. Purification by column chromatography (SiO$_2$, ethyl acetate/hexane gradient) afforded 1-methyl-6-bromoindazole (402B) (2.71 g, 51%) as a yellow oil and 2-methyl-6-bromoindazole (402C) (2.28 g, 43%) as a yellow crystalline solid.

402B: HPLC-MS $t_R$=1.69 min (UV$_{254\ nm}$); mass calculated for formula $C_8H_7BrN_2$ 209.98, observed LCMS m/z 211.0 (M+H).

402C: HPLC-MS $t_R$=1.54 min (UV$_{254\,nm}$); mass calculated for formula $C_8H_7BrN_2$ 209.98, observed LCMS m/z 211.0 (M+H).

Example 403

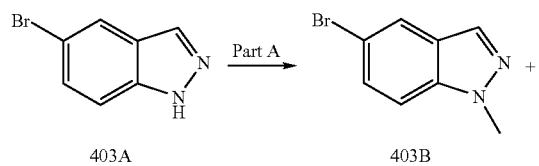

Part A:

Using the procedure described in Example 402 403B (53%) and 403C (39% were prepared.

403B: HPLC-MS $t_R$=1.69 min (UV$_{254\,nm}$); mass calculated for formula $C_8H_7BrN_2$ 209.98, observed LCMS m/z 211.0 (M+H).

403C: HPLC-MS $t_R$=1.46 min (UV$_{254\,nm}$); mass calculated for formula $C_8H_7BrN_2$ 209.98, observed LCMS m/z 211.0 (M+H).

Example 409

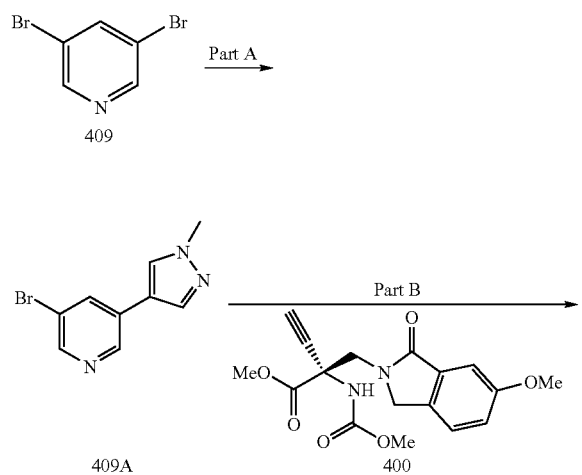

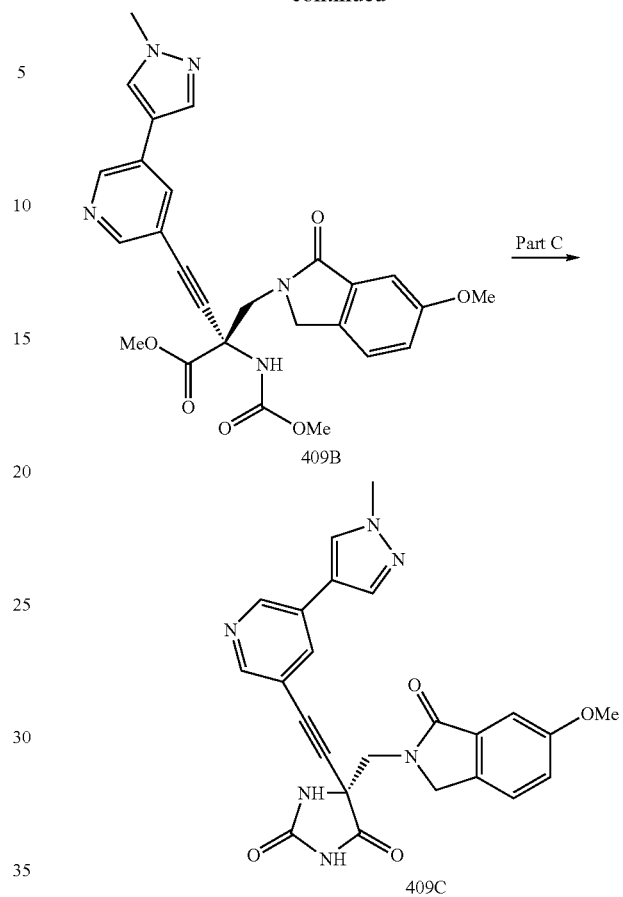

Part A:

Compound 409 (545 mg, 2.3 mmol) was combined with 1-methyl-4-(4,4,5,5-tetramethyl-1,3,2-dioxaborolan-2-yl)-1H-pyrazole (526 mg, 2.53 mmol), PdCl$_2$dppf.CH$_2$Cl$_2$ (94 mg, 0.11 mmol) and K$_3$PO$_4$ (1.46 g, 6.9 mmol) in 1,4-dioxane (10 mL) and heated overnight at 80° C. The reaction mixture was diluted with ethyl acetate and filtered through Celite. The organic filtrate was concentrated and purified by column chromatography (SiO$_2$, 50% to 80% ethyl acetate/hexane to ethyl acetate) to afford desired product 409A (0.250 g, 46%) as a yellow solid. HPLC-MS $t_R$=1.24 min (UV$_{254\,nm}$); mass calculated for formula $C_9H_8BrN_3$ 236.99, observed LCMS m/z 238.1, 240.0 (M+H, Br isotope).

Part B:

Compound 409B was prepared using procedures described in Example 400, part H. Purification by column chromatography (SiO$_2$, ethyl acetate to 5% methanol/ethyl acetate) afforded the desired product 409B (0.1 g, 59%). HPLC-MS $t_R$=1.38 min (UV$_{254\,nm}$); mass calculated for formula $C_{26}H_{25}N_5O_6$ 503.18, observed LCMS m/z 504.2 (M+H).

Part C:

Compound 409C was prepared using procedures described in Example 400, part I. Purification by reverse-phase prepLC afforded the desired product 409C (46 mg, 50%). HPLC-MS $t_R$=1.14 min (UV$_{254\ nm}$); mass calculated for formula C$_{24}$H$_{20}$N$_6$O$_4$ 456.15, observed LCMS m/z 457.1 (M+H).

Example 410

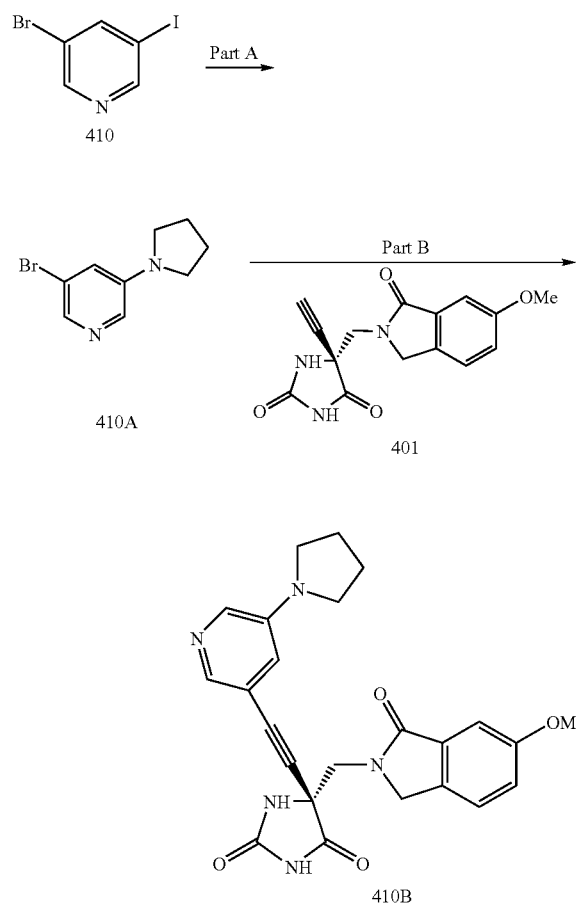

Part A:

According to a modification of a procedure by Xue, C-B et. al. (WO 2006/004741) a mixture of compound 410 (1.0 g, 3.52 mmol), pyrrolidine (0.31 mL, 3.7 mmol), CuI (67 mg, 0.35 mmol), K$_3$PO$_4$ (1.57 g, 7.4 mmol) and ethylene glycol (0.4 mL, 7.04 mmol) in isopropanol (10 mL) was heated at 85° C. in a sealed tube for 60 h. The reaction mixture was diluted with ethyl acetate and filtered through Celite. The organic filtrate was concentrated and purified by column chromatography (SiO$_2$, 10% to 30% ethyl acetate/hexane) to afford desired product 410A (0.39 g, 49%) as a white solid. HPLC-MS $t_R$=1.26 min (UV$_{254\ nm}$); mass calculated for formula C$_9$H$_{11}$BrN$_2$ 226.01, observed LCMS m/z 227.1, 229.1 (M+H, Br isotope).

Part B:

Compound 410B was prepared using procedures described in Example 400, part H. Purification by reverse-phase prepLC afforded the desired product 410B (54 mg, 24%). HPLC-MS $t_R$=1.11 min (UV$_{254\ nm}$); mass calculated for formula C$_{24}$H$_{23}$N$_5$O$_4$ 445.18, observed LCMS m/z 446.2 (M+H).

Example 412

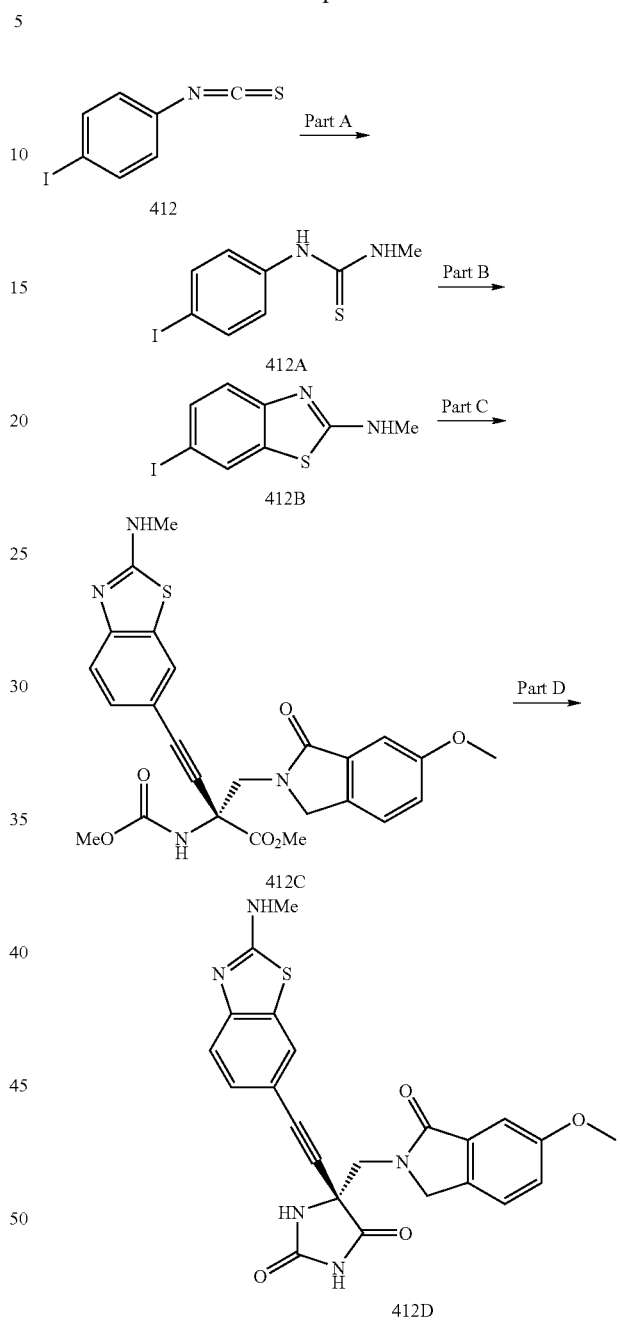

Part A:

Compound 412 (500 mg, 1.92 mmol) was dissolved in methylene chloride (15 mL) and triethylamine (0.53 mL, 3.84 mmol). Methylamine hydrochloride (186 mg, 2.3 mmol) was added and the solution was stirred for two hours. The reaction mixture was washed with water and the organic layer was dried over sodium sulfate and concentrated to provide compound 412A (430 mg, 77%).

Part B:

Compound 412A (430 mg, 1.47 mmol) was dissolved in acetic acid (10 mL) and bromine (0.091 mL, 1.76 mmol) was added dropwise. The reaction mixture was stirred overnight at room temperature. The solvent was removed and the residue was dissolved in ethyl acetate and water. The organic layer was dried over sodium sulfate and concentrated to provide the desired product (230 mg, 43%). HPLC-MS $t_R$=1.53 min (UV$_{254\,nm}$); mass calculated for formula $C_8H_7IN_2S$ 290.12, observed LCMS m/z 291.0 (M+H).

Part C:

See Example 400, Part H for similar experimental procedure. HPLC-MS $t_R$=1.47 min (UV$_{254\,nm}$); mass calculated for formula $C_{25}H_{24}N_4O_6S$ 508.55, observed LCMS m/z 509.1 (M+H).

Part D:

See Example 400, Part I for similar experimental procedure. HPLC-MS $t_R$=1.19 min (UV$_{254\,nm}$); mass calculated for formula $C_{23}H_{19}N_5O_4S$ 461.49, observed LCMS m/z 462.1 (M+H).

Example 413

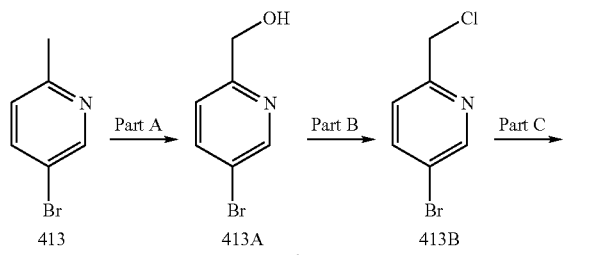

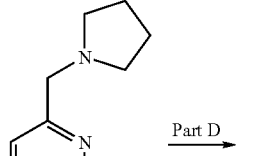

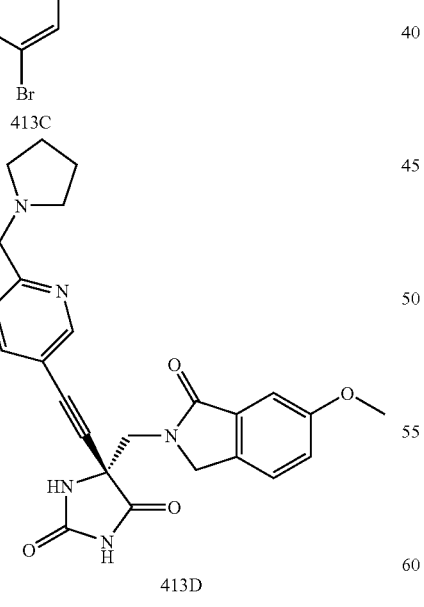

Part A:

Compound 413 (3.5 g, 20.7 mmol) was dissolved in methylene chloride (100 mL) and m-CPBA (4.95 g, 28.9 mmol) was added. The reaction mixture was stirred for two hours and then quenched with saturated sodium carbonate and stirred overnight. The organic layer was dried over sodium sulfate and the concentrated to provide a yellow solid (3.8 g). The solid was placed under argon and trifluoroacetic anhydride (15 mL) was added slowly. The reaction was stirred for 30 minutes at room temperature and then refluxed for 30 minutes. The reaction was cooled to room temperature and quenched slowly with saturated sodium bicarbonate. Methylene chloride was added and the organic layer was washed dried over sodium sulfate and concentrated. Column chromatography (2 to 1 ethyl acetate/hexanes) provided the desired product (3.0 g, 78%).

$^1$H NMR (400 MHz, CDCl$_3$) δ 8.65 (d, 1H), 7.8 (m, 1H), 7.2 (d, 1H), 4.7 (s, 2H).

Part B:

Compound 413A (500 mg, 2.7 mmol) was dissolved in methylene chloride (5 mL) and cooled in an ice bath. Thionyl chloride (480 mg, 4.05 mmol) was added dropwise and stirred at room temperature for 3 hours. The reaction was quenched with saturated sodium bicarbonate. The organic layer was dried over sodium sulfate and concentrated to provide the desired product (510 mg, 92%).

Part C:

Compound 413B (255 mg, 1.25 mmol) was dissolved in DMF (8 mL) and cesium carbonate (812 mg, 2.5 mmol) and pyrrolidine (108 mg, 1.5 mmol) added. The reaction mixture was stirred at 80° C. for one hour. The reaction was diluted with ethyl acetate and water. The organic layer was dried over sodium sulfate and concentrated to provide the desired product (250 mg, 81%).

$^1$H NMR (400 MHz, CDCl$_3$) δ 8.6 (d, 1H), 7.8 (m, 1H), 7.35 (d, 1H), 3.75 (s, 2H), 2.55 (m, 2H), 1.8 (m, 2H).

Part D:

Compound 401 (100 mg, 0.334 mmol), 413C (104 mg, 0.43 mmol), Pd(PPh$_3$)$_2$Cl$_2$ (15 mg, 0.021 mmol), CuI (8 mg, 0.041 mmol), diisopropylamine (0.1 mL) and DMF (1 mL) were stirred overnight at 80° C. The solvent was evaporated and the residue was washed with ethyl acetate and water. The remaining residue was purified by reverse phase HPLC to provide the desired product (50 mg, 32%). HPLC-MS $t_R$=0.981 min (UV$_{254\,nm}$); mass calculated for formula $C_{25}H_{25}N_5O_4$ 459.50, observed LCMS m/z 460.2 (M+H).

Example 414

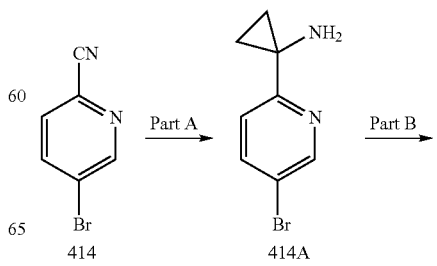

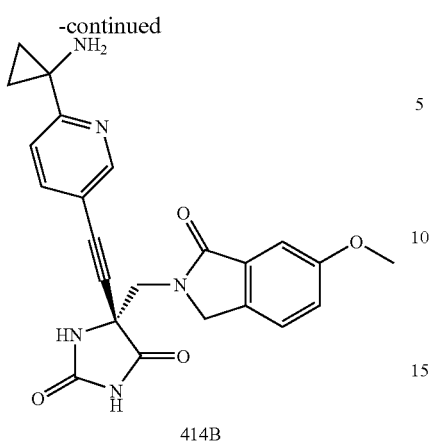

414B

Part A:

Compound 414 (1.0 g, 5.46 mmol) was suspended in diethylether (30 mL) and cooled to −78° C. Titanium (IV) isopropoxide (1.7 mL, 6.01 mmol) was added dropwise and stirred for 5 minutes. Ethyl magnesium bromide (3M in diethylether, 4.0 mL) was added dropwise and stirred for 30 minutes at the same temperature and 1 hour at room temperature. Boron trifluoride dietherate (1.55 g, 10.92 mmol) was added dropwise and the reaction was stirred for 2 hours. The reaction was quenched with 1M hydrochloric acid and the aqueous layer was washed with diethyl ether. The aqueous layer was made basic (pH=10) and extracted with ethyl acetate. The organic layer was dried over sodium sulfate and concentrated. Column chromatography (1:1 hexanes/ethyl acetate) provided the desired product (350 mg, 30%).

$^1$H NMR (400 MHz, CDCl$_3$) δ 8.5 (d, 1H), 7.7 (m, 1H), 7.3 (d, 1H), 1.25 (m, 2H), 1.15 (m, 2H).

Part B:

See Example 413, Part D for similar experimental. HPLC-MS $t_R$=0.85 min (UV$_{254\ nm}$); mass calculated for formula C$_{23}$H$_{21}$N$_5$O$_4$ 431.44, observed LCMS m/z 432.1 (M+H).

Example 555

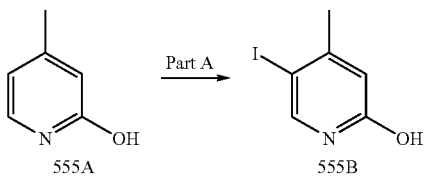

Part A:

Compound 555B was prepared according to a modification of a procedure described in WO-9846609. A mixture of 2-hydroxy-4-methylpyridine 555A (1.50 g, 13.7 mmol), iodine (3.68 g, 13.7 mmol) and sodium carbonate (3.06 g, 28.9 mmol) in water (70 mL) was heated at 70° C. overnight. The mixture was acidified with concentrated HCl to pH=3, and the resulting brown solid residue was washed twice with ethyl acetate, and then taken in hot ethanol. The solid which did not dissolve (diiodo byproduct) was filtered off, and the ethanol filtrate was concentrated to give the desired product 555B as a white solid (0.67 g, 21%); HPLC-MS $t_R$=1 min (UV$_{254\ nm}$); mass calculated for formula C$_6$H$_6$INO 234.95, observed LCMS m/z 236.0.

Example 1039

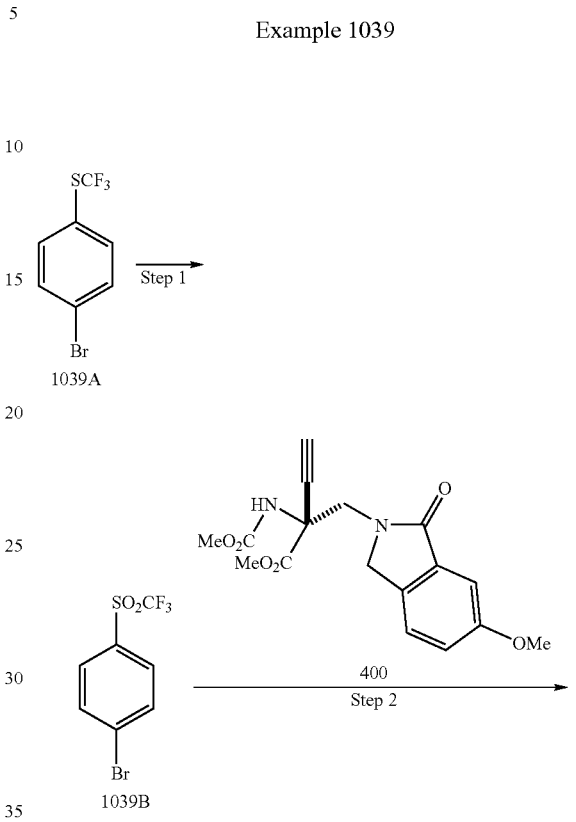

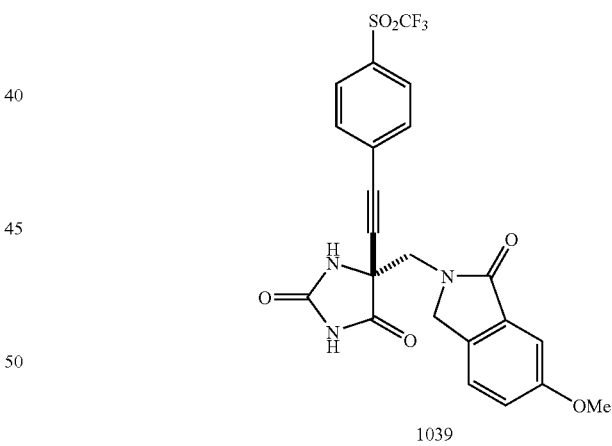

1039

Step 1 mCPBA (3.49 g, 77%, 15.6 mmol) was added to an ice-cold solution of Compound 1039A (1 g, 3.9 mmol) in CH$_2$Cl$_2$ (19 mL). The reaction mixture was allowed to warm to rt, and was stirred overnight. The mixture was diluted with CH$_2$Cl$_2$ and was washed sequentially with saturated aq sodium bicarbonate and brine. The organic solution was dried over MgSO$_4$, filtered and concentrated. The resulting crude product was purified by sgc (0-50% EtOAc-hexanes gradient) to afford Compound 1039B (787 mg, 70%).

Step 2

Compounds 1039B and 400 were converted to Compound 1039 by applying the procedure described for Examples 300A and 300B.

Example 1055

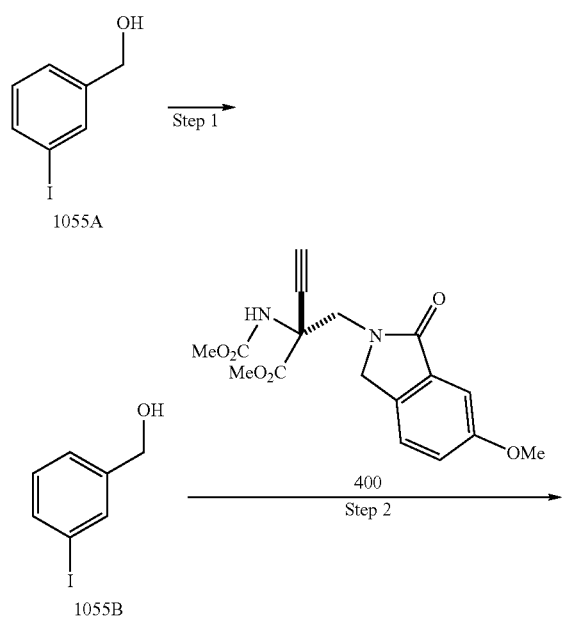

Example 1061

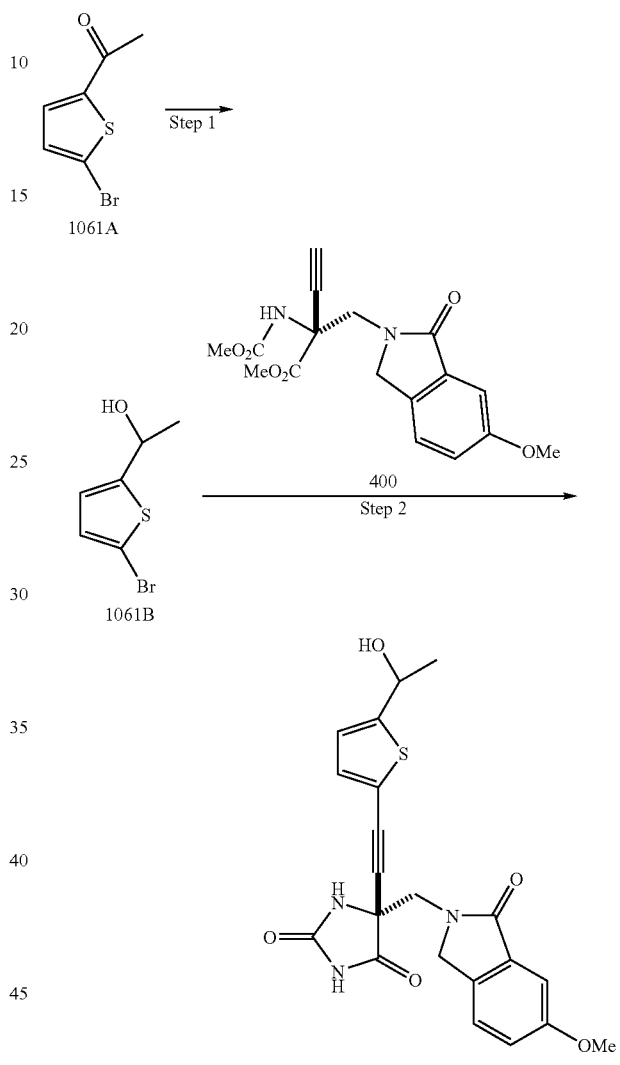

Step 1

A solution of Compound 1055A (300 mg, 1.28 mmol) in DMF (4.3 mL) was treated with solid cesium carbonate (835 mg, 2.56 mmol) followed by iodomethane (0.09 mL, 218 mg, 1.54 mmol). The reaction mixture was stirred overnight at rt. The reaction mixture was diluted with EtOAc, then washed sequentially with water (3×) and brine. The organic layer was dried over anhydrous MgSO4, filtered, and concentrated. The residue was purified by sgc (0-50% EtOAc-hexanes gradient) to afford Compound 1055B (150 mg).

Step 2

Compounds 1055B and 400 were converted to Compound 1055 by applying the procedure described for Examples 300A and 300B.

Compounds 1046, 1050, 1057, 1058, and 1059 were prepared using the same procedure as for Compound 1055.

Example 1061

Step 1

Compound 1061A (620 mg, 3.02 mmol) was dissolved in methanol (30 mL) and the solution was cooled to 0° C. Solid sodium borohydride (230 mg, 6.04 mmol) was added in small portions. The resulting cloudy reaction mixture was stirred at 0° C. for 40 min. The reaction was quenched by dropwise addition of glacial acetic acid (0.4 mL). Solvents were removed under reduced pressure, and the resulting white solid was partitioned between EtOAc (100 mL) and water (50 mL). The aqueous layer was extracted once more with EtOAc (~25 mL). The combined organic layers were washed with brine (25 mL), dried over anhydrous MgSO$_4$, filtered, and concentrated to afford a colorless oil. The crude product was purified by sgc (10-40% EtOAc-hexanes gradient) to give Compound 1061B (591 mg, 95%) as a clear, colorless oil.

Step 2

Compounds 1061B and 400 were converted to Compound 1061 by applying the procedure described for Examples 300A and 300B.

The same procedure was used for the preparation of Compounds 1075, 1078 and 1079.

Example 1070

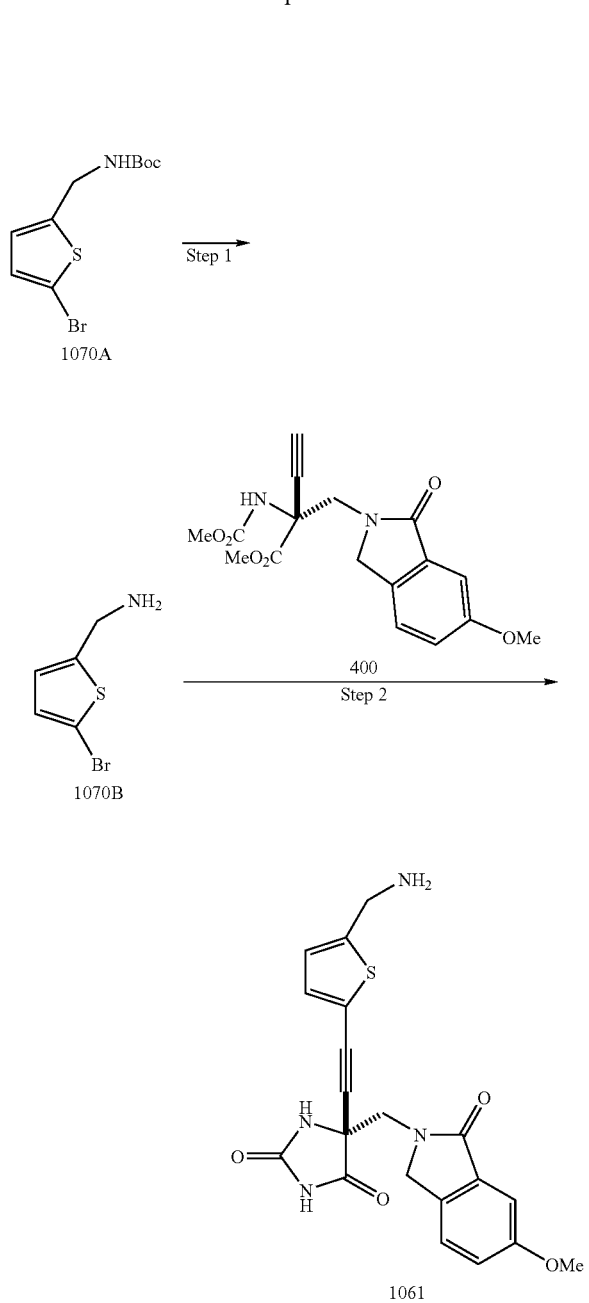

1061

Step 1

HCl (17 mL, 4 M in dioxane, 68 mmol) was added to an ice-cold solution of Compound 1070A in CH$_2$Cl$_2$ (27 mL). The reaction mixture was stirred at 0° C. for 30 min, and at rt for 18 h. The solvent was concentrated to dryness to give Compound 1070B as an off-white solid (1.51 g).

Step 2

Compounds 1070B and 400 were converted to Compound 1070 by applying the procedure described for Examples 300A and 300B.

Example 1071

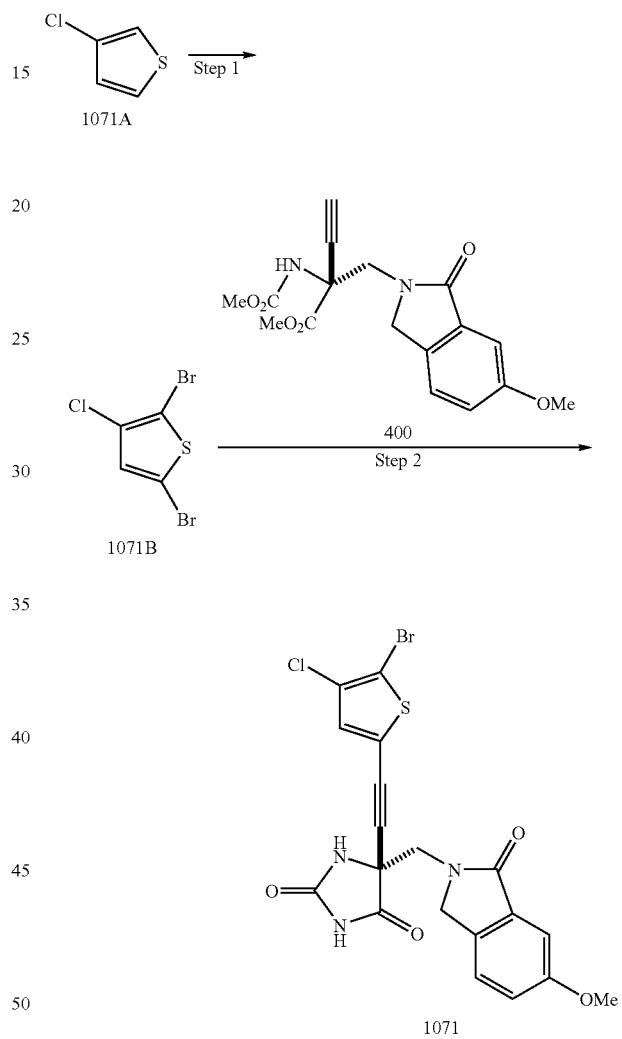

1071

Step 1

Neat bromine (1.4 mL, 28 mmol, 1.1 eq) was added dropwise to a stirred solution of Compound 1071A (3.0 g, 26 mmol) in dioxane (8 mL) at 0° C. Upon completion of the addition, the reaction mixture was heated at 60° C. for 18 h. The reaction mixture was diluted with Et$_2$O (50 mL), and was washed sequentially with saturated aq sodium bicarbonate (50 mL) and brine (~50 mL). The organic phase was dried over anhydrous MgSO$_4$, filtered, and concentrated. The desired product, Compound 1071B, was separated from the crude product by sgc (0-10% EtOAc-hexanes). Yield: 0.987 g, 15% yield.

281

Step 2

Compounds 1071B and 400 were converted to Compound 1071 by applying the procedure described for Examples 300A and 300B.

Example 1077

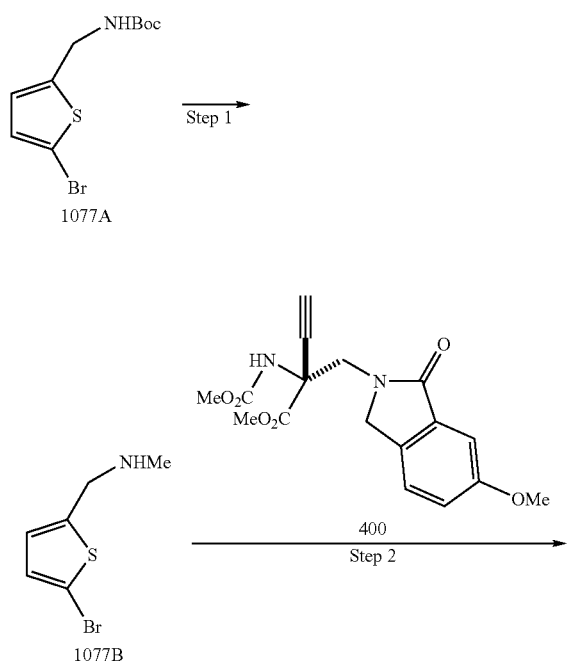

Step 1

A solution of Compound 1077A (200 mg, 0.68 mmol) in DMF (3 mL) was treated with sodium hydride (41 mg, 60% dispersion in oil; 0.82 mmol) followed by iodomethane (0.05 mL, 117 mmol). The reaction mixture was stirred for 3 d. The reaction mixture was diluted with EtOAc and washed sequentially with water and brine. The organic layer was dried over anhydrous MgSO$_4$, filtered and concentrated to dryness to afford an intermediate (191 mg). This intermediate was re-dissolved in CH$_2$Cl$_2$ and treated with HCl solution (0.78 mL).

282

The solution was stirred at rt overnight, then concentrated to afford the desired product (152 mg, 100% yield (HCl salt)), which was used without further purification.

Step 2

Compounds 1077B and 400 were converted to Compound 1077A by applying the procedure described for Examples 300A and 300B.

Example 1080

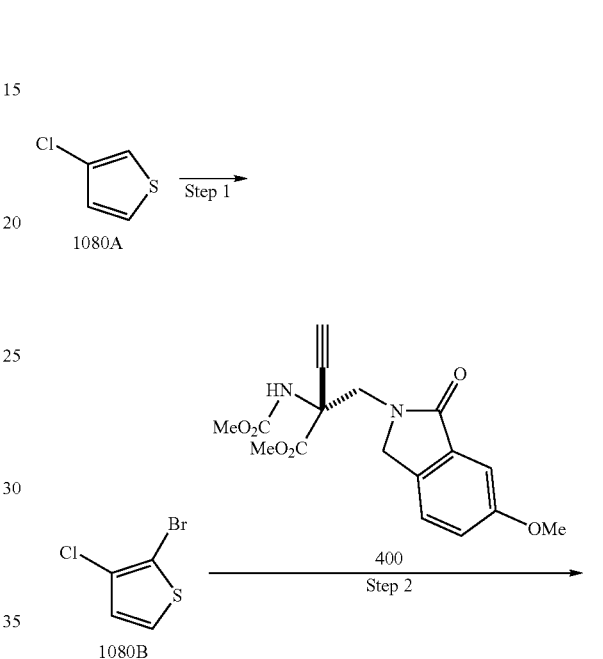

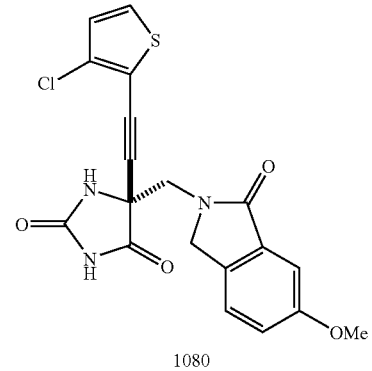

Neat bromine (0.8 mL, 24 mmol, 0.9 eq) was added dropwise over ~20 min to a stirred solution of Compound 1080A (2.00 g, 0.026 mmol) in carbon tetrachloride (4 mL) at 0° C. Upon completion of the addition, the reaction mixture was heated at 60° C. for 18 h. The reaction mixture was diluted with Et$_2$O (50 mL), and was washed sequentially with saturated aq sodium bicarbonate (50 mL) and brine (~50 mL). The organic phase was dried over anhydrous MgSO$_4$, filtered, and concentrated. The desired product 1080B was purified by sgc (100% hexanes, isocratic) to give Compound 1080B as a clear, colorless liquid (1.78 g, 53%)

283

Step 2

Compounds 1080B and 400 were converted to Compound 1080 by applying the procedure described for Examples 300A and 300B.

Example 1081

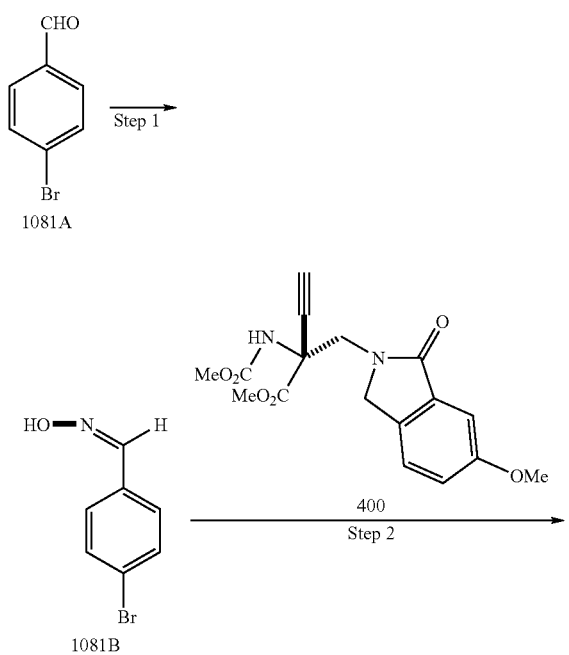

Step 1

A pressure tube containing a mixture of Compound 1081A (500 mg, 2.7 mmol) hydroxylamine hydrochloride (375 mg, 5.40 mmol), and sodium acetate (443 g, 5.6 mmol) in absolute ethanol (10 mL) was heated, with stirring, at 80° C. for 18 h. The mixture was allowed to cool, after which the solvent was removed. The residue was redissolved in EtOAc, and was washed with water and brine. The organic layer was dried over anhydrous MgSO4, filtered, and concentrated. The product was purified by PTLC (5% EtOAc-hexanes) to give Compound 1081B (504 mg, 93%).

284

Step 2

Compounds 1081B and 400 were converted to Compound 1081 by applying the procedure described for Examples 300A and 300B.

Analogous procedures were used for the preparation of Compounds 1082, 1083, 1084, 1085, 1086, 1089, 1090, and 1091.

Example 1095

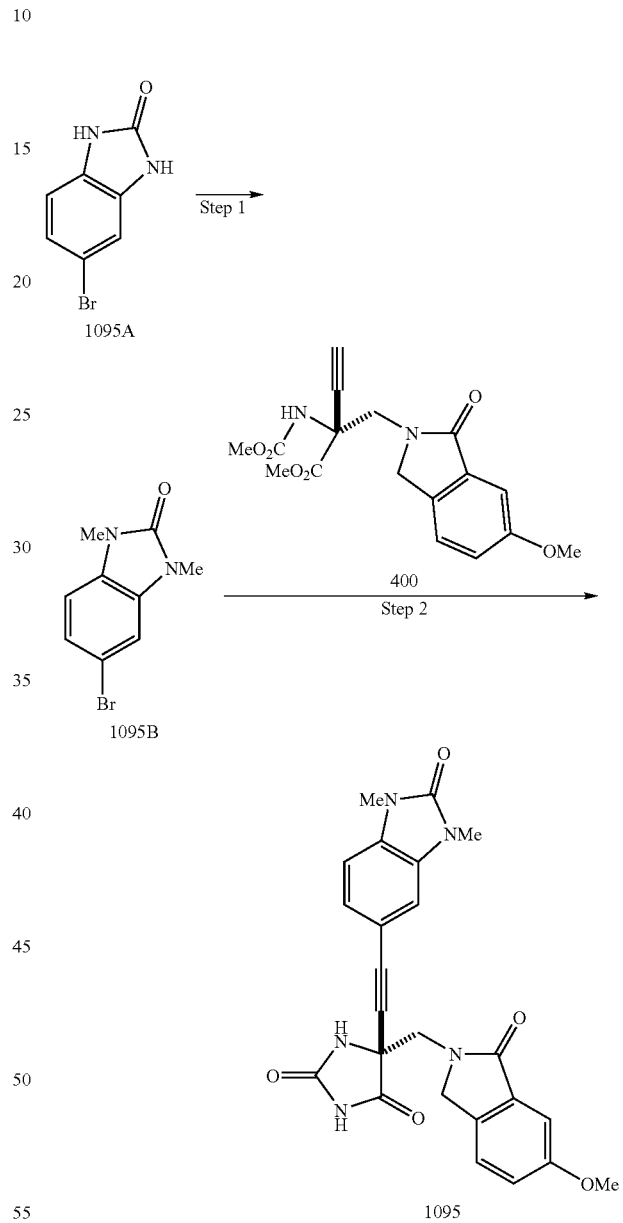

Step 1

A solution of Compound 1095A in DMF (2 mL) was treated sequentially with sodium hydride (28 mg, 60% dispersion in oil, 0.70 mmol) and iodomethane (0.04 mL, 80 mg, 0.56 mmol). The reaction mixture was stirred overnight at rt. The reaction was quenched with water, diluted with EtOAc, and washed sequentially with water and brine. The organic phase was dried over anhydrous MgSO4, filtered and concentrated to give crude Compound 1095B (37 mg, 68%), which was used without further purification.

Step 2
Compounds 1095B and 400 were converted to Compound 1095 by applying the procedure described for Examples 300A and 300B.
Example 973
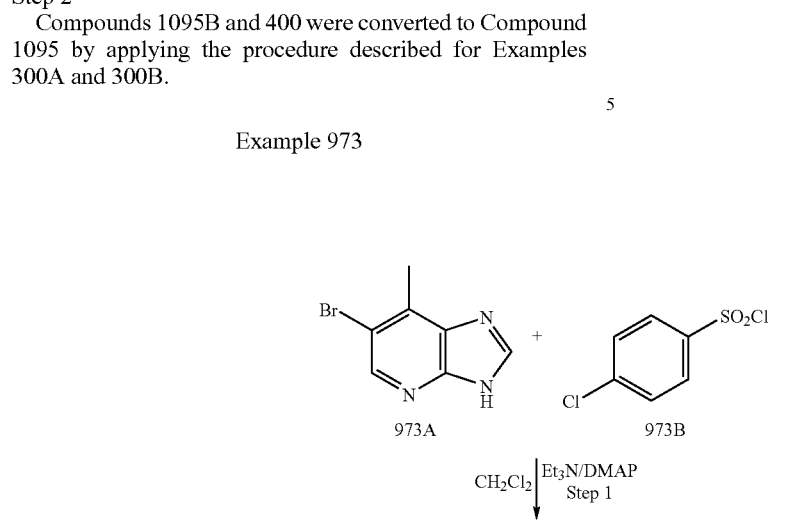
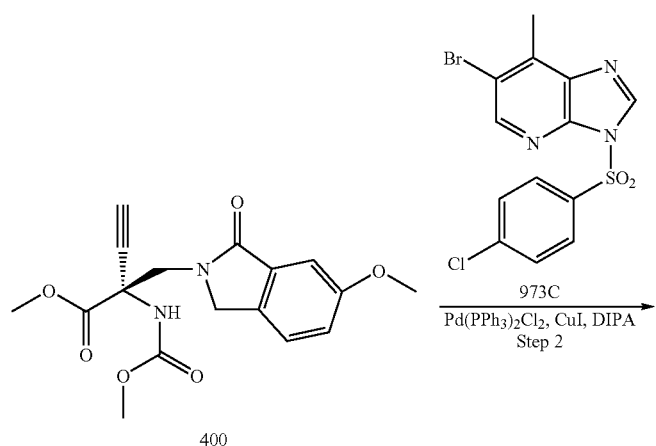
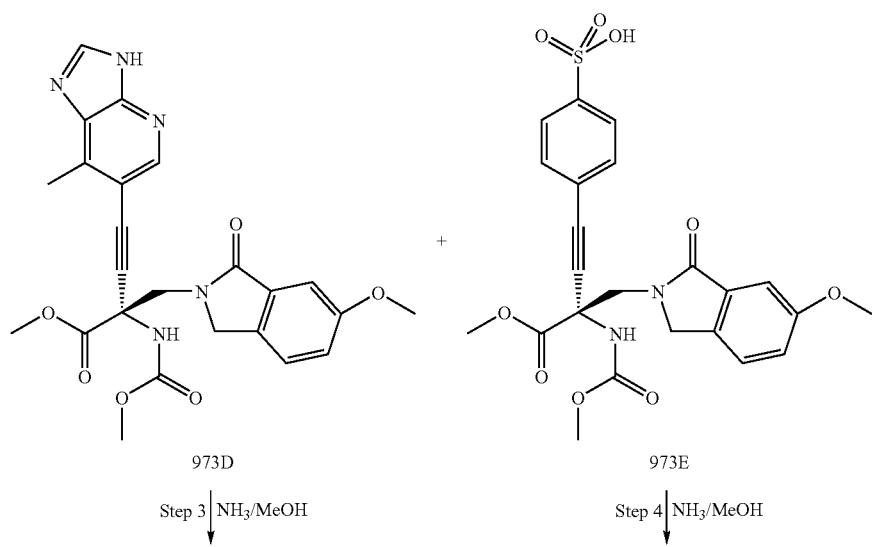
| 973D | 973E |
Step 3 | NH₃/MeOH
Step 4 | NH₃/MeOH

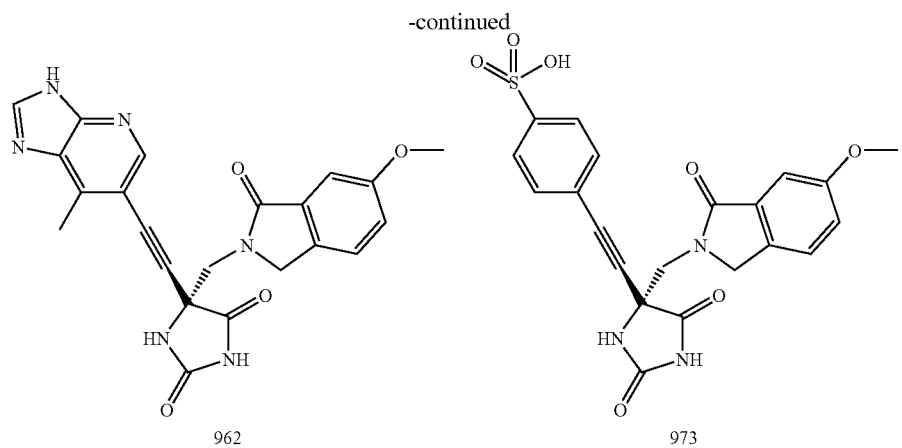

Step 1. To a solution of 973A (320 mg, 1.62 mmol) in CH₂Cl₂ (10 mL) at rt was added Et₃N (0.45 mL, 3.2 mmol), 973B (375 mg, 1.78 mmol) and DMAP (cat.). After 30 min, the solvent was removed and the crude material was purified by column chromatography (SiO₂, 40% EtOAc/Hexanes) to afford 973C (520 mg, 43%).

Step 2. Compound 400 (100 mg, 0.29 mmol) was combined with compound 973C (133 mg, 0.34 mmol), Pd(PPh₃)₂Cl₂ (2.2 mg, 0.003 mmol), CuI (5.5 mg, 0.03 mmol), diisopropylamine (0.05 mL, 0.36 mmol) in DMF (1 mL) and stirred overnight at 85° C. The reaction mixture was concentrated and the crude material was purified with TLC plates (SiO₂, 10% 7N NH₃ in methanol/CH₂Cl₂) afforded the desired product 973D (20 mg, 15%) and 973E (20 mg, 14%).

Step 3. Compound 973D (20 mg, 0.042 mmol) was dissolved in 7 M NH₃ in MeOH solution (2 mL) and stirred in a sealed pressure tube at 90° C. overnight. The reaction mixture was cooled to room temperature and concentrated. The residue was purified with prepative TLC (SiO₂, 10% 7N NH₃ in methanol/CH₂Cl₂) afforded the desired product 962 (12 mg, 67%).

Step 4. Compound 973E (20 mg, 0.04 mmol) was dissolved in 7 M ammonia solution (2 mL) and stirred in a sealed pressure tube at 90° C. overnight. The reaction mixture was cooled to room temperature and concentrated. The residue was purified with prepative TLC (SiO₂, 10% 7N NH₃ in methanol/CH₂Cl₂) afforded the desired product 973 (12 mg, 60%).

Example 1221

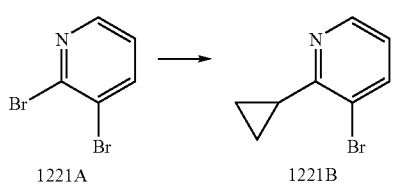

Compound 1221A (1.0 g, 4.22 mmol), cyclopropyl boronic acid (326 mg, 3.80 mmol) and [PdCl₂(dppf)]CH₂Cl₂ (150, 0.21 mmol) in CH₃CN (15 mL) was treated with potassium carbonate (5 mL, 5 mmol, 1M in H₂O). The mixture was subjected to vacuum and refilled with Nitrogen three times. The reaction mixture was stirred at 80° C. (oil bath) for 3 days. Additional [PdCl₂(dppf)]CH₂Cl₂ (150 mg) was added in day two. After cooling down, the water layer was separated and extracted with EtOAc (20 mL) once. The organic layers were combined, filtered through a Celite pad, and concentrated. The product was purified by silica gel chromatography (Hexane/EtOAc, 1:0 to 10:1 to 5:1) to give 1221B (280 mg, 33.5%)

Example 1250

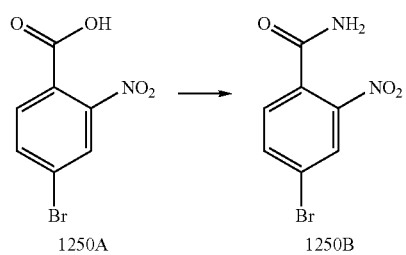

Compound 1250A (5.0 g, 20.3 mmol) was dissolved in thionyl chloride (40 mL) and stirred at reflux for two hours. After cooling down, thionyl chloride was removed by rotary evaporator. The residue was dissolved in CH₂Cl₂ and was added to NH₃—H₂O (conc. 50 mL) slowly with stirring. The solid was collected by filtration, washed with water, dried under vacuum for overnight to give compound 1250B.

Example 1251

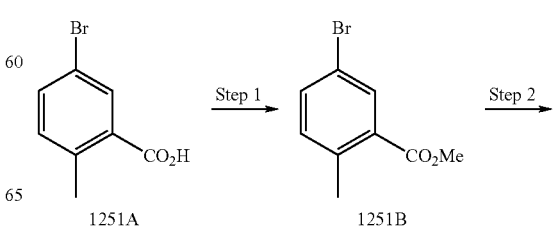

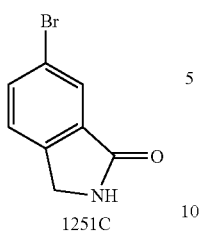

1251C

Step 1

Compound 1251A (2.0 g), MeOH (20 mL), and H₂SO₄ (conc., 2 mL) were stirred at RT for three days. Hexane (50 mL) was added. The organic layer was washed by water, dried over Na₂SO₄, concentrated by rotary evaporator. The product was purified by sgc (Hexane/EtOAc 10:1) to give compound 1251B (1.219 g)

Step 2

Compound 1251B (1.219 g, 5.32 mmol) was dissolved in CCl₄ (30 mL). NBS (947 mg, 5.32 mmol) and benzoyl peroxide (66 mg, 0.27 mmol) was added. The solution was stirred at 85° C. for 2 hours. After cooling down, the solid was filtered and the organic layer was washed with water (10 mL). The organic layer was dried over Na₂SO₄, concentrated by rotary evaporator, dried under vacuum. The residue was then dissolved in NH₃-MeOH (7N, 10 mL) and transferred into a 75 mL pressure bottle. The solution was stirred at 90° C. for over night. The product was purified by C18 chromatography (CH₃CN/water: 5% to 90%, with addition of 0.1% HCO₂H) to give compound 1251C (800 mg, 71%).

Example 1254

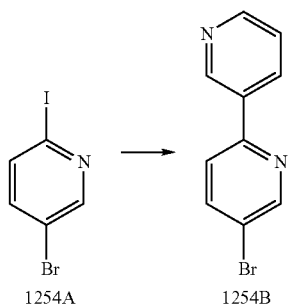

1254A    1254B

Compound 1254A (5.0 g, 17.61 mmol), 4-pyridine boronic acid (2.06 g, 16.73 mmol), and Pd(dppf)Cl₂-CH₂Cl₂ (644 mg, 0.88 mmol) were placed in a 500 mL flask. The flask was vacuumed for 1 minutes and then it was filled with N₂. This process was repeated twice. CH₃CN (200 mL) and K₂CO₃ (1M, 100 mL) were added. The solution was stirred in at 35° C. for two days. Additional Pd(dppf)Cl₂—CH₂Cl₂ (400 mg) was added in the second day. The aqueous layer was separated and extracted with EtOAc (50 mL) once. The organic layers were combined, washed with brine (100 mL) and dried over Na₂SO₄. The solution was concentrated and purified by sgc (Hexane/EtOAc 3:1 to 2:1) to give compound 1254B (3.1 g, 74.9%).

Example 1256

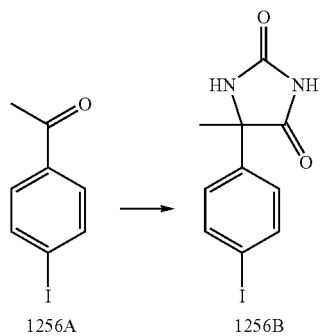

1256A    1256B

Compound 1256A (5.00 g, 20.3 mmol), KCN (1.59 g, 24.4 mmol), and (NH₄)₂CO₃ (7.80 g, 81.3 mmol) were placed in a 150 mL pressure bottle. EtOH (30 mL) and water (30 mL) were added. The bottle was sealed and stirred at 80° C. oil bath for overnight. A white solid appeared. After cooling down, 30 mL water was added and the solid was collected by filtration. The solid was washed by water (20 mL) twice, dried under vacuum at 50° C. for overnight to give compound 1256B (6.18 g, 96.2%).

Example 1555

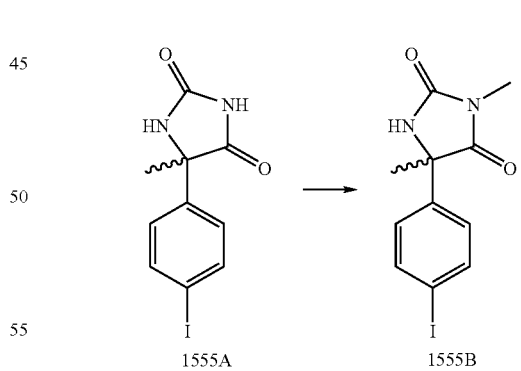

1555A    1555B

Compound 1555A (1.0 g, 3.16 mmol) was dissolved in anhydrous DMF (20 mL). Methyl iodide (0.236 mL, 3.80 mL) and DIPEA (1.1 mL, 6.32 mL) was added and the solution was stirred at RT for two days. More methyl iodide (0.472 mL, 7.6 mL) was added in day two. The solvent was removed by rotary evaporator. The product was purified by sgc (Hexane/EtOAc: 3:1 to 1:1) to give compound 1555B (766 mg, 73.4%).

Example 1566

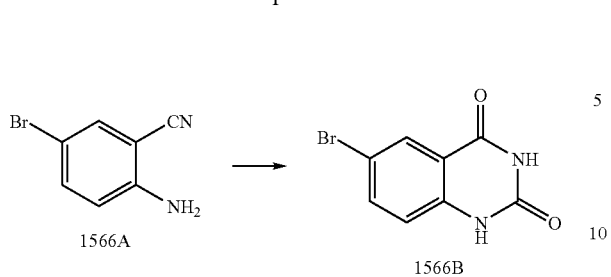

Compound 1566A (200 mg, 1.02 mmol) and 1,8-diazabicyclo[5.4.0]undec-7-ene (DBU, 459 µl, 3.06 mmol) were dissolved in DMF (2 mL) in a two-neck flask. The mixture was subjected to vacuum and the atmosphere refilled with $CO_2$ supplied from the evaporation of dry ice at 23° C. in a separate flask through a vacuum adapter. The mixture was allowed to stir at 23° C. for overnight and the atmosphere of $CO_2$ was allowed to gradually escape through a pin hole in a septum. The solvent was removed and the remaining yellow oil was redissolved in THF (2 mL). 2M HCl (5 mL) was added dropwise with stirring. A cloudy white precipitate formed which was briefly sonicated. The solid was filtered, washed with THF (10 mL), and dried under reduced pressure to yield compound 1566B (206.3 mg, 84.0%) as a white solid.

Example 925

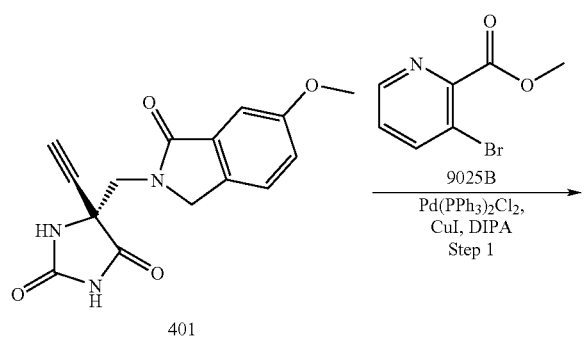

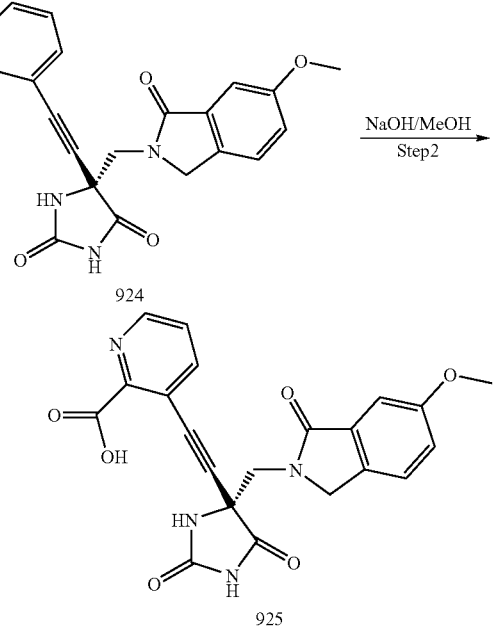

Step 1. Compound 401 (130 mg, 0.43 mmol) was combined with compound 925B (112 mg, 0.52 mmol), $Pd(PPh_3)_2Cl_2$ (6 mg, 0.009 mmol), CuI (12 mg, 0.06 mmol), diisopropylamine (0.1 mL, 0.71 mmol) in DMF (1 mL) and stirred at 85° C. for 2 h. The reaction mixture was purified on a Gilson reverse phase HPLC (0-40% acetonitrile with Formic acid 0.01% in $H_2O$ with formic acid 0.01%) afforded the desired product 924 (107 mg, 57%).

Step 2. Compound 924 (100 mg, 0.23 mmol) was stirred in MeOH (5 mL) and LiOH (1N, aq., 5 mL) was added. The reaction was stirred at rt for 2 h. Solvent was removed and the crude material was purified on a Gilson reverse phase HPLC (0-40% acetonitrile in $H_2O$ with 0.1% formic acid) afforded the desired product 925 (40 mg, 41%).

Example 2000

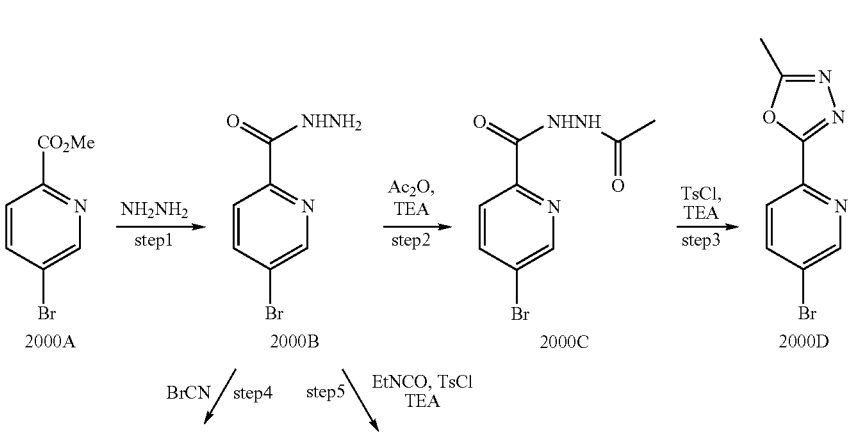

-continued

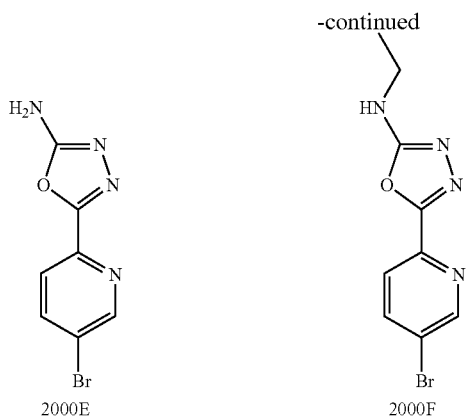

2000E    2000F

Step 1

To a solution of 2000A (1 g, 4.6 mmol) in EtOH (12 mL) was added hydrazine (0.22 mL, 6.9 mmol) at 25° C. and the mixture was heated to reflux for 3 h. The reaction mixture was cooled to 0° C. and the resulting precipitate was filtered and washed with cold EtOH to afford 2000B (0.86 g, 86% yield).

Step 2

To a suspension of 2000B (300 mg, 1.39 mmol) and triethylamine (0.39 mL, 2.78 mmol) in CH$_2$Cl$_2$ (9 mL) was added acetic anhydride (0.15 mL, 1.53 mmol) at 25° C. After stirring at the temperature for 1.5 h, the mixture was poured to a cold water and the resulting precipitate was collected by filtration. The white solid was washed with water and dried under reduced pressure to afford 2000C (323 mg, 90% yield).

Step 3

A suspension of 2000C (120 mg, 0.47 mmol) in CH$_3$CN (3 mL) and CH$_2$Cl$_2$ (3 mL) was treated with triethylamine (0.39 mL, 2.82 mmol) and TsCl (94 mg, 0.49 mmol) at 25° C. The mixture was stirred at the temperature for 5 h and added to aqueous NaHCO$_3$ solution. The organic layers were extracted by CH$_2$Cl$_2$ and the combined organic solution was washed with brine solution, dried (Na$_2$SO$_4$), and concentrated in vacuo. The crude product was purified by SiO$_2$ column chromatography (0 to 5% MeOH in CH$_2$Cl$_2$) to afford 2000D (80 mg, 71% yield).

Step 4

A suspension of 2000B (100 mg, 0.46 mmol) in MeOH (3 mL) and 1,4-dioxane (1.5 mL) was treated with BrCN (3 M solution in CH$_2$Cl$_2$, 0.17 mL, 0.51 mmol) dropwisely at 25° C. After stirring for 1 h at the temperature, NaHCO$_3$ (80 mg, 0.95 mmol) was added and the resulting suspension was continued stirring for 18 h. The white precipitate formed was filtered, washed with water, and dried in the air to afford 2000E (95 mg, 86% yield).

Step 5

A suspension of 2000B (100 mg, 0.46 mmol) in CH$_2$Cl$_2$ (6 mL) was treated with ethylisocyanate (0.04 mL, 0.50 mmol) at 0° C. and the mixture was stirred at 25° C. for 6 h. To this suspension were added triethylamine (0.32 mL, 2.2 mmol) and TsCl (95 mg, 0.50 mmol) and the mixture was stirred at the temperature for 18 h followed by addition to aqueous NaHCO$_3$ solution. The organic layers were extracted by CH$_2$Cl$_2$ and the combined organic solution was washed with brine solution, dried (Na$_2$SO$_4$), and concentrated in vacuo.

The residue was purified by SiO$_2$ column chromatography (0 to 5% MeOH in CH$_2$Cl$_2$) to afford 2000F (102 mg, 82% yield).

Example 2001

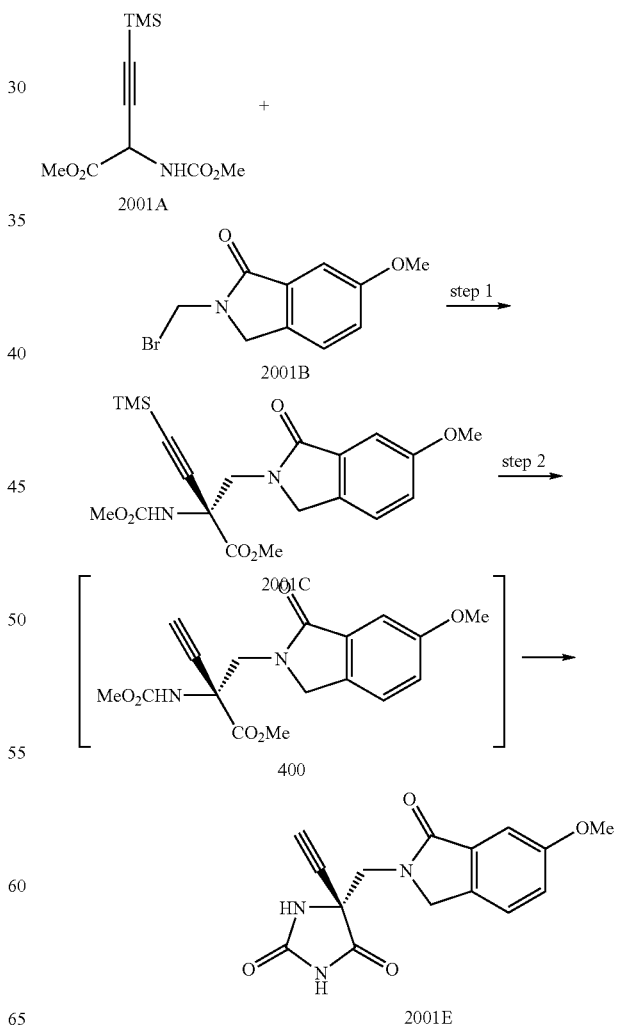

Step 1

A solution of 2001A (11.7 g, 48 mmol) and 2001B (10.3 g, 40 mmol) in THF (400 mL) was cooled to −7~8° C. and treated with NaH (60% dispersion, 6 g, 150 mmol) portionwisely. The mixture was stirred for 2 h at the temperature and quenched by slow addition of acetic acid (15 mL). The mixture was poured to a mixture of cold aqueous NaHCO$_3$ solution and EtOAc. After stirring for 0.5 h, the organic layers were extracted by EtOAc and the combined organic solution was washed with brine solution, dried (Na$_2$SO$_4$), and concentrated in vacuo. The oily residue was solidified in EtOAc/hexane (1:1 mixture) to afford racemic 2001C (8.5 g) as a white solid after filtration. The filtrate was concentrated and the residue was purified by SiO$_2$ column chromatography (EtOAc:hexane=1:2) to afford 2001C (1.5 g, 60% combined yield). The active chiral isomer 2001C (0.32 g from racemic 0.8 g per loading) was obtained by HPLC separation using preparative chiral OD column (EtOH: hexane=1:4).

Step 2

A solution of 2001C (3 g, 7.16 mmol) in THF (30 mL) was treated with TBAF (1 M solution in THF, 10 mL, 10 mmol) at 0° C. The mixture was stirred for 1.5 h at the temperature and poured to a mixture of ice-water and EtOAc. The organic layers were extracted by EtOAc and the combined organic solution was washed with brine solution, dried (Na$_2$SO$_4$), and concentrated in vacuo to provide crude 400. The crude 400 was placed in a pressure vessel and dissolved in ammonia in MeOH (7 N solution, 60 mL). The solution was heated to 80° C. for 14 h and cooled to 25° C. followed by concentration. The residue was treated with CH$_2$Cl$_2$ in an ice bath and the resulting solid was filtered to afford 2001E (1.38 g) and the filtrate was concentrated and the residue was solidified in CH$_2$Cl$_2$ and hexane to afford 2001E (0.24 g, 76% combined yield).

Example 2002

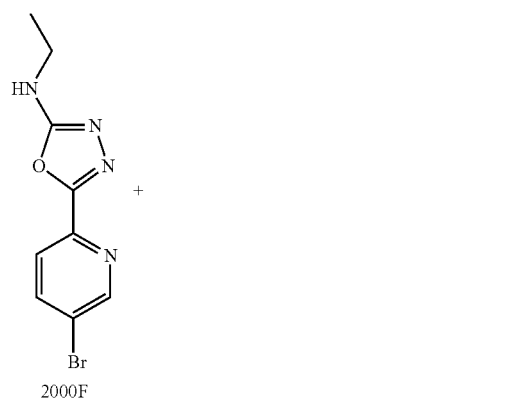

2000F

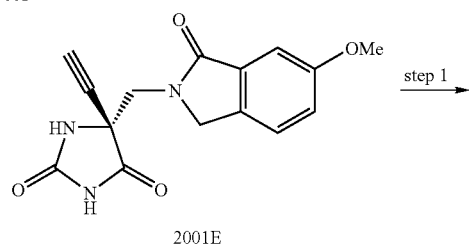

2001E

-continued

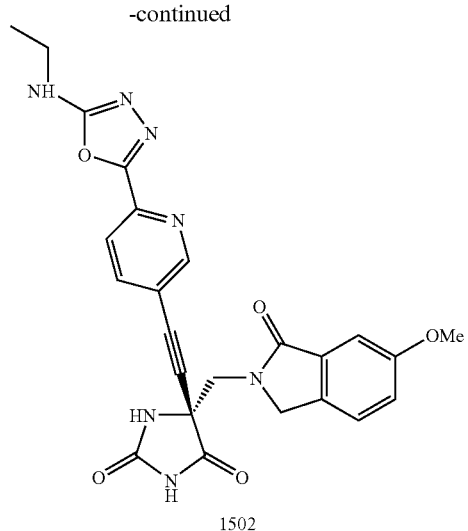

1502

Step 1

A mixture of 2001E (52 mg, 0.17 mmol), 2000F (68 mg, 0.26 mmol), Pd(PPh$_3$)$_2$Cl$_2$ (2.4 mg, 3.4 μmol), CuI (3.2 mg, 17 μmol), and diisopropylethylamine (65 μL, 0.37 mmol) in DMF (1.5 ml) was purged with N$_2$ and heated to 70° C. After heating for 17 h, the mixture was cooled to 25° C. and purified by column chromatography on a reverse phase C-18 column (0.01% HCO$_2$H in water/0.01% HCO$_2$H in CH$_3$CN) to afford compound 1502 (47 mg, 57% yield).

Example 2003

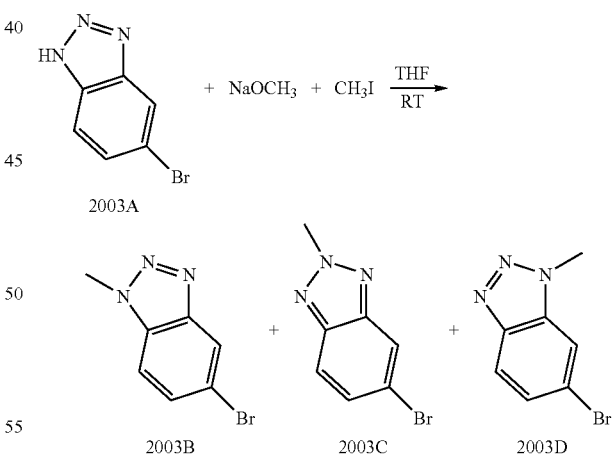

Compound 2003A (400 mg, 2.0 mmol) was dissolved in 10 mL of THF and reacted with sodium methoxide (4 mL, 2.0 mmol). After 30 min iodomethane (0.5 mL, 8.0 mmol) was added. Reaction mixture was stirred for 4 hours at room temp, then it was added to ethyl acetate and water. The aqueous layer was extracted with ethyl acetate twice. All the organic layers were combined, washed with brine solution and dried over sodium sulfate. The solvent was removed by rotary evaporator and further purified by SiO$_2$ column chromatography to give 2003B (105 mg, 25% yield), 2003C (110 mg, 26% yield) and 2003D (106 mg, 25% yield).

Example 2004

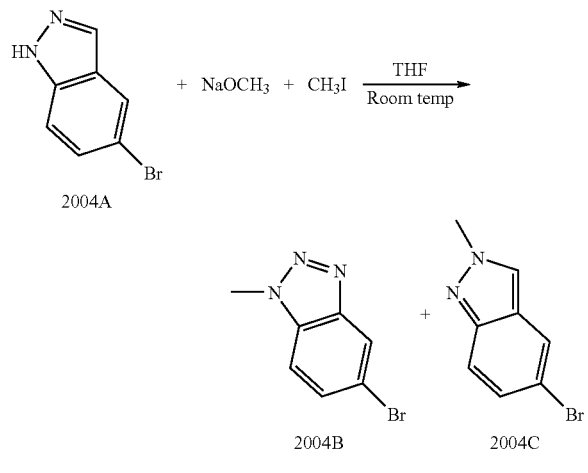

Compound 2004A (1 g, 5.07 mmol) was dissolved in 20 mL of THF and reacted with sodium methoxide (10 mL, 5.07 mmol). After 30 min, iodomethane (1.3 mL, 20.3 mmol) was added. Reaction mixture was stirred for 5 hours at room temp, then it was added to ethyl acetate and water. The aqueous layer was extracted with ethyl acetate twice. All the organic layers were combined, washed with brine solution and dried over sodium sulfate. The solvent was removed by rotary evaporator and further purified by $SiO_2$ column chromatography to give 2004B (470 mg, 44% yield) and 2004C (450 mg, 42% yield).

Example 2005

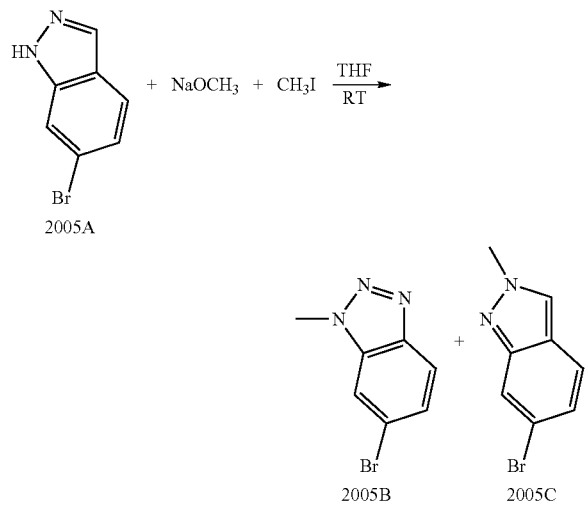

Compound 2005A (400 mg, 2.03 mmol) was dissolved in 10 mL of THF and reacted with sodium methoxide (4 mL, 2.03 mmol). After 30 min iodomethane (0.5 mL, 8.12 mmol) was added. Reaction mixture was stirred for 3 hours at room temp, then it was added to ethyl acetate and water. The aqueous layer was extracted with ethyl acetate twice. All the organic layers were combined, washed with brine solution and dried over sodium sulfate. The solvent was removed by rotary evaporator and further purified by $SiO_2$ column chromatography to give 2005B (200 mg, 47% yield), 2005C (150 mg, 35% yield).

Example 2007

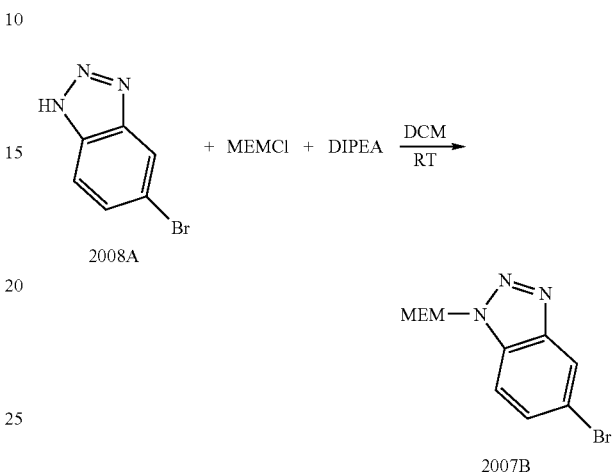

Compound 2007A (200 mg, 1.01 mmol) was dissolved in 10 mL of $CH_2Cl_2$ and reacted with DIPEA (0.5 ml, 3.04 mmol), followed by addition of MEMCl (0.15 mL, 1.31 mmol). The reaction mixture was stirred for 5 hours at room temp, then it was added to $CH_2Cl_2$ and sodium bicarbonate aqueous solution. The organic layers were extracted with $CH_2Cl_2$, combined and dried over sodium sulfate. The solvent was removed by rotary evaporator to yield compound 2007B (205 mg, 71% yield).

Example 2008

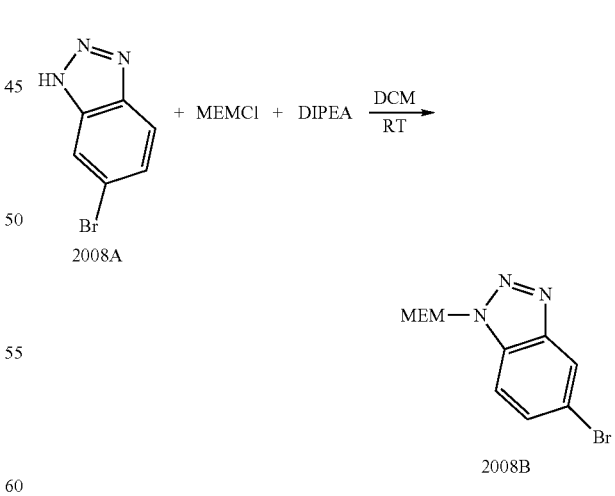

Compound 2008A (200 mg, 1.02 mmol) was dissolved in 10 mL of $CH_2Cl_2$ and reacted with DIPEA (0.53 ml, 3.03 mmol), followed by addition of MEMCl (0.15 mL, 1.31 mmol). The reaction mixture was stirred for 16 hours at room temp, then it was added to $CH_2Cl_2$ and sodium bicarbonate aqueous solution. The organic layers were extracted with CH₂Cl₂, combined and dried over sodium sulfate. The solvent was removed by rotary evaporator to yield compound 2008B (210 mg, 72% yield).

Example 2009

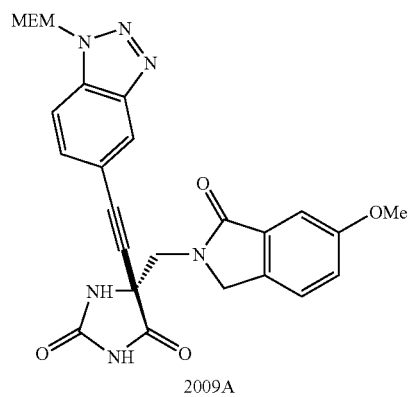
2009A

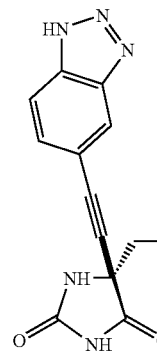
1522

Compound 2009A (20 mg, 0.04 mmol) was dissolved in 2 mL of MeOH—CH₂Cl₂ (1:1 mixture) and reacted with trifluoroacetic acid (0.4 ml). The reaction mixture was stirred for 3 days at room temp and then at 40° C. for 20 hours. The solvent was removed by rotary evaporator and the residue was purified by preparative TLC to yield compound 1522 (2 mg, 12% yield).

Example 943

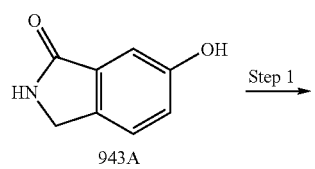
943A

Step 1

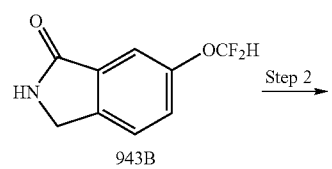
943B

Step 2

-continued

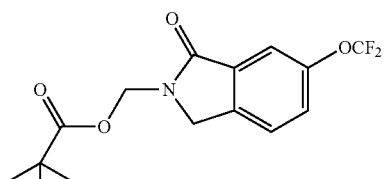
943C

Step 3

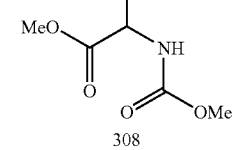
308

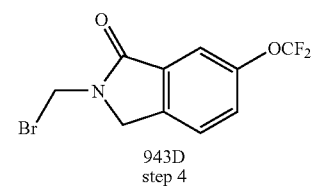
943D
step 4

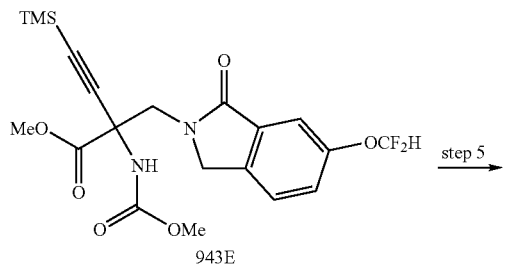
943E step 5

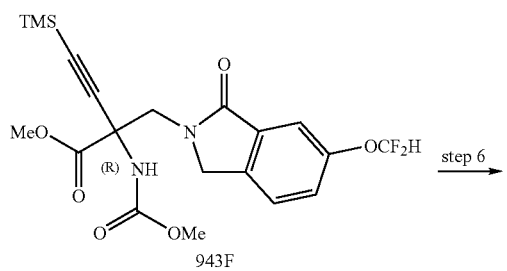
943F step 6

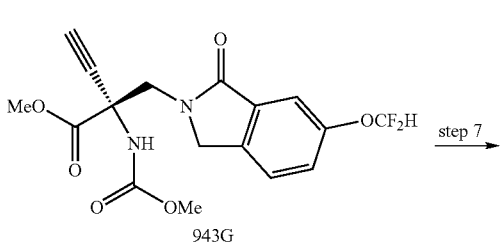
943G step 7

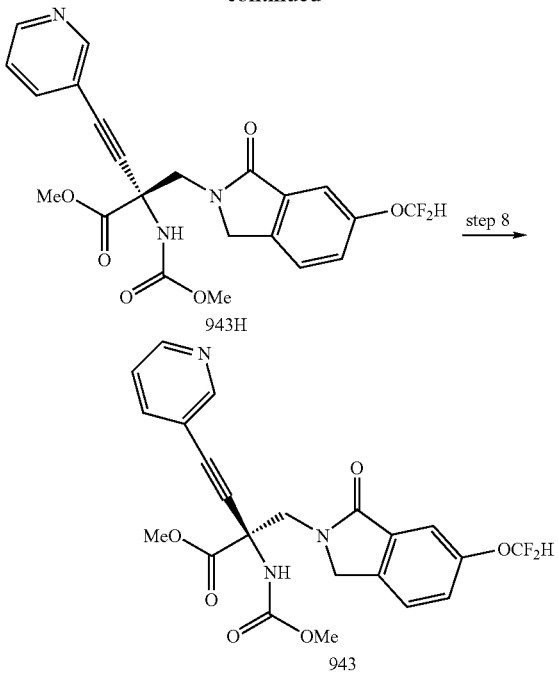

Step 1.

943A (0.35 g, 2.35 mmol) in 5 mL NMP was treated with Cs$_2$CO$_3$ (1.15 g, 3.5 mmol). The flask was equipped with a dry ice acetone trap and difluoro choro methane gas was bubbled for 2 h. another portion of Cs$_2$CO$_3$ (2.68 g, 8.2 mmol) was added excess of difluoro chloro methane gas was bubbled in before the bubbling was stopped and the reaction was stirred overnight. Another portion of Cs$_2$CO$_3$ (2.68 g, 8.2 mmol) was added excess of difluoro chloro methane gas was bubbled in and the reaction was stirred at rt for 3 h. The reaction was diluted with 15 mL CH$_2$Cl$_2$ and washed with water (2×15 mL) and brine (1×15 mL). The organics were dried and concentrated to yield a crude which was purified by silica-gel prep plate chromatography using 3:1 ethyl acetate: hexane to yield 230 mg of pure product 943B.

Step 2.

Compound 943B (600 mg, 3.01 mmol) was dissolved in THF (40 mL) and DMPU (6 mL) and potassium t-butoxide (406 mg, 3.61 mmol) was added and stirred at rt for 2 h. Chloro pivalate (0.656 mL, 4.52 mmol) was added dropwise and stirred at rt for 2 h. The reaction was quenched with NH$_4$Cl—H$_2$O and extracted with ethyl acetate (3×20 mL). The combined organic layers were dried and concentrated to yield a crude which was purified by silica-gel prep plate chromatography using 1:3 ethyl acetate:hexane to yield 700 mg of pure product 943C.

Step 3.

Compound 943C (1.4 g, 4.47 mmol) was dissolved in CH$_2$Cl$_2$ (20 mL) and cooled to 0° C. TMS bromide (1.13 mL, 8.58 mmol) was added dropwise. The reaction was stirred at 0° C. for 2 h and it was slowly warmed up to rt. Solvent was removed and it was dried under vacuum to give compound 943D (1.2 g, 92%).

Step 4.

Compound 308 (1.05 g, 4.3 mmol) and compound 943D (1.1 g, 3.76 mmol) were dissolved in THF (40 mL) and cooled to −30° C. NaH (518 mg, 12.95 mmol) was added portionwise and the reaction mixture was stirred for 2 hours at −12° C. Acetic acid was added slowly and the reaction was allowed to warm to room temperature. The aqueous layer was extracted with ethyl acetate. The combined organic layers were washed with water, brine, dried over sodium sulfate, and concentrated. Purification by column chromatography (SiO$_2$, 30% ethyl acetate/hexanes to 50% ethyl acetate/hexanes) afforded the desired product 943E (1.3 g, 76%).

Step 5

The two isomers were separated using a chiral AD column. One gram of material was injected into the column and the two peaks were separated by using a solvent mixture of 90% hexanes/2-propanol. The first isomer was the desired compound 943F (400 mg, 80%).

Step 6:

Compound 943F (450 mg, 1 mmol) was dissolved in THF (10 mL) and cooled to 0° C. Tetrabutylammonium fluoride (1 M in THF, 1.5 mL, 1.5 mmol) was added dropwise and the reaction was stirred for 20 min at 0° C. The reaction mixture was diluted with ethyl acetate and water. The organic layer was washed with water, saturated sodium bicarbonate, brine, dried over sodium sulfate and concentrated to provide compound 943G (380 g, 99%). The product was used without purification.

Step 7

Compound 943G (50 mg, 0.13 mmol) was combined with 3-iodopyridine (40 mg, 2.0 mmol), Pd(PPh$_3$)$_2$Cl$_2$ (1 mg, cat.), CuI (2.5 mg, cat.), diisopropylamine (0.04 mL, 0.29 mmol) in DMF (5 mL) and stirred at 70° C. for 1 h. The reaction mixture was diluted with ethyl acetate and water. The organic layer was washed with water, brine, dried over sodium sulfate and concentrated. Purification by column chromatography (SiO$_2$, 66% EtOAc/Hexanes) afforded the desired product 943H (46 mg, 77%).

Step 8.

Compound 943H (46 mg, 0.1 mmol) was dissolved in 7 M ammonia solution (2 mL) and stirred in a sealed pressure tube at 90° C. overnight. The reaction mixture was cooled to room temperature and concentrated. The crude material was treated with EtOEt and the solid was collected by suction filtration to provide compound 943 (28 mg, 68%).

Example 2014

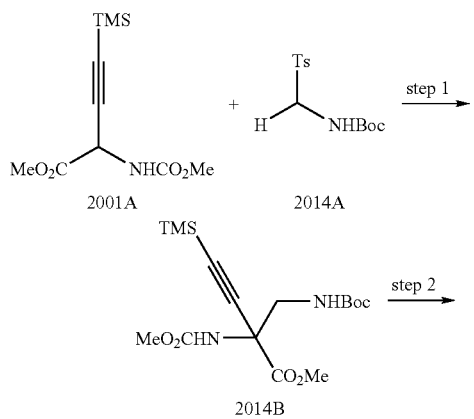

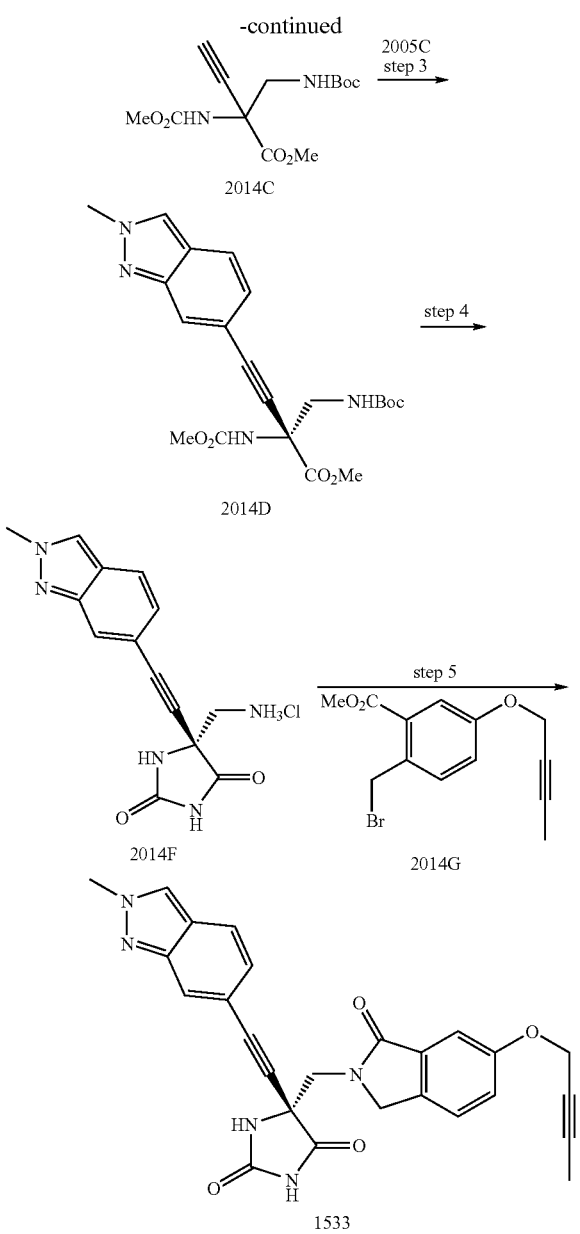

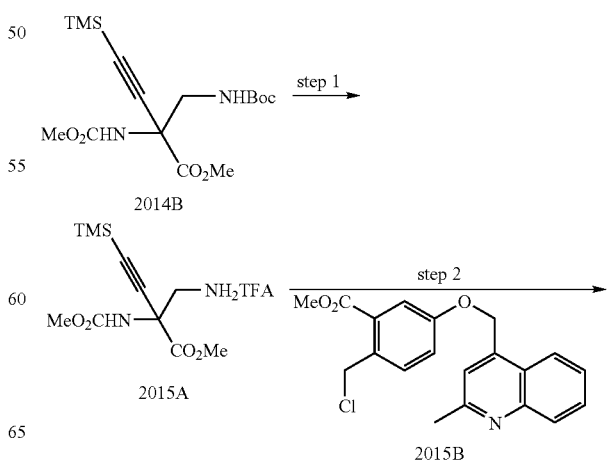

organic layers were extracted by EtOAc and the combined organic solution was washed with brine solution, dried (Na$_2$SO$_4$), and concentrated in vacuo. The residue was purified by SiO$_2$ column chromatography (30% EtOAc in hexane) to afford 2014C (329 mg, 73% yield).

Step 3

A mixture of 2014C (168 mg, 0.56 mmol), 2005C (124 mg, 0.58 mmol), Pd(PPh$_3$)$_2$Cl$_2$ (4.0 mg, 6 µmol), CuI (21 mg, 110 µmol), and diisopropylethylamine (0.39 mL, 0.24 mmol) in DMF (4 ml) was purged with N$_2$ and heated to 70° C. After heating for 17 h, the mixture was cooled to 25° C. and the mixture was poured to an ice-water. The organic layers were extracted with EtOAc and the combined organic solution was washed with brine solution, dried (Na$_2$SO$_4$), and concentrated in vacuo. The residue was purified by SiO$_2$ column chromatography (1 to 5% MeOH in CH$_2$Cl$_2$) to afford racemic 2014D (183 mg, 76% yield). The active enantiomer of 2014D was separated by chiral HPLC on chiral OD column (IPA/hexane=1:3) to afford active isomer 2014D (50 mg).

Step 4

2014D (49 mg, 0.11 mmol) was placed in a pressure vessel and dissolved in ammonia in MeOH (7 N solution, 7 mL). The solution was heated to 80° C. for 18 h and cooled to 25° C. followed by concentration. The residue was purified by preparative TLC (7% MeOH in CH$_2$Cl$_2$) to afford hydantoin 2014E (not shown, 35 mg, 84% yield). 2014E (34 mg, 0.089 mmol) was dissolved in 10% MeOH in CH$_2$Cl$_2$ (3 mL) and was treated with 4 N HCl in dioxane (0.3 mL). The mixture was stirred at 25° C. for 18 h and concentrated in vacuo to afford 2014F (34 mg, quant.).

Step 5

A mixture of 2014F (18 mg, 0.055 mmol), 2014G (18 mg, 0.06 mmol), and diisopropylethylamine (48 µL, 0.28 mmol) in DMF (0.5 mL) was heated to 60° C. The mixture was stirred for 16 h at the temperature and concentrated in vacuo. The residue was dissolved in EtOAc and washed with water, brine solution, dried (Na$_2$SO$_4$), and concentrated in vacuo. The residue was purified by preparative TLC (10% MeOH in CH$_2$Cl$_2$) to afford 1533 (7 mg, 28% yield).

Example 2015

Step 1

A solution of 2001A (515 mg, 2.12 mmol) and 2014A (730 mg, 2.54 mmol) in THF (15 mL) was cooled to −5° C. and treated with NaH (60% dispersion, 370 mg, 9.25 mmol) portionwisely. The mixture was stirred for 8 h at the temperature and was poured to a mixture of cold aqueous NH$_4$Cl solution and EtOAc. After stirring for 0.5 h, the organic layers were extracted by EtOAc and the combined organic solution was washed with brine solution, dried (Na$_2$SO$_4$), and concentrated in vacuo. The residue was purified by SiO$_2$ column chromatography (1 to 7% MeOH in CH$_2$Cl$_2$) to afford 2014B (600 mg, 72% yield).

Step 2

A solution of 2014B (600 mg, 1.51 mmol) in THF (10 mL) was treated with TBAF (1 M solution in THF, 1.8 mL, 1.8 mmol) at 0° C. The mixture was stirred for 3 h at the temperature and poured to a mixture of ice-water and EtOAc. The

305

-continued

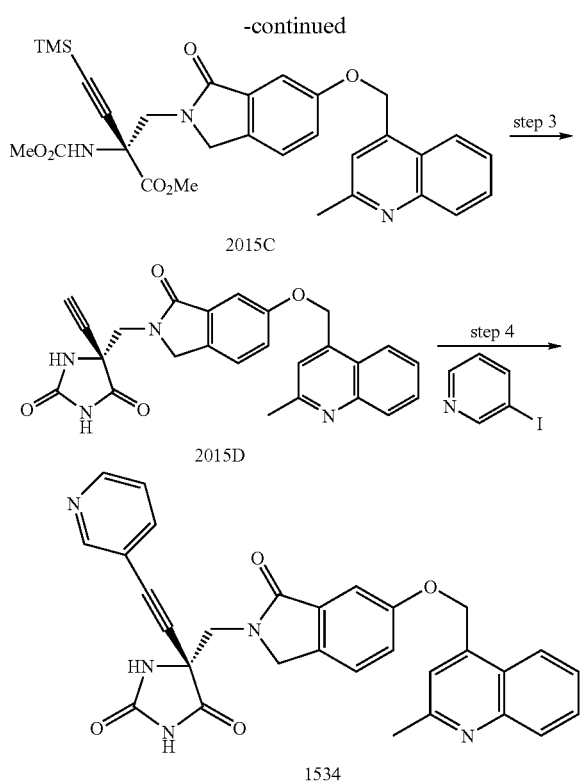

Step 1

A solution of 2014B (193 mg, 0.52 mmol) in $CH_2Cl_2$ (3 mL) was treated with trifluoroacetic acid (0.3 mL) at 25° C. The mixture was stirred for 2 h at the temperature and concentrated in vacuo to afford 2015A (280 mg, quant.).

Step 2

A mixture of 2015A (580 mg, 1.2 mmol), 2015B (435 mg, 1.22 mmol), and diisopropylethylamine (0.85 mL, 4.88 mmol) in DMF (7 mL) was heated to 80° C. The mixture was stirred for 48 h at the temperature and concentrated in vacuo. The residue was dissolved in EtOAc and washed with water, brine solution, dried ($Na_2SO_4$), and concentrated in vacuo. The residue was purified by $SiO_2$ column chromatography (0 to 5% MeOH in $CH_2Cl_2$) to afford racemic 2015C (180 mg, 28% yield). The active enantiomer of 2015C was separated by chiral HPLC on chiral OD column (IPA/hexane=1:3) to afford active isomer 2015C (68 mg).

Step 3

A solution of 2015C (68 mg, 0.12 mmol) in THF (2 mL) was treated with TBAF (1 M solution in THF, 0.16 mL, 0.16 mmol) at 0° C. The mixture was stirred for 1.5 h at the temperature and poured to a mixture of ice-water and EtOAc. The organic layers were extracted by EtOAc and the combined organic solution was washed with brine solution, dried ($Na_2SO_4$), and concentrated in vacuo to provide desilylated compound after $SiO_2$ column separation (0 to 5% MeOH in $CH_2Cl_2$). The desilylated compound (48 mg, 0.098 mmol) was placed in a pressure vessel and dissolved in ammonia in MeOH (7 N solution, 10 mL). The solution was heated to 70° C. for 18 h and cooled to 25° C. followed by concentration to afford crude 2015D (39 mg, 82% yield in 2 steps).

306

Step 4

A mixture of 2015D (39 mg, 0.089 mmol), 3-iodopyridine (37 mg, 0.18 mmol), $Pd(PPh_3)_2Cl_2$ (1.4 mg, 9 μmol), CuI (1.4 mg, 2 μmol), and diisopropylethylamine (0.027 mL, 0.20 mmol) in DMF (1 ml) was purged with $N_2$ and heated to 70° C. After heating for 3 h, the mixture was cooled to 25° C. and purified by column chromatography on a reverse phase C-18 column (0.01% $HCO_2H$ in water/0.01% $HCO_2H$ in $CH_3CN$) to afford 1534 (27 mg, 59% yield).

Example 2016

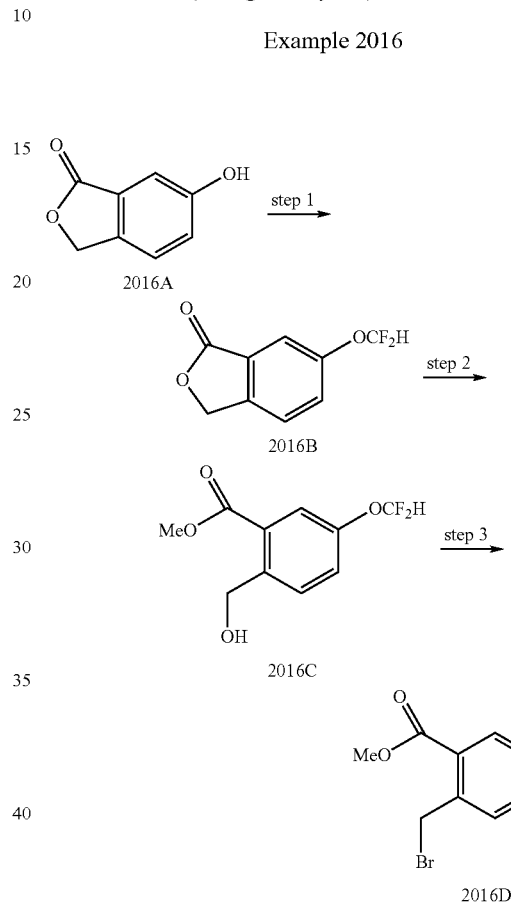

Step 1

To a suspension of 2016A (1.46 g, 9.73 mmol) and $K_2CO_3$ (4.03 g, 29.2 mmol) in DMF (35 mL) in a 3-neck 100 mL flask equipped with dry ice condenser was bubbled $CF_2ClH$ gas and the mixture was heated to 70° C. After 16 h stirring at the temperature, the mixture was cooled to 25° C. and diluted in EtOAc. The organic solution was washed with water, brine solution, dried ($Na_2SO_4$), and concentrated in vacuo. The residue was purified by $SiO_2$ column chromatography ($CH_2Cl_2$) to afford 2016B (900 mg, 46% yield).

Step 2

A suspension of 2016B (428 mg, 2.14 mmol) in water (2.5 mL) was treated with 1N NaOH solution (2.14 mL, 2.14 mmol) and the mixture was stirred at 100° C. for 2 h. The mixture was cooled and concentrated in vacuo. The residual solid was dried by azeotropic distillation with toluene and dissolved in DMF (2.5 mL). The solution was treated with iodomethane (0.4 mL, 6.42 mmol) at 25° C. for 4 h followed by addition to ice-water. The organic layers were extracted with EtOAc and the combined organic solution was washed with brine solution, dried ($Na_2SO_4$) and concentrated in vacuo. The residue was purified by SiO₂ column chromatography (CH₂Cl₂) to afford 2016C (326 mg, 66% yield).

Step 3

A solution of 2016C (50 mg, 0.22 mmol) in THF (1 mL) was treated with tribromophosphine (20 μL, 0.22 mmol) at 25° C. The reaction mixture was stirred at the temperature for 20 h and added to aqueous NaHCO₃ solution. The organic layers were extracted with CH₂Cl₂ and the combined organic solution was washed with brine solution, dried (Na₂SO₄), and concentrated in vacuo. The residue was purified by SiO₂ column chromatography (CH₂Cl₂/hexane 1:1) to afford 2016D (16 mg, 25% yield).

Example 2017

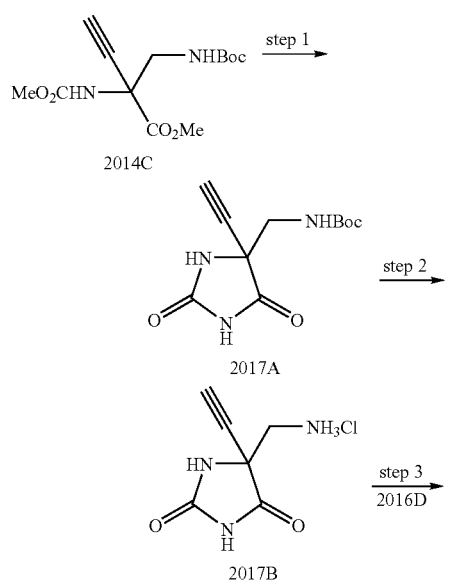

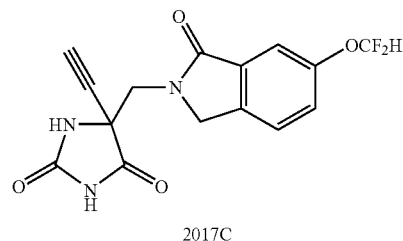

Step 1

2014C (73 mg, 0.24 mmol) was placed in a pressure vessel and dissolved in ammonia in MeOH (7 N solution, 5 mL). The solution was heated to 80° C. for 18 h and cooled to 25° C. followed by concentration. The residue was purified by SiO₂ column chromatography (1 to 10% MeOH in CH₂Cl₂) to afford 2017A (20 mg, 33% yield).

Step 2

2017A (20 mg, 0.08 mmol) in MeOH (2 mL) was treated with 4 N HCl in dioxane (1 mL) at 25° C. The mixture was stirred at the temperature for 20 h and concentrated in vacuo to afford crude 2017B (19.6 mg).

Step 3

A mixture of 2017B (19.6 mg, 0.103 mmol), 2016B (37 mg, 0.12 mmol), and diisopropylethylamine (0.11 mL, 0.6 mmol) in DMF (0.5 mL) was heated to 60° C. The mixture was stirred for 48 h at the temperature and concentrated in vacuo. The residue was purified by preparative TLC (5% MeOH in CH₂Cl₂) to afford 2017C (11 mg, 32% yield).

Example 1087

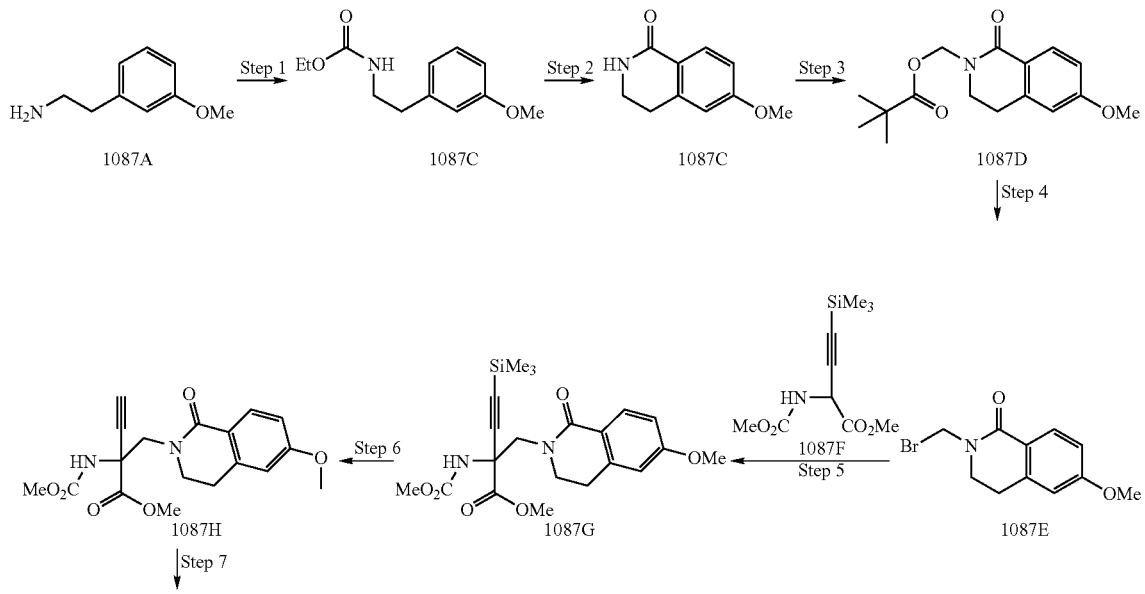

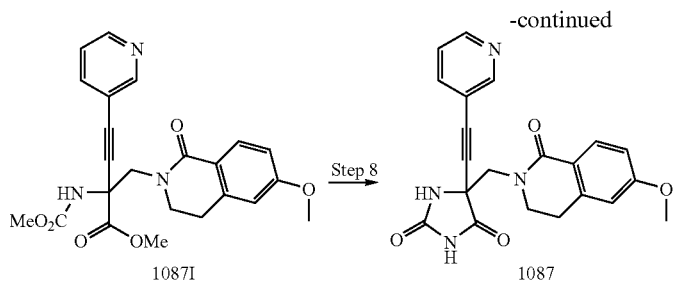

Step 1

Neat ethyl chloroformate (12.5 mL, 14.3 g, 132 mmol) was added dropwise over ~10 min to a stirred, ice-cold solution of Compound 1087A (18.9 g, 125 mmol) and triethylamine (18.2 mL, 13.3 g, 132 mmol) in $CH_2Cl_2$ (400 mL). The solution was stirred at 0° C. for 1.5 h, after which solvents were removed by evaporation. The resulting liquid was dissolved in EtOAc (~400 mL) and the resulting solution was washed sequentially with water (2×100 mL) and brine (~100 mL). The organic layer was dried over anhydrous MgSO4, filtered, and concentrated to give Compound 1087B as a pale yellow liquid (26.9 g, 96%).

Step 2

The transformation of Compound 1087B to Compound 1087C was carried out following the procedure of Sall and Grunewald, in Sall, D. J.; Grunewald, G. L. *J. Med. Chem.* 1987, 30, 2208-2216.

Step 3

The conversion of Compound 1087C to Compound 1087D was carried out following the procedure given in Example 300A, Step D.

Step 4

The conversion of Compound 1087D to Compound 1087E was carried out following the procedure given in Example 300A, Step E.

Step 5

Compounds 1087F (2.45 g, 10.1 mmol) and 1087E (2.86 g, 10.6 mmol) were admixed. Dry THF (80 mL) was added and the resulting suspension was cooled to −78° C. and stirred for 30 min. LHMDS solution (20 mL, 1 M in THF, 20 mmol) was added dropwise over 15 min. The reaction mixture was stirred at −78° C. for 2 h. Saturated aq. ammonium chloride solution (100 mL), followed by EtOAc (250 mL), were added to the stirred reaction mixture and the temperature was allowed to rise to rt. The organic layer was separated and the aqueous layer was extracted with EtOAc (200 mL). The combined organic layers were washed with brine, dried over anhydrous $MgSO_4$, filtered, and concentrated. The resulting crude product was purified by sgc (10-100% EtOAc-hexane gradient) to afford Compound 1087G (2.70 g, 62%) as a beige solid.

Steps 6, 7, 8

Compound 1087G was converted to Compound 1087 in a three-step sequence following the procedure given in Example 300B, Steps D through F.

Example 1099

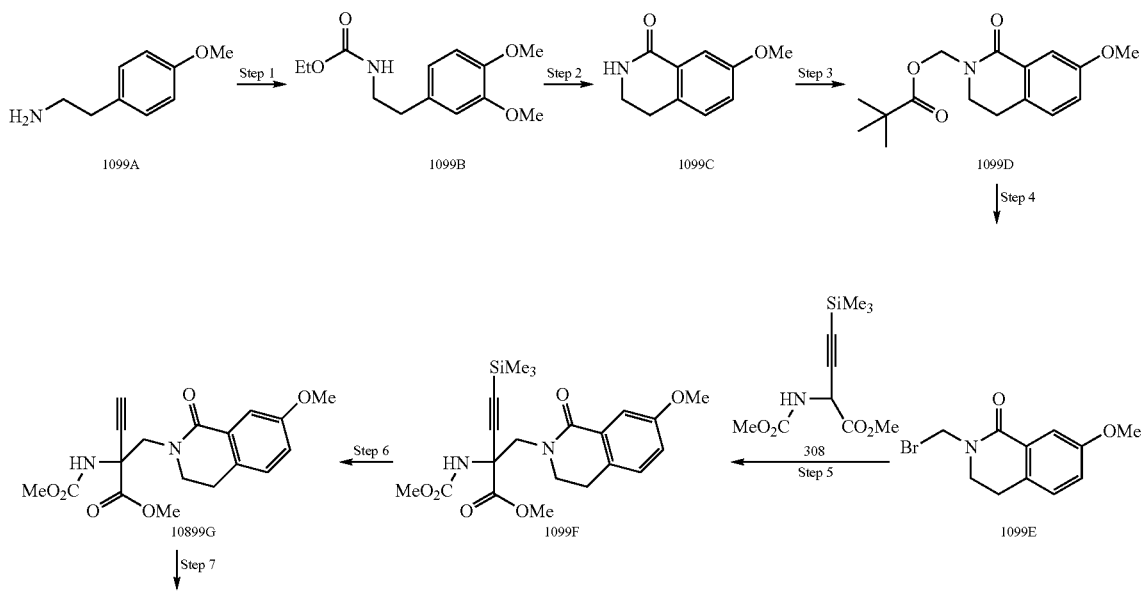

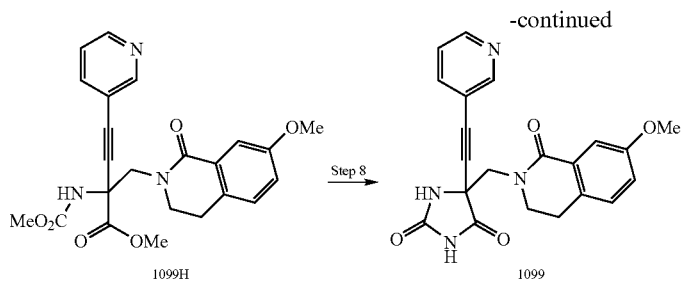

Compound 1099 was prepared by following the procedure given in Example 1087, but starting with commercially available 4-methoxyphenethylamine (Compound 1099A) instead of 3-methoxyphenethylamine (Compound 1087A).

Example 1570

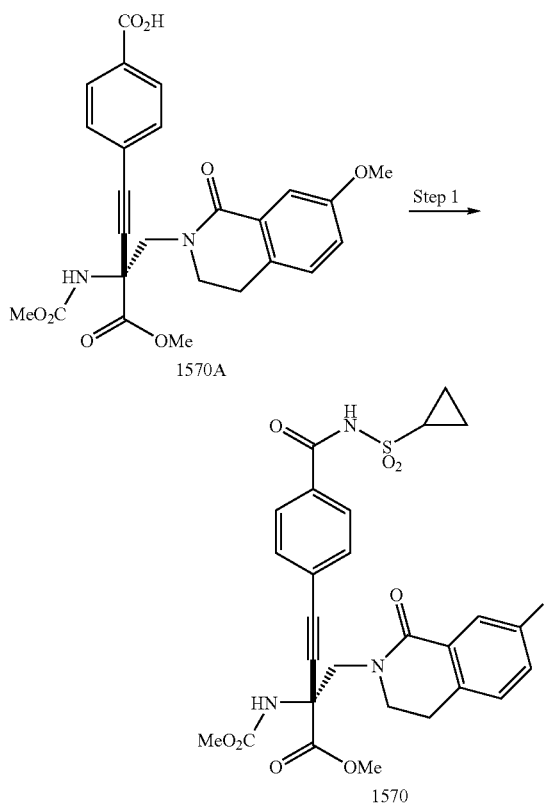

Compound 1570A was prepared from Compound 400 and 4-iodobenzoic acid by sequential application of the procedures given in Parts H and I in Example 400. Solid carbonyl diimidazole (19 mg, 0.12 mmol) was added in one portion to a stirred solution of Compound 1570A in THF (200 µL). The solution was stirred at 70° C. for 1.5 h, and was subsequently allowed to cool to rt. Solid cyclopropanesulfonamide (17 mg, 0.14 mmol) and DBU (43 µL, 43 mg, 0.29 mmol) were added sequentially and the reaction mixture was stirred at rt for 18 h. The solvent was evaporated and the residue was dissolved in DCM (50 mL). The solution was washed sequentially with 0.1 N aq hydrochloric acid (~25 mL), water (~25 mL) and brine (~25 mL). The organic phase was dried over anhydrous MgSO$_4$, filtered and concentrated under reduced pressure to afford an off-white solid. The crude product was purified by PTLC (3:1 EtOAc-hexanes+1% HCO$_2$H) to afford the desired Compound 1570 (24 mg, 48% yield) as a beige solid.

Proton NMR spectral data for certain of the Compounds are set forth below:

Compound 400B. $^1$H NMR (400 Hz, DMSO-d$_6$) δ11.2 (s, 1H), 8.8 (s, 1H), 8.6 (m, 2H), 8.0 (d, 1H), 7.6 (m, 2H), 7.2 (m, 2H), 4.6 (m, 2H), 4.05 (m, 2H), 3.8 (s, 3H).

Compound 417C. $^1$H NMR (400 Hz, DMSO-d$_6$) δ12.05 (s, 1H), 11.14 (s, 1H), 8.84 (d, J=1.6 Hz, 1H), 6.63 (m, 1H), 7.27 (m, 2H), 7.18 (m, 2H), 6.19 (m, 1H), 4.59 (dd, J=6.4 Hz, 16.8 Hz, 2H), 4.02 (m, 2H), 3.80 (s, 3H)

Compound 424. $^1$H NMR (400 Hz, DMSO-d$_6$) δ11.22 (s, 1H), 8.90 (d, 1H, J=1.0 Hz), 8.38 (s, 1H), 7.72 (m, 2H), 7.55 (d, 1H, J=8.4 Hz), 7.19 (m, 2H), 6.97 (m, 1H), 4.60 (m, 2H), 4.18 (s, 3H), 4.12 (m, 2H), 3.83 (s, 3H).

Compound 447. $^1$H NMR (400 Hz, DMSO-d$_6$) δ8.85 (br s, 1H), 7.02 (br s, 1H), 7.91-7.88 (m, 2H), 7.77-7.74 (m, 1H), 7.61 (t, J=8.20 Hz, 1H), 7.55 (d, J=8.53 Hz, 1H), 7.23-7.17 (m, 2H), 4.64-4.5 (m, 2H), 4.15-4.01 (m, 2H), 3.82 (s, 3H).

Compound 494. $^1$H NMR (400 Hz, DMSO-d$_6$) δ11.2 (s, 1H), 8.9 (s, 1H), 8.7 (bs, 1H), 7.8 (s, 1H), 7.5 (d, 1H), 7.4-7.3 (m, 2H), 7.2-7.1 (m, 2H), 4.5 (dd, 2H, J=17 Hz, 33 Hz), 4.05 (dd, 2H, J=14 Hz, 20 Hz), 3.8 (s, 3H).

Compound 507. $^1$H NMR (400 Hz, DMSO-d$_6$) δ11.2 (s, 1H), 8.9 (s, 1H), 7.8 (d, 1H), 7.5 (m, 1H), 7.4 (s, 1H), 7.2-7.1 (m, 3H), 4.6 (dd, 2H, J=17 Hz, 26 Hz), 4.05 (dd, 2H, J=14 Hz, 30 Hz), 3.8 (s, 3H), 3.0 (s, 3H).

Compound 554. $^1$H NMR (400 Hz, DMSO-d$_6$) δ 11.27 (s, 1H), 8.93 (d, 1H, J=1.2 Hz), 7.96 (bs, 2H) 7.52 (d, 1H, J=8.4 Hz), 7.23 (m, 2H), 1.17 (m, 1H), 4.54 (m, 2H), 4.07 (m, 2H), 3.8 (s, 3H).

Compound 555. $^1$H NMR (400 Hz, DMSO-d$_6$) δ11.73 (s, 1H), 11.14 (s, 1H), 8.79 (s, 1H), 7.54 (m, 2H), 7.17 (m, 2H), 6.20 (s, 1H), 4.52 (dd, J=25.6 Hz, 17.6 Hz, 2H), 4.03 (m, 2H), 3.79 (s, 3H), 2.03 (s, 3H).

Compound 516. $^1$H NMR (400 MHz, DMSO-d$_6$) δ8.91 (s, 1H), 7.49 (m, 3H), 7.30 (m, 1H), 7.20 (m, 3H), 4.55 (dd, J=36.8 Hz, 17.2 Hz, 2H), 4.07 (s, 2H), 3.80 (s, 3H).

Compound 490. $^1$H NMR (400 MHz, DMSO-d$_6$) δ 10.9 (bs, 1H), 8.95 (s, 1H), 7.6 (m, 1H), 7.5 (d, 1H), 7.4 (m, 1H), 7.2-7.1 (m, 3H), 4.5 (m, 2H), 4.05 (s, 2H), 3.8 (s, 3H).

Compound 442. $^1$H NMR (400 MHz, DMSO-d$_6$) δ 11.36 (s, 1H), 9.74 (s, 1H), 9.08 (d, 1H, J=1.7 Hz), 8.66 (d, 1H, J=6.1 Hz), 8.45 (d, 1H, J=8.5 Hz), 8.29 d, 1H, J=6.3 Hz), 8.19 (dd, 1H, J=0.9, 7.2 Hz), 7.89 (dd, 1H, J=7.6, 8.2 Hz), 7.55 (d, 1H, J=8.0 Hz), 7.25-7.10 (m, 2H), 4.63 (m, 2H), 4.29 (d, 1H, J=14.0 Hz), 4.15 (d, 1H, J=13.9 Hz), 3.82 (s, 3H)

Compound 930. $^1$H NMR (500 Hz, MeOH-d$_4$) δ7.95 (d, 1H, J=4 Hz), 7.67 (dd, 1H, J=10 Hz, 1.5 Hz), 7.48 (d, 1H, J=8.5 Hz), 7.33 (d, 1H, J=2.5 Hz), 7.22 (dd, 1H, J=2.5 Hz, 8.5

Hz), 6.67 (dd, 1H, J=8 Hz, 5 Hz), 4.67 (q, 2H, J=17 Hz), 4.36 (d, 1H, J=14 Hz), 4.15 (d, 1H, J=14.5 Hz), 3.88 (s, 3H).

Compound 943. $^1$H NMR (500 Hz, MeOH-d$_4$) δ 8.630 (s, 1H), 8.568 (dd, J=2.0 Hz, 5.1 Hz, 1H), 7.925 (dt, J=1.5 Hz, 8.2 Hz, 1H), 7.648 (d, J=8.8 Hz, 1H), 7.57 (s, 1H), 7.452 (m, 2H), 6.940 (t, J=73.1 Hz, 1H), 4.731 (dd, J=16.4 Hz, 56.7 Hz, 2H), 4.267 (dd, J=23.1 Hz, 14.2 Hz, 2H).

Compound 960. $^1$H NMR (500 Hz, MeOH-d$_4$) δ 8.492 (s, 2H), 8.137 (d, J=2.2 Hz, 1H), 7.490 (d, J=8.5 Hz, 1H), 7.337 (d, J=2.8 Hz, 1H), 7.217 (dd, J=8.5 Hz, 2.5 Hz, 1H), 4.673 (dd, J=55.2 Hz, 17.3 Hz, 2H), 4.280 (dd, J=37.8 Hz, 14.2 Hz, 2H), 3.877 (s, 3H).

Compound 972. $^1$H NMR (500 Hz, MeOH-d$_4$) δ 9.319 (s, 1H), 8.159 (s, 1H), 8.083 (d, J=8.5 Hz, 1H), 7.547 (dd, J=2.3 Hz, 8.6 Hz, 1H), 7.482 (d, J=8.8 Hz, 1H), 7.334 (d, J=2.5 Hz, 1H), 7.209 (dd, J=8.5 Hz, 2.5 Hz, 1H), 4.669 (dd, J=59.9 Hz, 16.7 Hz, 2H), 4.277 (dd, J=29.6 Hz, 14.8 Hz, 2H), 3.871 (s, 3H).

Compound 1003. $^1$H NMR (500 MHz, DMSO-d$_6$) δ11.32 (s, 1H), 9.01 (s, 1H), 8.59 (d, 1H, J=4.5 Hz), 8.07 (d, 1H, J=7.5 Hz), 7.55 (d, 1H, J=8 Hz), 7.50 (t, 1H, J=5.5 Hz), 7.21 (m, 2H), 4.62 (d, 1H, J=17 Hz), 4.56 (d, 1H, J=17 Hz), 4.18 (d, 1H, J=14 Hz), 4.09 (d, 1H, J=14 Hz), 3.83 (s, 3H), 2.58 (s, 3H).

Compound 1256. $^1$H NMR (500 MHz, DMSO-d$_6$) δ11.23 (s, 1H), 10.84 (s, 1H), 8.91 (s, 1H), 8.66 (s, 1H), 7.55 (H, J=8 Hz), 7.50 (d, 1H, J=9 Hz), 7.48 (d, 1H, J=9 Hz), 7.23 (d, 1H, J=2.5 Hz), 7.20 (dd, 1H, J=8, 2.5 Hz), 4.62 (d, 1H, J=17 Hz), 4.54 (d, 1H, J=17 Hz), 4.11 (d, 1H, J=15 Hz), 4.07 (d, 1H, J=15 Hz), 3.83 (s, 3H), 1.65 (s, 3H).

Compound 1009. $^1$H NMR (500 MHz, DMSO-d$_6$) δ12.63 (bs, 1H), 11.24 (s, 1H), 8.90 (S, 1H), 8.57 (bs, 1H), 7.55 (d, 1H, J=8 Hz), 7.40 (bs, 1H), 7.33 (bs, 1H), 7.27 (m, 2H), 7.20 (d, 1H, J=8.5 Hz), 4.62 (d, 1H, J=16.5 Hz), 4.56 (d, 1H, J=16.5 Hz), 4.15 (d, 1H, J=14.5 Hz), 4.06 (d, 1H, J=14.5 Hz), 3.84 (s, 3H).

Compound 1012. $^1$H NMR (500 MHz, DMSO-d$_6$) δ11.27 (s, 1H), 8.94 (s, 1H), 7.89 (s, 1H), 7.79 (d, 1H, J=8.5 Hz), 7.56 (d, 1H, J=8.5 Hz), 7.50 (d, 1H, J=8.5 Hz), 7.26 (d, 1H, J=2.5 Hz), 7.20 (dd, 1H, J=9, 2.5 Hz), 4.64 (d, 1H, J=17.5 Hz), 4.58 (d, 1H, J=17.5 Hz), 4.18 (d, 1H, J=14.5 Hz), 4.09 (d, 1H, J=14.5 Hz), 3.84 (s, 3H).

Compound 1253. $^1$H NMR (500 MHz, DMSO-d$_6$) δ11.27 (s, 1H), 8.95 (s, 1H), 8.72 (s, 1H), 7.67 (d, 1H, J=8 Hz), 7.63 (s, 1H), 7.55 (d, 1H, J=8 Hz), 7.53 (d, 1H, J=8 Hz), 7.25 (d, 1H, J=2.5 Hz), 7.20 (dd, 1H, J=8, 2.5 Hz), 4.63 (d, 1H, J=17.5 Hz), 4.56 (d, 1H, J=17.5 Hz), 4.41 (s, 2H), 4.15 (d, 1H, J=14 Hz), 4.09 (d, 1H, J=14 Hz), 3.84 (s, 3H).

Compound 1015. $^1$H NMR (500 MHz, DMSO-d$_6$) δ11.27 (s, 1H), 8.84 (s, 1H), 8.21 (s, 1H), 7.88 (d, 1H, J=8 Hz), 7.56 (d, 1H, J=8 Hz), 7.48 (d, 1H, J=7.5 Hz), 7.25 (d, 1H, J=2 Hz), 7.20 (dd, 1H, J=8, 2 Hz), 7.14 (d, 1H, J=7.5 Hz), 4.65 (d, 1H, J=17.5 Hz), 4.61 (d, 1H, J=17.5 Hz), 4.30 (d, 1H, J=14 Hz), 4.15 (d, 1H, J=14 Hz), 3.83 (s, 3H).

Compound 1155. $^1$H NMR (500 MHz, MeOH-d$_6$) δ8.90 (bs, 1H), 8.51 (d of d, 1H, J=8 Hz, J=2 Hz), 7.94 (d, 1H, 8 Hz), 7.49 (d, 1H, 9 Hz), 7.31 (d, 1H, J=2 Hz), 7.23 (d of d, 1H, J=9 Hz, 2 Hz), 4.69 (d, 1H, J=17 Hz), 4.60 (d, 1H, J=17 Hz), 4.35 (d, 1H, J=14 Hz), 4.22 (d, 1H, 14 Hz), 3.88 (s, 3H).

Compound 1152. $^1$H NMR (500 MHz, MeOH-d$_8$) δ7.46-7.51 (m,3H), 7.31 (s, 1H), 7.20 (d, 1H, J=9 Hz), 6.66 (bs, 1H), 4.68 (d, 1H, J=17 Hz). 4.57 (d, 1H, J=17 Hz), 4.30 (d, 1H, J=14 Hz), 4.23 (d, 1H, J=14 Hz), 3.87 (s, 3H).

Compound 1129. $^1$H NMR (500 MHz, MeOH-d$_6$) δ7.67 (s, 1H), 7.51-7.46 (m, 1H), 7.39-7.26 (m, 3H), 7.24-7.13 (m, 2H), 6.46 (s, 1H), 4.74 (d, 1H, J=17 Hz), 4.61 (d, 1H, J=17 Hz), 4.25 (s, 2H), 3.88 (s, 3H).

Compound 1133. $^1$H NMR (500 MHz, MeOH-d$_6$) δ7.90-7.84 (m, 1H), 7.57-7.46 (m, 3H), 7.35-7.32 (m, 1H), 7.25-7.20 (m, 1H), 4.70 (d, 1H, J=17 Hz), 4.60 (d, 1H, J=17 Hz), 4.28 (d, 1H, J=15 Hz), 4.22 (d, 1H, J=15 Hz), 3.88 (s, 3H).

Compound 1134. $^1$H NMR (500 MHz, MeOH-d$_6$) δ67.97 (s, 1H), 7.93-7.88 (m, 1H), 7.66-7.61 (m, 1H), 7.52-7.47 (m, 2H), 7.33 (s, 1H), 7.24-7.19 (m, 1H), 4.71 (d, 1H, J=17 Hz), 4.60 (d, 1H, J=17 Hz), 4.28 (d, 1H, J=15 Hz), 4.23 (d, 1H, J=15 Hz), 3.88 (s, 3H).

Compound 1136. $^1$H NMR (500 MHz, MeOH-d$_6$) δ7.88-7.83 (m, 2H), 7.55-7.45 (m, 3H), 7.34-7.29 (m, 1H), 7.23-7.15 (m, 3H), 4.69 (d, 1H, J=17 Hz), 4.59 (d, 1H, J=17 Hz), 4.28 (d, 1H, J=14 Hz), 4.21 (d, 1H, J=14 Hz), 3.87 (s, 3H).

Compound 1146. $^1$H NMR (400 MHz, MeOH-d$_6$) δ7.50-7.48 (m, 2H), 7.42 (d, 2H, J=8 Hz), 7.37-7.33 (m, 1H), 7.30-7.24 (m, 2H), 7.18-7.14 (m, 1H), 5.48 (s, 1H), 4.69 (d, 1H, J=17 Hz), 4.55 (d, 1H, J=17 Hz), 4.23 (d, 1H, J=14 Hz), 4.20 (d, 1H, J=14 Hz), 3.83 (s, 3H).

Compound 1132. $^1$H NMR (500 MHz, MeOH-d$_6$) δ7.47-7.41 (m, 2H), 7.34-7.28 (m, 2H), 7.22-7.13 (m, 2H), 7.10-7.04 (m, 1H), 6.55-6.52 (m, 1H), 4.73 (d, 1H, J=17 Hz), 4.60 (d, 1H, J=17 Hz), 4.30 (d, 1H, J=15 Hz), 4.27 (d, 1H, J=15 Hz), 3.86 (s, 3H).

Compound 1091. $^1$H NMR (500 MHz, CD$_3$OD) δ8.09 (s, 1H), 7.60 (d, 2H, J=8 Hz), 7.44-7.51 (m, 3H), 7.33 (d, 1H, J=2H), 7.22 (dd, 1H, J=8 Hz, 2 Hz), 4.70 (d, 1H, J=17 Hz), 4.59 (d, 1H, J=17 Hz), 4.27 (d, 1H, J=14.5 Hz), 4.21 (d, 1H, J=14.5 Hz), 3.88 (s, 3H).

Compound 1063. $^1$H NMR (500 MHz, CD$_3$OD) δ7.48 (d, 1H, J=8.5 Hz), 7.33 (d, 1H, J=2.5 Hz), 7.28 (bs, 1H), 7.20-7.30 (m, 2H), 7.11-7.19 (m, 1H), 4.70 (d, 1H, J=17 Hz), 4.58 (d, 1H, J=17 Hz), 4.28 (d, 1H, J=14.5 Hz), 4.21 (d, 1H, J=14.5 Hz), 3.88 (s, 3H).

Compound 1070. $^1$H NMR (500 MHz, CD$_3$OD) δ7.68 (s, 1H), 7.48 (d, 1H, J=8.5 Hz), 7.32 (d, 1H, J=2 Hz), 7.22 (dd, 1H, J=8.5 Hz, 2 Hz), 7.17 (s, 1H), 4.67 (d, 1H, J=16.5 Hz), 4.57 (d, 1H, J=16.5 Hz), 4.16-4.28 (m, 4H), 3.88 (s, 3H).

Compound 1090. $^1$H NMR (500 MHz, CD$_3$OD) δ7.48 (d, 1H, J=8.5 Hz), 7.33 (d, 1H, J=2.5 Hz), 7.18-7.23 (m, 3H), 4.69 (d, 1H, J=17 Hz), 4.57 (d, 1H, J=17 Hz), 2.24 (d, 1H, J=14.5 Hz), 2.21 (d, 1H, J=14.5 Hz), 3.88 (s, 3H).

Compound 1092. $^1$H NMR (500 MHz, DMSO-d$_6$) δ8.80 (s, 1H), 8.62 (bd, 1H, J=12 Hz), 7.89 (dt, 1H, J=8.3 Hz, 2 Hz), 7.83 (d, 1H, J=8.3 Hz), 7.43-7.47 (m, 1H), 6.91 (dd, 1H, J=8 Hz, 2.5 Hz), 6.86 (d, 1H, J=2.5 Hz), 4.14 (d, 1H, J=13.5 Hz), 4.02 (d, 1H, J=13.5 Hz), 3.81 (s, 3H), 3.68-3.74 (m, 1H), 3.60-3.67 (m, 1H), 2.88-3.01 (m, 2H).

Compound 1098. $^1$H NMR (500 MHz, DMSO-d$_6$) δ8.91 (s, 1H), 8.21 (bs, 1H), 7.55 (d, 1H, J=6 Hz), 7.17-7.26 (m, 2H), 4.63 (d, 1H, J=17 Hz), 4.57 (d, 1H, J=17 Hz), 4.17 (d, 1H, J=13.5 Hz), 4.08 (d, 1H, J=13.5 Hz), 3.83 (s, 3H), 2.47 (s, 3H).

Compound 1069. $^1$H NMR (500 MHz, CD$_3$OD) δ7.47 (d, 1H, J=8.5 Hz), 7.32 (d, 1H, J=2.5 Hz), 7.21 (dd, 1H, J=8.5 Hz, 2.5 Hz), 7.15 (dd, 1H, J=8 Hz, 1 Hz), 7.12 (d, 1H, J=1 Hz), 7.01 (d, 1H, J=8 Hz), 4.70 (d, 1H, J=17 Hz), 4.59 (d, 1H, J=17 Hz), 4.26 (d, 1H, J=14 Hz), 4.20 (d, 1H, J=14 Hz), 3.84 (s, 3H).

Compound 1099. $^1$H NMR (500 MHz, DMSO-d$_6$) δ11.2 (s, 1H), 8.83 (s, 1H), 8.71 (s, 1H), 8.66 (bd, 1H, J=4 Hz), 7.99 (dt, 1H, J=8 Hz, 2 Hz), 7.52-7.56 (m, 1H), 7.40 (d, 1H, J=3 Hz), 7.24 (d, 1H, J=8.5 Hz), 7.08 (dd, 1H, J=8.5 Hz, 3 Hz), 4.17 (d, 1H, J=14 Hz), 4.07 (d, 1H, J=14 Hz), 3.78 (s, 3H), 3.69-3.75 (m, 1H), 3.61-3.67 (m, 1H), 2.84-2.96 (m, 2H).

Compound 1502. $^1$H NMR (500 MHz, DMSO-d$_6$) δ11.31 (s, 1H), 8.98 (s, 1H), 8.71 (s, 1H), 8.01 (m, 2H), 7.56 (d, 1H, J=8.2 Hz), 7.24 (d, 1H, J=2.6 Hz), 7.21 (dd, 1H, J=8.2 Hz, 2.6

Hz), 4.63 (d, 1H, J=17.1 Hz), 4.57 (d, 1H, J=17.1 Hz), 4.16 (d, 1H, J=13.9 Hz), 4.11 (d, 1H, J=13.9 Hz), 3.84 (s, 3H), 3.30 (m, 2H), 1.19 (t, 3H, J=7.2 Hz).

Compound 1505. $^1$H NMR (500 MHz, DMSO-$d_6$) δ11.25 (s, 1H), 8.93 (s, 1H), 8.76 (s, 1H), 7.69 (s, 1H), 7.56 (d, 1H, J=8.5 Hz), 7.45 (d, 1H, J=9.4 Hz), 7.25 (d, 1H, J=2.6 Hz), 7.21 (dd, 1H, J=8.5 Hz, 2.6 Hz), 7.13 (dd, 1H, J=9.4 Hz, 1.6 Hz), 4.63 (d, 1H, J=17.1 Hz), 4.55 (d, 1H, J=17.1 Hz), 4.13 (d, 1H, J=14.2 Hz), 4.08 (d, 1H, J=14.2 Hz), 3.83 (s, 3H), 2.33 (s, 3H).

Compound 1513. $^1$H NMR (500 MHz, DMSO-$d_6$) δ11.31 (s, 1H), 8.98 (s, 1H), 8.68 (s, 1H), 8.20 (s, 1H), 8.06 (dd, 1H, J=8.2 Hz, 1.9 Hz), 8.04 (d, 1H, J=8.2 Hz), 7.78 (brs, 1H), 7.56 (d, 1H, J=8.5 Hz), 7.24 (d, 1H, J=2.4 Hz), 7.21 (dd, 1H, J=8.5 Hz, 2.4 Hz), 4.63 (d, 1H, J=17.1 Hz), 4.57 (d, 1H, J=17.1 Hz), 4.17 (d, 1H, J=13.9 Hz), 4.11 (d, 1H, J=13.9 Hz), 3.84 (s, 3H).

Compound 1519. $^1$H NMR (500 MHz, DMSO-$d_6$) δ11.18 (s, 1H), 8.85 (d, 1H, J=1.2 Hz), 7.91 (d, 1H, J=2.6 Hz), 7.55 (d, 1H, J=8.3 Hz), 7.20 (m, 3H), 4.60 (d, 1H, J=17.0 Hz), 4.51 (d, 1H, J=17.0 Hz), 4.05 (s, 2H), 3.83 (s, 3H), 3.42 (s, 3H), 1.97 (s, 3H).

Compound 1520. $^1$H NMR (500 MHz, DMSO-$d_6$) δ11.28 (s, 1H), 8.97 (d, 1H, J=1.2 Hz), 8.06 (m, 2H), 7.57 (d, 1H, J=8.5 Hz), 7.41 (dd, 1H, J=8.7 Hz, 1.6 Hz), 7.25 (d, 1H, J=2.4 Hz), 7.21 (dd, 1H, J=8.5 Hz, 2.4 Hz), 4.64 (d, 1H, J=17.1 Hz), 4.57 (d, 1H, J=17.1 Hz), 4.31 (s, 3H), 4.16 (d, 1H, J=13.8 Hz), 4.12 (d, 1H, J=13.8 Hz), 3.84 (s, 3H).

Compound 1523. $^1$H NMR (500 MHz, CD$_3$OD) δ8.08 (s, 1H), 7.92 (d, 1H, J=1.0 Hz), 7.53 (d, 1H, J=8.4 Hz), 7.48 (d, 1H, J=8.4 Hz), 7.43 (dd, 1H, J=8.6 Hz, 1.4 Hz), 7.34 (d, 1H, J=2.6 Hz), 7.21 (dd, 1H, J=8.2 Hz, 2.6 Hz), 4.71 (d, 1H, J=17.1 Hz), 4.62 (d, 1H, J=17.1 Hz), 4.30 (d, 1H, J=14.2 Hz), 4.19 (d, 1H, J=14.2 Hz), 3.88 (s, 3H).

Compound 1220B. $^1$H NMR (500 Hz, dmso-$d_6$) δ8.9 (bs, 1H,) 7.95 (d, 2H, J=5 Hz), 7.64 (d, 2H, J=5 Hz), 7.6 (d, 1H, J=3 Hz), 7.28 (s, 1H), 7.2 (d, 1H, J=3 Hz), 4.6 (dd, 2H, J=16 Hz, 9 Hz), 4.15 (dd, 2H, J=16 Hz, 9 Hz), 3.82 (s, 3H).

Compound 1206. $^1$H NMR (500 Hz, dmso-$d_6$) δ8.9 (bs, 1H,) 7.52 (d, 1H, J=5 Hz), 7.2 (m, 2H), 4.6 (dd, 2H, J=8 Hz, 28 Hz), 4.2 (s, 2H), 3.81 (s, 3H), 212 (s, 3H).

Compound 1201. $^1$H NMR (500 Hz, dmso-$d_6$) δ8.92 (s, 1H,), 7.64 (d, 1H, J=6 Hz), 7.2-7.42 (m, 4H), 7.4 (d, 1H, J=6 Hz), 6.72 (bs, 1H), 4.62 (d, 1H, J=8 Hz), 4.58 (d, 2H, J=8 Hz), 4.05 (m, 2H), 3.88 (s, 3H).

Compound 1200. $^1$H NMR (500 Hz, dmso-$d_6$) δ8.92 (s, 1H,), 8.65 (m, 2H), 7.4-7.75 (m, 5H), 4.66 (dd, 2H, J=16 Hz, 24 Hz), 4.15 (m, 2H).

Compound 1220. $^1$H NMR (500 Hz, dmso-$d_6$). 8.449 (s. 1H), 7.93 (s, 1H), 7.73 (t, 1H, J=1.892 Hz), 6.55 (d, 1H, J=2.522 Hz), 6.69 (d, 1H, J=8.512 Hz), 6.41 (dd, 1H, J=2.52 Hz, J=8.51 Hz), 4.46-4.40 (m, 1H), 3.87 (dd, 2H, J=17.02 Hz, J=54.85 Hz), 3.48 (dd, 2H, J=14.187 Hz, J=51.703 Hz), 3.067 (s, 3H), 0.92 (d, 6H, J=6.62 Hz).

Compound 1552. $^1$H NMR (500 Hz, CD$_3$OD) δ8.11 (s, 1H), 7.49 (d, 1H, J=8.5 Hz), 7.33 (d, 1H, J=2 Hz), 7.11-7.25 (m, 3H), 4.72 (d, 1H, J=17 Hz), 4.60 (d, 1H, J=17 Hz), 4.31 (d, 1H, J=14.5 Hz), 4.23 (d, 1H, J=14.5 Hz), 3.88 (s, 3H), 2.24 (s, 3H).

Compound 1562. $^1$H NMR (500 MHz, MeOH-$d_6$) δ7.63-7.61 (m, 2H) (bs, 1H), 7.57-7.55 (m, 2H), 7.48 (d, 1H, 9 Hz), 7.32 (d, 1H, J=3 Hz), 7.22 (d of d, 1H, J=9 Hz, 3 Hz), 4.69 (d, 1H, J=18 Hz), 4.58 (d, 1H, J=18 Hz), 4.27 (d, 1H, J=15 Hz), 4.21 (d, 1H, 15 Hz), 3.88 (s, 3H), 3.89-3.86 (m, 1H), 3.40-3.37 (m, 1H).

Compound 1576. $^1$H NMR (500 MHz, DMSO-$d_6$) δ11.23 (s, 1H), 10.83 (s, 1H), 8.91 (s, 1H), 8.46 (s, 1H), 7.56 (d, J=8.5 Hz, 1H), 7.35 (br. s, 1H), 7.32 (d, J=8.5 Hz, 1H), 7.24 (d, J=2.5 Hz, 1H), 7.20 (m, 2H), 4.63 (d, J=17 Hz, 1H), 4.54 (d, J=17 Hz, 1H), 4.11 (d, J=14 Hz, 1H), 4.07 (d, J=14 Hz, 1H), 3.83 (s, 3H), 2.98 (m, 2H), 2.54 (m, 1H), 2.16 (m, 1H).

It will be appreciated by those skilled in the art that changes could be made to the embodiments described above without departing from the broad inventive concept thereof. It is understood, therefore, that this invention is not limited to the particular embodiments disclosed, but it is intended to cover modifications that are within the spirit and scope of the invention, as defined by the appended claims.

Each document referred to herein is incorporated by reference in its entirety for all purposes.

We claim:

1. A method of treating a condition or disease selected from the group consisting of septic shock, sepsis syndrome, post ischaemic reperfusion injury, meningitis, psoriasis, an inflammatory bowel disease, osteo and rheumatoid arthritis, ankylosing spondylitis, psoriatic arthritis, adult Still's disease, non-insulin dependent diabetes mellitus, asthma, and chronic obstructive pulmonary disease (COPD) in a subject comprising administering to the subject in need of such treatment a therapeutically effective amount of a compound, or a pharmaceutically acceptable salt thereof;

wherein the compound is represented by Formula (I):

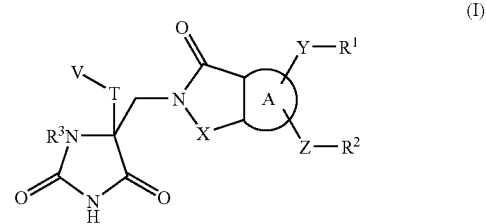

wherein:

ring A is phenyl, which is substituted with —Y—R$^1$ and —Z—R$^2$ as shown;

X is selected from the group consisting of —S—, —O—, —S(O)$_2$—, S(O)—, —(C(R$^3$)$_2$)$_m$— and —N(R$^3$)—;

T is alkynyl;

V is selected from the group consisting H, alkyl, cycloalkyl, cycloalkenyl, aryl, heteroaryl, heterocyclyl, and N-oxides of said heteroaryl and heterocyclyl, wherein when each of said cycloalkyl, cycloalkenyl, aryl, heteroaryl, heterocyclyl, and N oxides of said heteroaryl and heterocyclyl contains two radicals on same or adjacent carbon atoms, said radicals may optionally be taken together with the carbon atom(s) to which they are attached to form a five- to eight-membered cycloalkyl, cycloalkenyl, aryl, heterocyclyl or heteroaryl ring, wherein each of the aforementioned cycloalkyl, cycloalkenyl, aryl, heteroaryl, and heterocyclyl, optionally with said five- to eight-membered cycloalkyl, cycloalkenyl, aryl, heterocyclyl, or heteroaryl is independently unsubstituted or substituted with one to four R$^{10}$ moieties which can be the same or different;

Y is selected from the group consisting of a covalent bond, —(C(R$^4$)$_2$)$_n$—, —N(R$^4$)—, —C(O)N(R$^4$)—, —N(R$^4$)C(O)—, —N(R$^4$)C(O)N(R$^4$)—, —S(O)$_2$N(R$^4$)—, —N(R$^4$)—S(O)$_2$—, —O—, —S—, —C(O)—, —S(O)—, and —S(O)$_2$—;

Z is selected from the group consisting of a covalent bond, —(C(R$^4$)$_2$)$_n$—, —N(R$^4$)—, —C(O)N(R$^4$)—, —N(R⁴)C(O)—, —N(R⁴)C(O)N(R⁴)—, —S(O)₂N(R⁴)—, —N(R⁴)—S(O)₂—, —O—, —S—, —C(O)—, —S(O)—, and —S(O)₂—;

m is 1 to 3:

n is 1 to 3;

R¹ is selected from the group consisting of H, cyano, alkynyl, halogen, alkyl, cycloalkyl, haloalkyl, aryl, heteroaryl, and heterocyclyl, wherein when each of said cycloalkyl, heterocyclyl, aryl and heteroaryl contains two radicals on adjacent carbon atoms, said radicals may optionally be taken together with the carbon atoms to which they are attached to form a five- to eight-membered cycloalkyl, aryl, heterocyclyl or heteroaryl ring; wherein each of the R¹ alkyl, alkynyl, aryl, heteroaryl, and heterocyclyl, optionally with the five- to eight-membered cycloalkyl, aryl, heterocyclyl or heteroaryl ring is unsubstituted or optionally independently substituted with one to four R²⁰ moieties which can be the same or different; with the proviso that when Y is —N(R⁴)—, —S— or —O—, then R¹ is not halogen or cyano;

R² is selected from the group consisting of H, cyano, alkynyl, halogen, alkyl, cycloalkyl, haloalkyl, aryl, heteroaryl, and heterocyclyl, wherein when each of said cycloalkyl, heterocyclyl, aryl and heteroaryl contains two radicals on adjacent carbon atoms, said radicals may optionally be taken together with the carbon atoms to which they are attached to form a five- to eight-membered cycloalkyl, aryl, heterocyclyl or heteroaryl ring; wherein each of the R² alkyl, cycloalkyl, aryl, heteroaryl, and heterocyclyl, optionally with five- to eight-membered cycloalkyl, aryl, heterocyclyl or heteroaryl ring is unsubstituted or optionally independently substituted with one to four R²⁰ moieties which can be the same or different; with the proviso that when Z is —N(R⁴)—, —S— or —O—, then R² is not halogen or cyano;

each R³ is the same of different and is independently selected from the group consisting of H, alkyl, and aryl;

each R⁴ is the same or different and is independently selected from the group consisting of H, alkyl, cycloalkyl, haloalkyl, hydroxy, -alkylcycloalkyl, -alkyl-N(alkyl)₂, heterocyclyl, aryl, and heteroaryl;

R¹⁰ is selected from the group consisting of hydrogen, cyano, nitro, —C(R⁴)═N—OR⁴, —OR⁴, —SR⁴, —N(R⁴)₂, —S(O)R⁴, —S(O)₂R⁴, —N(R⁴)S(O)₂R⁴, —N(R⁴)—C(O)—R⁴, —C(O)N(R⁴)—S(O)₂R⁴, —S(O)₂N(R₄)—C(O)—R⁴, —C(O)N(R⁴)C(O)R⁴, —C(O)N(R⁴)C(O)NR⁴—S(O)₂N(R⁴)₂, —N(R⁴)—C(O)OR⁴, —OC(O)N(R⁴)₂, —N(R⁴)C(O)N(R⁴)₂, —S(O)₂N(R⁴)₂, —S(O)₂N(R₄)—C(O)—R⁴, —N(R⁴)—C(═NR⁴)—N(R⁴)₂, —N(R⁴)—C(═N—CN)—N(R⁴)₂, -haloalkoxy, —C(O)OR⁴, —C(O)R⁴, —C(O)N(R⁴)₂, halogen, alkyl, haloalkyl, aryl, heteroaryl, heterocyclyl, and cycloalkyl, wherein each of the R¹⁰ alkyl, aryl, heteroaryl, heterocyclyl, and cycloalkyl is unsubstituted or optionally independently substituted with one to four R³⁰ moieties which can be the same or different;

or wherein two R¹⁰ moieties, when attached to the same or adjacent carbon atoms may optionally be taken together with the carbon atom(s) to which they are attached to form a cycloalkyl, cycloalkenyl, heterocyclyl, aryl, or heteroaryl ring;

R²⁰ is selected from the group consisting of cyano, nitro, —C(R⁴)═N—OR⁴, —OR⁴, —SR⁴, —N(R⁴)₂, —S(O)R⁴, —S(O)₂R⁴, —N(R⁴)S(O)₂R⁴, —N(R⁴)—C(O)—R⁴, —C(O)N(R⁴)—S(O)₂R⁴, —S(O)₂N(R₄)—C(O)—R⁴, —C(O)N(R⁴)C(O)R⁴, —C(O)N(R⁴)C(O)NR⁴—S(O)₂N(R⁴)₂, —N(R⁴)—C(O)OR⁴, —OC(O)N(R⁴)₂, —N(R⁴)C(O)N(R⁴)₂, —S(O)₂N(R⁴)₂, —S(O)₂N(R₄)—C(O)—R⁴, —N(R⁴)—C(═NR⁴)—N(R⁴)₂, —N(R⁴)—C(═N—CN)—N(R⁴)₂, -haloalkoxy, —C(O)OR⁴, —C(O)R⁴, —C(O)N(R⁴)₂, halogen, alkyl, haloalkyl, aryl, heteroaryl, heterocyclyl, and cycloalkyl; wherein when each of said R²⁰ aryl, heteroaryl, heterocyclyl and cycloalkyl contains two radicals on adjacent carbon atoms, said radicals may optionally be taken together with the carbon atoms to which they are attached to form a five- to eight-membered cycloalkyl, aryl, heterocyclyl or heteroaryl ring; wherein each of said R²⁰ alkyl, aryl, heteroaryl, heterocyclyl, and cycloalkyl, optionally with said five- to eight-membered cycloalkyl, aryl, heterocyclyl or heteroaryl ring is unsubstituted or substituted with one to four moieties selected independently from the group consisting of alkyl, halo, haloalkyl, hydroxy, alkoxy, haloalkoxy, hydroxyalkyl, cyano, nitro, —NH₂, —NH(alkyl), and —N(alkyl)₂;

or when two R²⁰ moieties when attached to the same or adjacent carbon atoms may optionally be taken together with the carbon atom(s) to which they are attached to form a cycloalkyl, cycloalkenyl, heterocyclyl, aryl, or heteroaryl ring;

R³⁰ is selected from the group consisting of cyano, nitro, —C(R⁴)═N—OR⁴, —OR⁴, —SR⁴, —N(R⁴)₂, —S(O)R⁴, —S(O)₂R⁴, —N(R⁴)S(O)₂R⁴, —N(R⁴)—C(O)—R⁴, —C(O)N(R⁴)—S(O)₂R⁴, —S(O)₂N(R₄)—C(O)—R⁴, —C(O)N(R⁴)C(O)R⁴, —C(O)N(R⁴)C(O)NR⁴—S(O)₂N(R⁴)₂, —N(R⁴)—C(O)OR⁴, —OC(O)N(R⁴)₂, —N(R⁴)C(O)N(R⁴)₂, —S(O)₂N(R⁴)₂, —S(O)₂N(R₄)—C(O)—R⁴, —N(R⁴)—C(═NR⁴)—N(R⁴)₂, —N(R⁴)—C(═N—CN)—N(R⁴)₂, -haloalkoxy, —C(O)OR⁴, —C(O)R⁴, —C(O)N(R⁴)₂, halogen, alkyl, haloalkyl, aryl, heteroaryl, heterocyclyl, and cycloalkyl; wherein when each of said R³⁰ aryl, heteroaryl, heterocyclyl and cycloalkyl contains two radicals on adjacent carbon atoms, said radicals may optionally be taken together with the carbon atoms to which they are attached to form a five- to eight-membered cycloalkyl, aryl, heterocyclyl or heteroaryl ring; wherein each of said R³⁰ alkyl, aryl, heteroaryl, heterocyclyl, and cycloalkyl, optionally with said five- to eight-membered cycloalkyl, aryl, heterocyclyl or heteroaryl ring is unsubstituted or substituted with one to four moieties selected independently from the group consisting of alkyl, halo, haloalkyl, hydroxy, alkoxy, haloalkoxy, cyano, nitro, —NH₂, —NH(alkyl), and —N(alkyl)₂;

or when two R³⁰ moieties when attached to the same or adjacent carbon atoms may optionally be taken together with the carbon atom(s) to which they are attached to form a cycloalkyl, cycloalkenyl, heterocyclyl, aryl, or heteroaryl ring.

2. The method of claim 1, wherein the condition or disease is rheumatoid arthritis.

3. The method of claim 1, wherein the condition or disease is inflammatory bowel disease.

4. The method of claim 3, wherein the inflammatory bowel disease is Crohn's disease.

5. The method of claim 3, wherein the inflammatory bowel disease is colitis.

6. The method of claim 1, wherein the condition or disease is chronic obstructive pulmonary disorder.

7. The method of claim 1, wherein the condition or disease is psoriasis.

8. The method of claim 1, wherein the condition or disease is ankylosing spondylitis.

9. The method of claim 1, wherein the condition or disease is psoriatic arthritis.

10. The method of claim 1, wherein the compound of Formula (I) is represented by the compound of Formula (III):

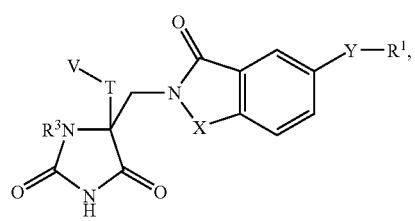

(III)

wherein in Formula (III), X is —(CH$_2$)$_{1-2}$—, and T, V, Y, R$^1$, and R$^3$ are as set forth in claim 1.

11. The method of claim 10, wherein X is —CH$_2$— in the compound of Formula (III).

12. The method of claim 1, wherein the compound of Formula (I) is represented by the compound of Formula (IV):

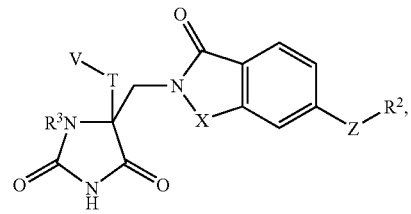

(IV)

wherein in Formula (IV), X is —(CH$_2$)$_{1-2}$—, T, V, Z, R$^2$, and R$^3$ are as set forth in claim 1.

13. The method of claim 12, wherein X is —CH$_2$— in the compound of Formula (IV).

14. The method of claim 1, wherein the compound is selected from the group of compounds set forth below:

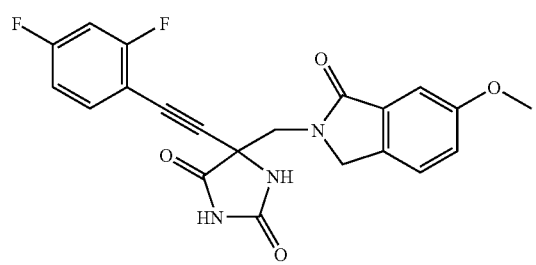

-continued

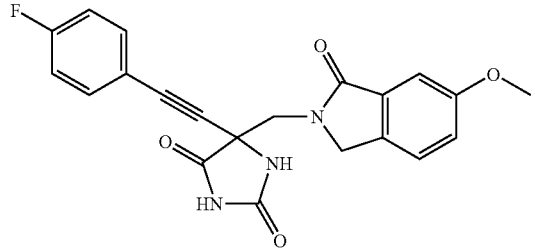

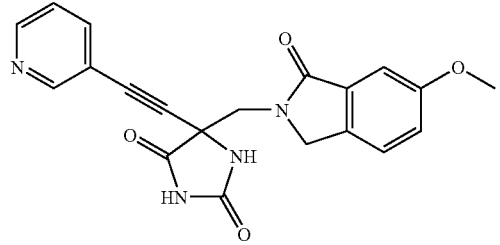

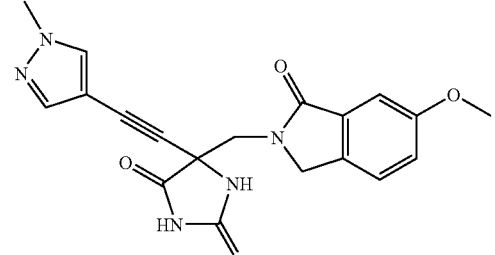

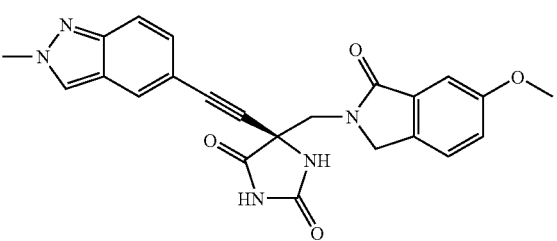

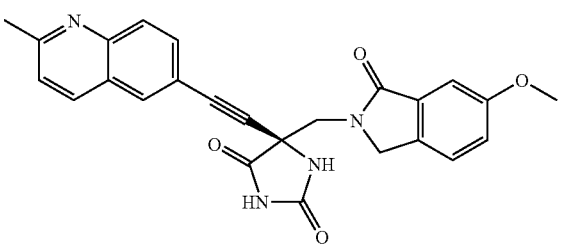

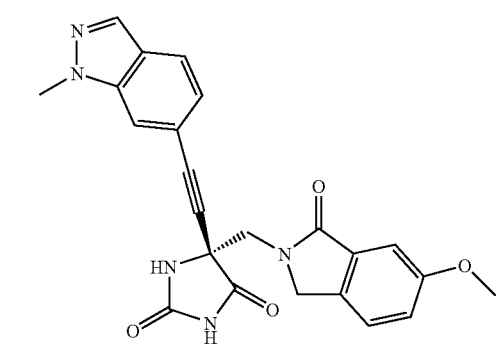

321
-continued
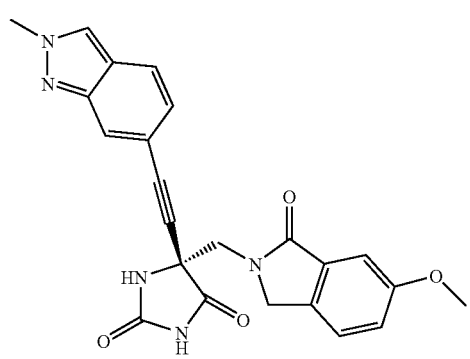
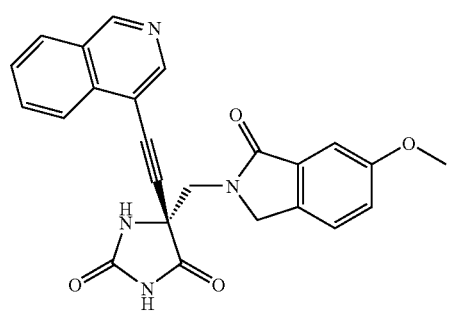
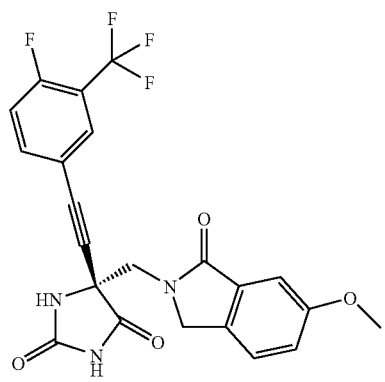
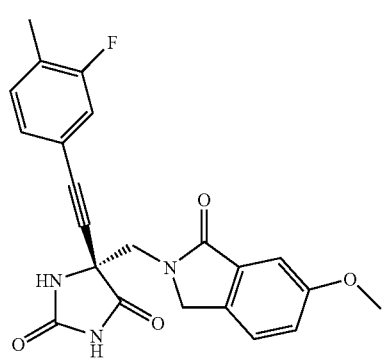
322
-continued
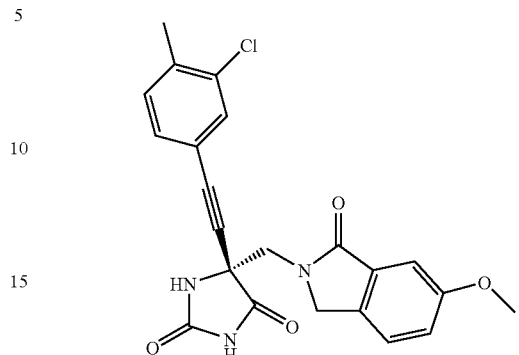
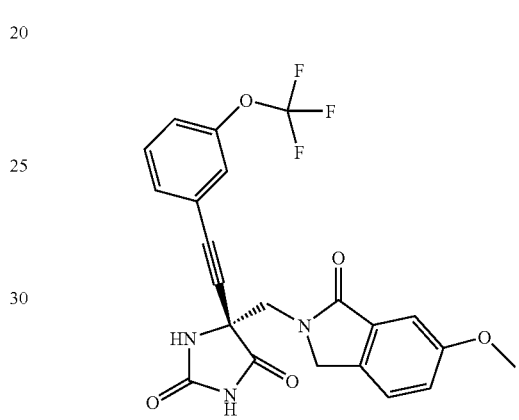
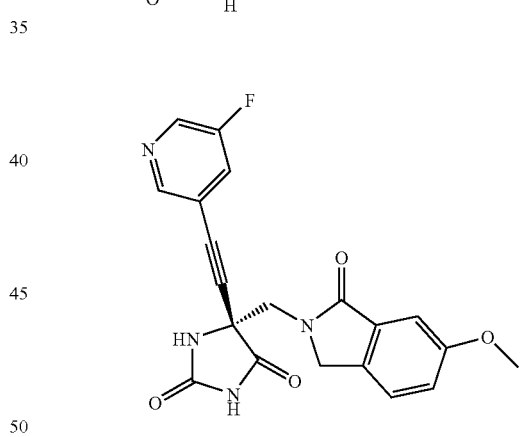
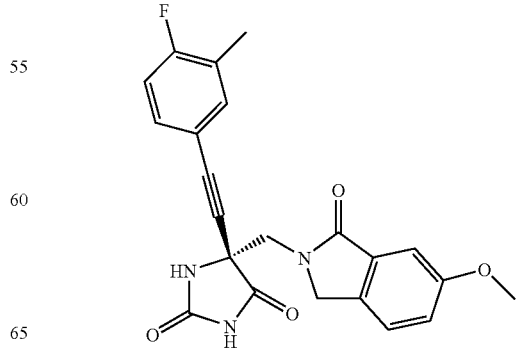

323
-continued
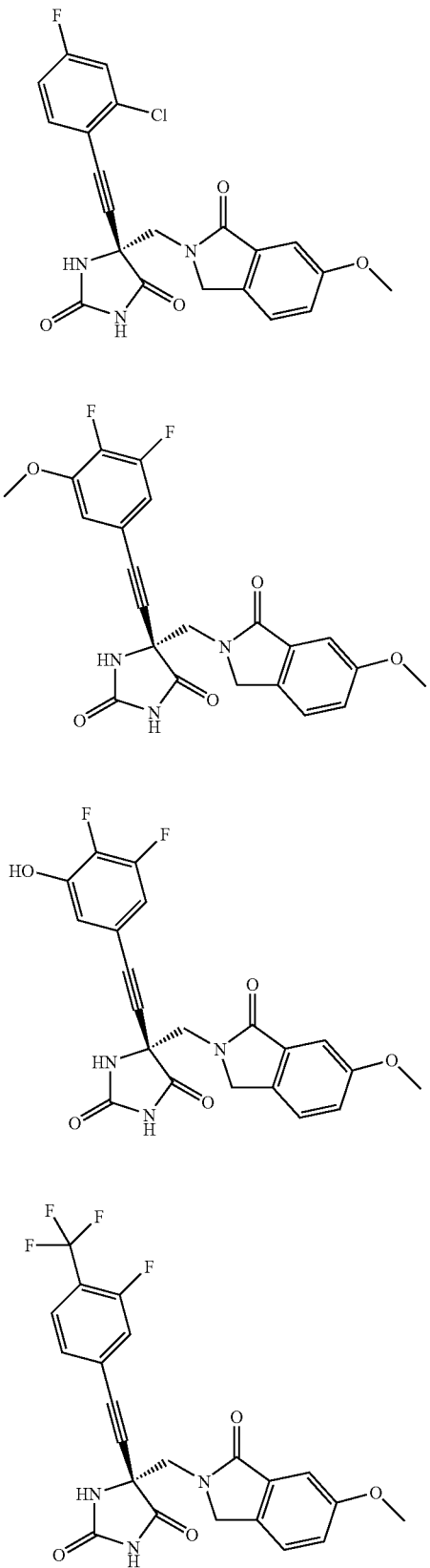
324
-continued
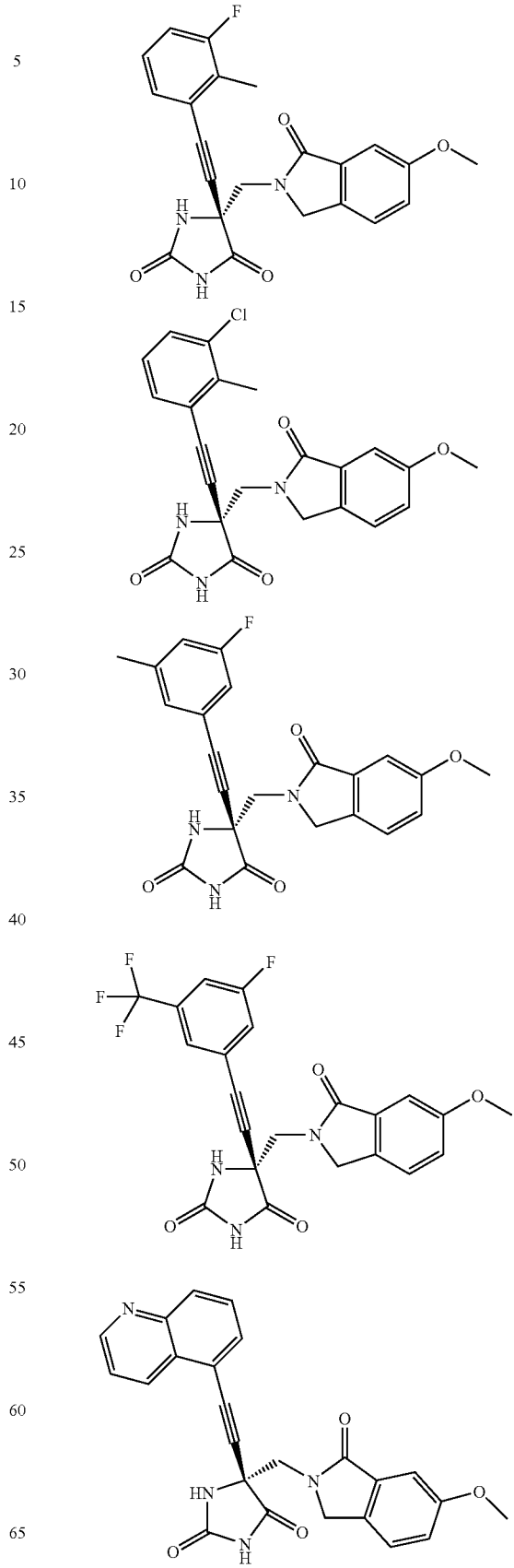

325
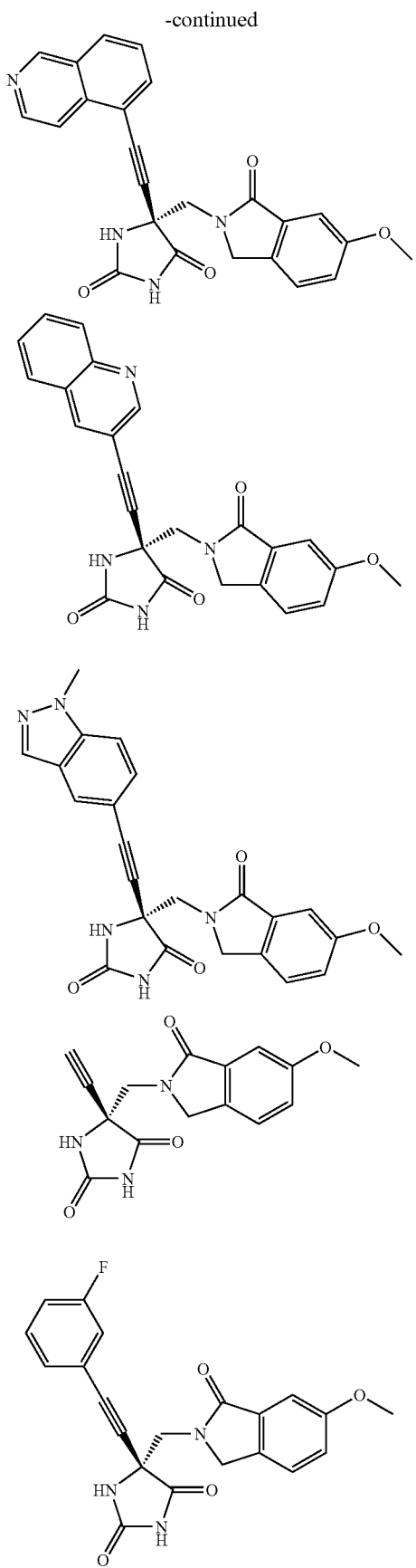
326
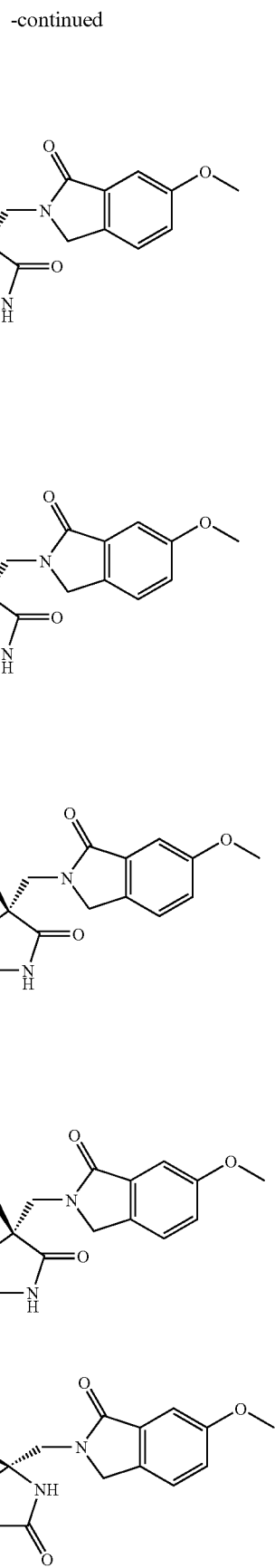

327
-continued
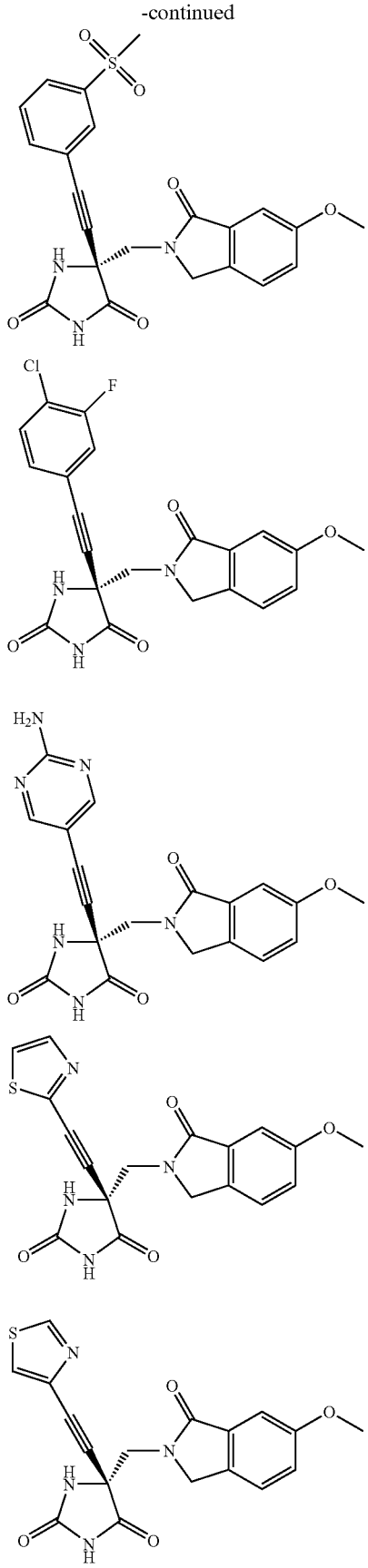
328
-continued
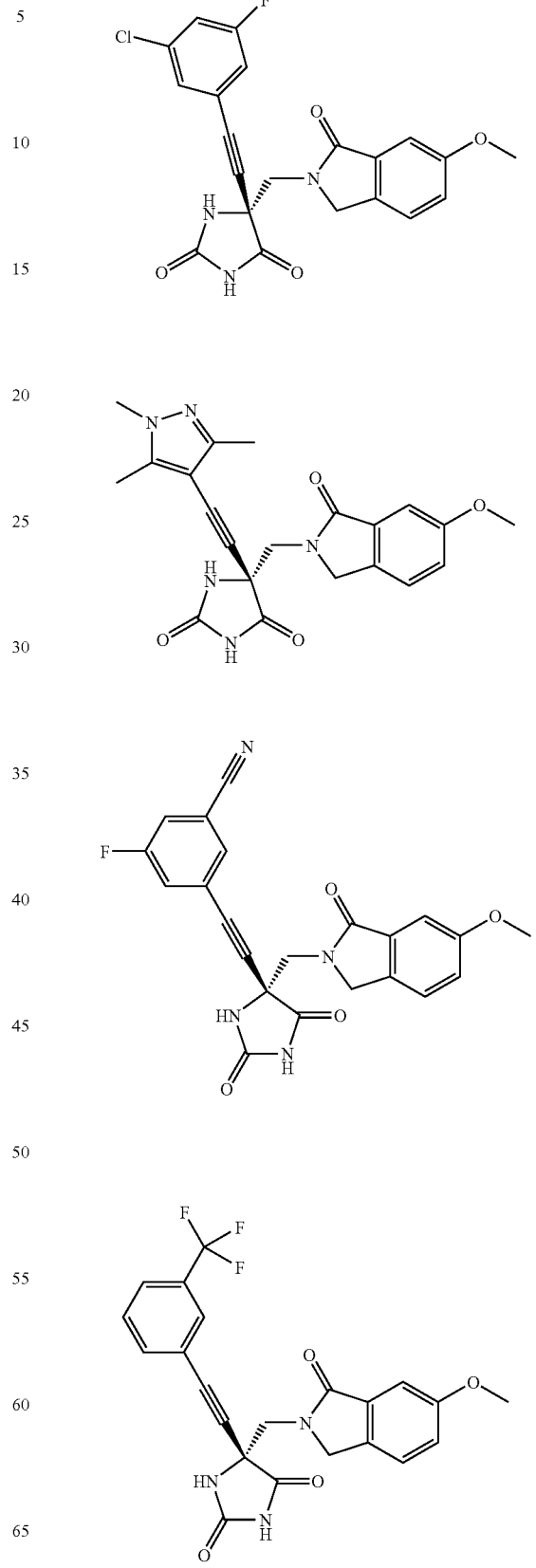

-continued
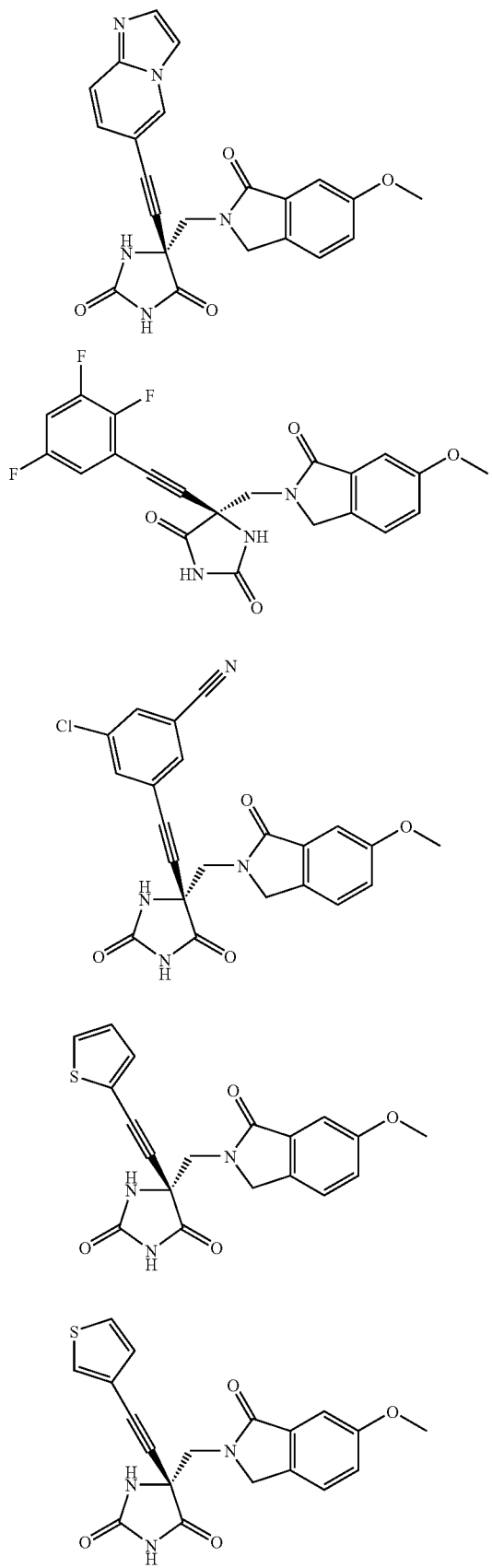
-continued
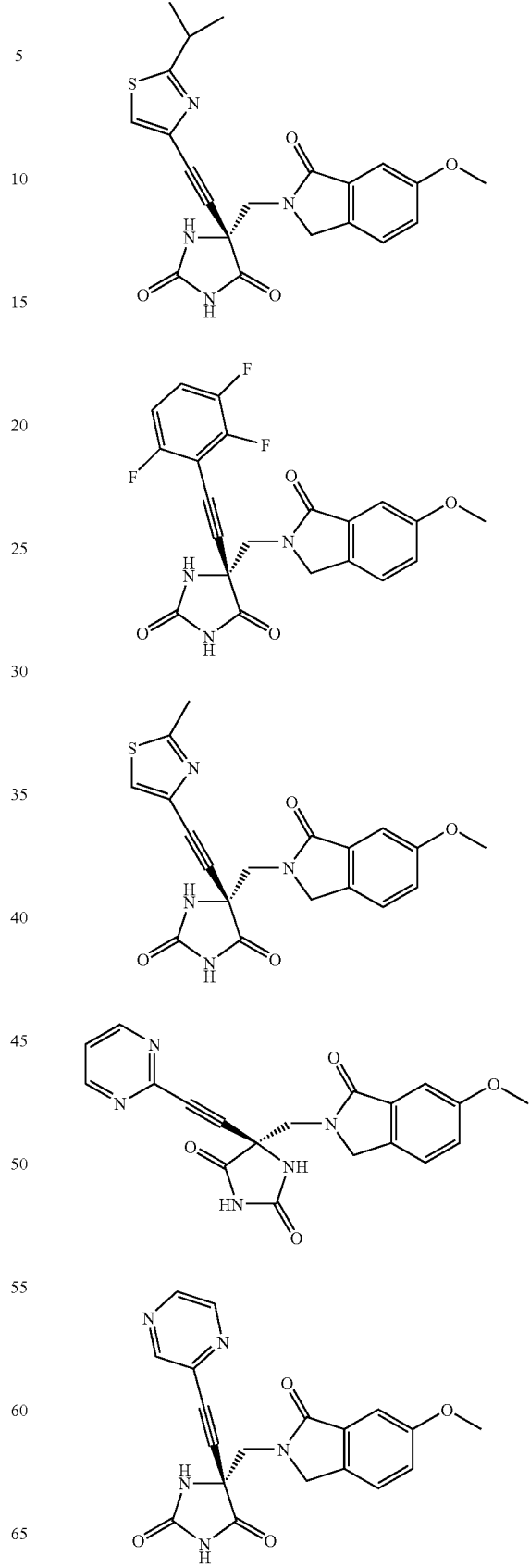

-continued
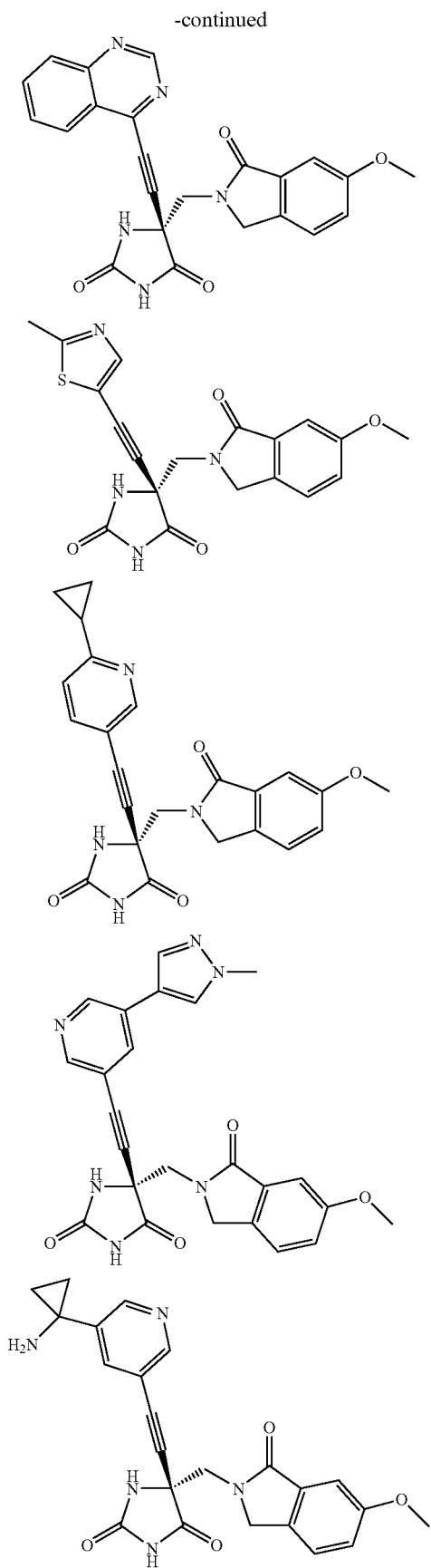
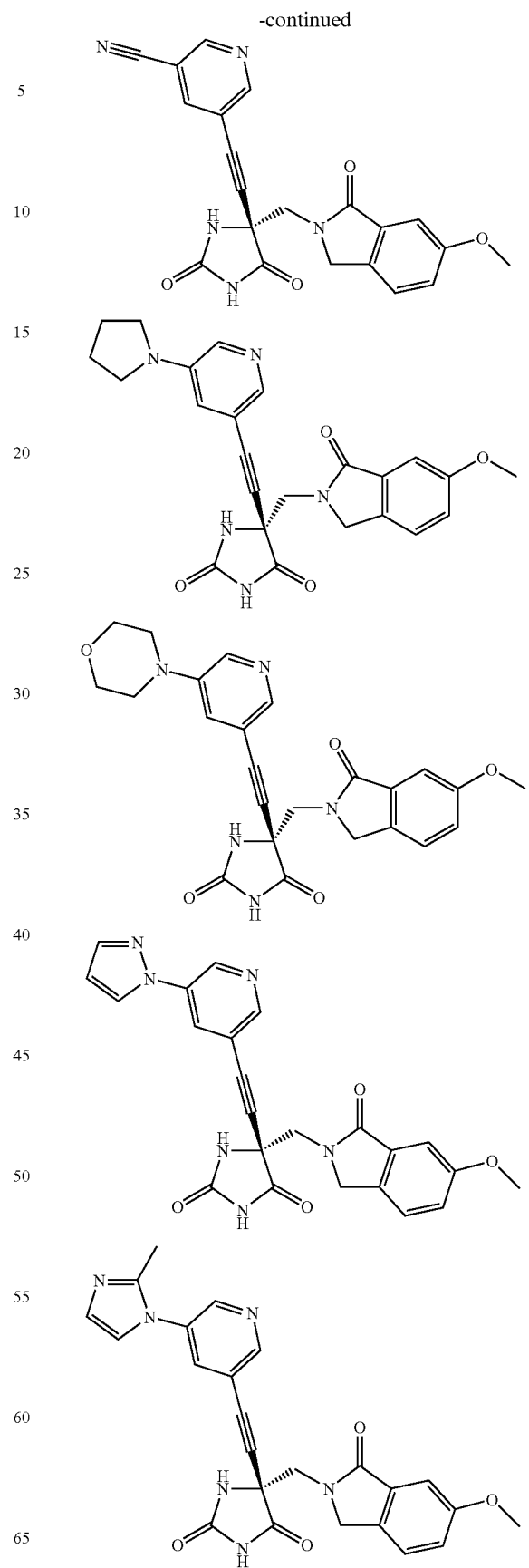

333
-continued
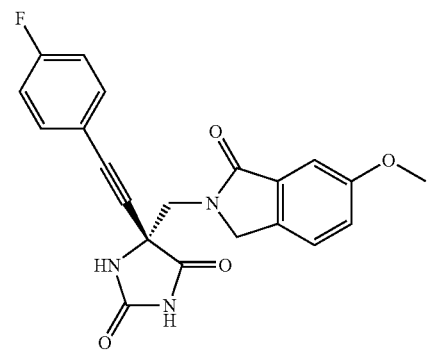
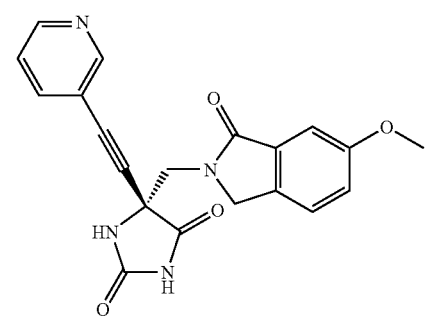
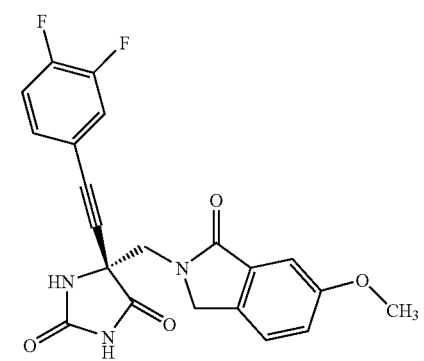
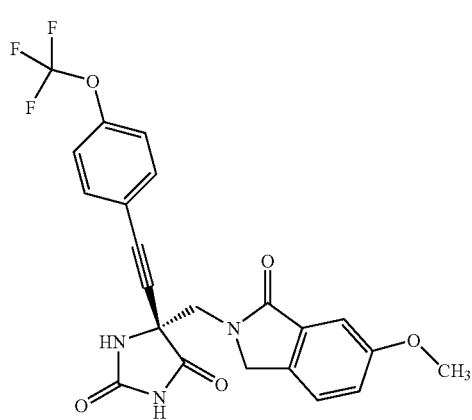
334
-continued
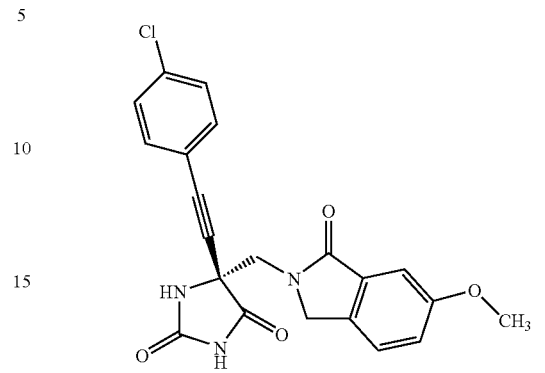
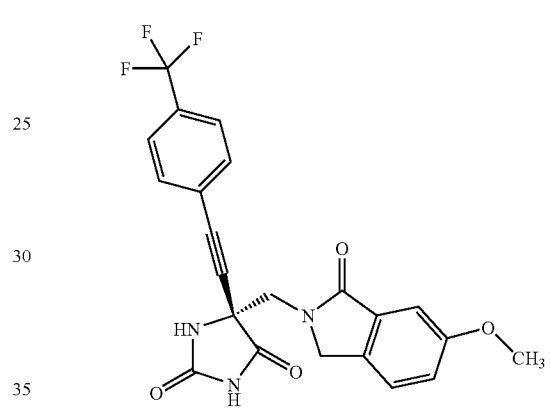
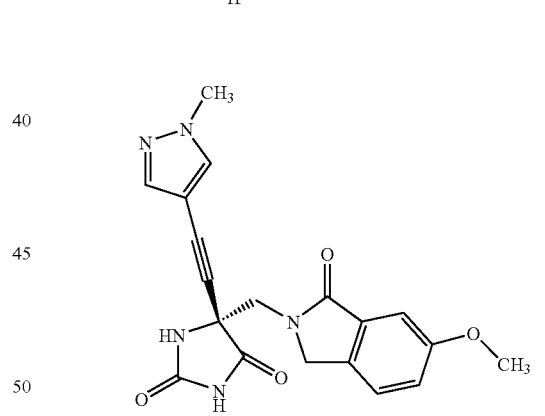
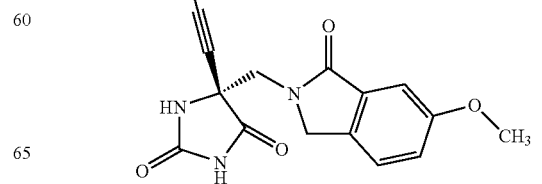

335
-continued
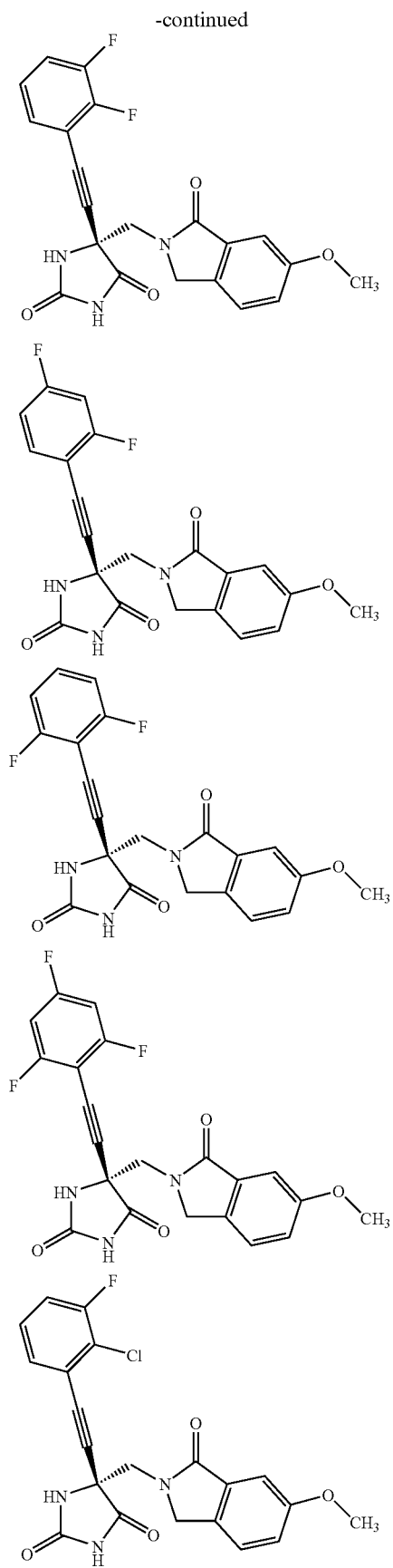
336
-continued
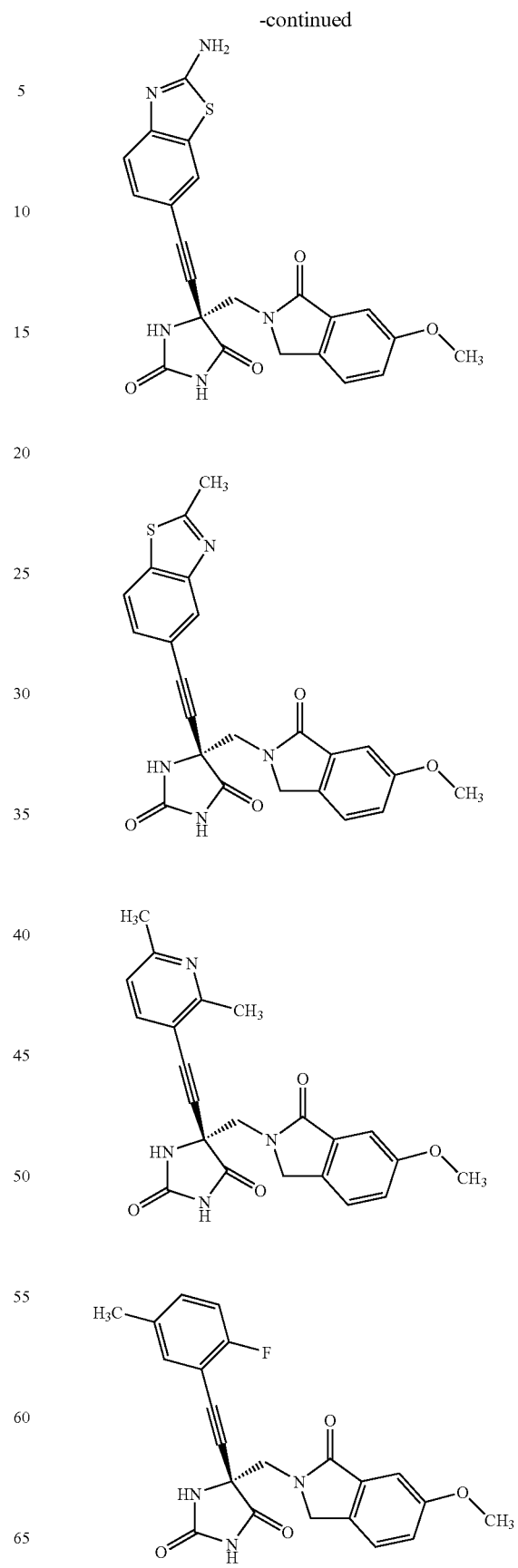

337
-continued
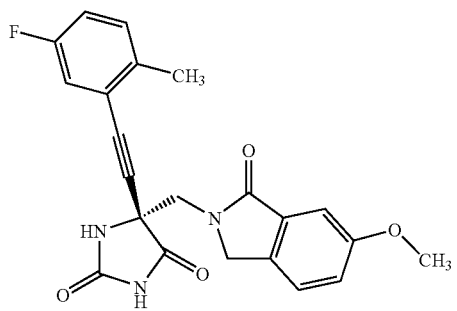
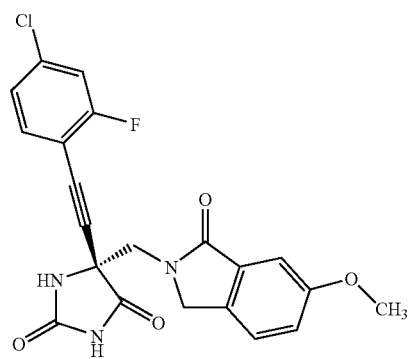
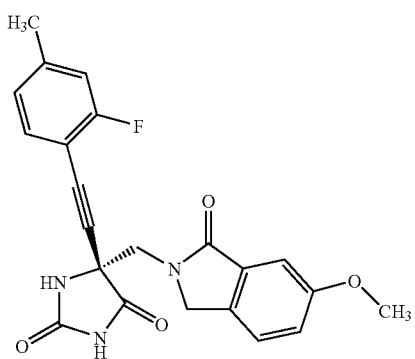
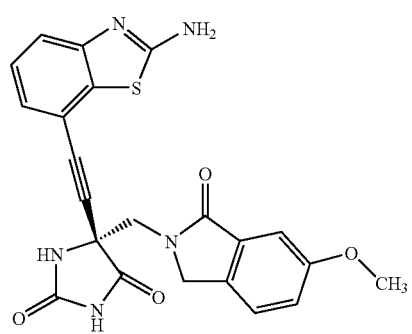
338
-continued
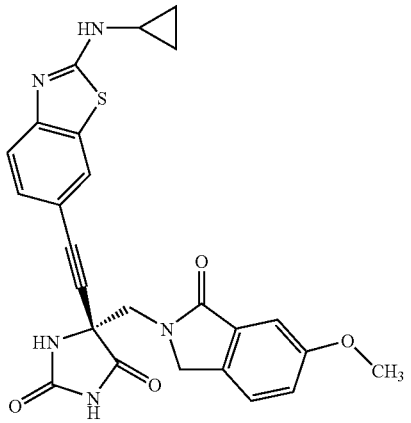
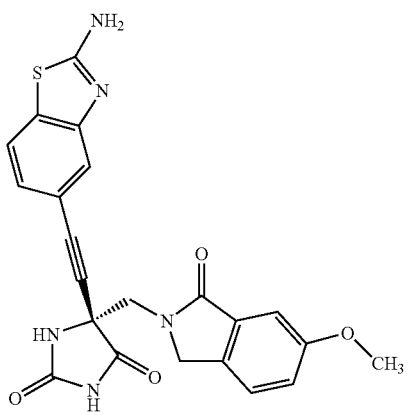
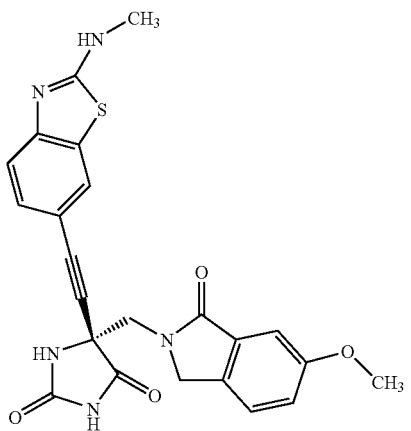
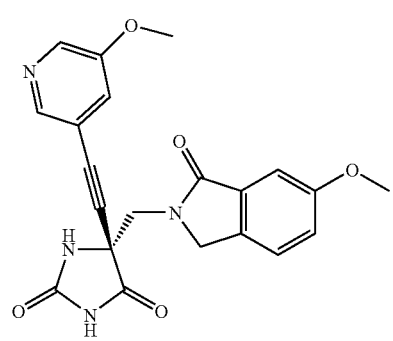

-continued
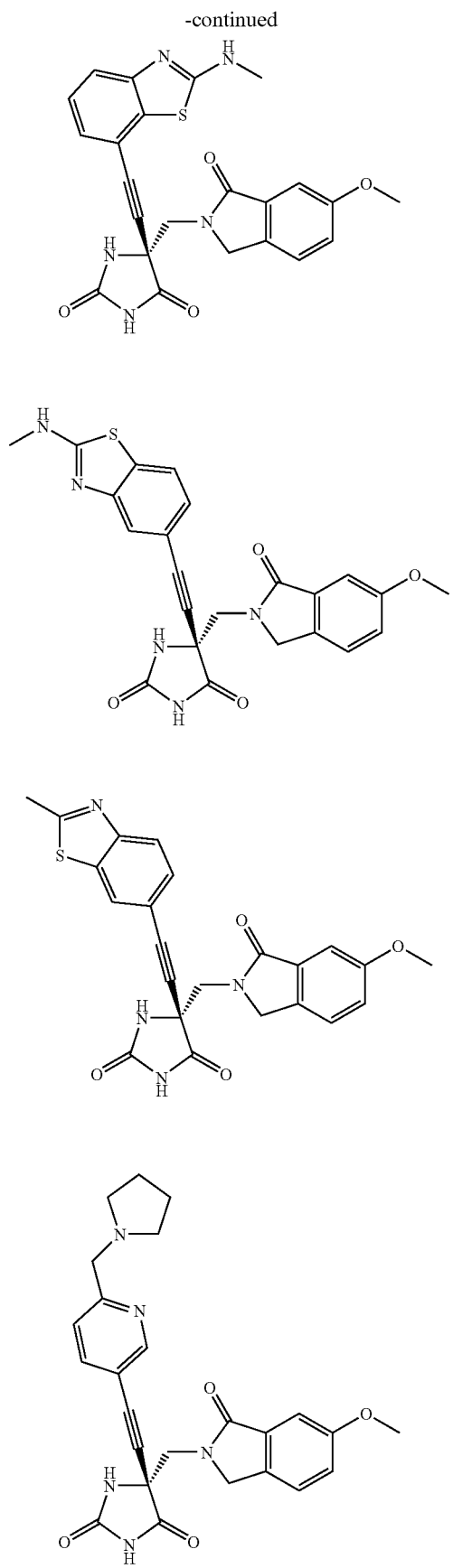
-continued
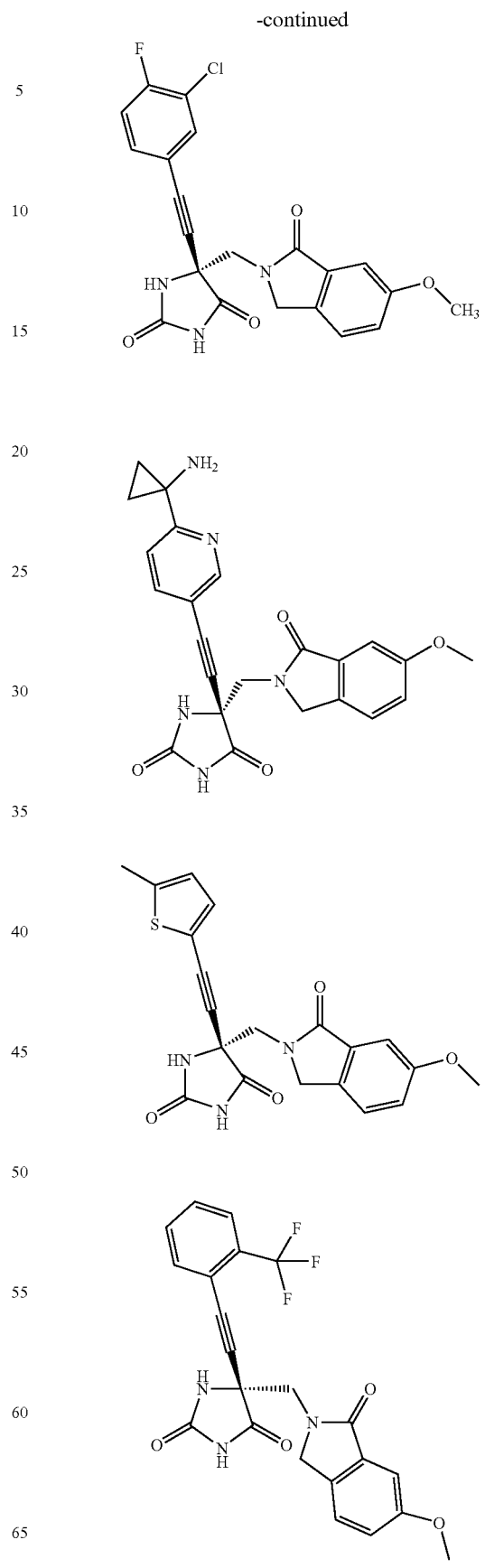

-continued
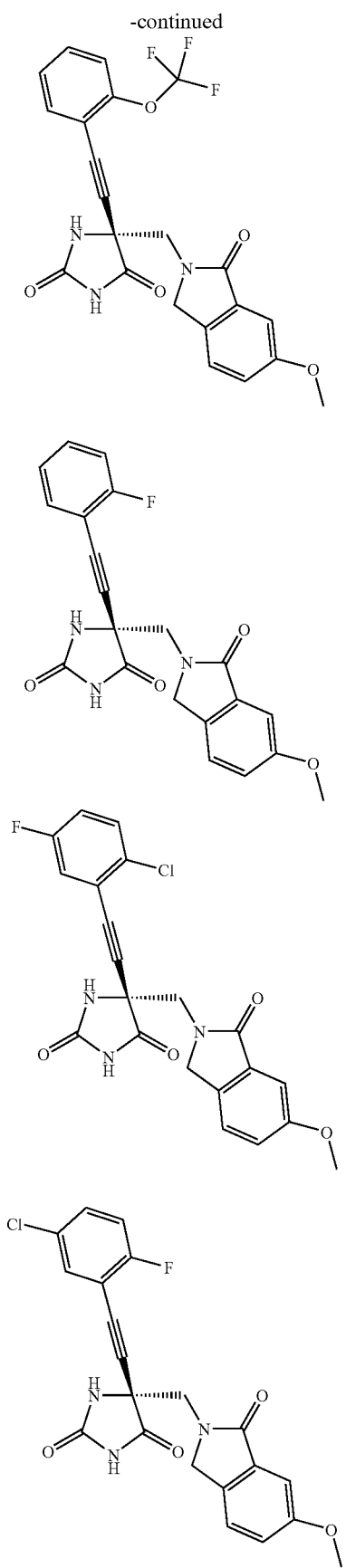
-continued
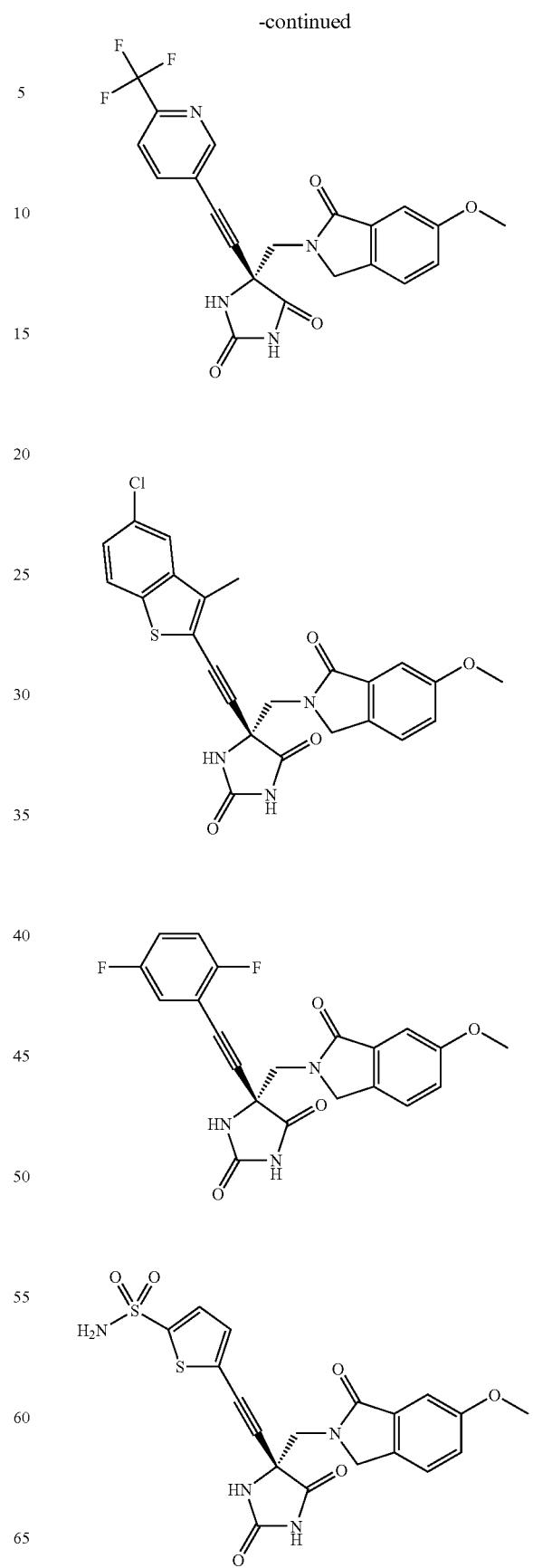

-continued
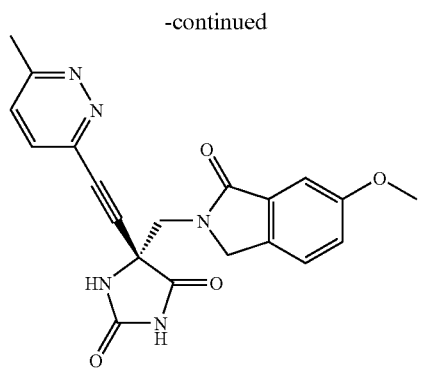
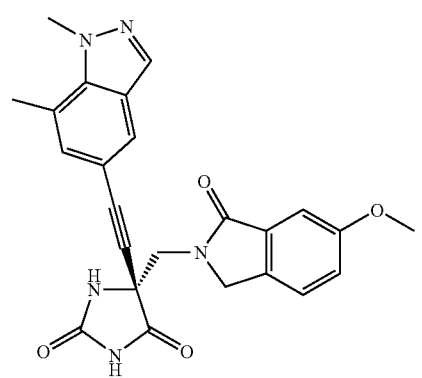
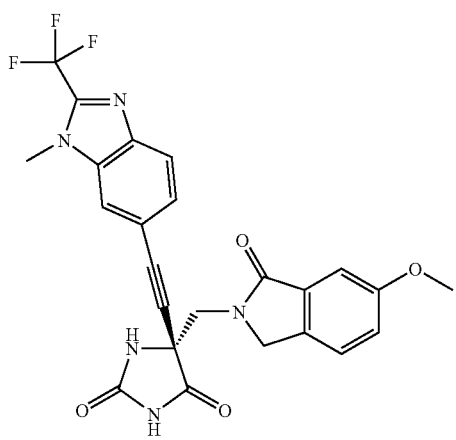
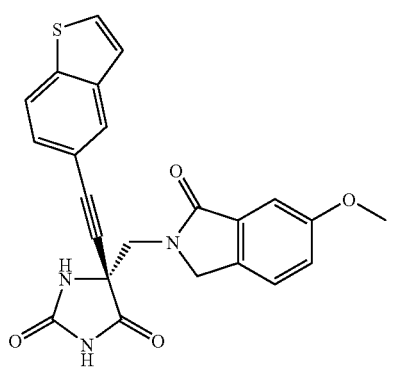
-continued
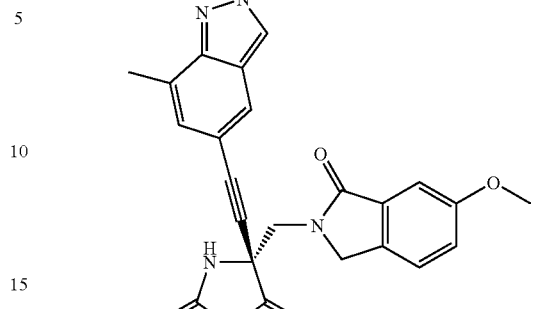
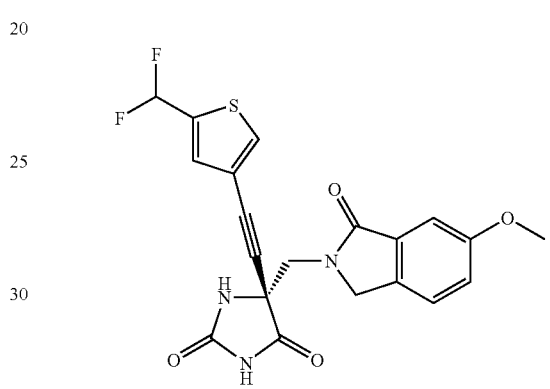
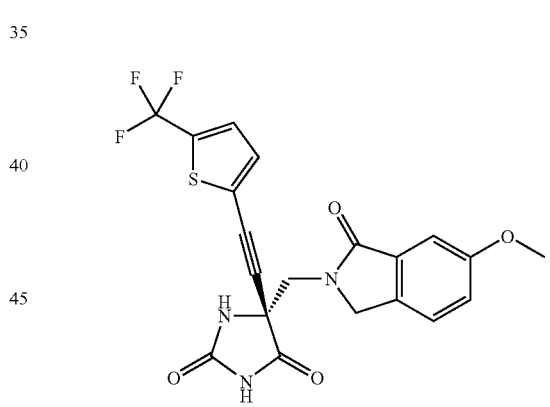
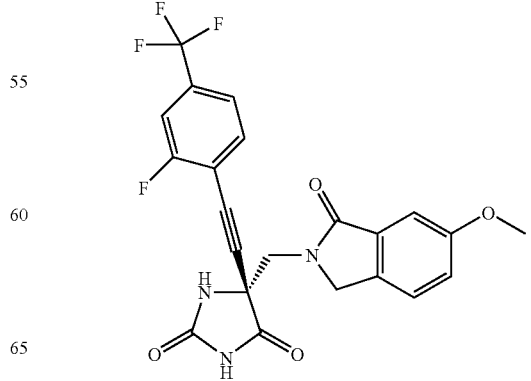

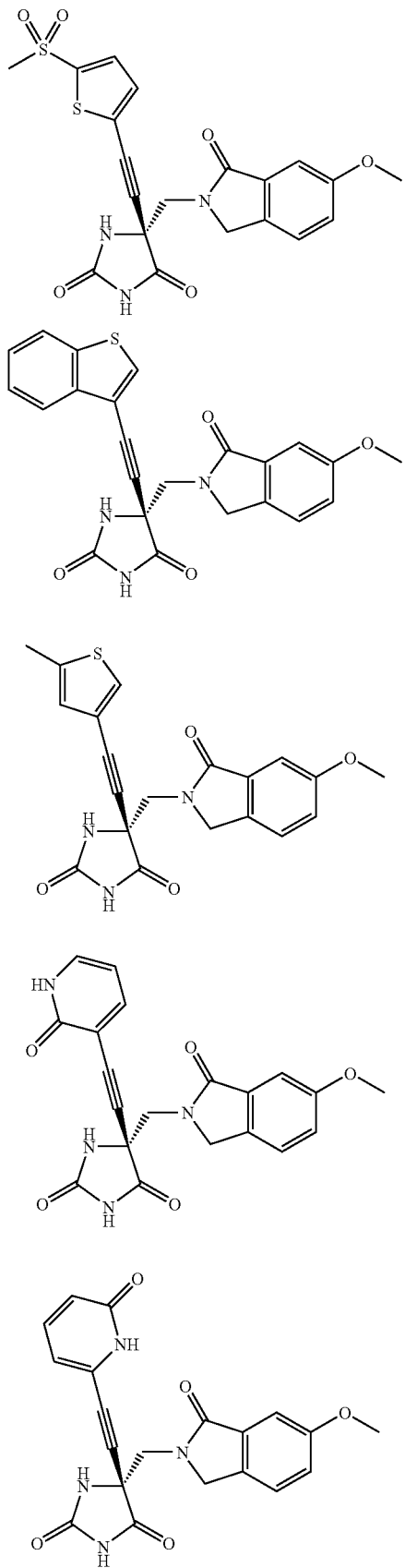
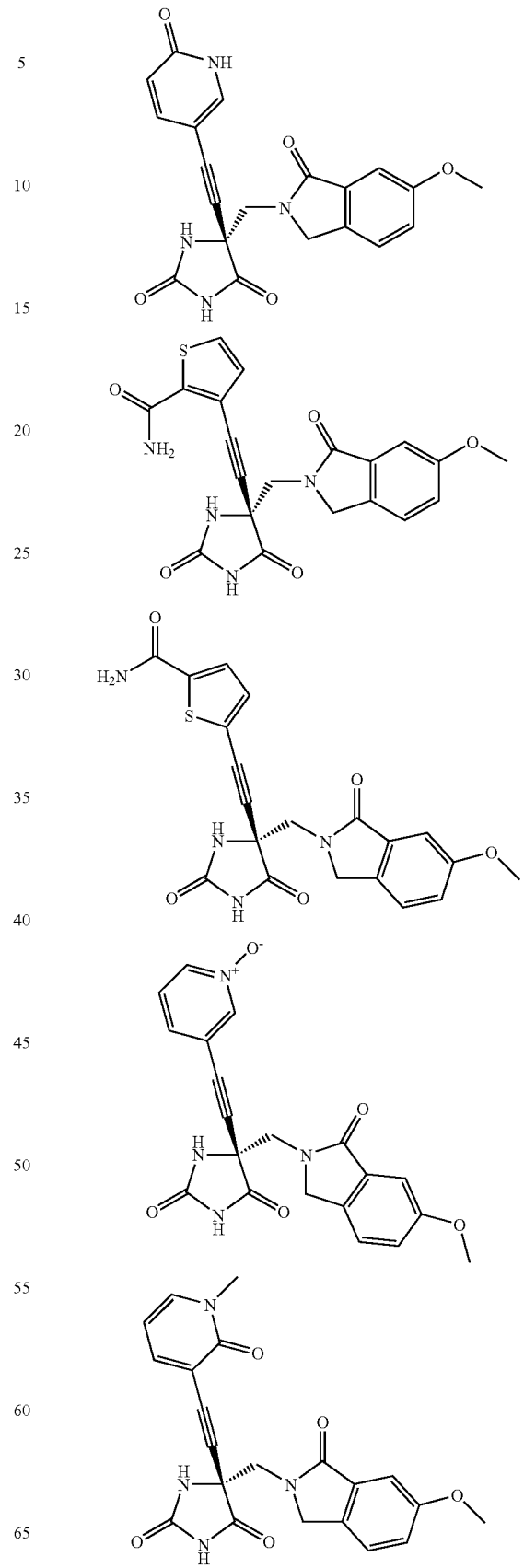

347
-continued
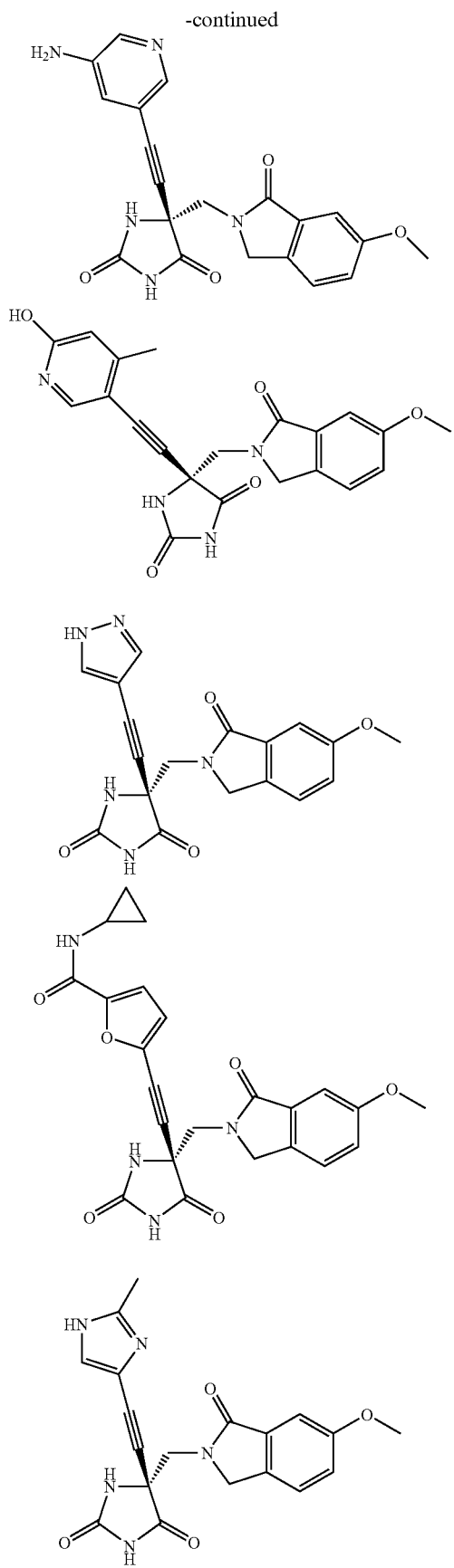
348
-continued
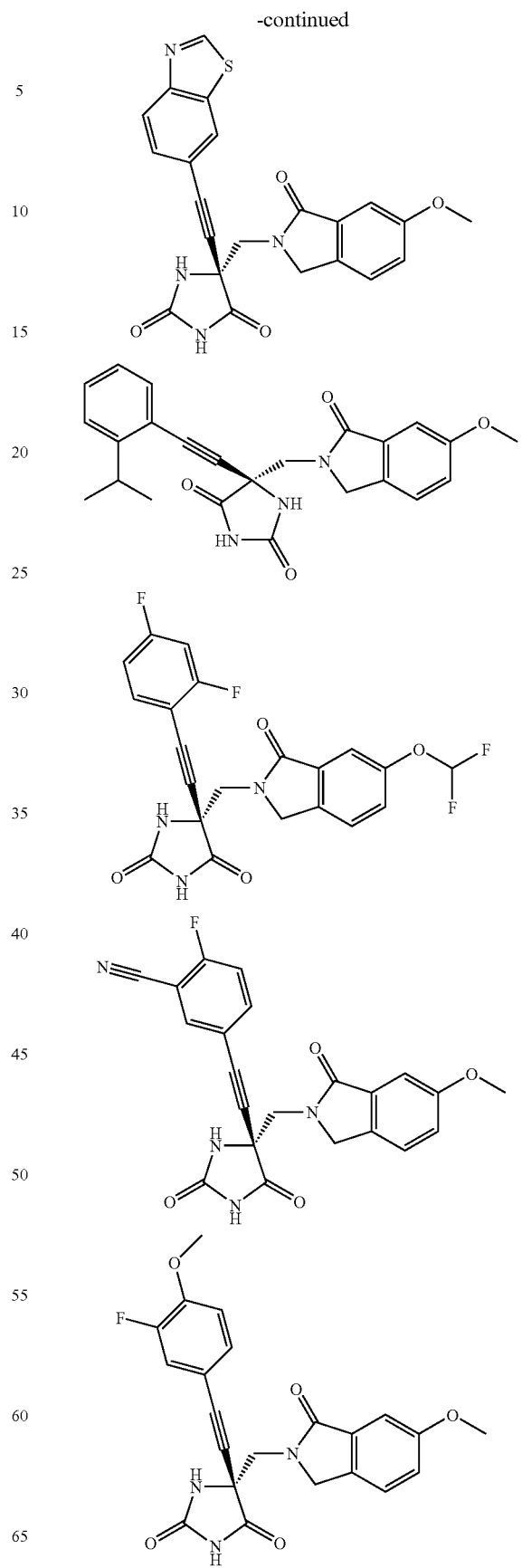

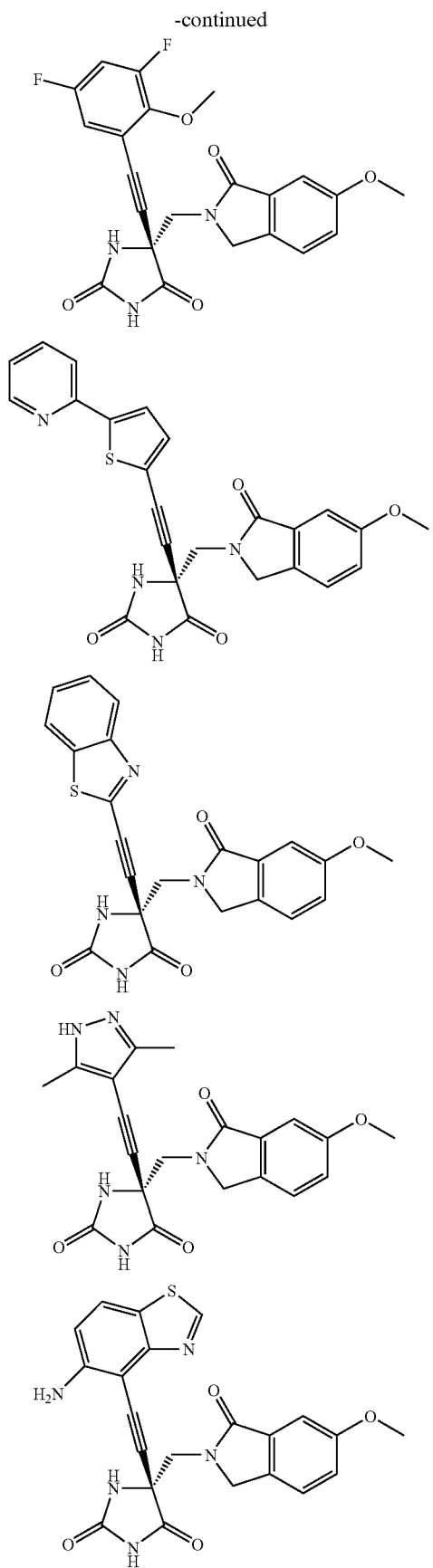
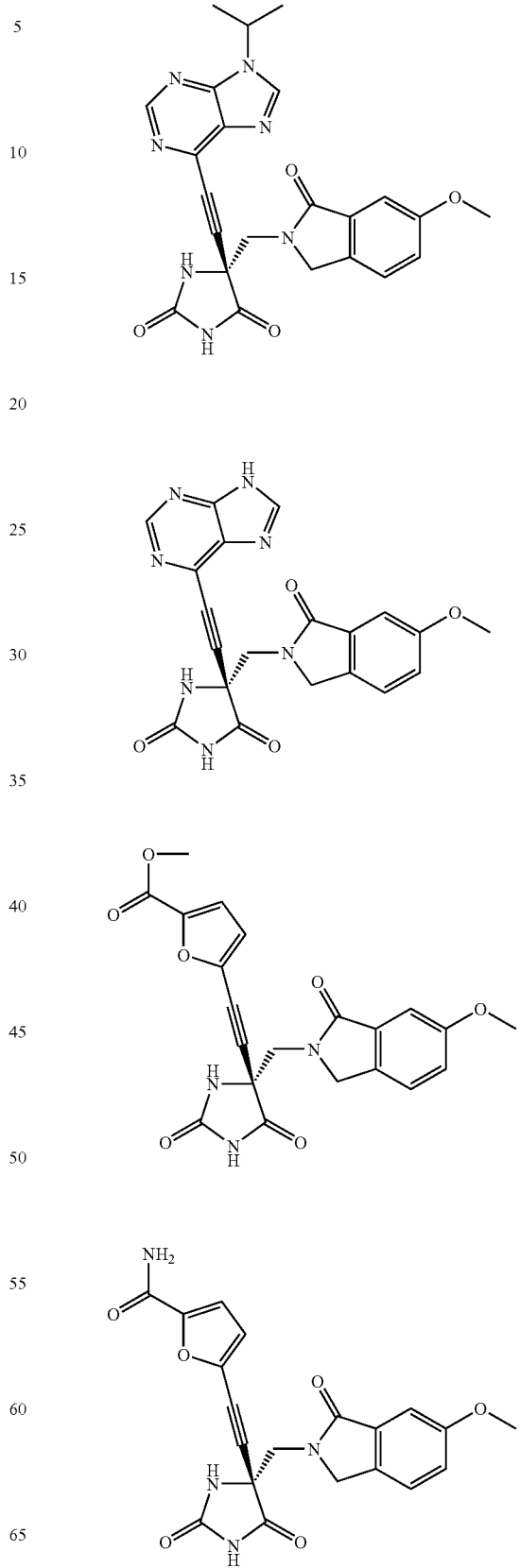

351
-continued
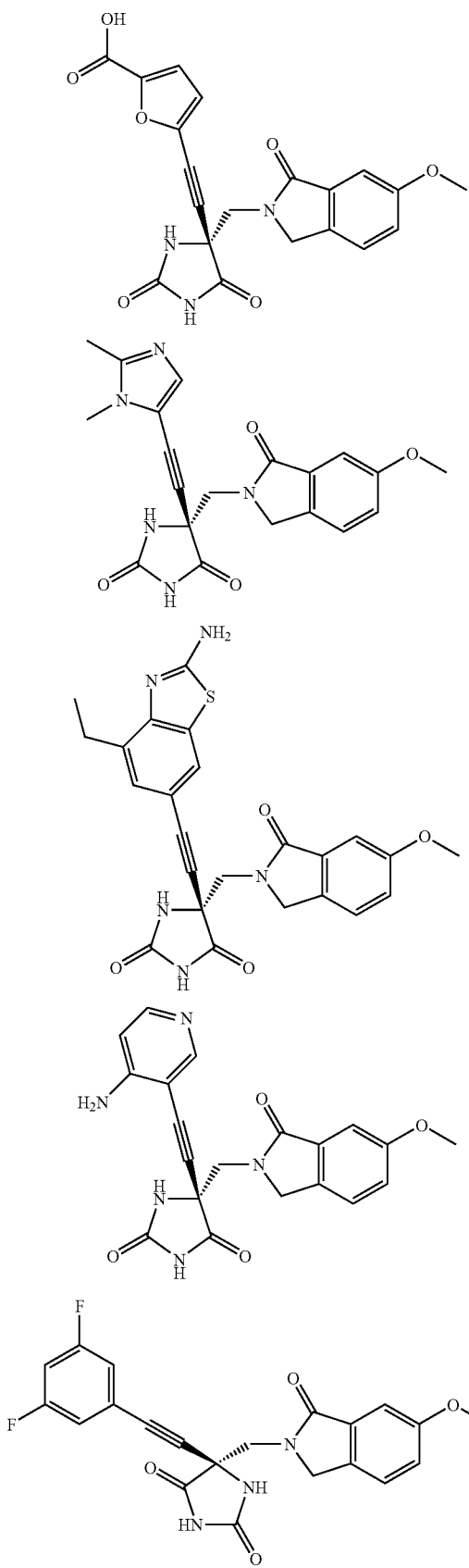
352
-continued
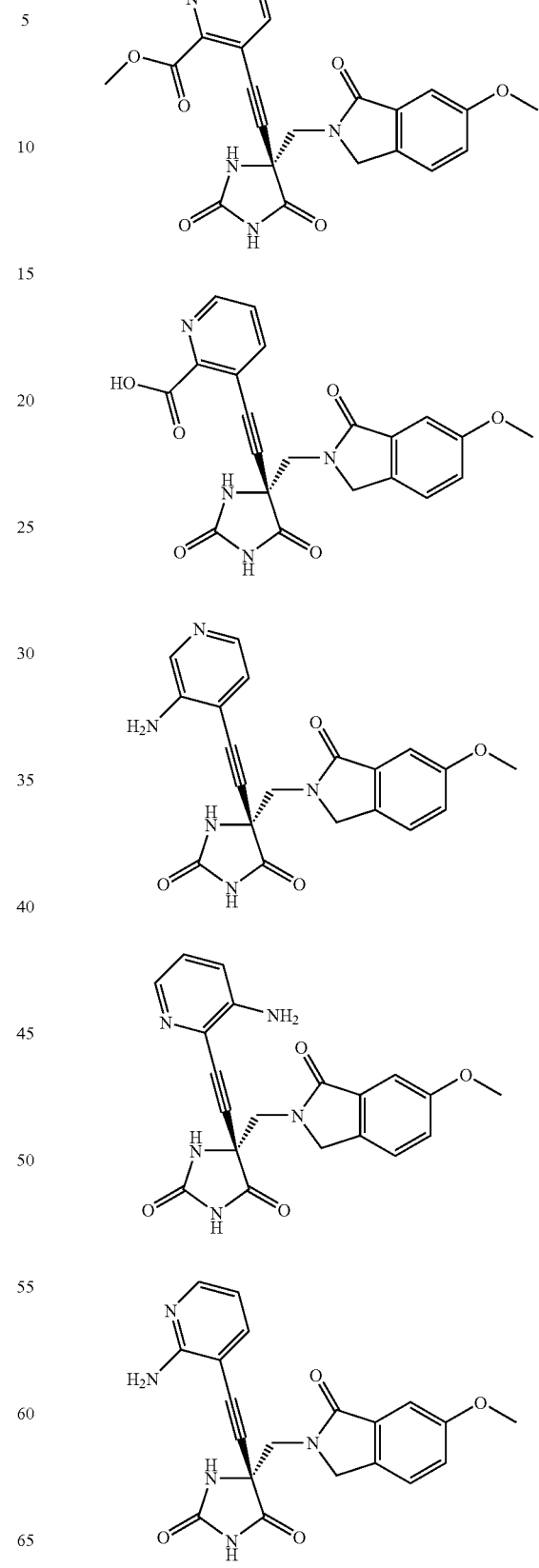

353
-continued
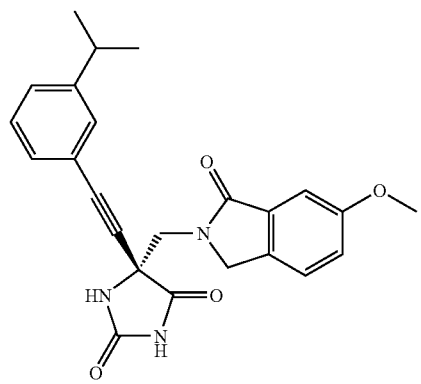
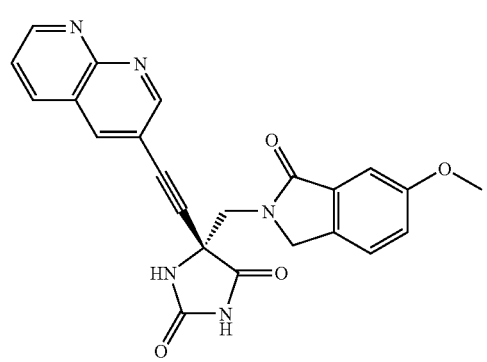
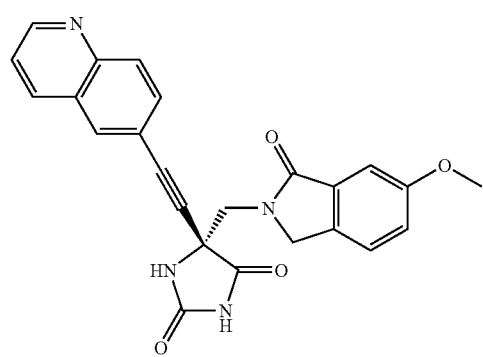
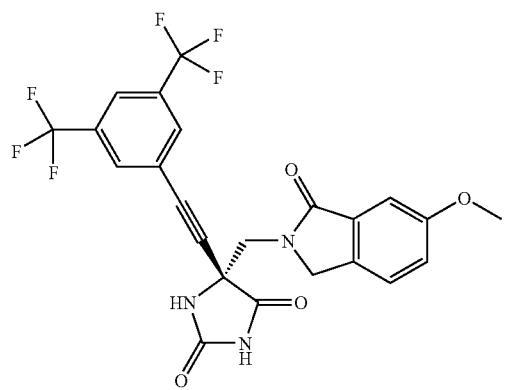
354
-continued
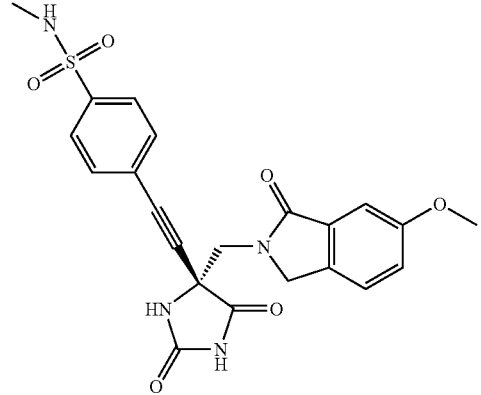
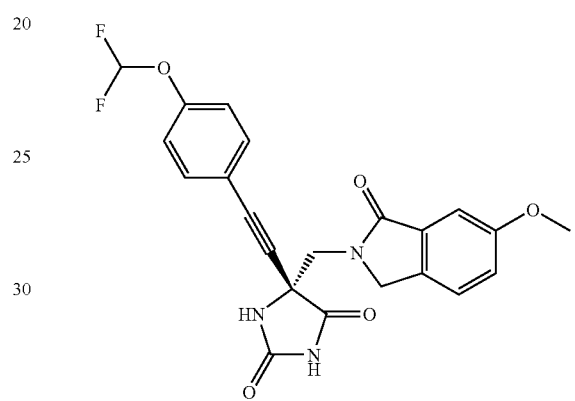
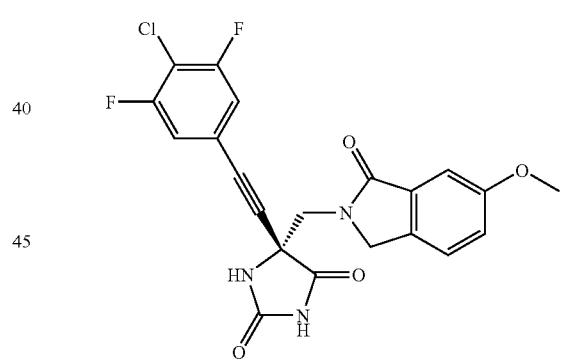
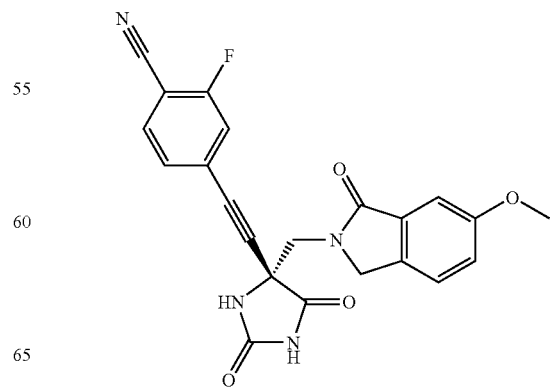

355
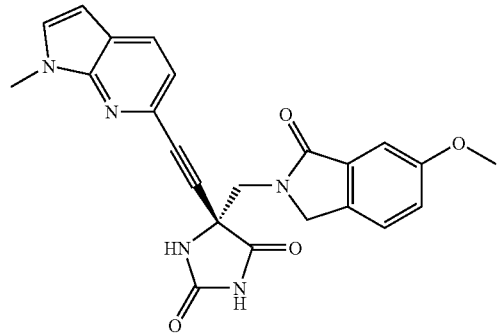
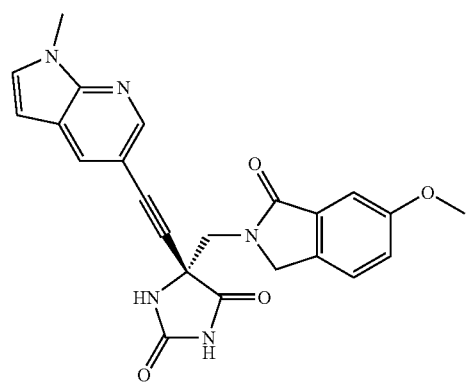
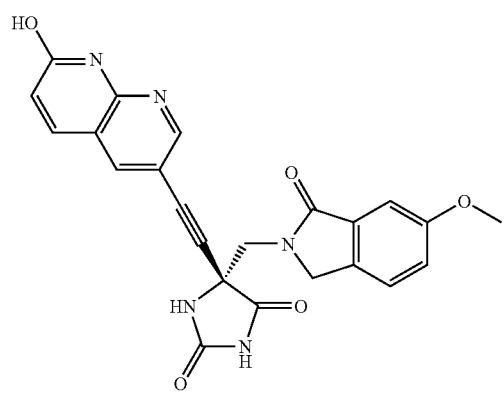
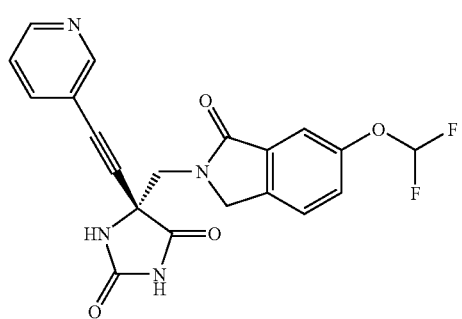
356
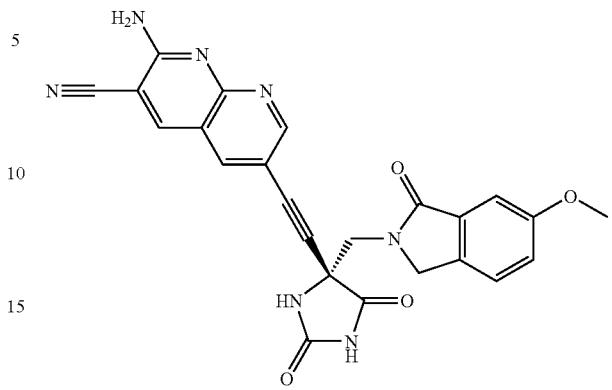
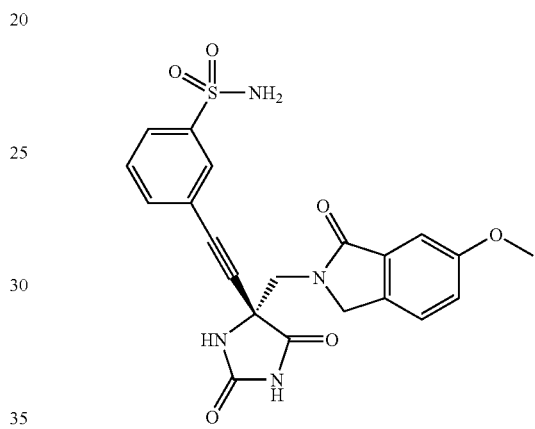
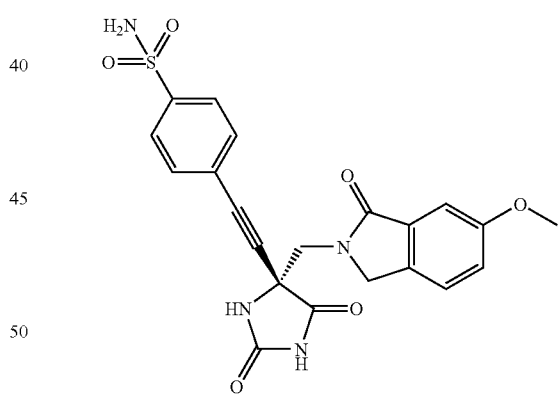
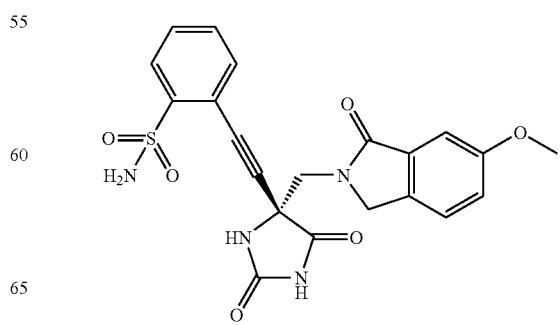

-continued
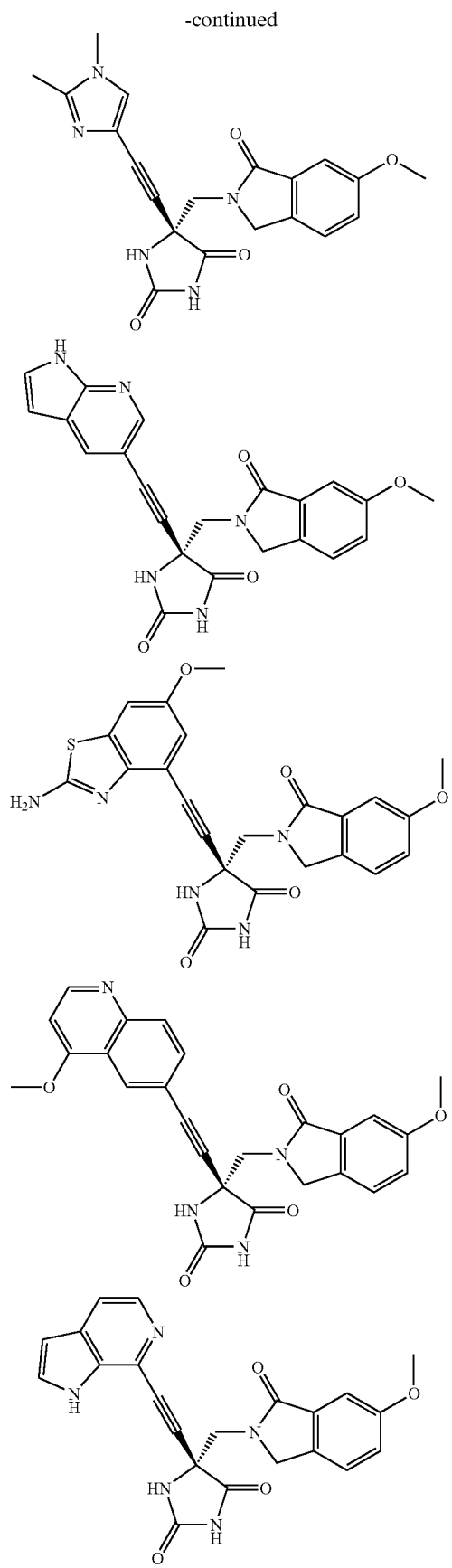
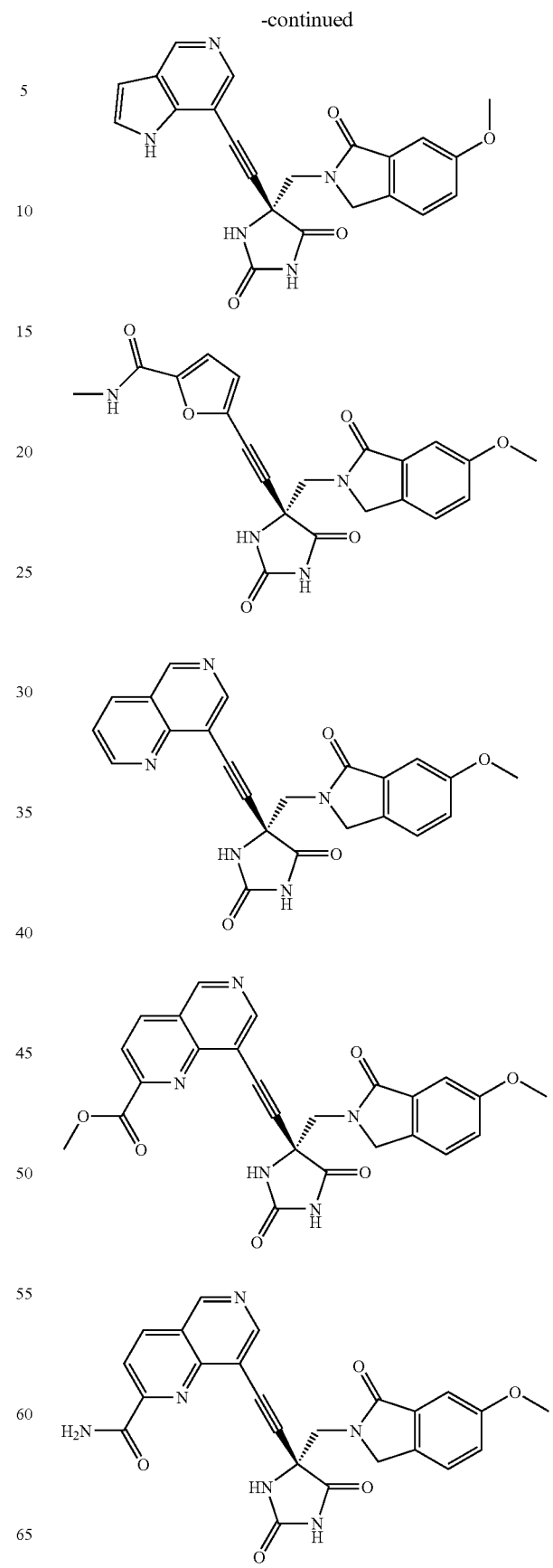

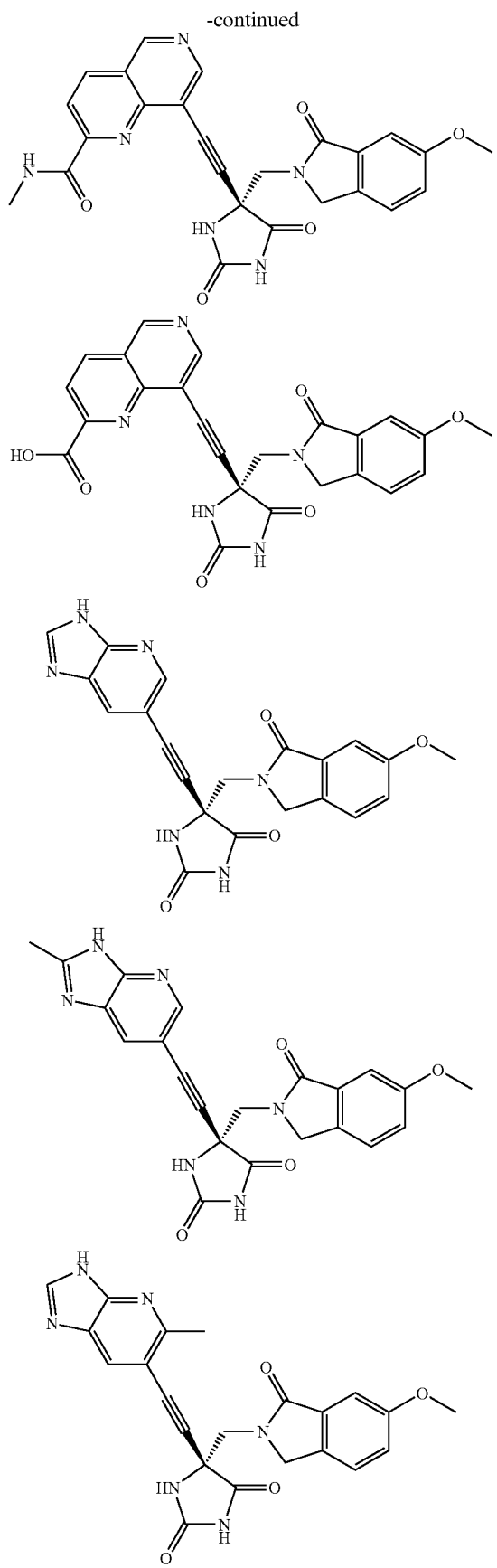
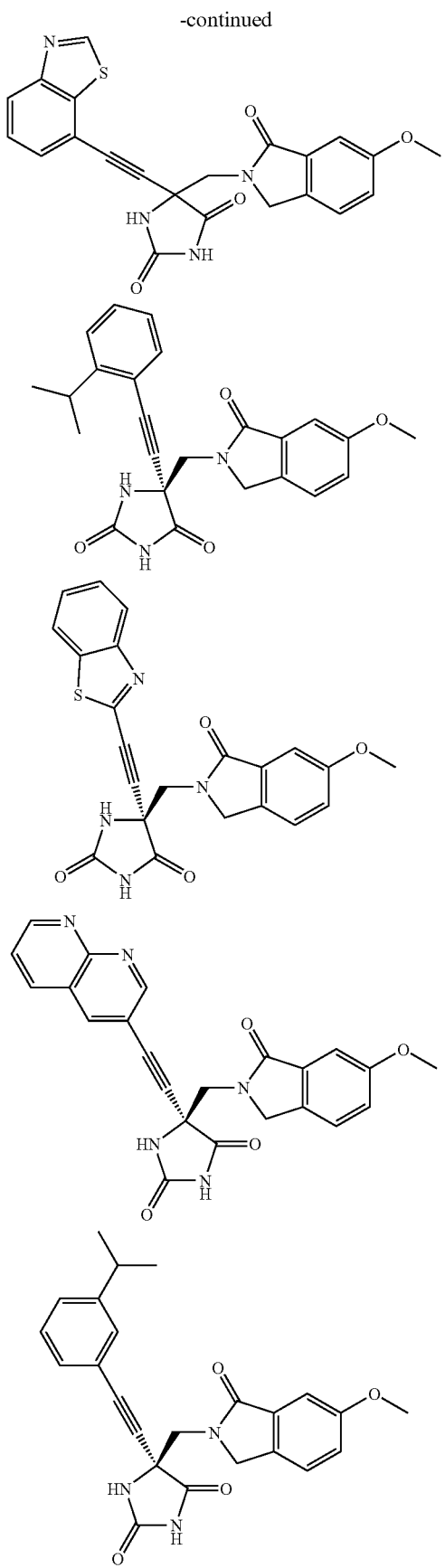

| 361 | 362 |
|---|---|
| -continued | -continued |
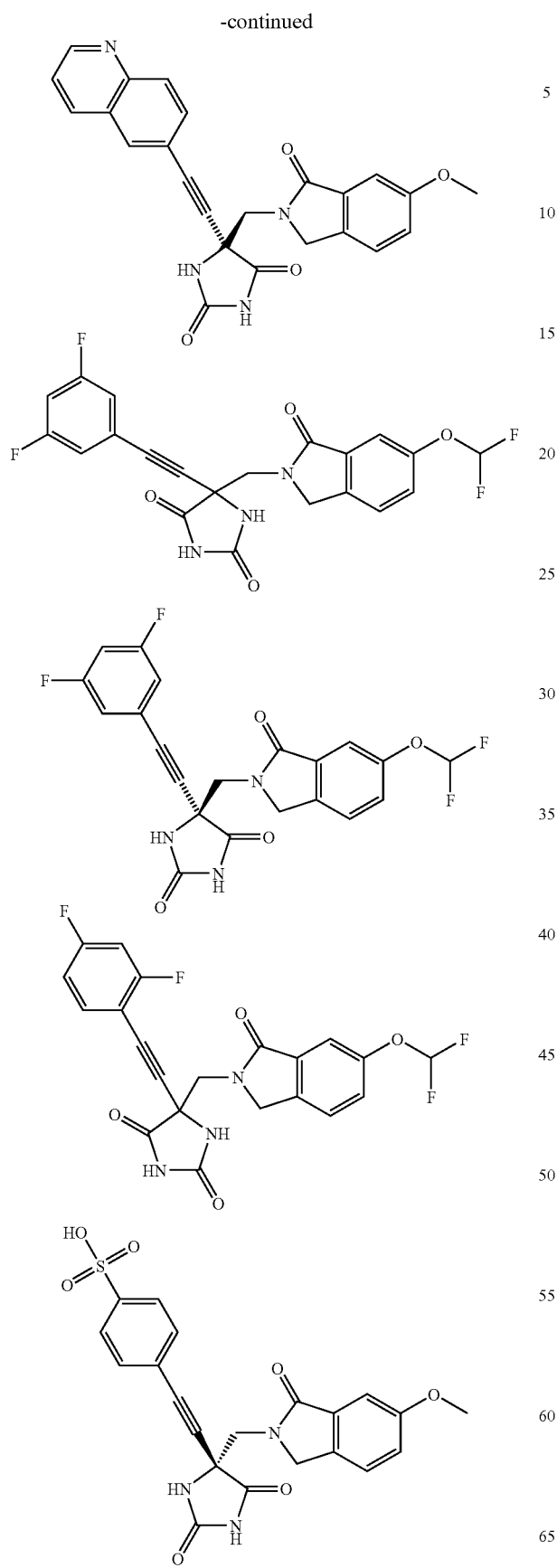
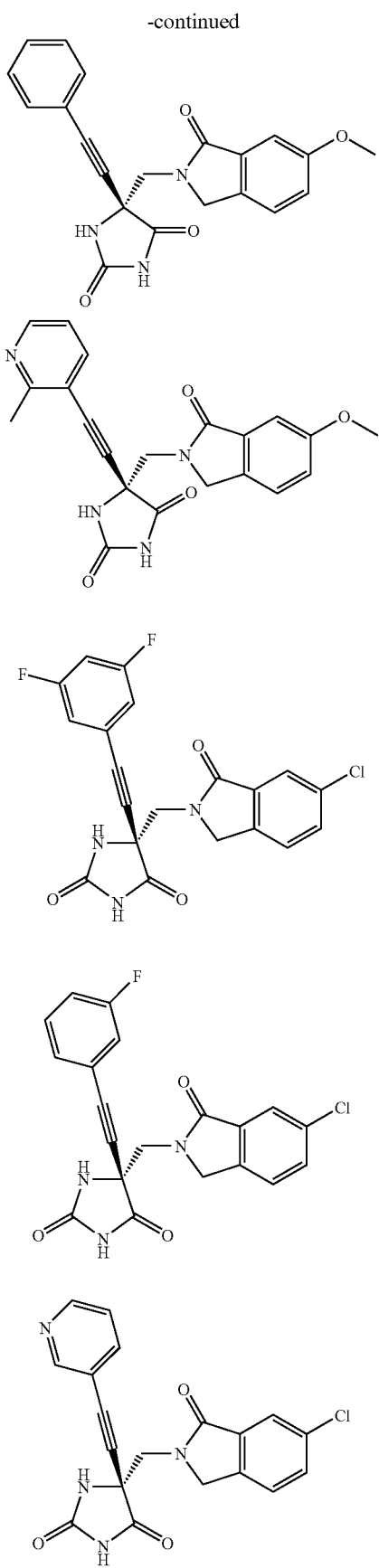

363
-continued
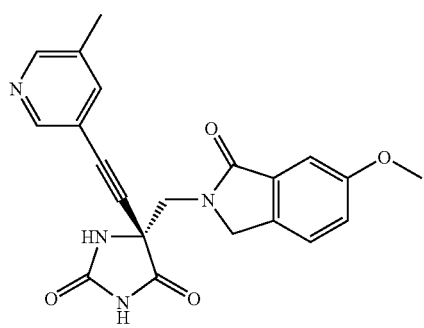
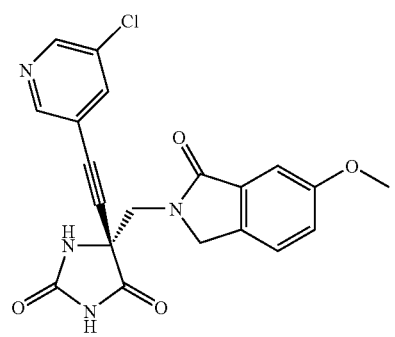
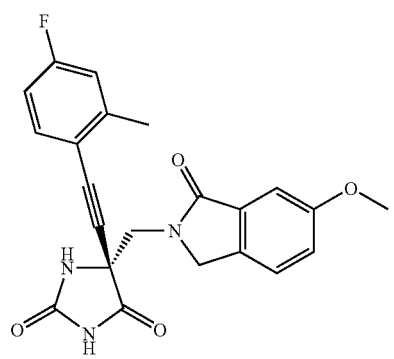
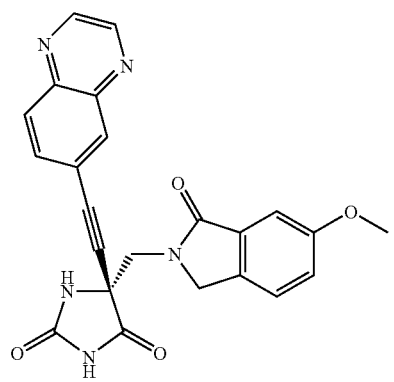
364
-continued
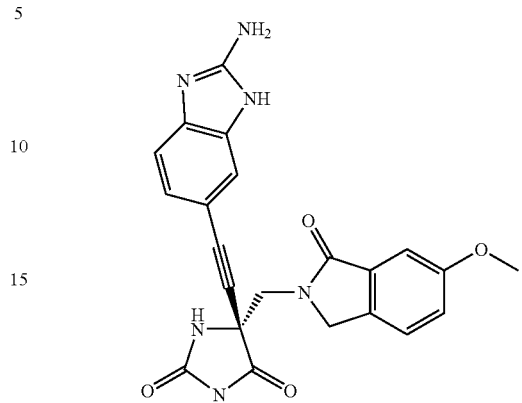
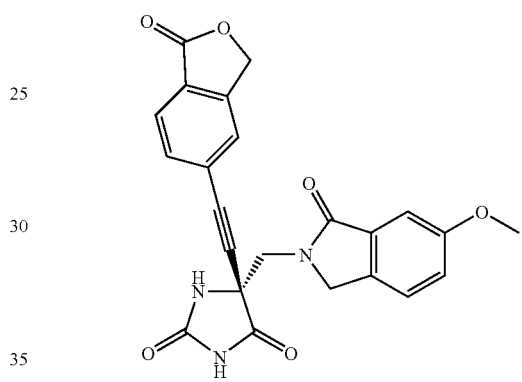
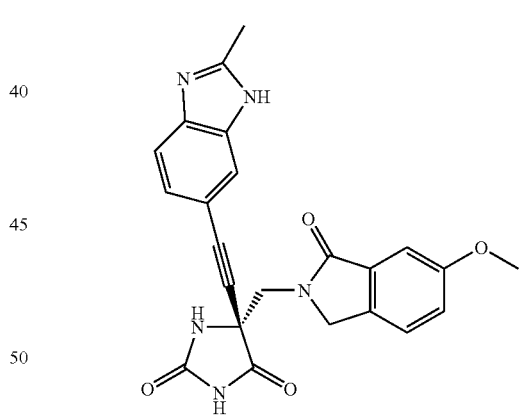
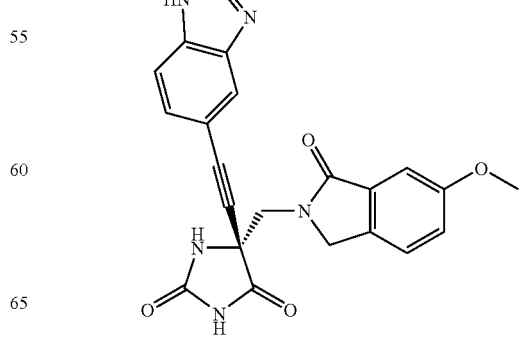

365
-continued
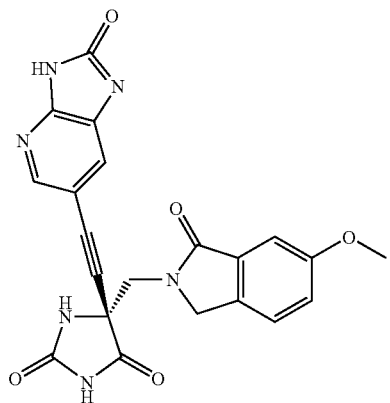
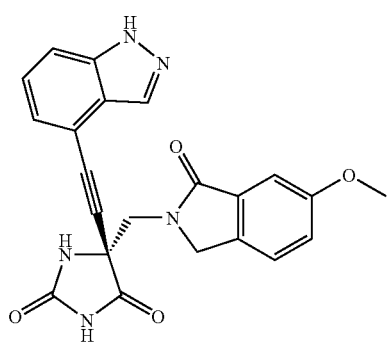
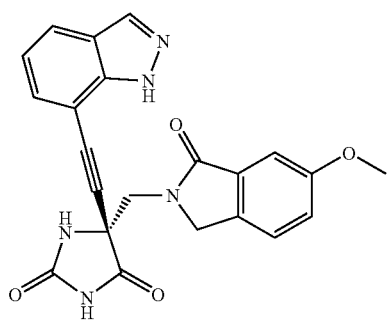
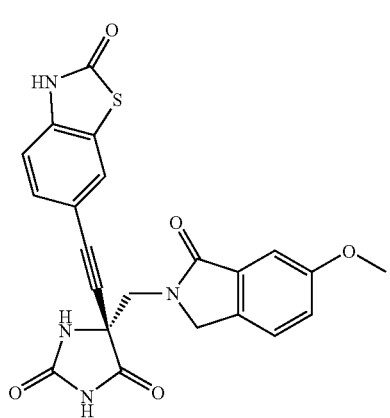
366
-continued
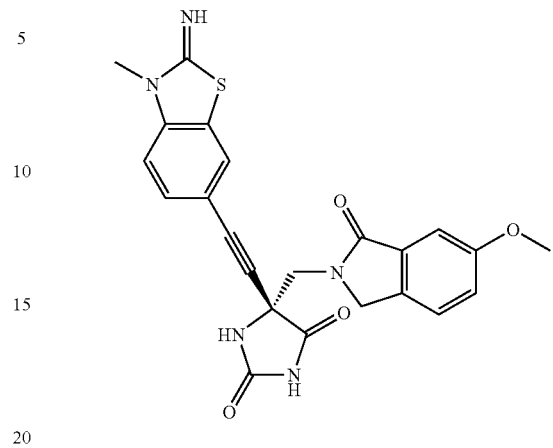
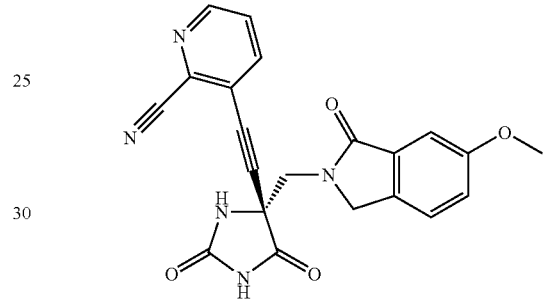
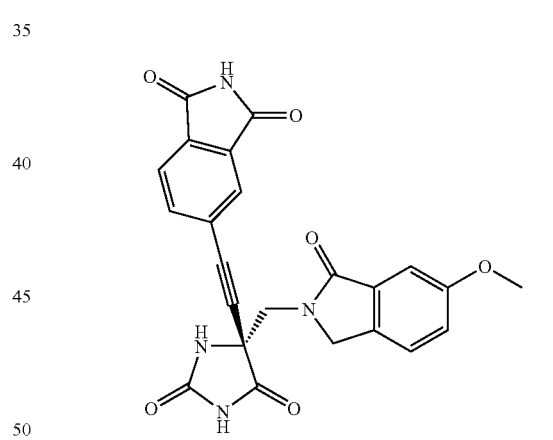
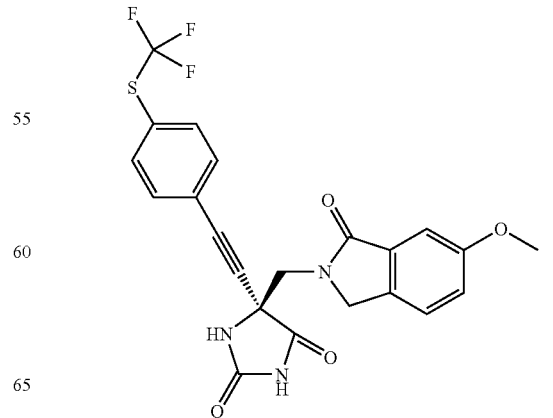

367
-continued
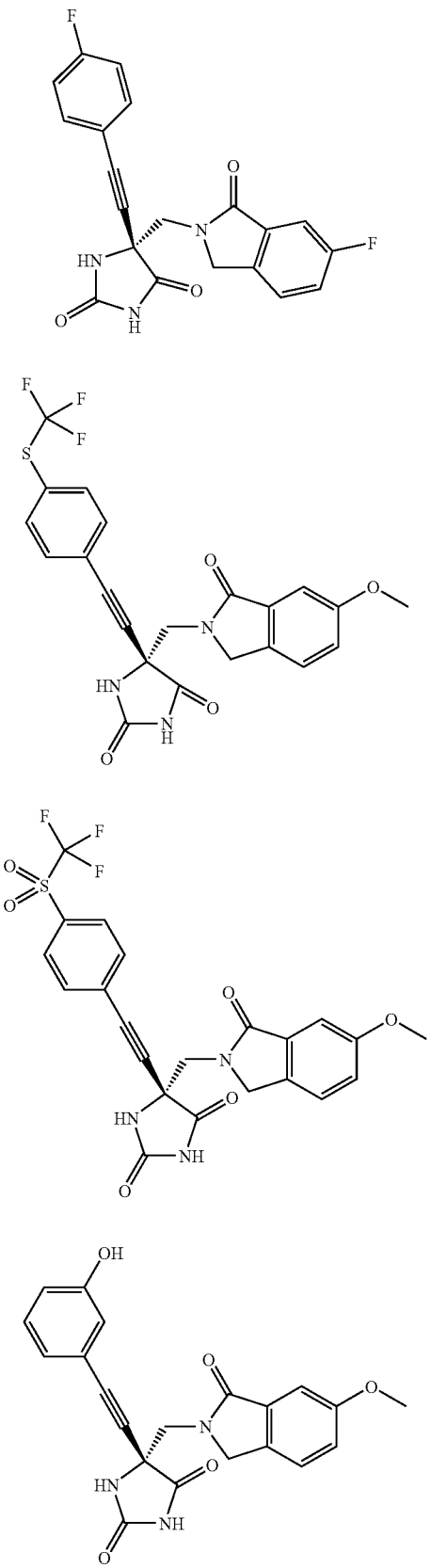
368
-continued
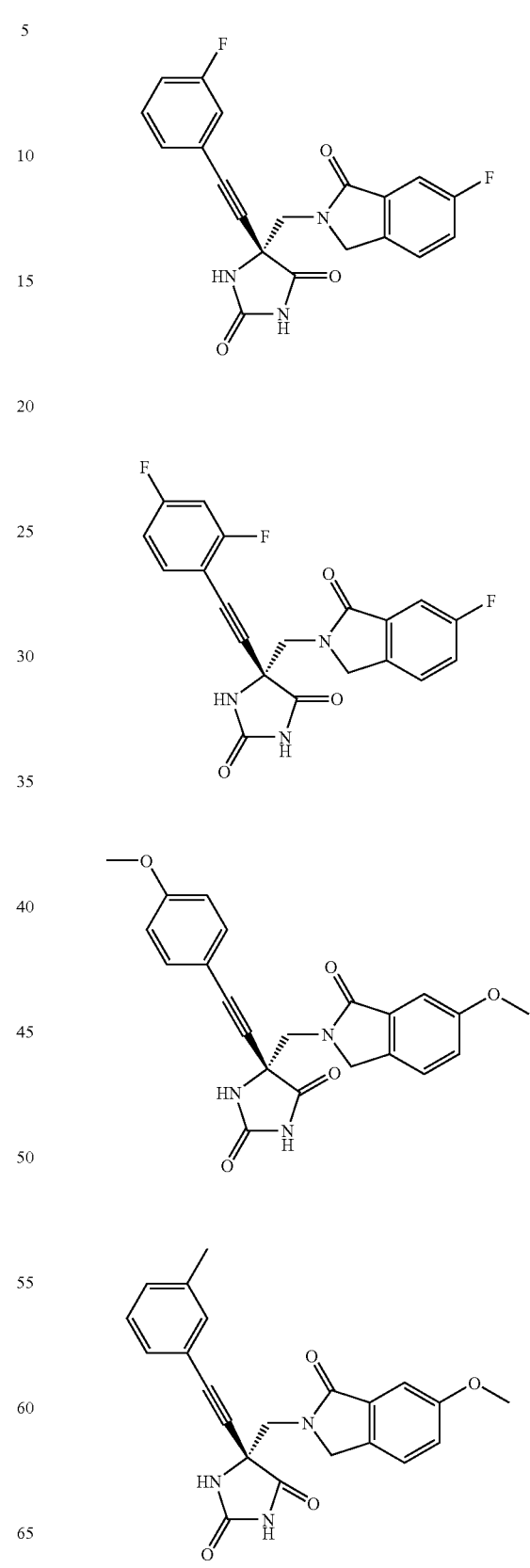

369
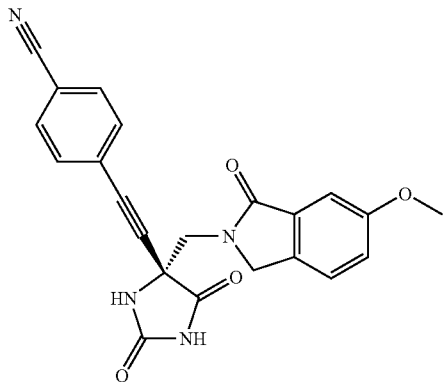
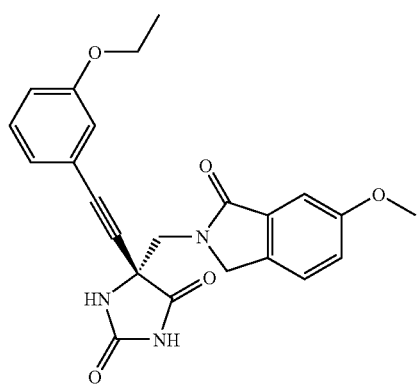
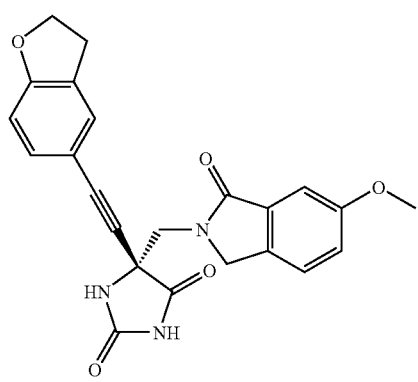
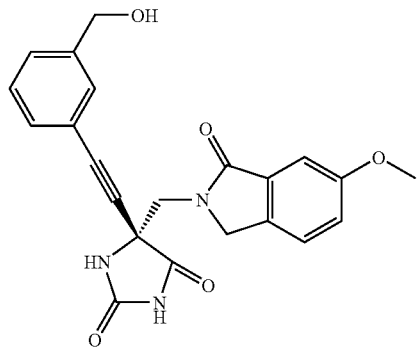
370
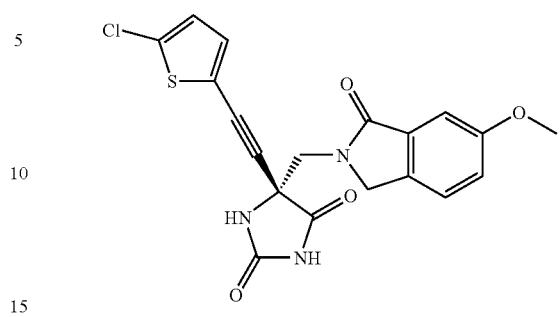
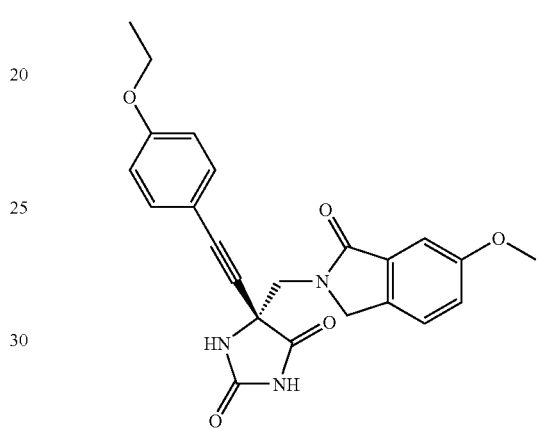
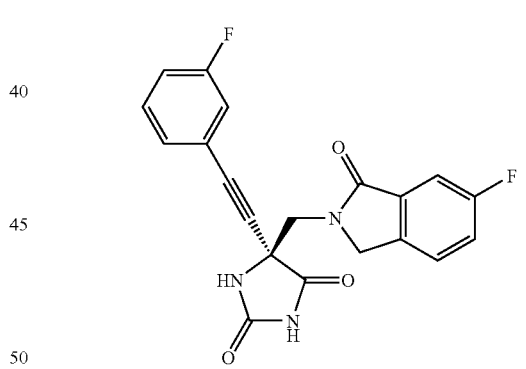
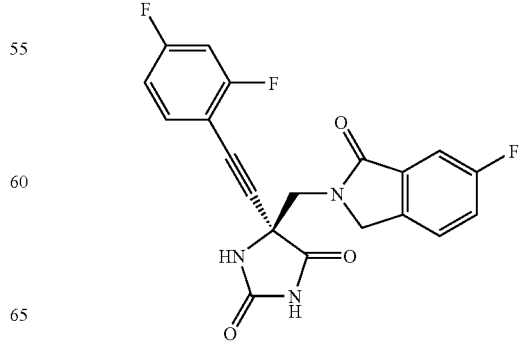

371
-continued
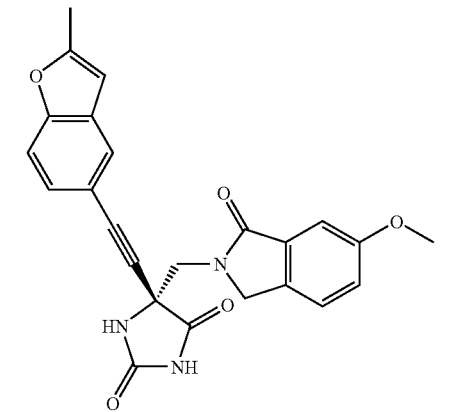
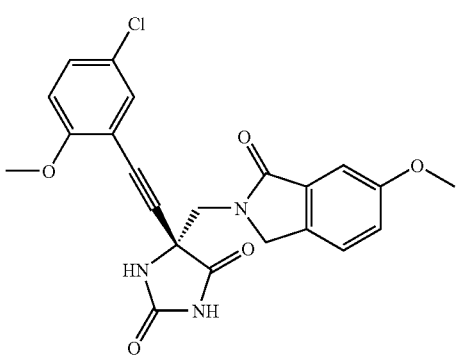
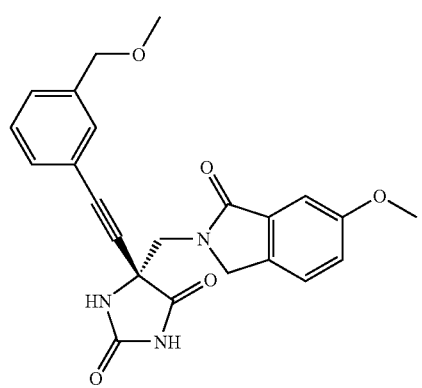
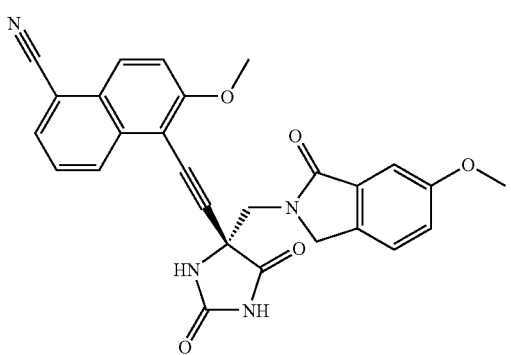
372
-continued
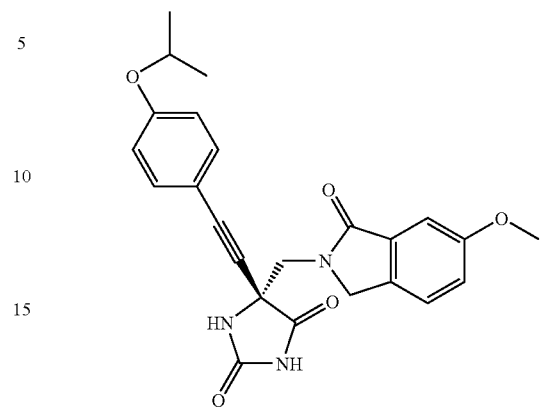
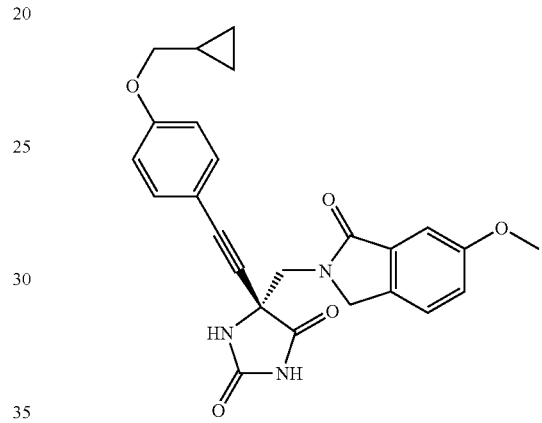
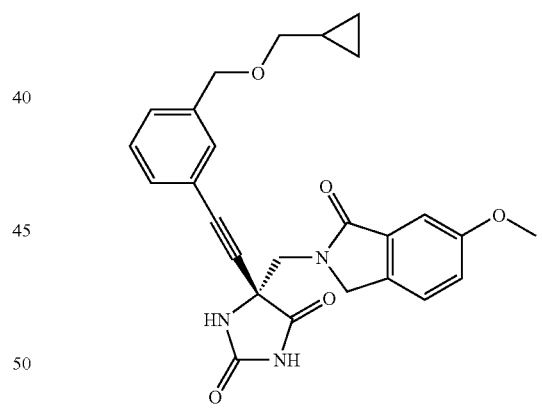
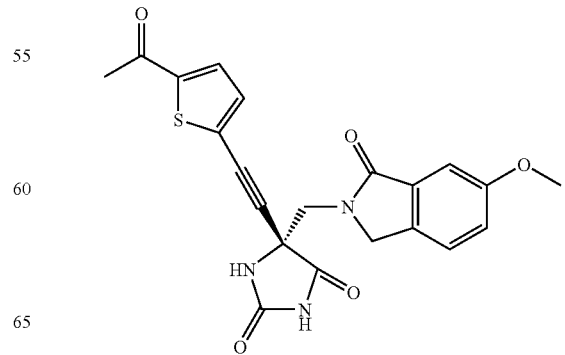

-continued
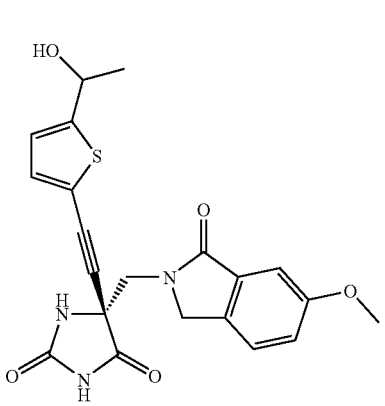
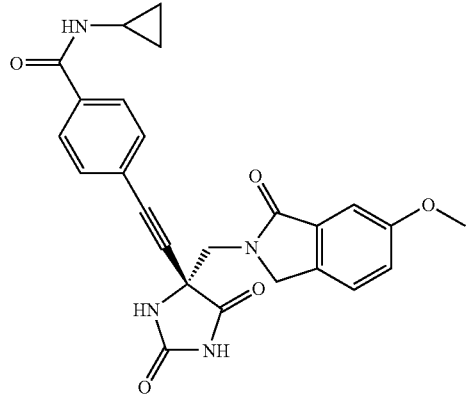
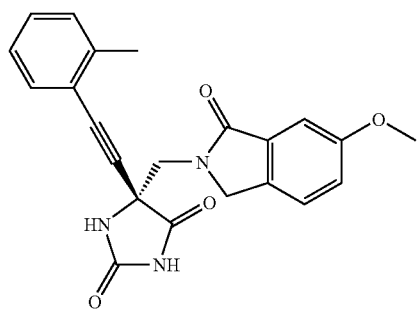
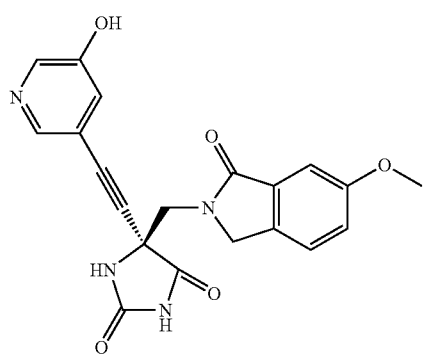
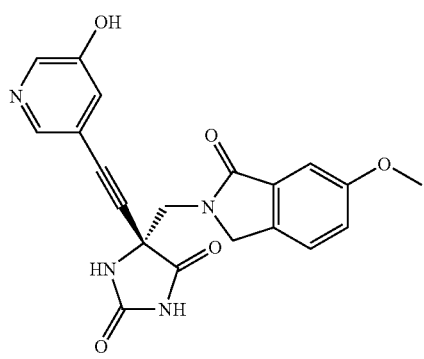
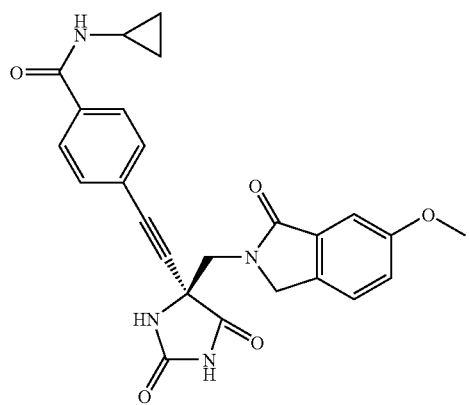
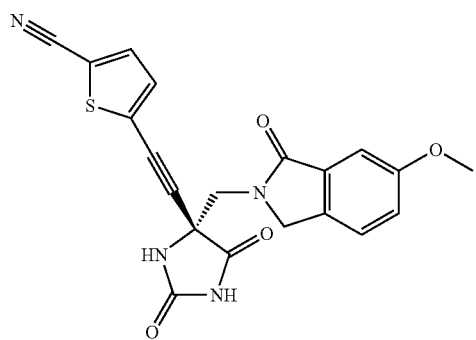

-continued
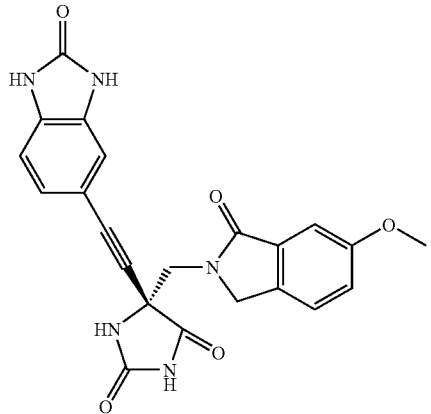
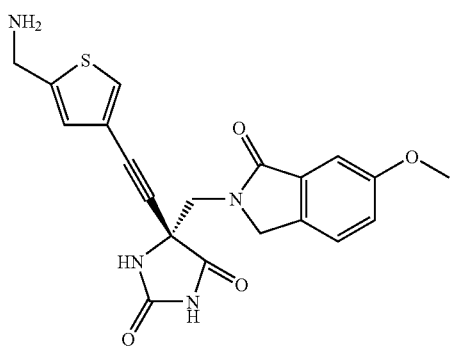
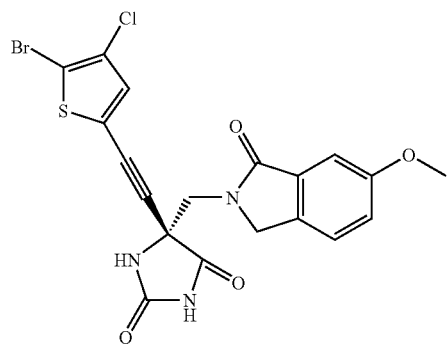
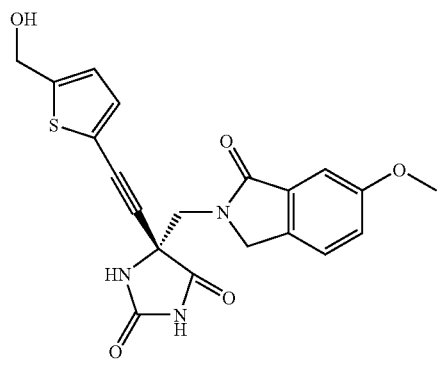
-continued
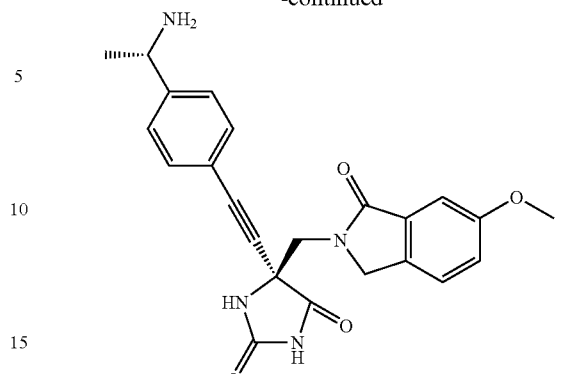
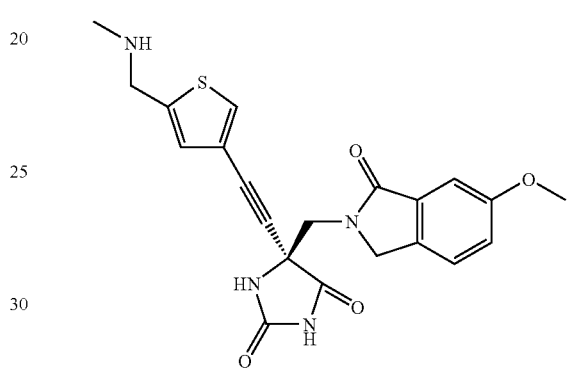
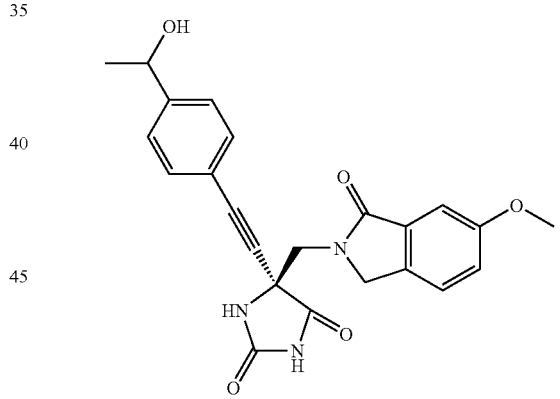
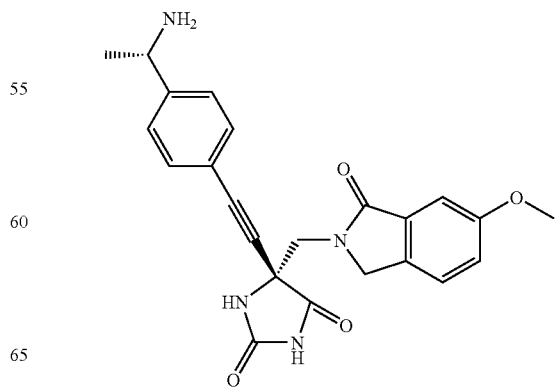

377
-continued
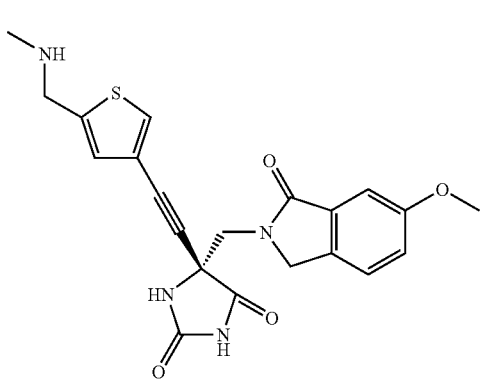
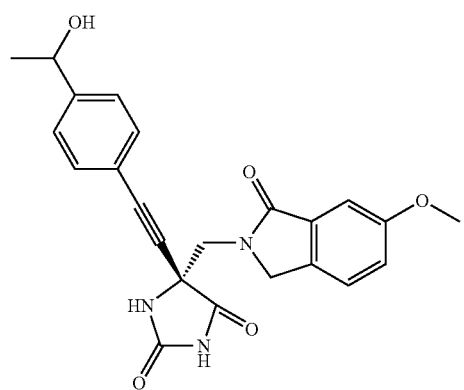
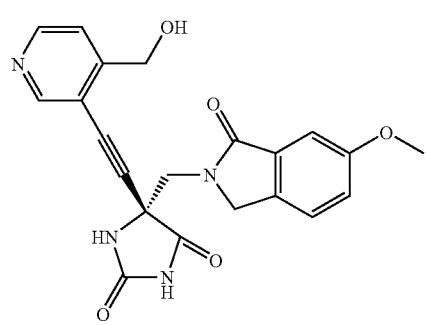
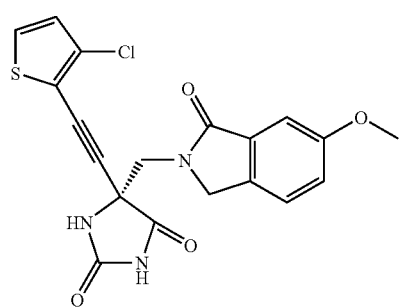
378
-continued
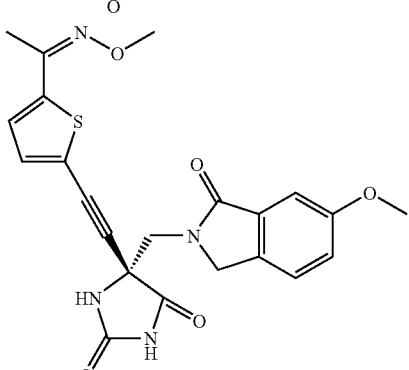
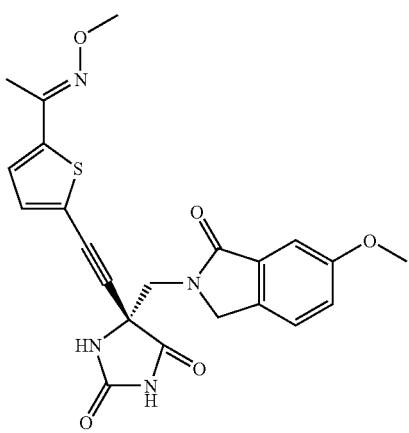
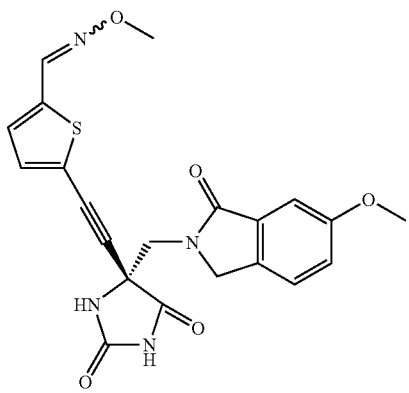

379
-continued
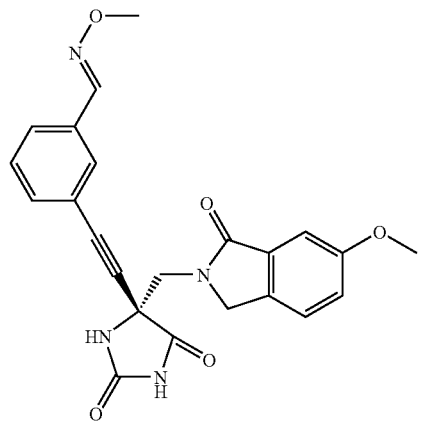
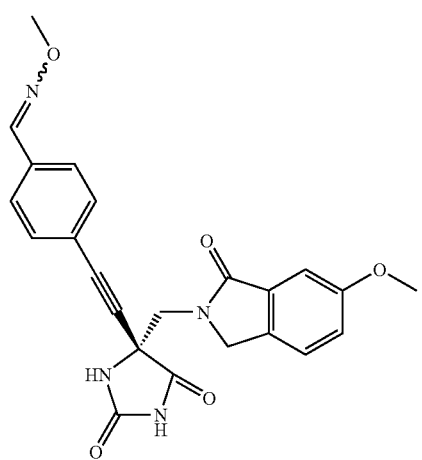
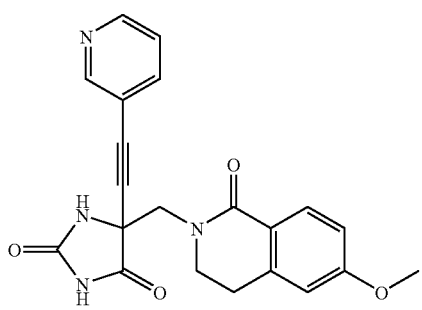
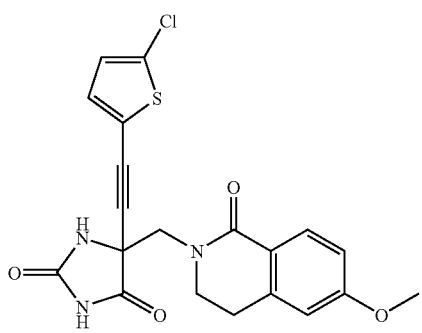
380
-continued
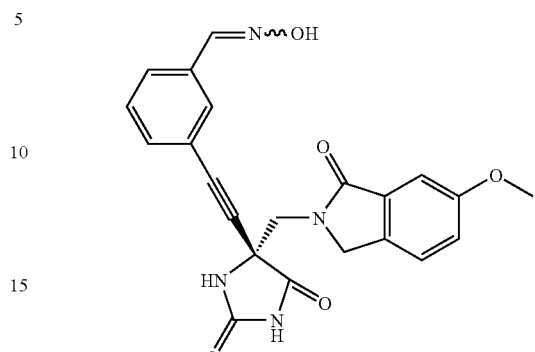
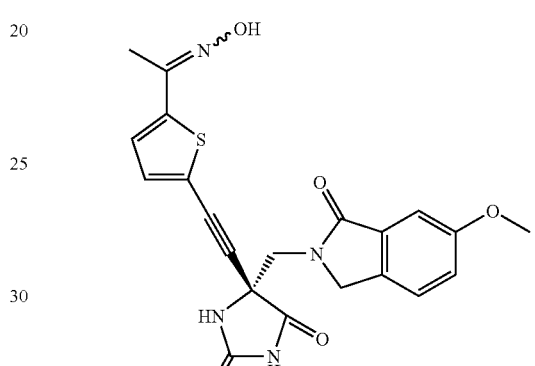
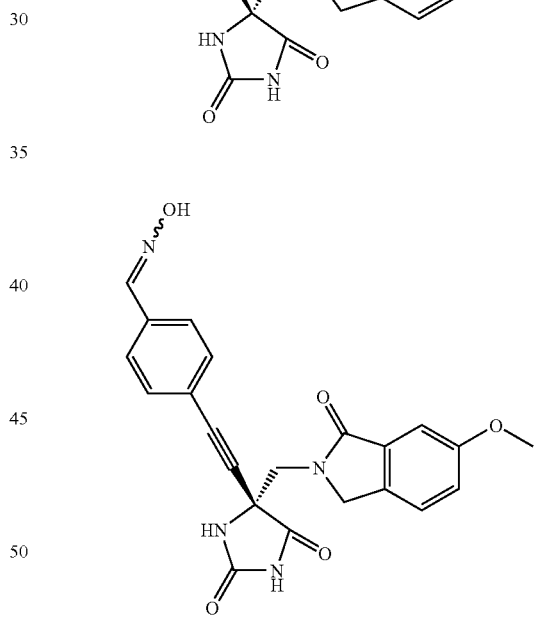
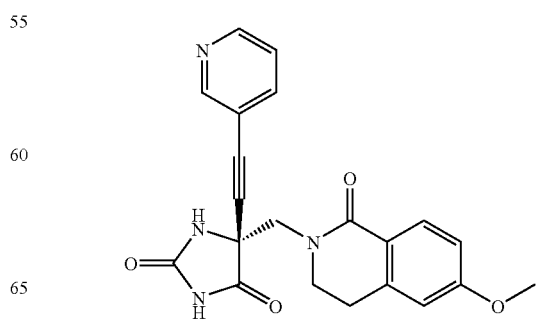

381 -continued
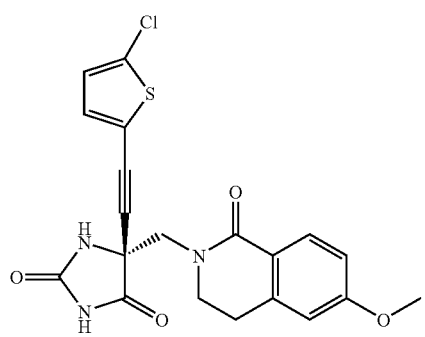
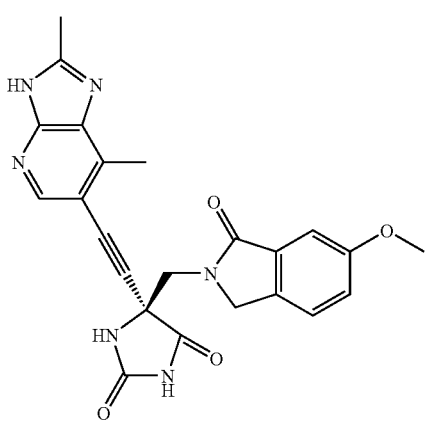
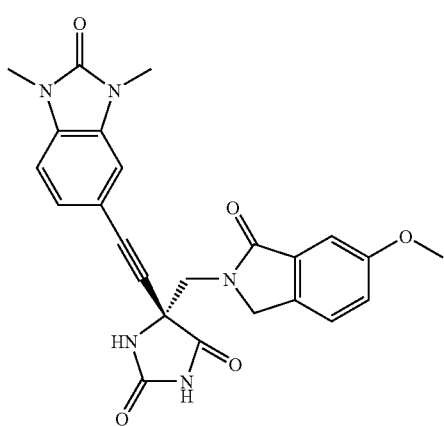
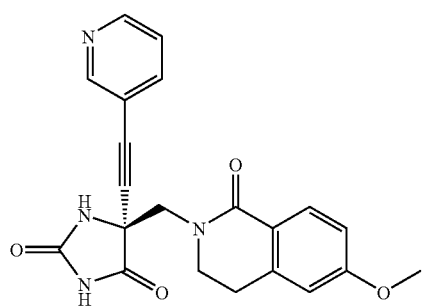
382 -continued
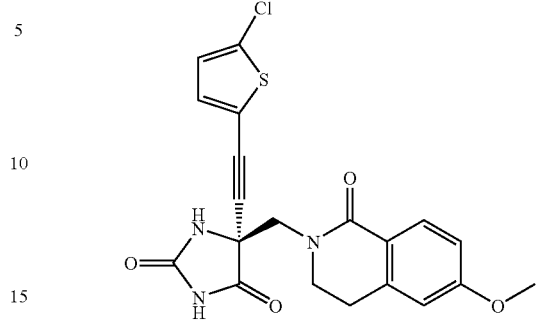
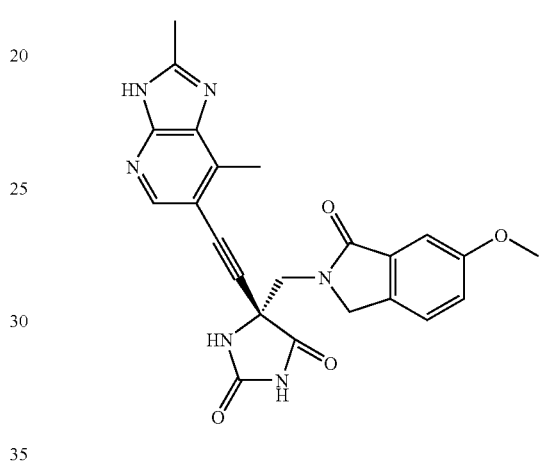
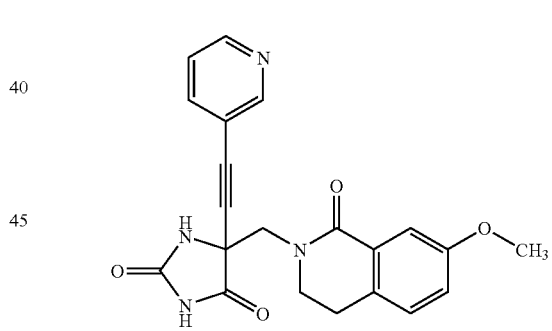
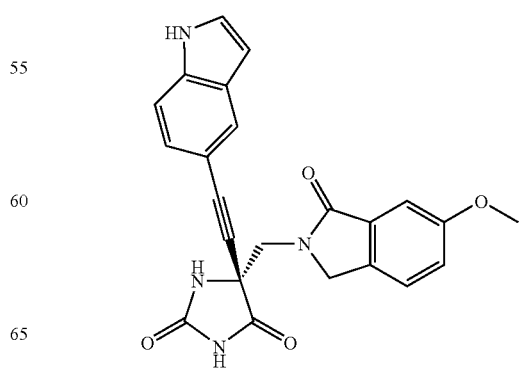

383
-continued
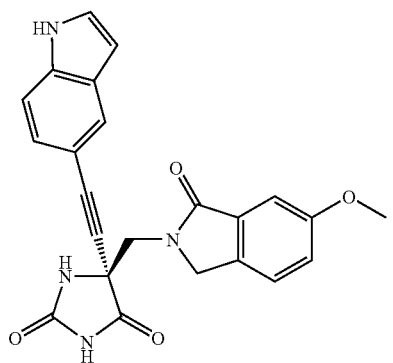
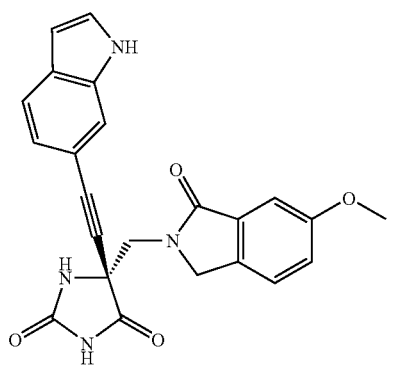
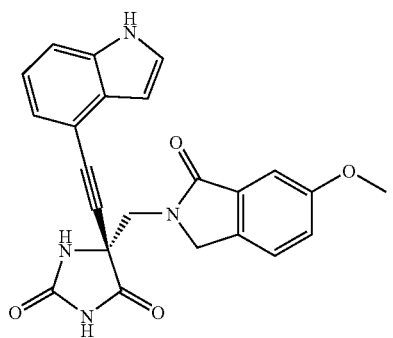
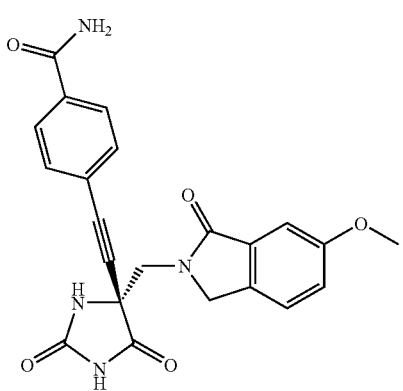
384
-continued
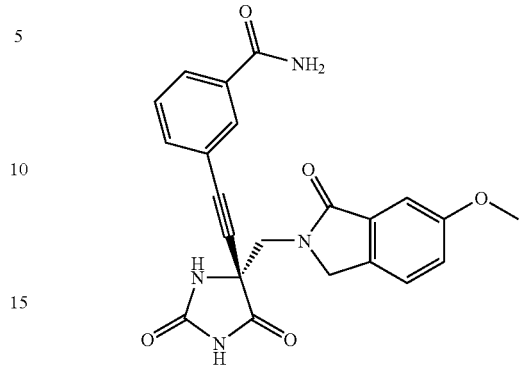
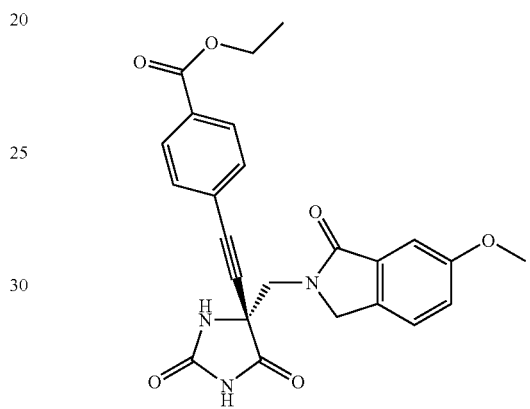
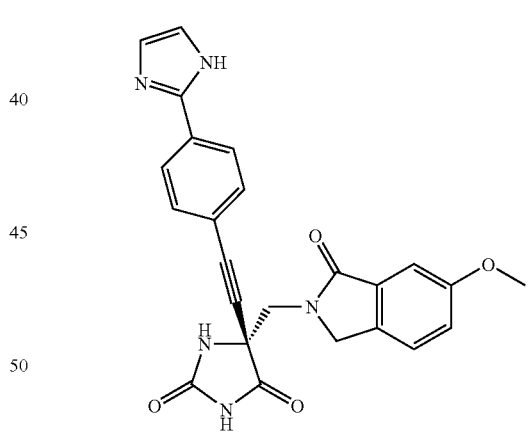
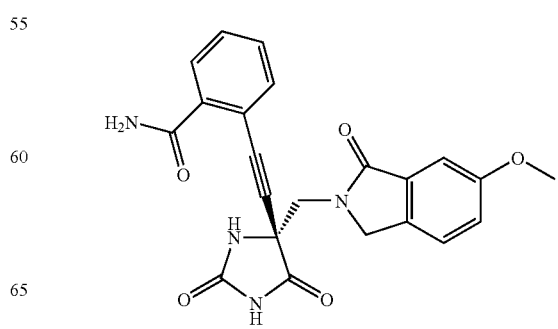

-continued
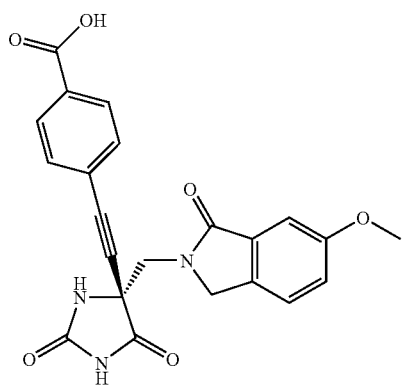
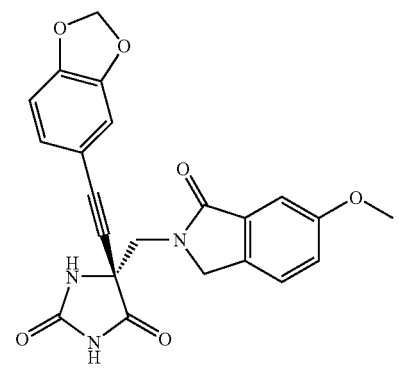
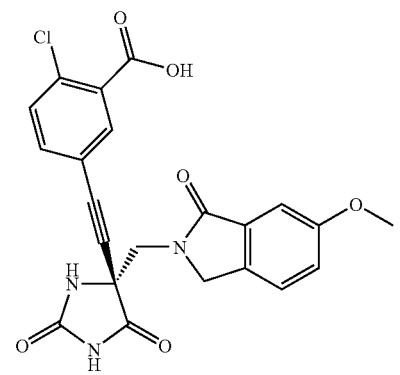
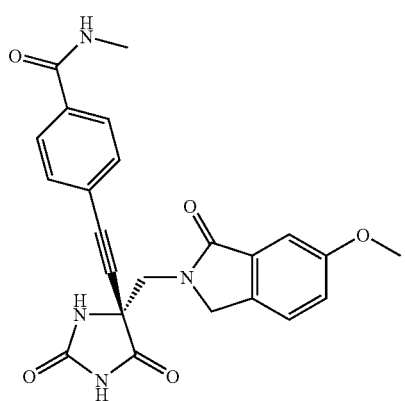
-continued
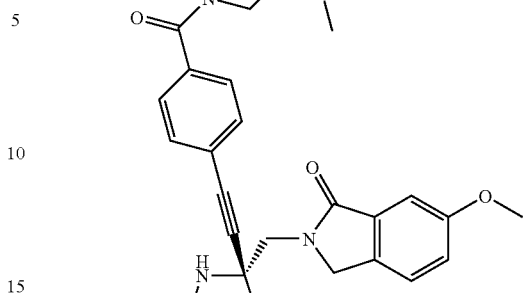
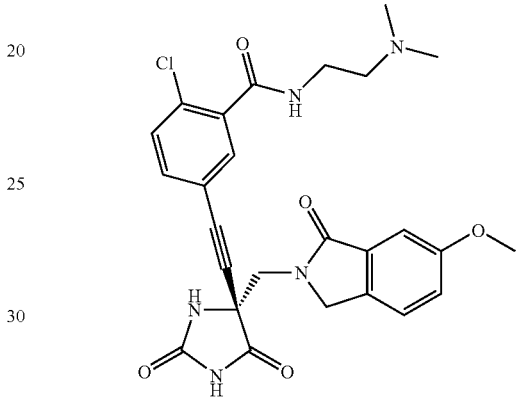
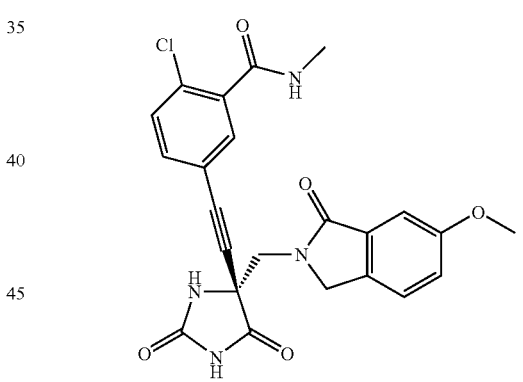
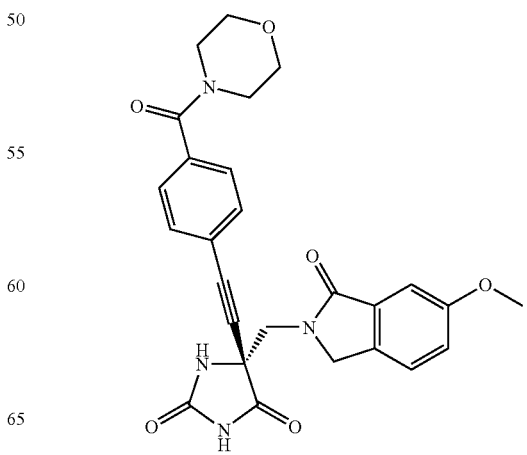

387
-continued
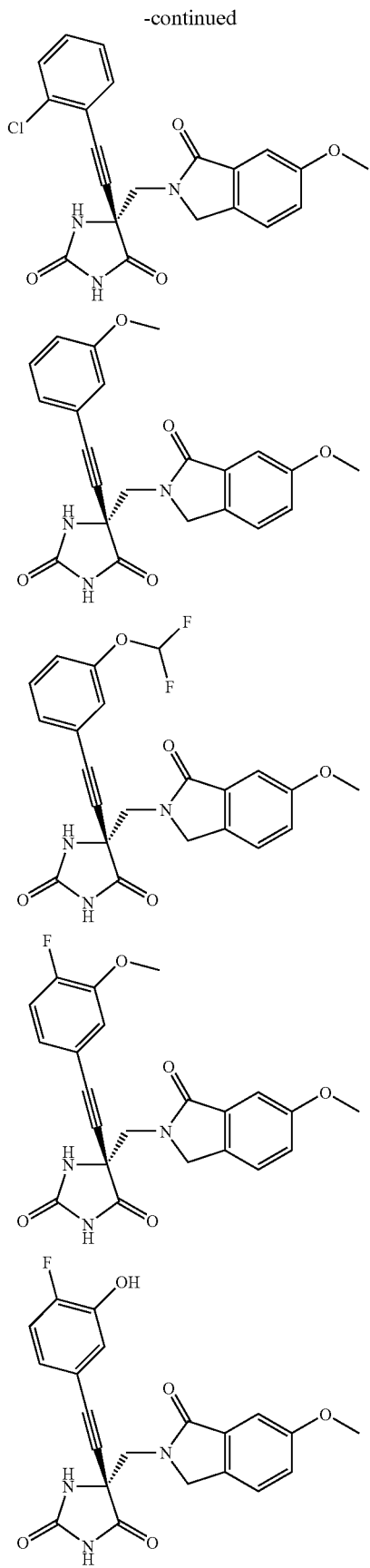
388
-continued
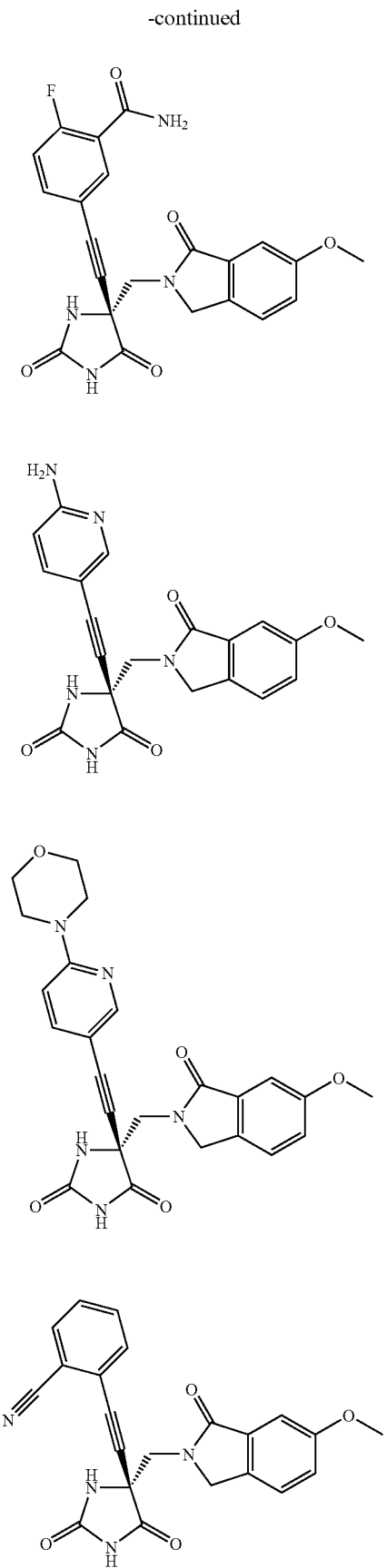

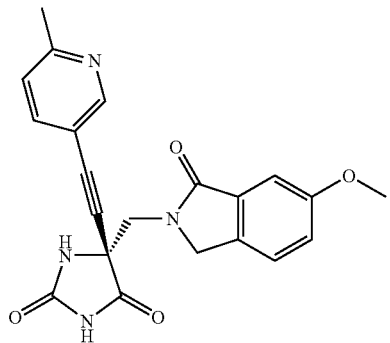
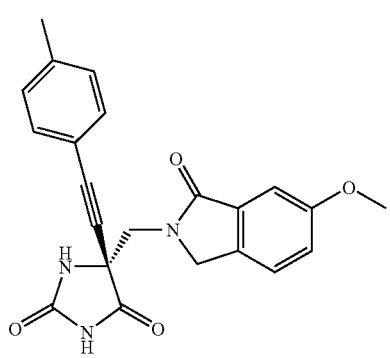
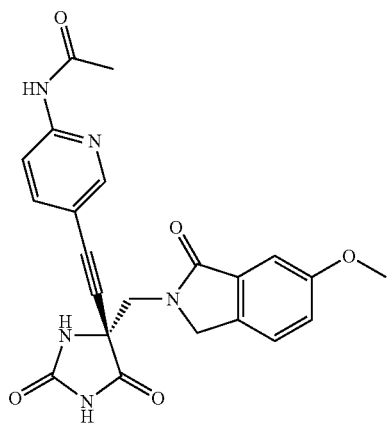
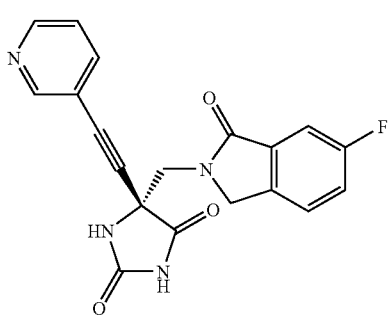
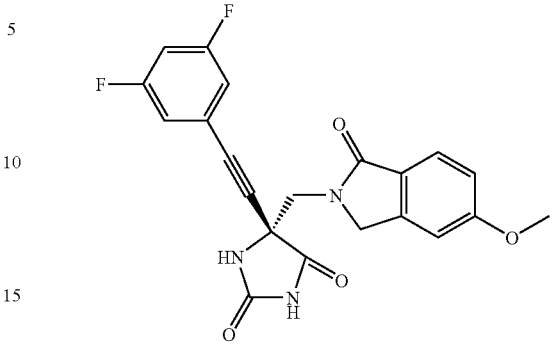
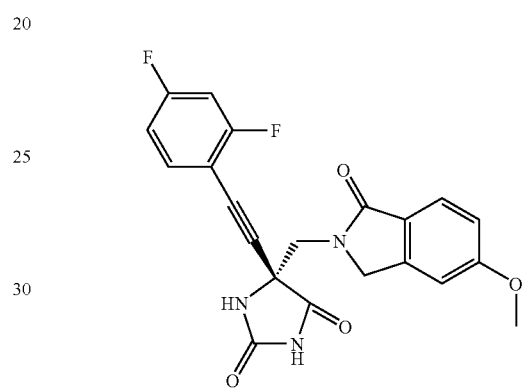
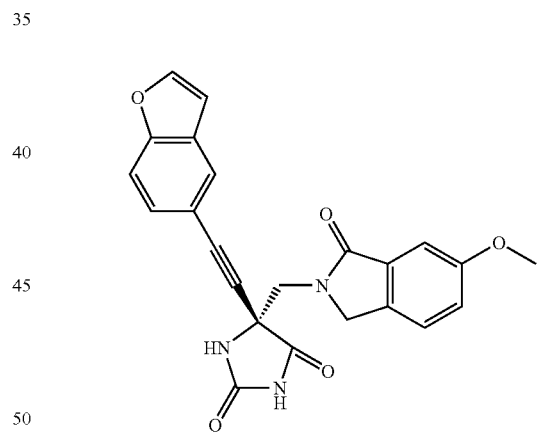
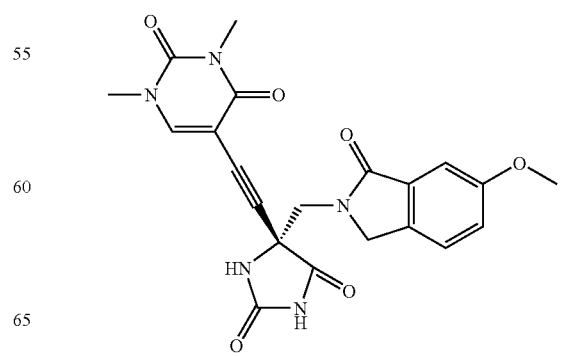

391
-continued
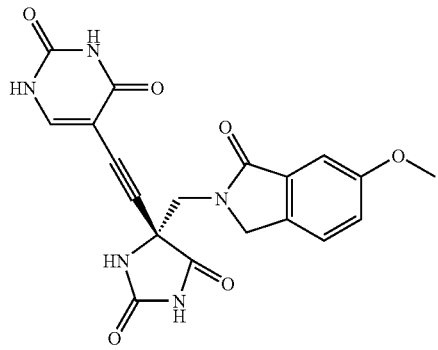
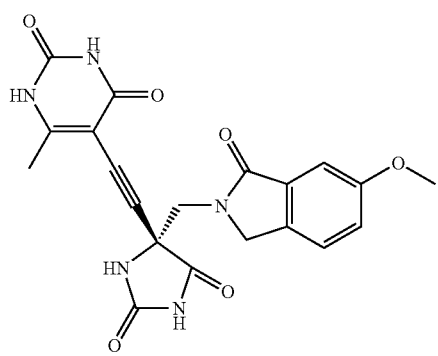
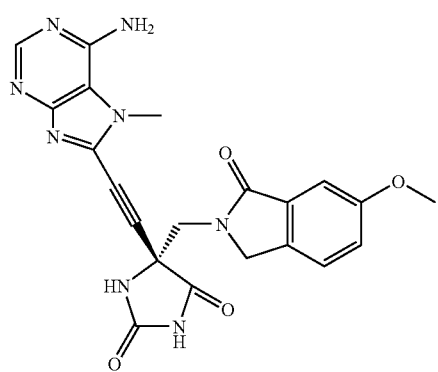
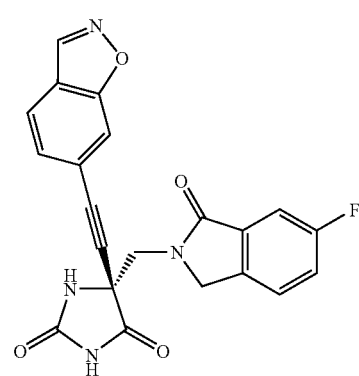
392
-continued
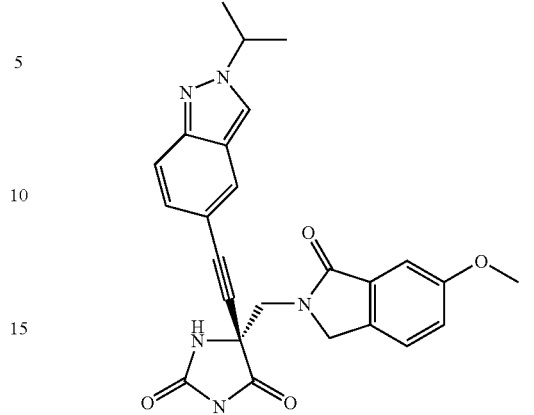
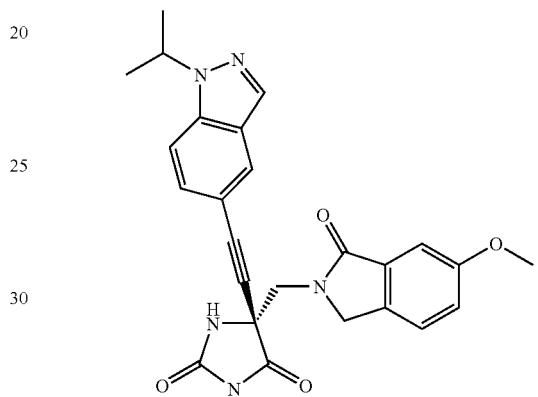
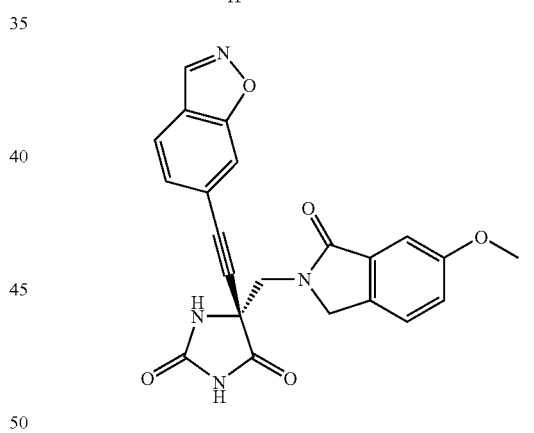
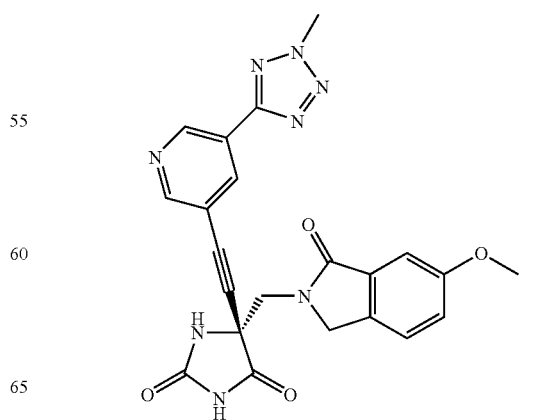

393
-continued
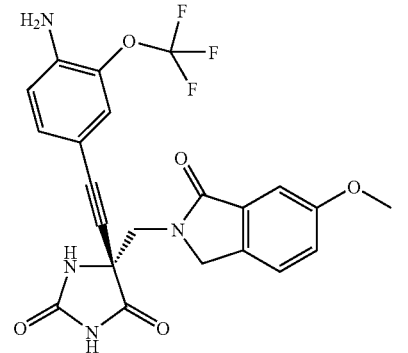
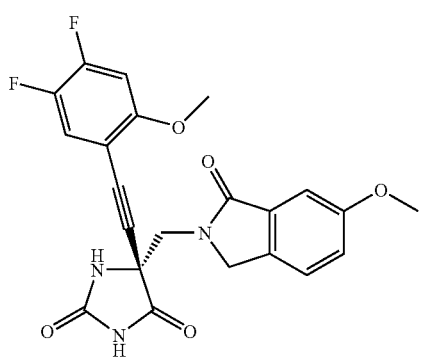
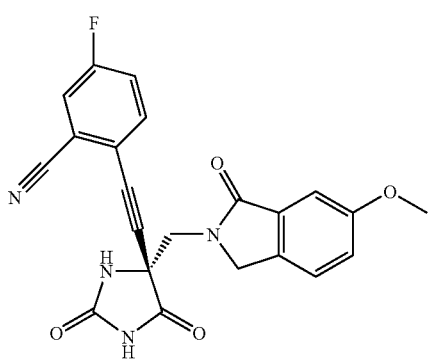
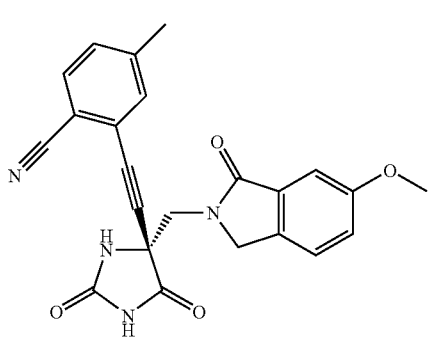
394
-continued
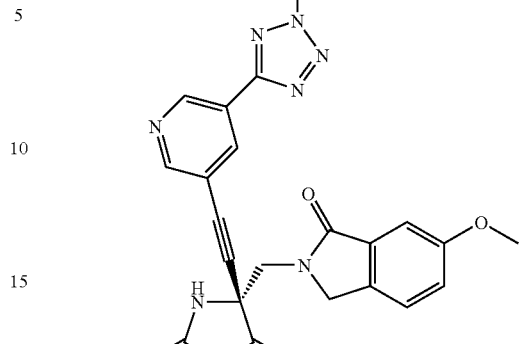
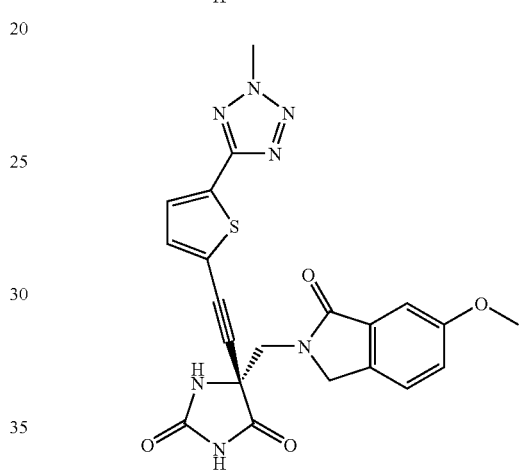
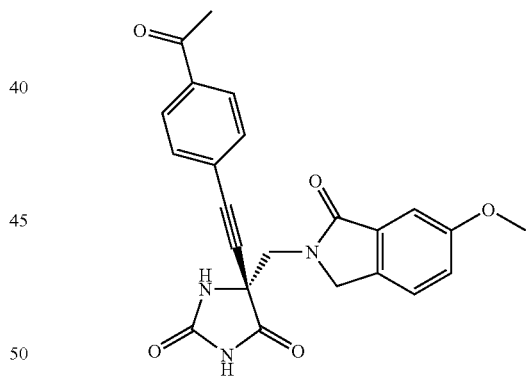
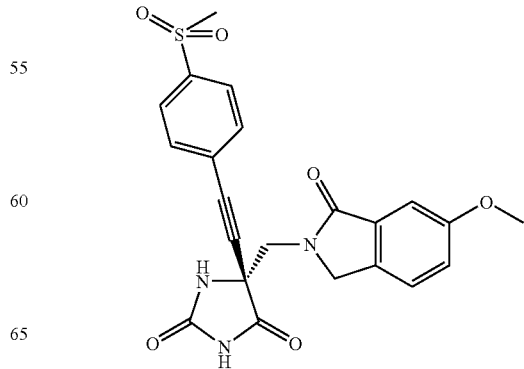

395
-continued
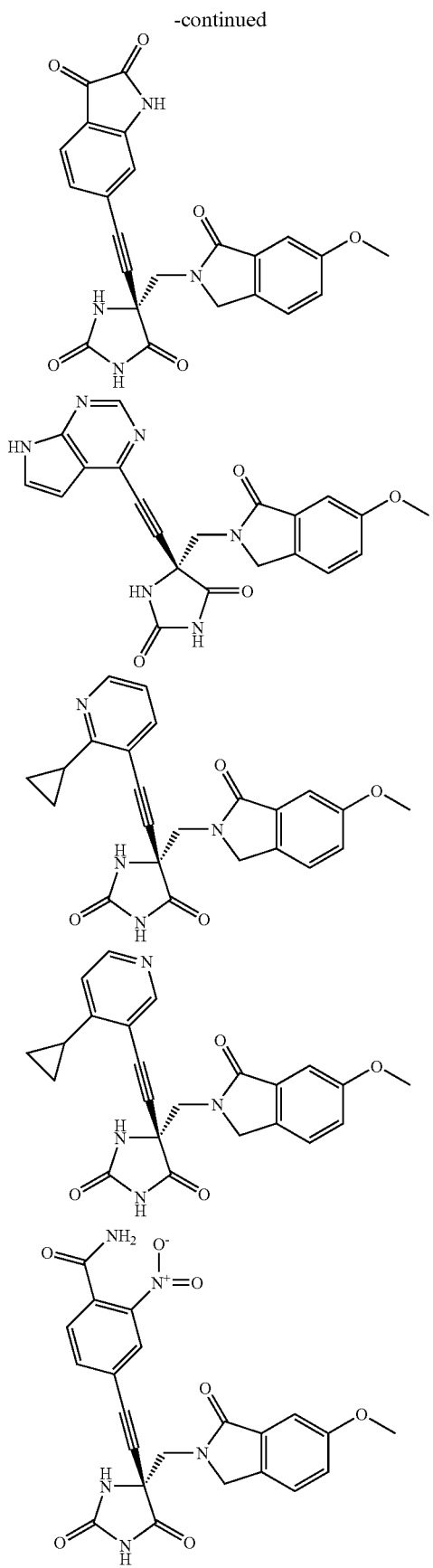
396
-continued
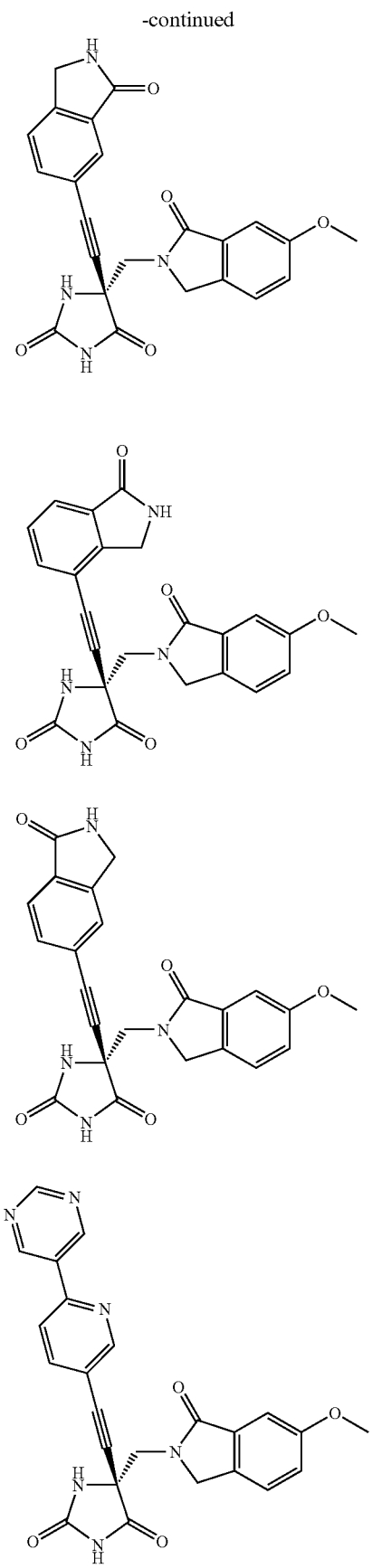

397
-continued
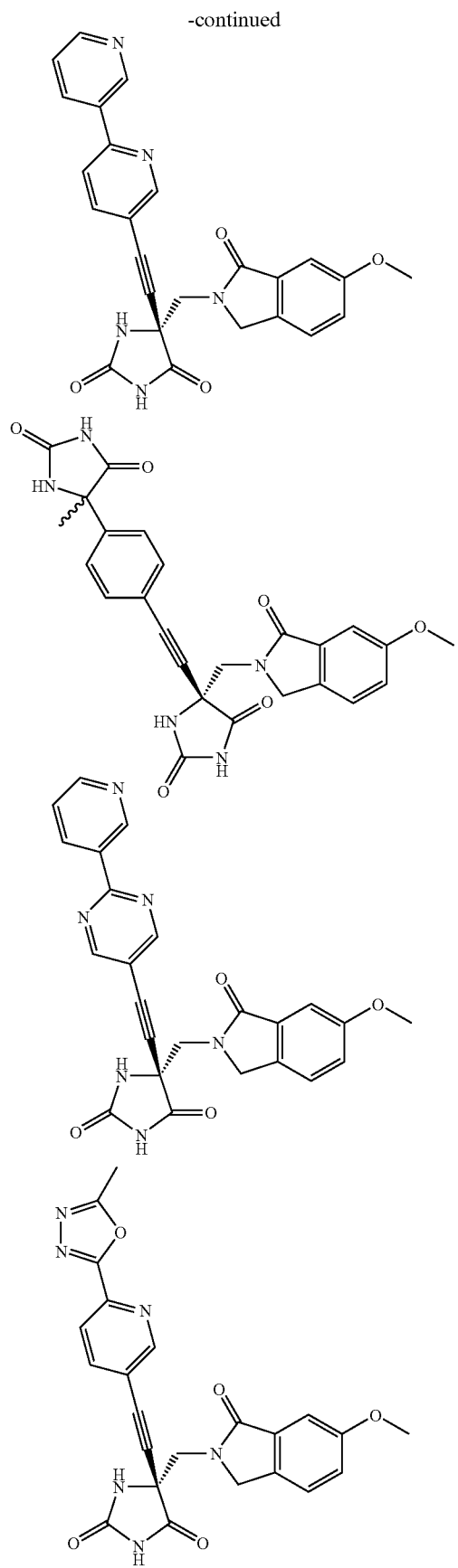
398
-continued
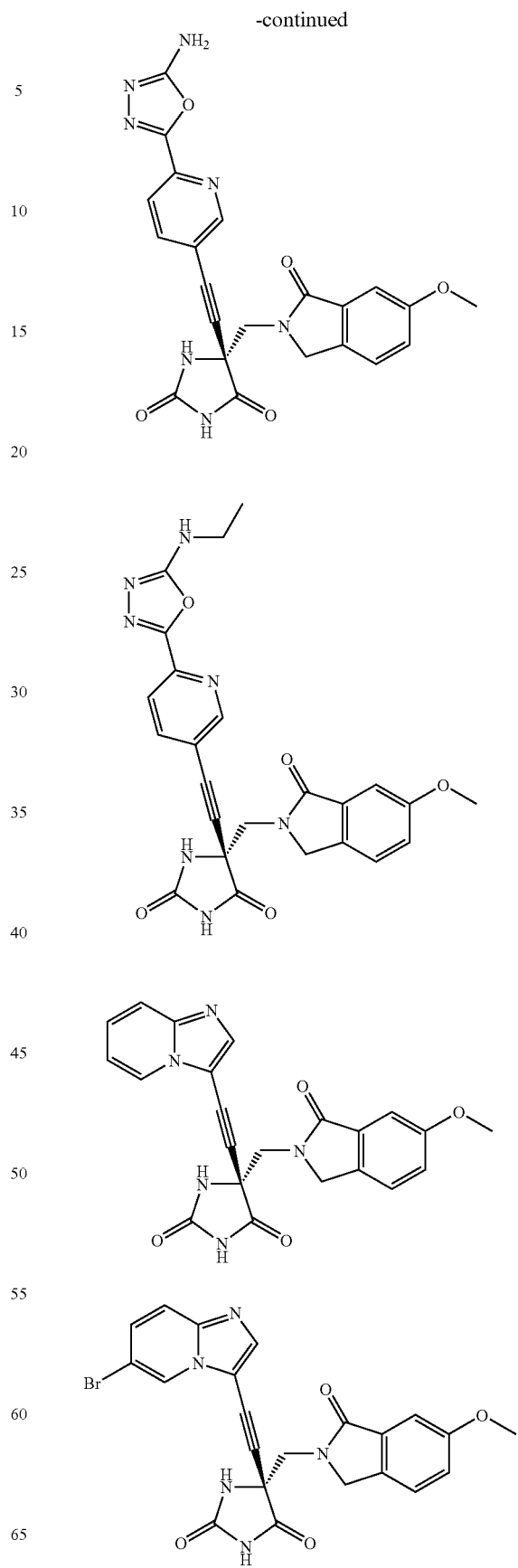

399
-continued
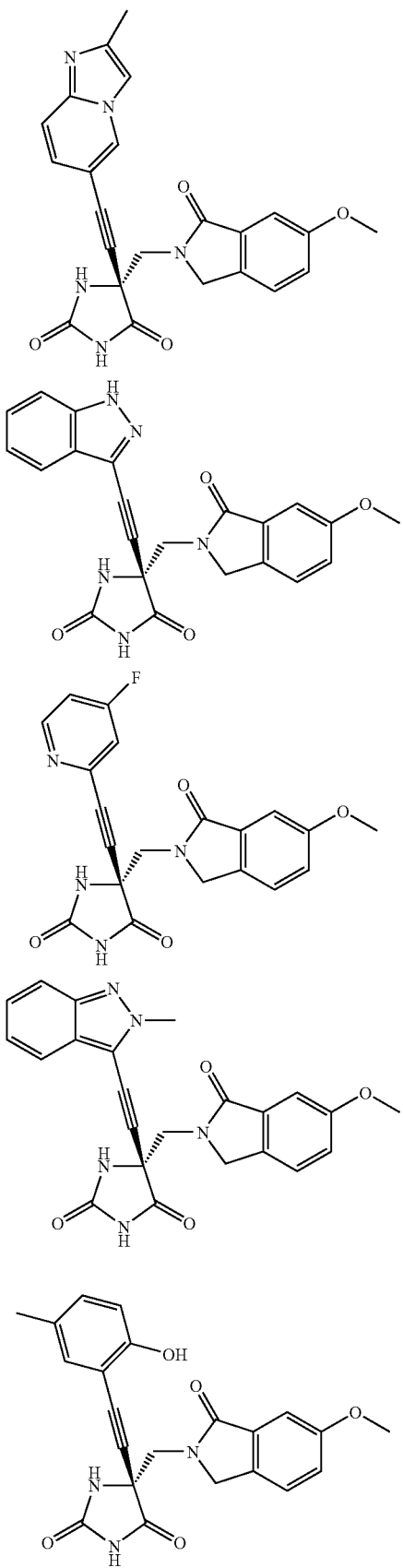
400
-continued
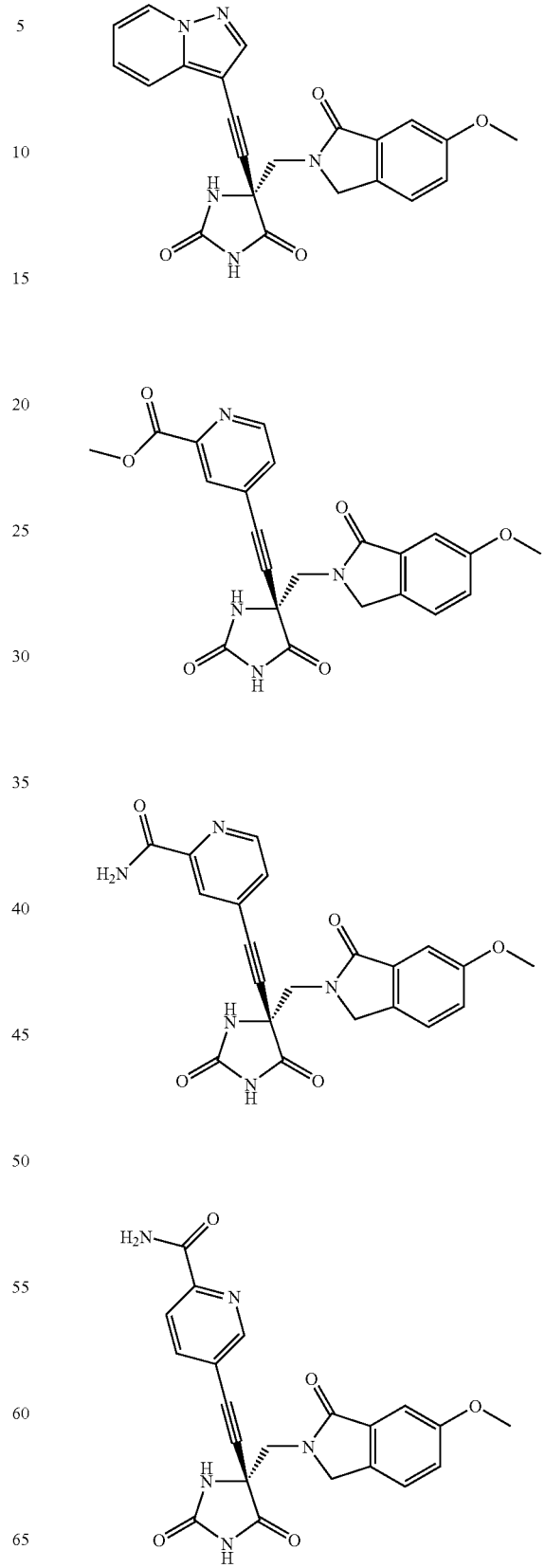

401
-continued
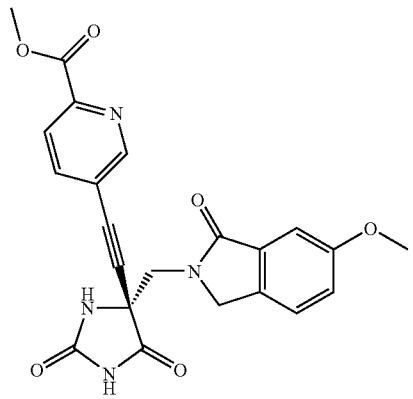
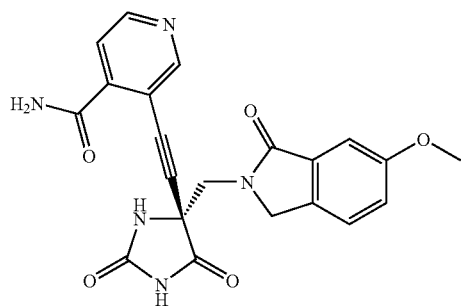
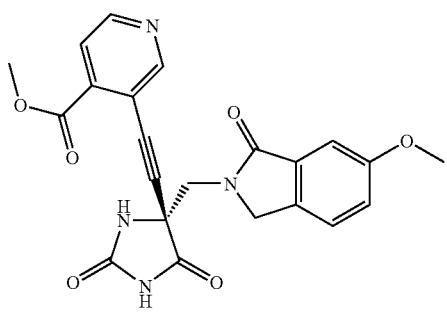
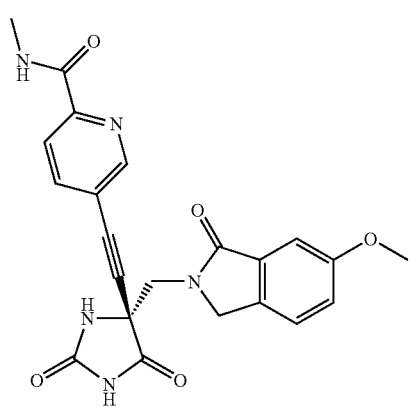
402
-continued
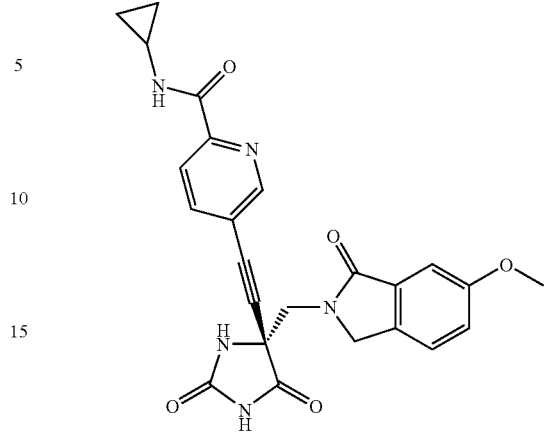
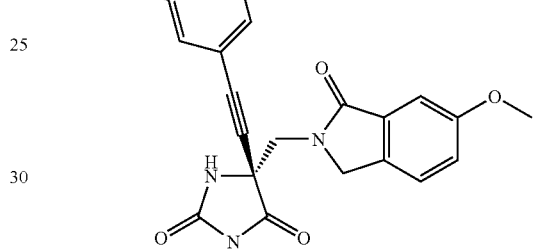
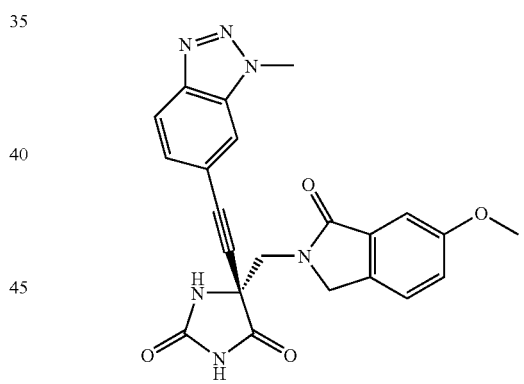
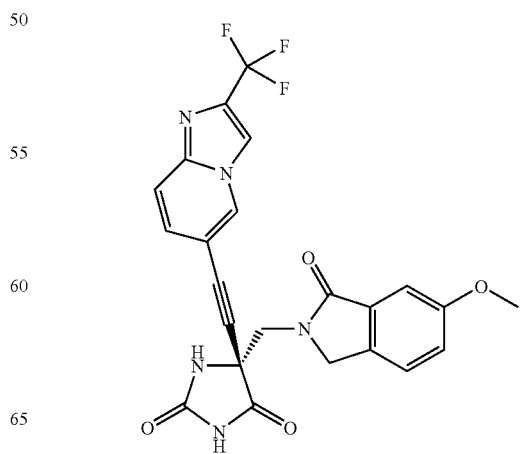

403
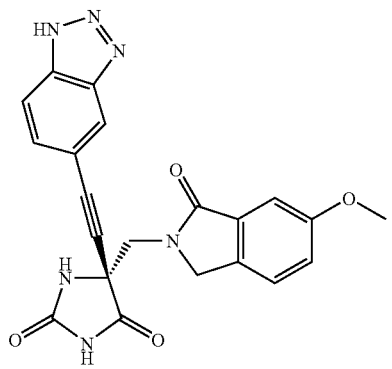
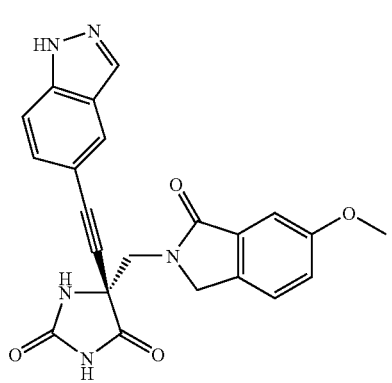
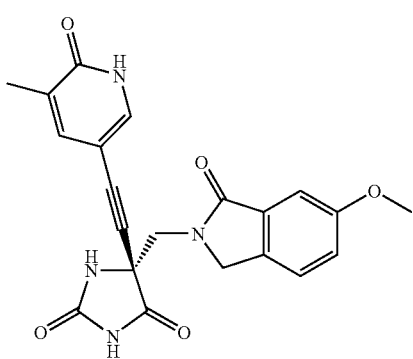
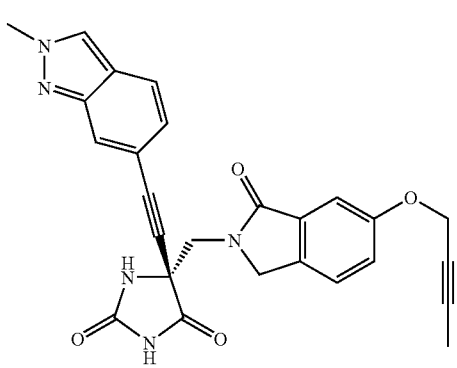
404
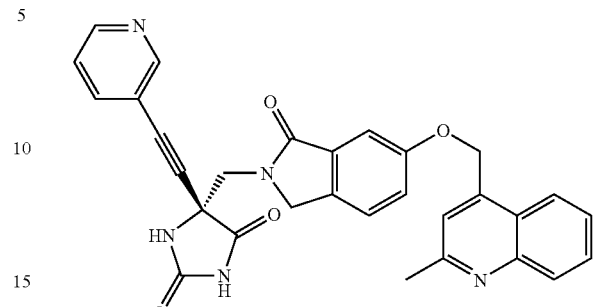
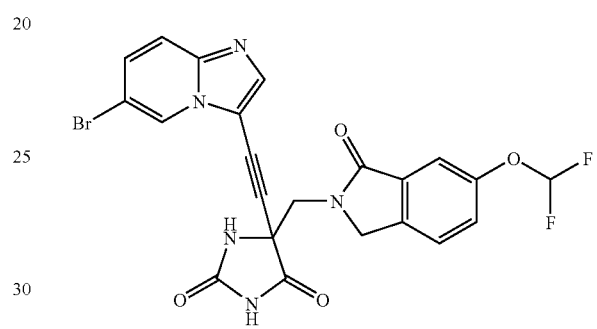
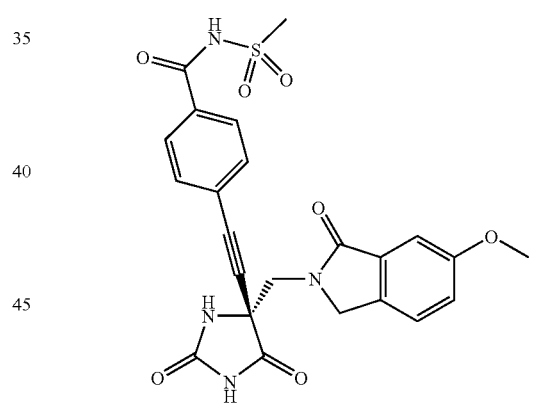
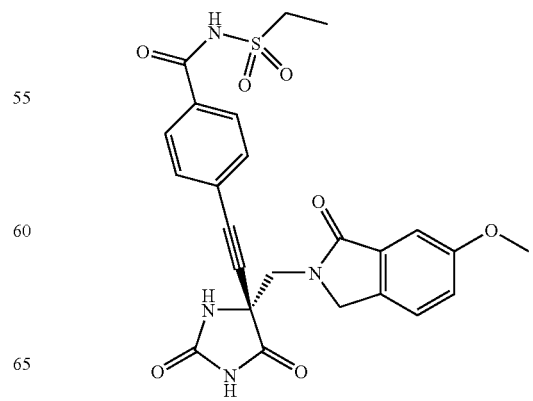

405
-continued
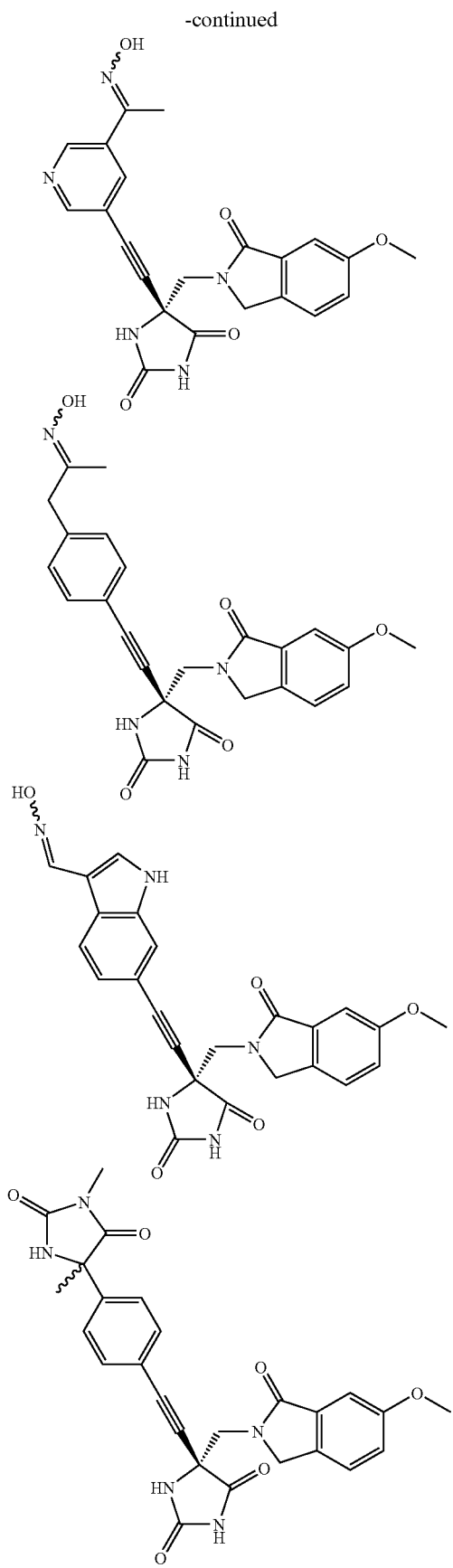
406
-continued
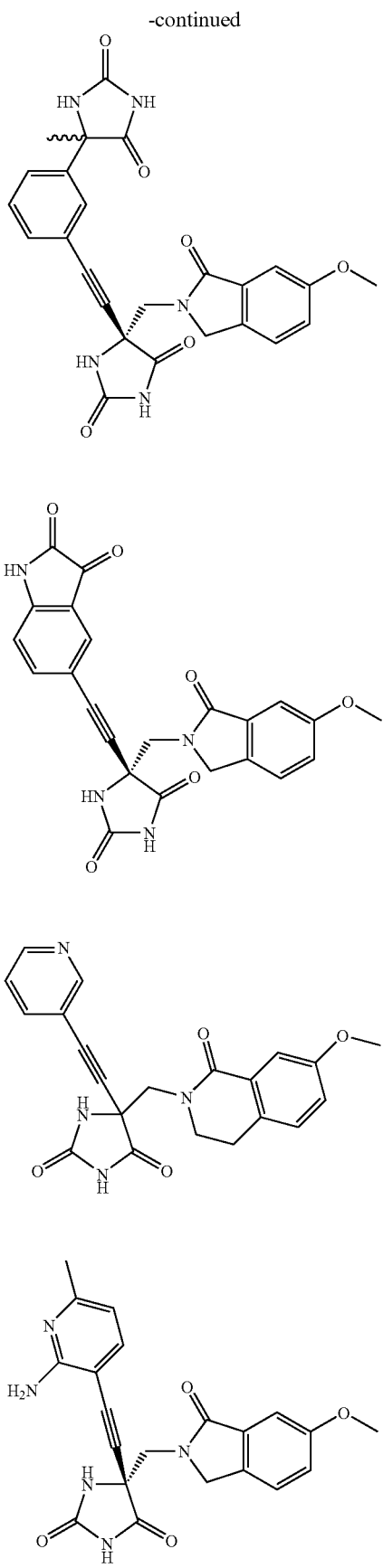

407
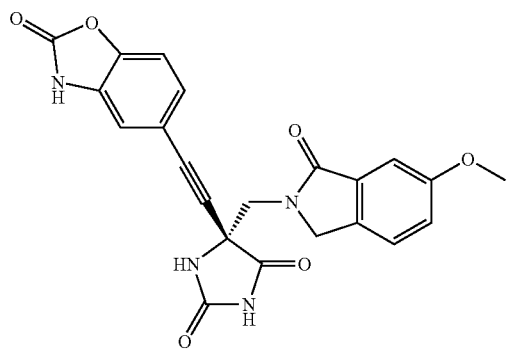
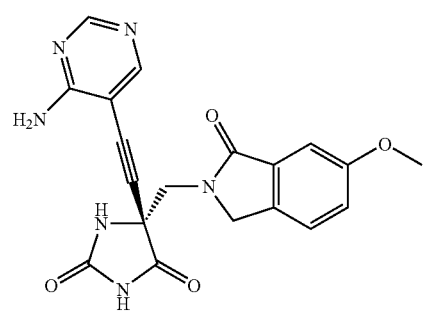
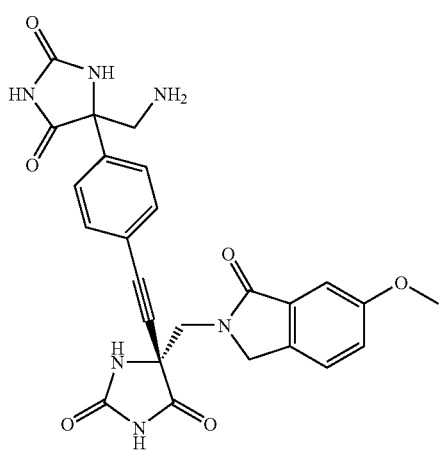
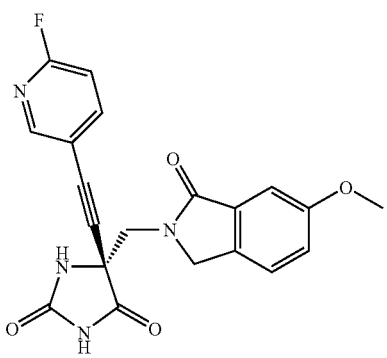
408
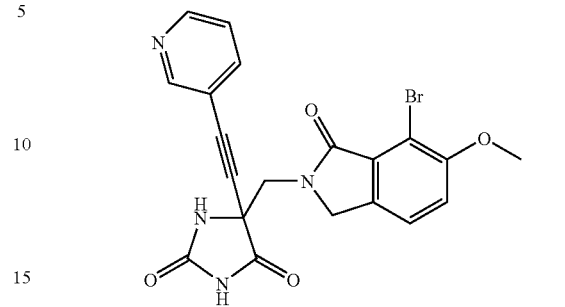
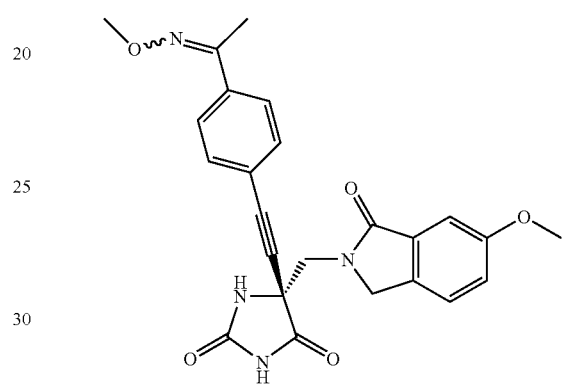
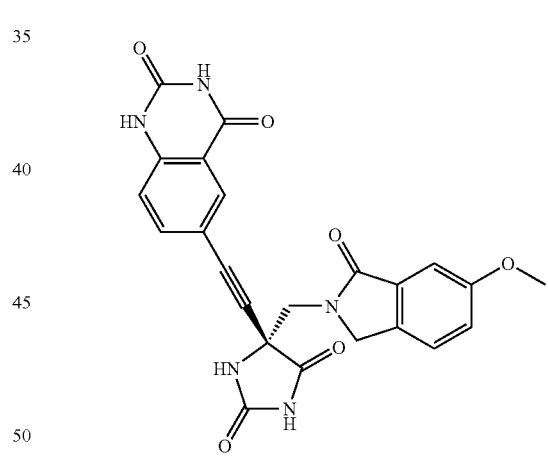
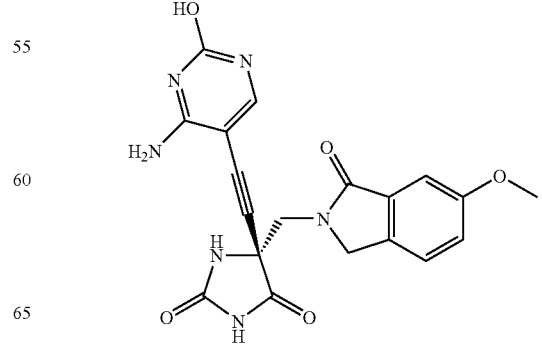

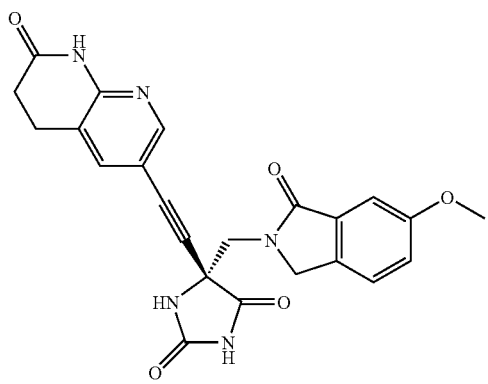
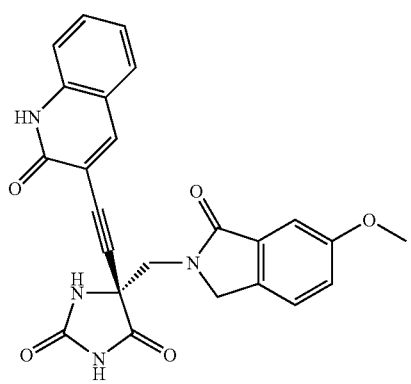
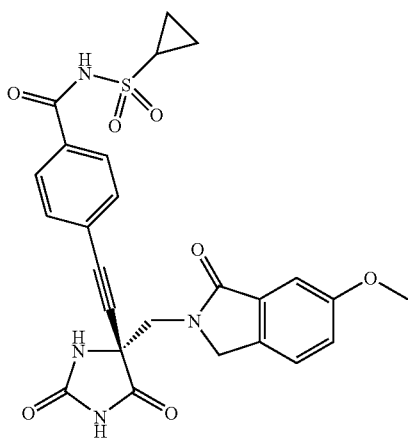
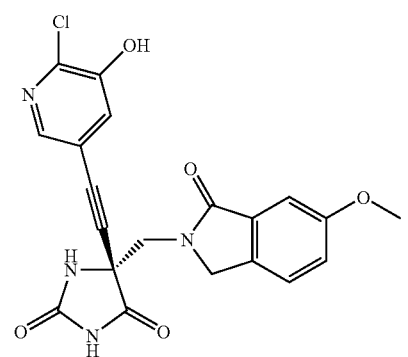
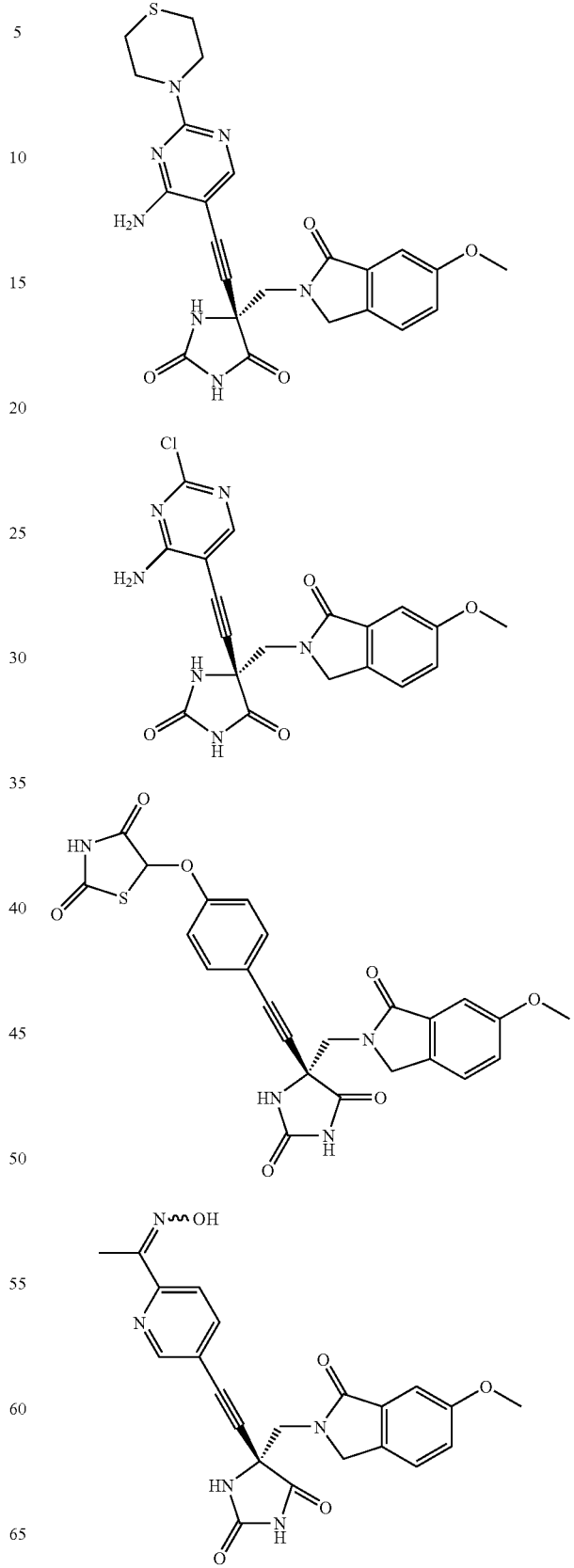

411

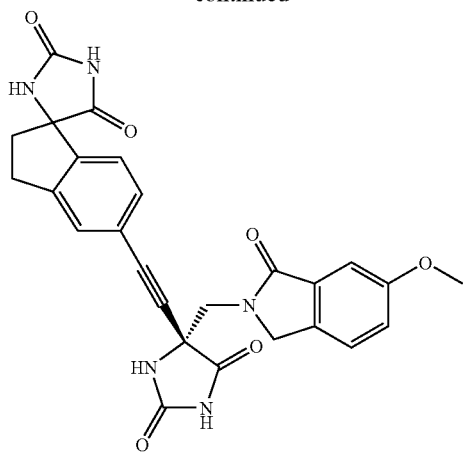

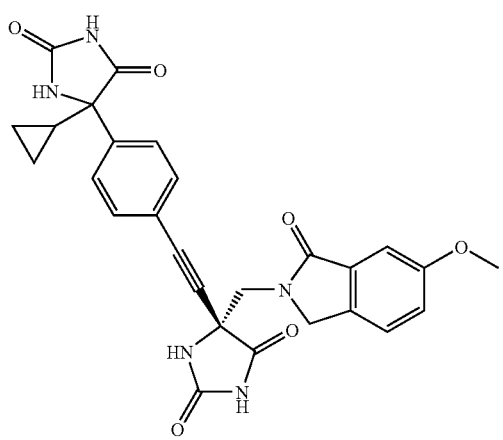

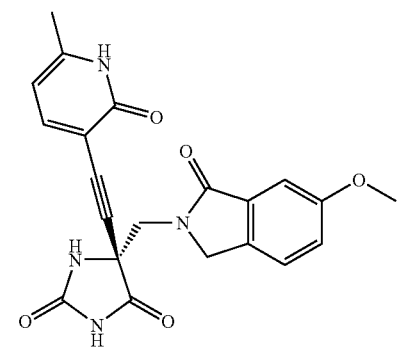

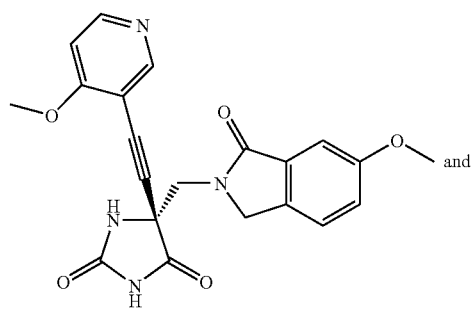

412

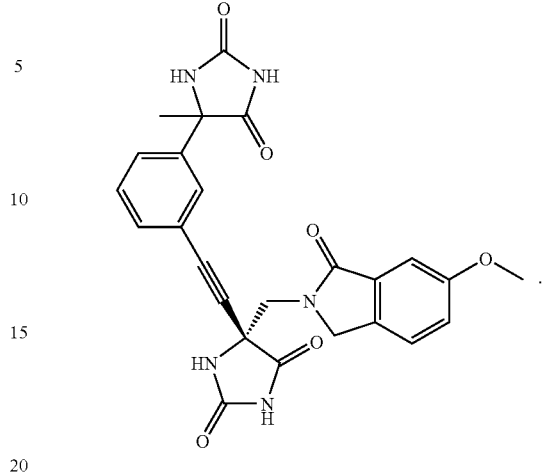

15. The method of claim 14, wherein the condition or disease is rheumatoid arthritis.

16. The method of claim 14, wherein the condition or disease is inflammatory bowel disease.

17. The method of claim 16, wherein the inflammatory bowel disease is Crohn's disease.

18. The method of claim 16, wherein the inflammatory bowel disease is colitis.

19. The method of claim 14, wherein the condition or disease is chronic obstructive pulmonary disorder.

20. The method of claim 14, wherein the condition or disease is psoriasis.

21. The method of claim 14, wherein the condition or disease is ankylosing spondylitis.

22. The method of claim 14, wherein the condition or disease is psoriatic arthritis.

23. The method of claim 1, wherein the compound is selected from the group of compounds set forth below:

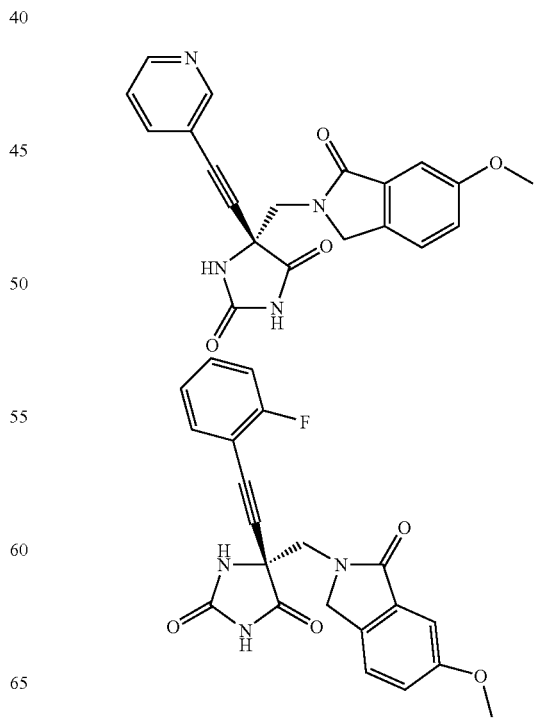

-continued

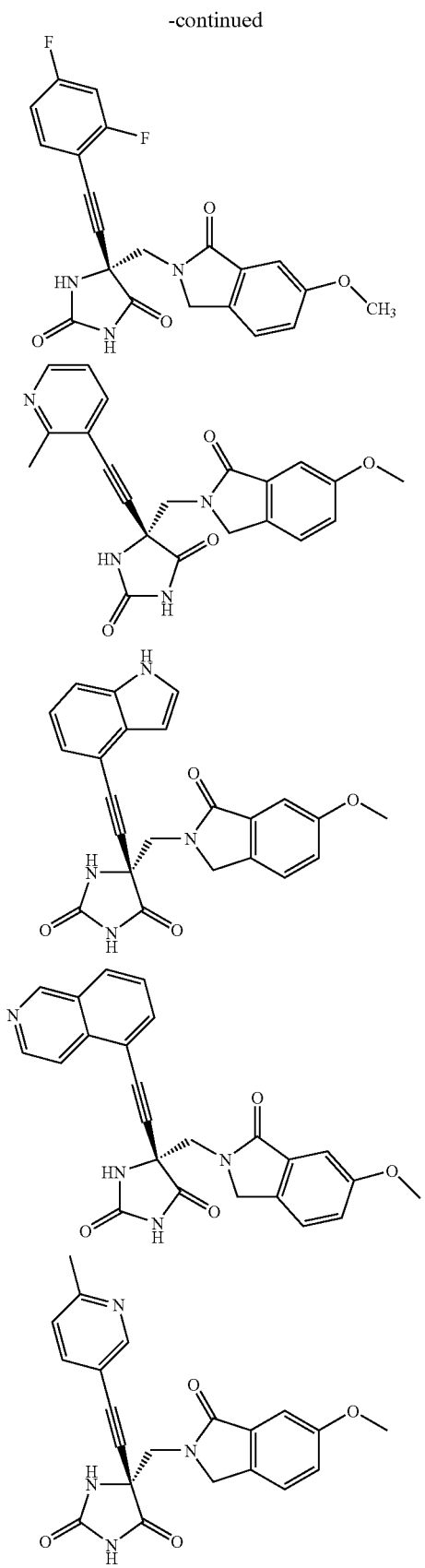

-continued

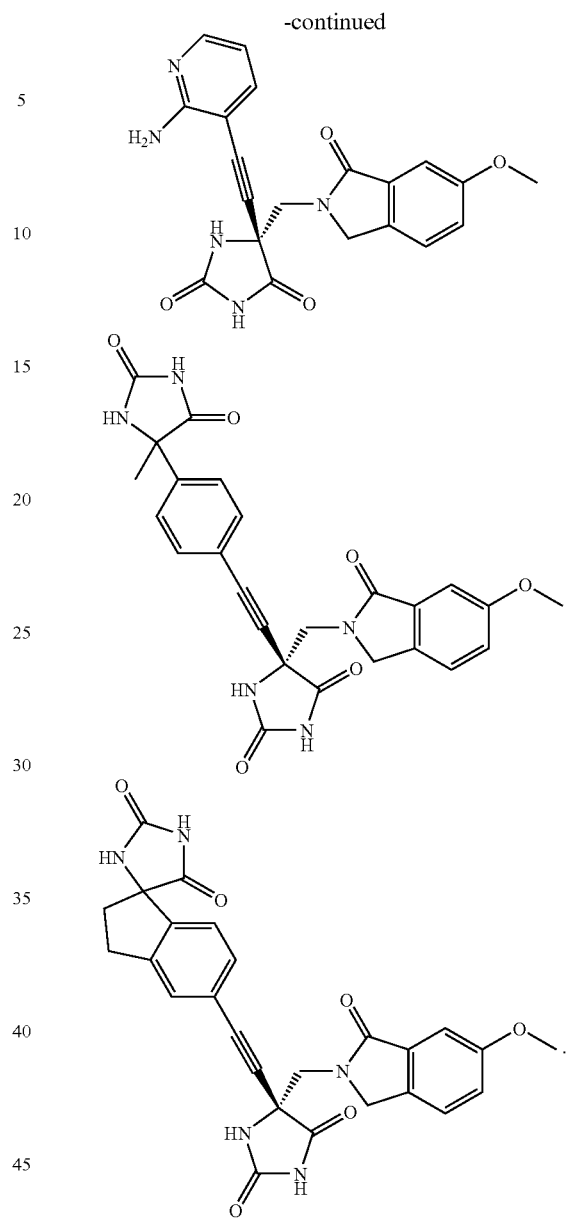

24. The method of claim 23, wherein the condition or disease is rheumatoid arthritis.

25. The method of claim 23, wherein the condition or disease is inflammatory bowel disease.

26. The method of claim 16, wherein the inflammatory bowel disease is Crohn's disease.

27. The method of claim 16, wherein the inflammatory bowel disease is colitis.

28. The method of claim 23, wherein the condition or disease is chronic obstructive pulmonary disorder.

29. The method of claim 23, wherein the condition or disease is psoriasis.

30. The method of claim 23, wherein the condition or disease is ankylosing spondylitis.

31. The method of claim 23, wherein the condition or disease is psoriatic arthritis.

* * * * *